United States Patent
Verdonck et al.

(10) Patent No.: US 10,822,425 B2
(45) Date of Patent: Nov. 3, 2020

(54) SINGLE VARIABLE DOMAIN ANTIBODIES AGAINST OX40L, CONSTRUCTS AND THERAPEUTIC USE

(71) Applicant: Ablynx N.V, Ghent-Zwijnaarde (BE)

(72) Inventors: Frank Verdonck, Sint-Gillis-Waas (BE); Sigrid Cornelis, Sint Martens Latem (BE); Stephanie Staelens, Wevelgem (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 285 days.

(21) Appl. No.: 15/795,442

(22) Filed: Oct. 27, 2017

(65) Prior Publication Data
US 2018/0171019 A1 Jun. 21, 2018
US 2018/0362656 A9 Dec. 20, 2018

Related U.S. Application Data

(63) Continuation of application No. 14/587,042, filed on Dec. 31, 2014, now Pat. No. 9,834,611, which is a continuation of application No. 13/515,876, filed as application No. PCT/EP2010/069606 on Dec. 14, 2010, now Pat. No. 8,962,807.

(60) Provisional application No. 61/286,163, filed on Dec. 14, 2009.

(51) Int. Cl.
*C07K 16/28* (2006.01)
*A61K 39/395* (2006.01)
*G01N 33/68* (2006.01)
*A61K 39/00* (2006.01)

(52) U.S. Cl.
CPC ...... *C07K 16/2896* (2013.01); *C07K 16/2875* (2013.01); *G01N 33/6845* (2013.01); *G01N 33/6854* (2013.01); *A61K 2039/505* (2013.01); *C07K 2317/22* (2013.01); *C07K 2317/24* (2013.01); *C07K 2317/31* (2013.01); *C07K 2317/565* (2013.01); *C07K 2317/569* (2013.01); *C07K 2317/76* (2013.01); *C07K 2317/92* (2013.01); *C07K 2319/00* (2013.01); *C07K 2319/31* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,632,927 B2 | 10/2003 | Adair et al. | |
| 8,962,807 B2 | 2/2015 | Verdonck et al. | |
| 9,834,611 B2 | 12/2017 | Verdonck et al. | |
| 2009/0297524 A1 | 12/2009 | Grant et al. | |
| 2013/0018175 A1 | 1/2013 | Verdonck et al. | |

FOREIGN PATENT DOCUMENTS

| | | |
|---|---|---|
| WO | WO 95/12673 A1 | 5/1995 |
| WO | WO 95/21915 A1 | 8/1995 |
| WO | WO 99/15200 A1 | 4/1999 |
| WO | WO 2005/094879 A2 | 10/2005 |
| WO | WO 2006/029879 A2 | 3/2006 |
| WO | WO 2006/030220 A1 | 3/2006 |
| WO | WO 2007/133290 A2 | 11/2007 |
| WO | WO 2010/139808 A2 | 12/2010 |
| WO | WO 2010/142551 A2 | 12/2010 |

OTHER PUBLICATIONS

[No Author Listed] A Study of humab OX40L in the Prevention of Allergen-Induced Airway Obstruction in Adults With Mild Allergic Asthma. Clinical Trials Identifier: NCT00983658. Oct. 7, 2009. Last accessed at http://clinicaltrials.gov/archive/nct00983658/2009_10_07 on Aug. 3, 2012.
[No Author Listed] Dissociation constant. Wikipedia. Jun. 27, 2016. Retrieved from https://en.wikipedia.org/w/index. php?title=Dissociation _ constant&oldid=72 7236090 on Jul. 13, 2016.
[No Author Listed] IC50. Wikipedia. May 10, 2016. Retrieved from https://en.wikipedia.org/w/index.php?title=IC50&oldid=719591698 on Jul. 13, 2016.
[No Author Listed] Trademark search result. USPTO. Jun. 2014. 1 page.
Beiboer et al., Guided selection of a pan carcinoma specific antibody reveals similar binding characteristics yet structural divergence between the original murine antibody and its human equivalent. J Mol Biol. Feb. 25, 2000;296(3):833-49.
Catley et al., Monoclonal antibodies for the treatment of asthma. Pharmacol Ther. Dec. 2011;132(3):333-51. doi: 10.1016/j.pharmthera.2011.09.005. Epub Sep. 12, 2011.
Coppieters et al., Formatted anti-tumor necrosis factor alpha VHH proteins derived from camelids show superior potency and targeting to inflamed joints in a murine model of collagen-induced arthritis. Arthritis Rheum. Jun. 2006;54(6):1856-66.
Drescher, Characterization of biological interactions with Biacore. GE Healthcare. Jun. 27, 2011.

(Continued)

*Primary Examiner* — Ilia I Ouspenski
(74) *Attorney, Agent, or Firm* — Wolf, Greenfield & Sacks, P.C.

(57) ABSTRACT

The present invention relates to immunoglobulin single variable domain sequences that are directed against (as defined herein) OX40L, as well as to compounds or constructs, and in particular proteins and polypeptides, that comprise or essentially consist of one or more such immunoglobulin single variable domain sequences. In particular these immunoglobulin single variable domain sequences can block binding of OX40L to OX40.
The immunoglobulin single variable domains, compounds and constructs can be used for prophylactic, therapeutic or diagnostic purposes, such as for the treatment of inflammatory disease and/or disorder such as e.g. asthma, allergic asthma, chronic colitis, Crohn's disease, inflammatory bowel disease, and/or arthrosclerosis.

15 Claims, 2 Drawing Sheets
Specification includes a Sequence Listing.

(56) References Cited

OTHER PUBLICATIONS

Gough et al., OX40 (CD134) and OX40L. Adv Exp Med Biol. 2009;647:94-107.

Higgins et al., Regulation of T cell activation in vitro and in vivo by targeting the OX40-OX40 ligand interaction: amelioration of ongoing inflammatory bowel disease with an OX40-IgG fusion protein, but not with an OX40 ligand-IgG fusion protein. J Immunol. Jan. 1, 1999;162(1):486-93.

Klimka et al., Human anti-CD30 recombinant antibodies by guided phage antibody selection using cell panning. Br J Cancer. Jul. 2000;83(2):252-60.

Krimmer et al., CD40 and OX40 ligand are differentially regulated on asthmatic airway smooth muscle. Allergy. Jul. 2009;64(7):1074-82. Epub Feb. 12, 2009.

Mahmood et al., OX40L-OX40 interactions: a possible target for gastrointestinal autoimmune diseases. N Am J Med Sci. Nov. 2012;4(11):533-6. doi: 10.4103/1947-2714.103311.

Malmström et al., CD134L expression on dendritic cells in the mesenteric lymph nodes drives colitis in T cell-restored SCID mice. J Immunol. Jun. 1, 2001;166(11):6972-81.

Panka et al., Variable region framework differences result in decreased or increased affinity of variant anti-digoxin antibodies. Proc Natl Acad Sci U S A. May 1988;85(9):3080-4.

Rader et al., A phage display approach for rapid antibody humanization: designed combinatorial V gene libraries. Proc Natl Acad Sci U S A. Jul. 21, 1998;95(15):8910-5.

Redmond et al., Targeting OX40 and OX40L for the treatment of autoimmunity and cancer. Crit Rev Immunol. 2007;27(5):415-36.

Rentero et al., Screening of large molecule diversities by phage display. Chimia (Aarau). 2011;65(11):843-5. doi: 10.2533/chimia.2011.843.

Roche, Half Year Results 2011. Changes to the development pipeline. Jul. 21, 2011. 2 pages.

Rudikoff et al., Single amino acid substitution altering antigen-binding specificity. Proc Natl Acad Sci U S A. Mar. 1982;79(6):1979-83.

Sebaugh, Guidelines for accurate EC50/IC50 estimation. Pharm Stat. Mar.-Apr. 2011;10(2):128-34. doi: 10.1002/pst.426.

Seshasayee et al., In vivo blockade of OX40 ligand inhibits thymic stromal lymphopoietin driven atopic inflammation. J Clin Invest. Dec. 2007;117(12):3868-78.

Totsuka et al., Therapeutic effect of anti-OX40L and anti-TNF-alpha MAbs in a murine model of chronic colitis. Am J Physiol Gastrointest Liver Physiol. Apr. 2003;284(4):G595-603. Epub Jan. 10, 2003.

Wesolowski et al., Single domain antibodies: promising experimental and therapeutic tools in infection and immunity. Med Microbiol Immunol. Aug. 2009;198(3):157-74. Epub Jun. 16, 2009.

Xu et al., Diversity in the CDR3 region of V(H) is sufficient for most antibody specificities. Immunity. Jul. 2000;13(1):37-45.

PCT/EP2010/069606, Apr. 18, 2011, International Search Report and Written Opinion.

PCT/EP2010/069606, Jun. 28, 2012, International Preliminary Report on Patentability.

Amit et al., Three-dimensional structure of an antigen-antibody complex at 2.8 A resolution. Science. Aug. 15, 1986;233(4765):747-53.

```
                      SEQUENCE LISTING

<160> NUMBER OF SEQ ID NOS: 234

<210> SEQ ID NO 1
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 1

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ile Pro Phe Ser Xaa Xaa
                20                  25                  30

Xaa Xaa Xaa Trp Phe Arg Gln Ala Pro Gly Lys Gln Arg Asp Ser Val
            35                  40                  45
```

```
Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
 65                  70                  75                  80

Val Tyr Arg Cys Tyr Phe Xaa Xaa Xaa Xaa Trp Gly Gln Gly Thr
                 85                  90                  95

Gln Val Thr Val Ser Ser
            100

<210> SEQ ID NO 2
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 2

Gln Val Lys Leu Glu Glu Ser Gly Gly Gly Leu Val Gln Ala Gly Gly
 1               5                  10                  15

Ser Leu Arg Leu Ser Cys Val Gly Ser Gly Arg Thr Phe Ser Xaa Xaa
             20                  25                  30

Xaa Xaa Xaa Trp Phe Arg Leu Ala Pro Gly Lys Glu Arg Glu Phe Val
         35                  40                  45

Ala Xaa Xaa Xaa Xaa Xaa Arg Phe Thr Ile Ser Arg Asp Thr Ala Ser
    50                  55                  60

Asn Arg Gly Tyr Leu His Met Asn Asn Leu Thr Pro Glu Asp Thr Ala
 65                  70                  75                  80

Val Tyr Tyr Cys Ala Ala Xaa Xaa Xaa Xaa Xaa Trp Gly Gln Gly Thr
                 85                  90                  95

Gln Val Thr Val Ser Ser
            100

<210> SEQ ID NO 3
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 3

Ala Val Gln Leu Val Asp Ser Gly Gly Gly Leu Val Gln Ala Gly Asp
```

```
                1               5                   10                  15
Ser Leu Lys Leu Ser Cys Ala Leu Thr Gly Gly Ala Phe Thr Xaa Xaa
                20                  25                  30

Xaa Xaa Xaa Trp Phe Arg Gln Thr Pro Gly Arg Glu Arg Glu Phe Val
            35                  40                  45

Ala Xaa Xaa Xaa Xaa Arg Phe Thr Ile Ser Arg Asp Asn Ala Lys
    50                  55                  60

Asn Met Val Tyr Leu Arg Met Asn Ser Leu Ile Pro Glu Asp Ala Ala
65                  70                  75                  80

Val Tyr Ser Cys Ala Ala Xaa Xaa Xaa Xaa Xaa Trp Gly Gln Gly Thr
                85                  90                  95

Leu Val Thr Val Ser Ser
            100

<210> SEQ ID NO 4
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 4

Gln Val Gln Leu Val Glu Ser Gly Gly Gly Leu Val Glu Ala Gly Gly
1               5                   10                  15

Ser Leu Arg Leu Ser Cys Thr Ala Ser Glu Ser Pro Phe Arg Xaa Xaa
                20                  25                  30

Xaa Xaa Xaa Trp Phe Arg Gln Thr Ser Gly Gln Glu Arg Glu Phe Val
            35                  40                  45

Ala Xaa Xaa Xaa Xaa Xaa Arg Phe Thr Ile Ser Arg Asp Asp Ala Lys
    50                  55                  60

Asn Thr Val Trp Leu His Gly Ser Thr Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 5
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
```

```
<221> NAME/KEY: misc_feature
<222> LOCATION: (87)..(91)
<223> OTHER INFORMATION: Xaa is any amino acid

<400> SEQUENCE: 5

Ala Val Gln Leu Val Glu Ser Gly Gly Gly Leu Val Gln Gly Gly
1               5                   10                  15

Ser Leu Arg Leu Ala Cys Ala Ala Ser Glu Arg Ile Phe Asp Xaa Xaa
            20                  25                  30

Xaa Xaa Xaa Trp Tyr Arg Gln Gly Pro Gly Asn Glu Arg Glu Leu Val
            35                  40                  45

Ala Xaa Xaa Xaa Xaa Xaa Arg Phe Thr Ile Ser Met Asp Tyr Thr Lys
50                  55                  60

Gln Thr Val Tyr Leu His Met Asn Ser Leu Arg Pro Glu Asp Thr Gly
65                  70                  75                  80

Leu Tyr Tyr Cys Lys Ile Xaa Xaa Xaa Xaa Xaa Trp Gly Gln Gly Thr
                85                  90                  95

Gln Val Thr Val Ser Ser
            100

<210> SEQ ID NO 6
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 6

Asp Val Lys Phe Val Glu Ser Gly Gly Gly Leu Val Gln Ala Gly Gly
1               5                   10                  15

Ser Leu Arg Leu Ser Cys Val Ala Ser Gly Phe Asn Phe Asp Xaa Xaa
            20                  25                  30

Xaa Xaa Xaa Trp Phe Arg Gln Ala Pro Gly Lys Glu Arg Glu Glu Val
            35                  40                  45

Ala Xaa Xaa Xaa Xaa Xaa Arg Phe Thr Ile Ser Ser Glu Lys Asp Lys
50                  55                  60

Asn Ser Val Tyr Leu Gln Met Asn Ser Leu Lys Pro Glu Asp Thr Ala
65                  70                  75                  80

Leu Tyr Ile Cys Ala Gly Xaa Xaa Xaa Xaa Xaa Trp Gly Arg Gly Thr
                85                  90                  95

Gln Val Thr Val Ser Ser
            100

<210> SEQ ID NO 7
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
```

```
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 7

Gln Val Arg Leu Ala Glu Ser Gly Gly Gly Leu Val Gln Ser Gly Gly
1               5                   10                  15

Ser Leu Arg Leu Ser Cys Val Ala Ser Gly Ser Thr Tyr Thr Xaa Xaa
            20                  25                  30

Xaa Xaa Xaa Trp Tyr Arg Gln Tyr Pro Gly Lys Gln Arg Ala Leu Val
        35                  40                  45

Ala Xaa Xaa Xaa Xaa Xaa Arg Phe Thr Ile Ala Arg Asp Ser Thr Lys
    50                  55                  60

Asp Thr Phe Cys Leu Gln Met Asn Asn Leu Lys Pro Glu Asp Thr Ala
65                  70                  75                  80

Val Tyr Tyr Cys Tyr Ala Xaa Xaa Xaa Xaa Xaa Trp Gly Gln Gly Thr
                85                  90                  95

Gln Val Thr Val Ser Ser
            100

<210> SEQ ID NO 8
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Ser Asp Xaa Xaa
            20                  25                  30

Xaa Xaa Xaa Trp Phe Arg Gln Ala Pro Gly Lys Pro Arg Glu Gly Val
        35                  40                  45

Ser Xaa Xaa Xaa Xaa Xaa Arg Phe Thr Ile Ser Thr Asp Asn Ala Lys
    50                  55                  60

Asn Thr Val His Leu Leu Met Asn Arg Val Asn Ala Glu Asp Thr Ala
65                  70                  75                  80

Leu Tyr Tyr Cys Ala Val Xaa Xaa Xaa Xaa Xaa Trp Gly Arg Gly Thr
                85                  90                  95

Arg Val Thr Val Ser Ser
            100

<210> SEQ ID NO 9
```

```
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Gln Ala Ser Gly Asp Ile Ser Thr Xaa Xaa
            20                  25                  30

Xaa Xaa Xaa Trp Tyr Arg Gln Val Pro Gly Lys Leu Arg Glu Phe Val
        35                  40                  45

Ala Xaa Xaa Xaa Xaa Xaa Arg Phe Thr Ile Ser Gly Asp Asn Ala Lys
    50                  55                  60

Arg Ala Ile Tyr Leu Gln Met Asn Asn Leu Lys Pro Asp Asp Thr Ala
65                  70                  75                  80

Val Tyr Tyr Cys Asn Arg Xaa Xaa Xaa Xaa Xaa Trp Gly Gln Gly Thr
                85                  90                  95

Gln Val Thr Val Ser Pro
            100

<210> SEQ ID NO 10
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 10

Gln Val Pro Val Val Glu Ser Gly Gly Gly Leu Val Gln Ala Gly Asp
1               5                   10                  15

Ser Leu Arg Leu Phe Cys Ala Val Pro Ser Thr Phe Ser Thr Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asn Ala Thr Lys
    50                  55                  60

Asn Thr Leu Thr Leu Arg Met Asp Ser Leu Lys Pro Glu Asp Thr Ala
65                  70                  75                  80

Val Tyr Tyr Cys Ala Ala Xaa Xaa Xaa Xaa Xaa Trp Gly Gln Gly Thr
```

```
                    85                  90                  95

Gln Val Thr Val Ser Ser
            100

<210> SEQ ID NO 11
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 11

Glu Val Gln Leu Val Glu Ser Gly Gly Gly Leu Val Gln Ala Gly Asp
1               5                   10                  15

Ser Leu Arg Leu Phe Cys Thr Val Ser Gly Gly Thr Ala Ser Xaa Xaa
                20                  25                  30

Xaa Xaa Xaa Trp Phe Arg Gln Ala Pro Gly Glu Lys Arg Glu Phe Val
            35                  40                  45

Ala Xaa Xaa Xaa Xaa Xaa Arg Phe Thr Ile Ala Arg Glu Asn Ala Gly
50                  55                  60

Asn Met Val Tyr Leu Gln Met Asn Asn Leu Lys Pro Asp Asp Thr Ala
65                  70                  75                  80

Leu Tyr Thr Cys Ala Ala Xaa Xaa Xaa Xaa Xaa Trp Gly Arg Gly Thr
                85                  90                  95

Gln Val Thr Val Ser Ser
            100

<210> SEQ ID NO 12
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 12

Ala Val Gln Leu Val Glu Ser Gly Gly Asp Ser Val Gln Pro Gly Asp
1               5                   10                  15

Ser Gln Thr Leu Ser Cys Ala Ala Ser Gly Arg Thr Asn Ser Xaa Xaa
                20                  25                  30

Xaa Xaa Xaa Trp Phe Arg Gln Ala Pro Gly Lys Glu Arg Val Phe Leu
            35                  40                  45
```

```
Ala Xaa Xaa Xaa Xaa Xaa Arg Phe Thr Ile Ser Arg Asp Ser Ala Lys
 50                  55                  60

Asn Met Met Tyr Leu Gln Met Asn Asn Leu Lys Pro Gln Asp Thr Ala
 65                  70                  75                  80

Val Tyr Tyr Cys Ala Ala Xaa Xaa Xaa Xaa Xaa Trp Gly Gln Gly Thr
                 85                  90                  95

Gln Val Thr Val Ser Ser
            100
```

```
<210> SEQ ID NO 13
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 13
```

```
Ala Val Gln Leu Val Glu Ser Gly Gly Gly Leu Val Gln Ala Gly Gly
 1               5                  10                  15

Ser Leu Arg Leu Ser Cys Val Val Ser Gly Leu Thr Ser Ser Xaa Xaa
             20                  25                  30

Xaa Xaa Xaa Trp Phe Arg Gln Thr Pro Trp Gln Glu Arg Asp Phe Val
             35                  40                  45

Ala Xaa Xaa Xaa Xaa Xaa Arg Phe Thr Ile Ser Arg Asp Asn Tyr Lys
 50                  55                  60

Asp Thr Val Leu Leu Glu Met Asn Phe Leu Lys Pro Glu Asp Thr Ala
 65                  70                  75                  80

Ile Tyr Tyr Cys Ala Ala Xaa Xaa Xaa Xaa Xaa Trp Gly Gln Gly Thr
                 85                  90                  95

Gln Val Thr Val Ser Ser
            100
```

```
<210> SEQ ID NO 14
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 14
```

```
Ala Val Gln Leu Val Glu Ser Gly Gly Gly Leu Val Gln Ala Gly Ala
 1               5                  10                  15
```

Ser Leu Arg Leu Ser Cys Ala Thr Ser Thr Arg Thr Leu Asp Xaa Xaa
            20                  25                  30

Xaa Xaa Xaa Trp Phe Arg Gln Ala Pro Gly Arg Asp Arg Glu Phe Val
        35                  40                  45

Ala Xaa Xaa Xaa Xaa Xaa Arg Phe Thr Val Ser Arg Asp Ser Ala Glu
    50                  55                  60

Asn Thr Val Ala Leu Gln Met Asn Ser Leu Lys Pro Glu Asp Thr Ala
65                  70                  75                  80

Val Tyr Tyr Cys Ala Ala Xaa Xaa Xaa Xaa Trp Gly Gln Gly Thr
                85                  90                  95

Arg Val Thr Val Ser Ser
            100

<210> SEQ ID NO 15
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Thr Val Ser Arg Leu Thr Ala His Xaa Xaa
            20                  25                  30

Xaa Xaa Xaa Trp Phe Arg Gln Ala Pro Gly Lys Glu Arg Glu Ala Val
        35                  40                  45

Ser Xaa Xaa Xaa Xaa Xaa Arg Phe Thr Ile Ser Arg Asp Tyr Ala Gly
    50                  55                  60

Asn Thr Ala Phe Leu Gln Met Asp Ser Leu Lys Pro Glu Asp Thr Gly
65                  70                  75                  80

Val Tyr Tyr Cys Ala Thr Xaa Xaa Xaa Xaa Xaa Trp Gly Gln Gly Thr
                85                  90                  95

Gln Val Thr Val Ser Ser
            100

<210> SEQ ID NO 16
<211> LENGTH: 102
<212> TYPE: PRT
<213> ORGANISM: Artificial Sequence
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature

```
<222> LOCATION: (87)..(91)
<223> OTHER INFORMATION: Xaa is any amino acid

<400> SEQUENCE: 16

Glu Val Gln Leu Val Glu Ser Gly Gly Glu Leu Val Gln Ala Gly Gly
1               5                   10                  15

Ser Leu Lys Leu Ser Cys Thr Ala Ser Gly Arg Asn Phe Val Xaa Xaa
            20                  25                  30

Xaa Xaa Xaa Trp Phe Arg Arg Ala Pro Gly Lys Glu Arg Glu Phe Val
        35                  40                  45

Ala Xaa Xaa Xaa Xaa Xaa Arg Phe Thr Val Ser Arg Asp Asn Gly Lys
    50                  55                  60

Asn Thr Ala Tyr Leu Arg Met Asn Ser Leu Lys Pro Glu Asp Thr Ala
65                  70                  75                  80

Asp Tyr Tyr Cys Ala Val Xaa Xaa Xaa Xaa Leu Gly Ser Gly Thr
                85                  90                  95

Gln Val Thr Val Ser Ser
            100

<210> SEQ ID NO 17
<211> LENGTH: 102
<212> TYPE: PRT
<213> ORGANISM: Artificial Sequence
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 17

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Val Leu Glu Trp Val
        35                  40                  45

Ser Xaa Xaa Xaa Xaa Xaa Arg Phe Thr Ile Ser Arg Asp Asn Ala Lys
    50                  55                  60

Asn Thr Leu Tyr Leu Gln Met Asn Ser Leu Lys Pro Glu Asp Thr Ala
65                  70                  75                  80

Val Tyr Tyr Cys Val Lys Xaa Xaa Xaa Xaa Xaa Gly Ser Gln Gly Thr
                85                  90                  95

Gln Val Thr Val Ser Ser
            100

<210> SEQ ID NO 18
<211> LENGTH: 102
<212> TYPE: PRT
<213> ORGANISM: Artificial Sequence
<220> FEATURE:
<223> OTHER INFORMATION: GLEW-class Nanobody
<220> FEATURE:
<221> NAME/KEY: misc_feature
<222> LOCATION: (31)..(35)
```

<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100
```

<210> SEQ ID NO 19
<211> LENGTH: 102
<212> TYPE: PRT
<213> ORGANISM: Artificial Sequence
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 19

```
Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser Xaa Xaa
            20                  25                  30

Xaa Xaa Xaa Trp Val Arg His Thr Pro Gly Lys Ala Glu Glu Trp Val
        35                  40                  45

Ser Xaa Xaa Xaa Xaa Xaa Arg Phe Thr Ile Ser Arg Asp Asn Ala Lys
50                  55                  60

Asn Thr Leu Tyr Leu Glu Met Asn Ser Leu Ser Pro Glu Asp Thr Ala
65                  70                  75                  80

Met Tyr Tyr Cys Gly Arg Xaa Xaa Xaa Xaa Xaa Arg Ser Lys Gly Ile
                85                  90                  95

Gln Val Thr Val Ser Ser
            100
```

<210> SEQ ID NO 20
<211> LENGTH: 102

<212> TYPE: PRT
<213> ORGANISM: Artificial Sequence
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 20

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
65                  70                  75                  80

Val Tyr Tyr Cys Ala Ala Xaa Xaa Xaa Xaa Xaa Arg Gly Gln Gly Thr
                85                  90                  95

Gln Val Thr Val Ser Ser
            100

<210> SEQ ID NO 21
<211> LENGTH: 102
<212> TYPE: PRT
<213> ORGANISM: Artificial Sequence
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 21

Asp Val Gln Leu Val Glu Ser Gly Gly Asp Leu Val Gln Pro Gly Gly
1               5                   10                  15

Ser Leu Arg Leu Ser Cys Ala Ala Ser Gly Phe Ser Phe Asp Xaa Xaa
            20                  25                  30

Xaa Xaa Xaa Trp Leu Arg Gln Thr Pro Gly Lys Gly Leu Glu Trp Val
        35                  40                  45

Gly Xaa Xaa Xaa Xaa Xaa Arg Phe Thr Ile Ser Arg Asp Asn Ala Lys
    50                  55                  60

Asn Met Leu Tyr Leu His Leu Asn Asn Leu Lys Ser Glu Asp Thr Ala
65                  70                  75                  80

Val Tyr Tyr Cys Arg Arg Xaa Xaa Xaa Xaa Xaa Leu Gly Gln Gly Thr
                85                  90                  95

```
Gln Val Thr Val Ser Ser
            100

<210> SEQ ID NO 22
<211> LENGTH: 102
<212> TYPE: PRT
<213> ORGANISM: Artificial Sequence
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Glu Trp Val
        35                  40                  45

Ser Xaa Xaa Xaa Xaa Xaa Arg Phe Lys Ile Ser Arg Asp Asn Ala Lys
50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100

<210> SEQ ID NO 23
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 23

Gln Val Gln Arg Val Glu Ser Gly Gly Gly Leu Val Gln Ala Gly Gly
1               5                   10                  15

Ser Leu Arg Leu Ser Cys Ala Ala Ser Gly Arg Thr Ser Ser
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 24

Gln Val Gln Leu Val Glu Ser Gly Gly Gly Leu Val Gln Thr Gly Asp
1               5                   10                  15

Ser Leu Ser Leu Ser Cys Ser Ala Ser Gly Arg Thr Phe Ser
            20                  25                  30
```

```
<210> SEQ ID NO 25
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 25

Gln Val Lys Leu Glu Glu Ser Gly Gly Gly Leu Val Gln Ala Gly Asp
1               5                   10                  15

Ser Leu Arg Leu Ser Cys Ala Ala Thr Gly Arg Ala Phe Gly
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 26

Ala Val Gln Leu Val Glu Ser Gly Gly Gly Leu Val Gln Pro Gly Glu
1               5                   10                  15

Ser Leu Gly Leu Ser Cys Val Ala Ser Gly Arg Asp Phe Val
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 27

Glu Val Gln Leu Val Glu Ser Gly Gly Gly Leu Val Gln Ala Gly Gly
1               5                   10                  15

Ser Leu Arg Leu Ser Cys Glu Val Leu Gly Arg Thr Ala Gly
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 28

Gln Val Gln Leu Val Glu Ser Gly Gly Gly Trp Val Gln Pro Gly Gly
1               5                   10                  15

Ser Leu Arg Leu Ser Cys Ala Ala Ser Glu Thr Ile Leu Ser
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 29

Gln Val Gln Leu Val Glu Ser Gly Gly Gly Thr Val Gln Pro Gly Gly
1               5                   10                  15

Ser Leu Asn Leu Ser Cys Val Ala Ser Gly Asn Thr Phe Asn
            20                  25                  30
```

<210> SEQ ID NO 30
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 30

Glu Val Gln Leu Val Glu Ser Gly Gly Gly Leu Ala Gln Pro Gly Gly
1               5                   10                  15

Ser Leu Gln Leu Ser Cys Ser Ala Pro Gly Phe Thr Leu Asp
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: KERE-class Nanobody FW1 sequence

<400> SEQUENCE: 31

Ala Gln Glu Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 32
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 32

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 33
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 33

Val Asp Ser Gly Gly Gly Leu Val Gln Ala Gly Asp Ser Leu Lys Leu
1               5                   10                  15

Ser Cys Ala Leu Thr Gly
            20

<210> SEQ ID NO 34
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 34

Val Asp Ser Gly Gly Gly Leu Val Gln Ala Gly Asp Ser Leu Arg Leu
1               5                   10                  15

Ser Cys Ala Ala Ser Gly

```
                         20

<210> SEQ ID NO 35
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 35

Val Asp Ser Gly Gly Gly Leu Val Glu Ala Gly Gly Ser Leu Arg Leu
1               5                   10                  15

Ser Cys Gln Val Ser Glu
            20

<210> SEQ ID NO 36
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 36

Gln Asp Ser Gly Gly Gly Ser Val Gln Ala Gly Gly Ser Leu Lys Leu
1               5                   10                  15

Ser Cys Ala Ala Ser Gly
            20

<210> SEQ ID NO 37
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 37

Val Gln Ser Gly Gly Arg Leu Val Gln Ala Gly Asp Ser Leu Arg Leu
1               5                   10                  15

Ser Cys Ala Ala Ser Glu
            20

<210> SEQ ID NO 38
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 38

Val Glu Ser Gly Gly Thr Leu Val Gln Ser Gly Asp Ser Leu Lys Leu
1               5                   10                  15

Ser Cys Ala Ser Ser Thr
            20

<210> SEQ ID NO 39
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 39

Met Glu Ser Gly Gly Asp Ser Val Gln Ser Gly Gly Ser Leu Thr Leu
1               5                   10                  15
```

```
Ser Cys Val Ala Ser Gly
            20

<210> SEQ ID NO 40
<211> LENGTH: 22
<212> TYPE: PRT
<213> ORGANISM: Artificial Sequence
<220> FEATURE:
<223> OTHER INFORMATION: KERE-class Nanobody FW1 sequence

<400> SEQUENCE: 40

Gln Ala Ser Gly Gly Gly Leu Val Gln Ala Gly Gly Ser Leu Arg Leu
1               5                   10                  15

Ser Cys Ser Ala Ser Val
            20

<210> SEQ ID NO 41
<211> LENGTH: 14
<212> TYPE: PRT
<213> ORGANISM: Artificial Sequence
<220> FEATURE:
<223> OTHER INFORMATION: KERE-class Nanobody FW2 sequence

<400> SEQUENCE: 41

Trp Phe Arg Gln Ala Pro Gly Lys Glu Arg Glu Phe Val Ala
1               5                   10

<210> SEQ ID NO 42
<211> LENGTH: 14
<212> TYPE: PRT
<213> ORGANISM: Artificial Sequence
<220> FEATURE:
<223> OTHER INFORMATION: KERE-class Nanobody FW2 sequence

<400> SEQUENCE: 42

Trp Phe Arg Gln Thr Pro Gly Arg Glu Arg Glu Phe Val Ala
1               5                   10

<210> SEQ ID NO 43
<211> LENGTH: 14
<212> TYPE: PRT
<213> ORGANISM: Artificial Sequence
<220> FEATURE:
<223> OTHER INFORMATION: KERE-class Nanobody FW2 sequence

<400> SEQUENCE: 43

Trp Tyr Arg Gln Ala Pro Gly Lys Gln Arg Glu Met Val Ala
1               5                   10

<210> SEQ ID NO 44
<211> LENGTH: 14
<212> TYPE: PRT
<213> ORGANISM: Artificial Sequence
<220> FEATURE:
<223> OTHER INFORMATION: KERE-class Nanobody FW2 sequence

<400> SEQUENCE: 44

Trp Tyr Arg Gln Gly Pro Gly Lys Gln Arg Glu Leu Val Ala
1               5                   10

<210> SEQ ID NO 45
<211> LENGTH: 14
<212> TYPE: PRT
<213> ORGANISM: Artificial Sequence
<220> FEATURE:
<223> OTHER INFORMATION: KERE-class Nanobody FW2 sequence
```

```
<400> SEQUENCE: 45

Trp Ile Arg Gln Ala Pro Gly Lys Glu Arg Glu Gly Val Ser
1               5                   10

<210> SEQ ID NO 46
<211> LENGTH: 14
<212> TYPE: PRT
<213> ORGANISM: Artificial Sequence
<220> FEATURE:
<223> OTHER INFORMATION: KERE-class Nanobody FW2 sequence

<400> SEQUENCE: 46

Trp Phe Arg Glu Ala Pro Gly Lys Glu Arg Glu Gly Ile Ser
1               5                   10

<210> SEQ ID NO 47
<211> LENGTH: 14
<212> TYPE: PRT
<213> ORGANISM: Artificial Sequence
<220> FEATURE:
<223> OTHER INFORMATION: KERE-class Nanobody FW2 sequence

<400> SEQUENCE: 47

Trp Tyr Arg Gln Ala Pro Gly Lys Glu Arg Asp Leu Val Ala
1               5                   10

<210> SEQ ID NO 48
<211> LENGTH: 14
<212> TYPE: PRT
<213> ORGANISM: Artificial Sequence
<220> FEATURE:
<223> OTHER INFORMATION: KERE-class Nanobody FW2 sequence

<400> SEQUENCE: 48

Trp Phe Arg Gln Ala Pro Gly Lys Gln Arg Glu Glu Val Ser
1               5                   10

<210> SEQ ID NO 49
<211> LENGTH: 14
<212> TYPE: PRT
<213> ORGANISM: Artificial Sequence
<220> FEATURE:
<223> OTHER INFORMATION: KERE-class Nanobody FW2 sequence

<400> SEQUENCE: 49

Trp Phe Arg Gln Pro Pro Gly Lys Val Arg Glu Phe Val Gly
1               5                   10

<210> SEQ ID NO 50
<211> LENGTH: 32
<212> TYPE: PRT
<213> ORGANISM: Artificial Sequence
<220> FEATURE:
<223> OTHER INFORMATION: KERE-class Nanobody FW3 sequence

<400> SEQUENCE: 50

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Arg Cys Tyr Phe
            20                  25                  30

<210> SEQ ID NO 51
<211> LENGTH: 32
<212> TYPE: PRT
<213> ORGANISM: Artificial Sequence
<220> FEATURE:
```

```
<223> OTHER INFORMATION: KERE-class Nanobody FW3 sequence

<400> SEQUENCE: 51

Arg Phe Ala Ile Ser Arg Asp Asn Asn Lys Asn Thr Gly Tyr Leu Gln
 1               5                  10                  15

Met Asn Ser Leu Glu Pro Glu Asp Thr Ala Val Tyr Tyr Cys Ala Ala
             20                  25                  30

<210> SEQ ID NO 52
<211> LENGTH: 32
<212> TYPE: PRT
<213> ORGANISM: Artificial Sequence
<220> FEATURE:
<223> OTHER INFORMATION: KERE-class Nanobody FW3 sequence

<400> SEQUENCE: 52

Arg Phe Thr Val Ala Arg Asn Asn Ala Lys Asn Thr Val Asn Leu Glu
 1               5                  10                  15

Met Asn Ser Leu Lys Pro Glu Asp Thr Ala Val Tyr Tyr Cys Ala Ala
             20                  25                  30

<210> SEQ ID NO 53
<211> LENGTH: 32
<212> TYPE: PRT
<213> ORGANISM: Artificial Sequence
<220> FEATURE:
<223> OTHER INFORMATION: KERE-class Nanobody FW3 sequence

<400> SEQUENCE: 53

Arg Phe Thr Ile Ser Arg Asp Ile Ala Lys Asn Thr Val Asp Leu Leu
 1               5                  10                  15

Met Asn Asn Leu Glu Pro Glu Asp Thr Ala Val Tyr Tyr Cys Ala Ala
             20                  25                  30

<210> SEQ ID NO 54
<211> LENGTH: 32
<212> TYPE: PRT
<213> ORGANISM: Artificial Sequence
<220> FEATURE:
<223> OTHER INFORMATION: KERE-class Nanobody FW3 sequence

<400> SEQUENCE: 54

Arg Leu Thr Ile Ser Arg Asp Asn Ala Val Asp Thr Met Tyr Leu Gln
 1               5                  10                  15

Met Ser Ser Leu Lys Pro Glu Asp Thr Ala Val Tyr Tyr Cys Ala Ala
             20                  25                  30

<210> SEQ ID NO 55
<211> LENGTH: 32
<212> TYPE: PRT
<213> ORGANISM: Artificial Sequence
<220> FEATURE:
<223> OTHER INFORMATION: KERE-class Nanobody FW3 sequence

<400> SEQUENCE: 55

Arg Phe Thr Ile Ser Arg Asp Asn Ala Lys Asn Thr Val Tyr Leu Gln
 1               5                  10                  15

Met Asp Asn Val Lys Pro Glu Asp Thr Ala Ile Tyr Tyr Cys Ala Ala
             20                  25                  30

<210> SEQ ID NO 56
<211> LENGTH: 32
<212> TYPE: PRT
<213> ORGANISM: Artificial Sequence
```

<220> FEATURE:
<223> OTHER INFORMATION: KERE-class Nanobody FW3 sequence

<400> SEQUENCE: 56

Arg Phe Thr Ile Ser Lys Asp Ser Gly Lys Asn Thr Val Tyr Leu Gln
1               5                   10                  15
Met Thr Ser Leu Lys Pro Glu Asp Thr Ala Val Tyr Tyr Cys Ala Thr
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: KERE-class Nanobody FW3 sequence

<400> SEQUENCE: 57

Arg Phe Thr Ile Ser Arg Asp Ser Ala Lys Asn Met Met Tyr Leu Gln
1               5                   10                  15
Met Asn Asn Leu Lys Pro Gln Asp Thr Ala Val Tyr Tyr Cys Ala Ala
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: KERE-class Nanobody FW3 sequence

<400> SEQUENCE: 58

Arg Phe Thr Ile Ser Arg Glu Asn Asp Lys Ser Thr Val Tyr Leu Gln
1               5                   10                  15
Leu Asn Ser Leu Lys Pro Glu Asp Thr Ala Val Tyr Tyr Cys Ala Ala
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: KERE-class Nanobody FW3 sequence

<400> SEQUENCE: 59

Arg Phe Thr Ile Ser Arg Asp Tyr Ala Gly Asn Thr Ala Tyr Leu Gln
1               5                   10                  15
Met Asn Ser Leu Lys Pro Glu Asp Thr Gly Val Tyr Tyr Cys Ala Thr
            20                  25                  30

<210> SEQ ID NO 60
<211> LENGTH: 11
<212> TYPE: PRT
<213> ORGANISM: Artificial Sequence
<220> FEATURE:
<223> OTHER INFORMATION: KERE-class Nanobody FW4 sequence

<400> SEQUENCE: 60

Trp Gly Gln Gly Thr Gln Val Thr Val Ser Ser
1               5                   10

<210> SEQ ID NO 61
<211> LENGTH: 11
<212> TYPE: PRT
<213> ORGANISM: Artificial Sequence
<220> FEATURE:
<223> OTHER INFORMATION: KERE-class Nanobody FW4 sequence

```
<400> SEQUENCE: 61

Trp Gly Lys Gly Thr Leu Val Thr Val Ser Ser
1               5                   10

<210> SEQ ID NO 62
<211> LENGTH: 11
<212> TYPE: PRT
<213> ORGANISM: Artificial Sequence
<220> FEATURE:
<223> OTHER INFORMATION: KERE-class Nanobody FW4 sequence

<400> SEQUENCE: 62

Arg Gly Gln Gly Thr Arg Val Thr Val Ser Ser
1               5                   10

<210> SEQ ID NO 63
<211> LENGTH: 11
<212> TYPE: PRT
<213> ORGANISM: Artificial Sequence
<220> FEATURE:
<223> OTHER INFORMATION: KERE-class Nanobody FW4 sequence

<400> SEQUENCE: 63

Trp Gly Leu Gly Thr Gln Val Thr Ile Ser Ser
1               5                   10

<210> SEQ ID NO 64
<211> LENGTH: 30
<212> TYPE: PRT
<213> ORGANISM: Artificial Sequence
<220> FEATURE:
<223> OTHER INFORMATION: GLEW-class Nanobody FW1 sequence

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: GLEW-class Nanobody FW1 sequence

<400> SEQUENCE: 65

Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: GLEW-class Nanobody FW1 sequence

<400> SEQUENCE: 66

Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
            20                  25                  30
```

<210> SEQ ID NO 67
<211> LENGTH: 30
<212> TYPE: PRT
<213> ORGANISM: Artificial Sequence
<220> FEATURE:
<223> OTHER INFORMATION: GLEW-class Nanobody FW1 sequence

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: GLEW-class Nanobody FW1 sequence

<400> SEQUENCE: 68

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser
            20                  25                  30

<210> SEQ ID NO 69
<211> LENGTH: 22
<212> TYPE: PRT
<213> ORGANISM: Artificial Sequence
<220> FEATURE:
<223> OTHER INFORMATION: GLEW-class Nanobody FW1 sequence

<400> SEQUENCE: 69

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 70
<211> LENGTH: 22
<212> TYPE: PRT
<213> ORGANISM: Artificial Sequence
<220> FEATURE:
<223> OTHER INFORMATION: GLEW-class Nanobody FW1 sequence

<400> SEQUENCE: 70

Glu Glu Ser Gly Gly Gly Leu Ala Gln Pro Gly Gly Ser Leu Arg Leu
1               5                   10                  15

Ser Cys Val Ala Ser Gly
            20

<210> SEQ ID NO 71
<211> LENGTH: 22
<212> TYPE: PRT
<213> ORGANISM: Artificial Sequence
<220> FEATURE:
<223> OTHER INFORMATION: GLEW-class Nanobody FW1 sequence

<400> SEQUENCE: 71

Val Glu Ser Gly Gly Gly Leu Ala Leu Pro Gly Gly Ser Leu Thr Leu
1               5                   10                  15

Ser Cys Val Phe Ser Gly

```
<210> SEQ ID NO 72
<211> LENGTH: 14
<212> TYPE: PRT
<213> ORGANISM: Artificial Sequence
<220> FEATURE:
<223> OTHER INFORMATION: GLEW-class Nanobody FW2 sequence

<400> SEQUENCE: 72

Trp Val Arg Gln Ala Pro Gly Lys Val Leu Glu Trp Val Ser
1               5                   10

<210> SEQ ID NO 73
<211> LENGTH: 14
<212> TYPE: PRT
<213> ORGANISM: Artificial Sequence
<220> FEATURE:
<223> OTHER INFORMATION: GLEW-class Nanobody FW2 sequence

<400> SEQUENCE: 73

Trp Val Arg Arg Pro Pro Gly Lys Gly Leu Glu Trp Val Ser
1               5                   10

<210> SEQ ID NO 74
<211> LENGTH: 14
<212> TYPE: PRT
<213> ORGANISM: Artificial Sequence
<220> FEATURE:
<223> OTHER INFORMATION: GLEW-class Nanobody FW2 sequence

<400> SEQUENCE: 74

Trp Val Arg Gln Ala Pro Gly Met Gly Leu Glu Trp Val Ser
1               5                   10

<210> SEQ ID NO 75
<211> LENGTH: 14
<212> TYPE: PRT
<213> ORGANISM: Artificial Sequence
<220> FEATURE:
<223> OTHER INFORMATION: GLEW-class Nanobody FW2 sequence

<400> SEQUENCE: 75

Trp Val Arg Gln Ala Pro Gly Lys Glu Pro Glu Trp Val Ser
1               5                   10

<210> SEQ ID NO 76
<211> LENGTH: 14
<212> TYPE: PRT
<213> ORGANISM: Artificial Sequence
<220> FEATURE:
<223> OTHER INFORMATION: GLEW-class Nanobody FW2 sequence

<400> SEQUENCE: 76

Trp Val Arg Gln Ala Pro Gly Lys Asp Gln Glu Trp Val Ser
1               5                   10

<210> SEQ ID NO 77
<211> LENGTH: 14
<212> TYPE: PRT
<213> ORGANISM: Artificial Sequence
<220> FEATURE:
<223> OTHER INFORMATION: GLEW-class Nanobody FW2 sequence

<400> SEQUENCE: 77

Trp Val Arg Gln Ala Pro Gly Lys Ala Glu Glu Trp Val Ser
1               5                   10
```

```
<210> SEQ ID NO 78
<211> LENGTH: 14
<212> TYPE: PRT
<213> ORGANISM: Artificial Sequence
<220> FEATURE:
<223> OTHER INFORMATION: GLEW-class Nanobody FW2 sequence

<400> SEQUENCE: 78

Trp Val Arg Gln Ala Pro Gly Lys Gly Leu Glu Trp Val Ala
1               5                   10

<210> SEQ ID NO 79
<211> LENGTH: 14
<212> TYPE: PRT
<213> ORGANISM: Artificial Sequence
<220> FEATURE:
<223> OTHER INFORMATION: GLEW-class Nanobody FW2 sequence

<400> SEQUENCE: 79

Trp Val Arg Gln Ala Pro Gly Arg Ala Thr Glu Trp Val Ser
1               5                   10

<210> SEQ ID NO 80
<211> LENGTH: 32
<212> TYPE: PRT
<213> ORGANISM: Artificial Sequence
<220> FEATURE:
<223> OTHER INFORMATION: GLEW-class Nanobody FW3 sequence

<400> SEQUENCE: 80

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Val Lys
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: GLEW-class Nanobody FW3 sequence

<400> SEQUENCE: 81

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: GLEW-class Nanobody FW3 sequence

<400> SEQUENCE: 82

Arg Phe Thr Ser Ser Arg Asp Asn Ala Lys Ser Thr Leu Tyr Leu Gln
1               5                   10                  15

Met Asn Asp Leu Lys Pro Glu Asp Thr Ala Leu Tyr Tyr Cys Ala Arg
            20                  25                  30

<210> SEQ ID NO 83
<211> LENGTH: 32
<212> TYPE: PRT
```

```
<213> ORGANISM: Artificial Sequence
<220> FEATURE:
<223> OTHER INFORMATION: GLEW-class Nanobody FW3 sequence

<400> SEQUENCE: 83

Arg Phe Ile Ile Ser Arg Asp Asn Ala Lys Asn Thr Leu Tyr Leu Gln
1               5                   10                  15

Met Asn Ser Leu Gly Pro Glu Asp Thr Ala Met Tyr Tyr Cys Gln Arg
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: GLEW-class Nanobody FW3 sequence

<400> SEQUENCE: 84

Arg Phe Thr Ala Ser Arg Asp Asn Ala Lys Asn Thr Leu Tyr Leu Gln
1               5                   10                  15

Met Asn Ser Leu Lys Ser Glu Asp Thr Ala Arg Tyr Tyr Cys Ala Arg
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: GLEW-class Nanobody FW3 sequence

<400> SEQUENCE: 85

Arg Phe Thr Ile Ser Arg Asp Asn Ala Lys Asn Thr Leu Tyr Leu Gln
1               5                   10                  15

Met Asp Asp Leu Gln Ser Glu Asp Thr Ala Met Tyr Tyr Cys Gly Arg
            20                  25                  30

<210> SEQ ID NO 86
<211> LENGTH: 11
<212> TYPE: PRT
<213> ORGANISM: Artificial Sequence
<220> FEATURE:
<223> OTHER INFORMATION: GLEW-class Nanobody FW4 sequence

<400> SEQUENCE: 86

Gly Ser Gln Gly Thr Gln Val Thr Val Ser Ser
1               5                   10

<210> SEQ ID NO 87
<211> LENGTH: 11
<212> TYPE: PRT
<213> ORGANISM: Artificial Sequence
<220> FEATURE:
<223> OTHER INFORMATION: GLEW-class Nanobody FW4 sequence

<400> SEQUENCE: 87

Leu Arg Gly Gly Thr Gln Val Thr Val Ser Ser
1               5                   10

<210> SEQ ID NO 88
<211> LENGTH: 11
<212> TYPE: PRT
<213> ORGANISM: Artificial Sequence
<220> FEATURE:
<223> OTHER INFORMATION: GLEW-class Nanobody FW4 sequence

<400> SEQUENCE: 88
```

```
Arg Gly Gln Gly Thr Leu Val Thr Val Ser Ser
1               5                   10

<210> SEQ ID NO 89
<211> LENGTH: 11
<212> TYPE: PRT
<213> ORGANISM: Artificial Sequence
<220> FEATURE:
<223> OTHER INFORMATION: GLEW-class Nanobody FW4 sequence

<400> SEQUENCE: 89

Arg Ser Arg Gly Ile Gln Val Thr Val Ser Ser
1               5                   10

<210> SEQ ID NO 90
<211> LENGTH: 11
<212> TYPE: PRT
<213> ORGANISM: Artificial Sequence
<220> FEATURE:
<223> OTHER INFORMATION: GLEW-class Nanobody FW4 sequence

<400> SEQUENCE: 90

Trp Gly Lys Gly Thr Gln Val Thr Val Ser Ser
1               5                   10

<210> SEQ ID NO 91
<211> LENGTH: 11
<212> TYPE: PRT
<213> ORGANISM: Artificial Sequence
<220> FEATURE:
<223> OTHER INFORMATION: GLEW-class Nanobody FW4 sequence

<400> SEQUENCE: 91

Trp Gly Gln Gly Thr Gln Val Thr Val Ser Ser
1               5                   10

<210> SEQ ID NO 92
<211> LENGTH: 30
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 92

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 93
<211> LENGTH: 30
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 93

Gln Val Gln Leu Gln Glu Ser Gly Gly Gly Met Val Gln Pro Gly Gly
1               5                   10                  15

Ser Leu Arg Leu Ser Cys Ala Ala Ser Gly Phe Asp Phe Gly
            20                  25                  30

<210> SEQ ID NO 94
<211> LENGTH: 30
<212> TYPE: PRT
```

```
<213> ORGANISM: Artificial Sequence
<220> FEATURE:
<223> OTHER INFORMATION: P,R,S 103-class Nanobody FW1 sequence

<400> SEQUENCE: 94

Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
            20                  25                  30

<210> SEQ ID NO 95
<211> LENGTH: 30
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 95

Gln Val Gln Leu Ala Glu Ser Gly Gly Gly Leu Val Gln Pro Gly Gly
1               5                   10                  15

Ser Leu Lys Leu Ser Cys Ala Ala Ser Arg Thr Ile Val Ser
            20                  25                  30

<210> SEQ ID NO 96
<211> LENGTH: 30
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 96

Gln Glu His Leu Val Glu Ser Gly Gly Gly Leu Val Asp Ile Gly Gly
1               5                   10                  15

Ser Leu Arg Leu Ser Cys Ala Ala Ser Glu Arg Ile Phe Ser
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 97

Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 99
<211> LENGTH: 30
```

```
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 99

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser
            20                  25                  30

<210> SEQ ID NO 100
<211> LENGTH: 22
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 100

Val Glu Ser Gly Gly Gly Leu Val Gln Ala Gly Gly Ser Leu Arg Leu
1               5                   10                  15

Ser Cys Ala Ala Ser Gly
            20

<210> SEQ ID NO 101
<211> LENGTH: 22
<212> TYPE: PRT
<213> ORGANISM: Artificial Sequence
<220> FEATURE:
<223> OTHER INFORMATION: P,R,S 103-class Nanobody FW1 sequence

<400> SEQUENCE: 101

Ala Glu Ser Gly Gly Gly Leu Val Gln Pro Gly Gly Ser Leu Lys Leu
1               5                   10                  15

Ser Cys Ala Ala Ser Arg
            20

<210> SEQ ID NO 102
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 102

Trp Phe Arg Gln Ala Pro Gly Lys Glu Arg Glu Phe Val Ala
1               5                   10

<210> SEQ ID NO 103
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 103

Trp Val Arg Gln Ala Pro Gly Lys Val Leu Glu Trp Val Ser
1               5                   10

<210> SEQ ID NO 104
<211> LENGTH: 14
<212> TYPE: PRT
<213> ORGANISM: Artificial Sequence
<220> FEATURE:
<223> OTHER INFORMATION: P,R,S 103-class Nanobody FW2 sequence
```

```
<400> SEQUENCE: 104

Trp Val Arg Arg Pro Pro Gly Lys Gly Leu Glu Trp Val Ser
1               5                   10

<210> SEQ ID NO 105
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 105

Trp Ile Arg Gln Ala Pro Gly Lys Glu Arg Glu Gly Val Ser
1               5                   10

<210> SEQ ID NO 106
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 106

Trp Val Arg Gln Tyr Pro Gly Lys Glu Pro Glu Trp Val Ser
1               5                   10

<210> SEQ ID NO 107
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 107

Trp Phe Arg Gln Pro Pro Gly Lys Glu His Glu Phe Val Ala
1               5                   10

<210> SEQ ID NO 108
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 108

Trp Tyr Arg Gln Ala Pro Gly Lys Arg Thr Glu Leu Val Ala
1               5                   10

<210> SEQ ID NO 109
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 109

Trp Leu Arg Gln Ala Pro Gly Gln Gly Leu Glu Trp Val Ser
1               5                   10

<210> SEQ ID NO 110
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 110
```

Trp Leu Arg Gln Thr Pro Gly Lys Gly Leu Glu Trp Val Gly
1               5                   10

<210> SEQ ID NO 111
<211> LENGTH: 14
<212> TYPE: PRT
<213> ORGANISM: Artificial Sequence
<220> FEATURE:
<223> OTHER INFORMATION: P,R,S 103-class Nanobody FW2 sequence

<400> SEQUENCE: 111

Trp Val Arg Gln Ala Pro Gly Lys Ala Glu Glu Phe Val Ser
1               5                   10

<210> SEQ ID NO 112
<211> LENGTH: 32
<212> TYPE: PRT
<213> ORGANISM: Artificial Sequence
<220> FEATURE:
<223> OTHER INFORMATION: P,R,S 103-class Nanobody FW3 sequence

<400> SEQUENCE: 112

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 113
<211> LENGTH: 32
<212> TYPE: PRT
<213> ORGANISM: Artificial Sequence
<220> FEATURE:
<223> OTHER INFORMATION: P,R,S 103-class Nanobody FW3 sequence

<400> SEQUENCE: 113

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
            20                  25                  30

<210> SEQ ID NO 114
<211> LENGTH: 32
<212> TYPE: PRT
<213> ORGANISM: Artificial Sequence
<220> FEATURE:
<223> OTHER INFORMATION: P,R,S 103-class Nanobody FW3 sequence

<400> SEQUENCE: 114

Arg Phe Thr Ile Ser Arg Asp Asn Ala Lys Asn Glu Met Tyr Leu Gln
1               5                   10                  15

Met Asn Asn Leu Lys Thr Glu Asp Thr Gly Val Tyr Trp Cys Gly Ala
            20                  25                  30

<210> SEQ ID NO 115
<211> LENGTH: 32
<212> TYPE: PRT
<213> ORGANISM: Artificial Sequence
<220> FEATURE:
<223> OTHER INFORMATION: P,R,S 103-class Nanobody FW3 sequence

<400> SEQUENCE: 115

Arg Phe Thr Ile Ser Ser Asp Ser Asn Arg Asn Met Ile Tyr Leu Gln
1               5                   10                  15

Met Asn Asn Leu Lys Pro Glu Asp Thr Ala Val Tyr Tyr Cys Ala Ala 20                  25                  30

<210> SEQ ID NO 116
<211> LENGTH: 32
<212> TYPE: PRT
<213> ORGANISM: Artificial Sequence
<220> FEATURE:
<223> OTHER INFORMATION: P,R,S 103-class Nanobody FW3 sequence

<400> SEQUENCE: 116

Arg Phe Thr Ile Ser Arg Asp Asn Ala Lys Asn Met Leu Tyr Leu His
1               5                   10                  15

Leu Asn Asn Leu Lys Ser Glu Asp Thr Ala Val Tyr Tyr Cys Arg Arg
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: P,R,S 103-class Nanobody FW3 sequence

<400> SEQUENCE: 117

Arg Phe Thr Ile Ser Arg Asp Asn Ala Lys Lys Thr Val Tyr Leu Arg
1               5                   10                  15

Leu Asn Ser Leu Asn Pro Glu Asp Thr Ala Val Tyr Ser Cys Asn Leu
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: P,R,S 103-class Nanobody FW3 sequence

<400> SEQUENCE: 118

Arg Phe Lys Ile Ser Arg Asp Asn Ala Lys Lys Thr Leu Tyr Leu Gln
1               5                   10                  15

Met Asn Ser Leu Gly Pro Glu Asp Thr Ala Met Tyr Tyr Cys Gln Arg
            20                  25                  30

<210> SEQ ID NO 119
<211> LENGTH: 32
<212> TYPE: PRT
<213> ORGANISM: Artificial Sequence
<220> FEATURE:
<223> OTHER INFORMATION: P,R,S 103-class Nanobody FW3 sequence

<400> SEQUENCE: 119

Arg Phe Thr Val Ser Arg Asp Asn Gly Lys Asn Thr Ala Tyr Leu Arg
1               5                   10                  15

Met Asn Ser Leu Lys Pro Glu Asp Thr Ala Asp Tyr Tyr Cys Ala Val
            20                  25                  30

<210> SEQ ID NO 120
<211> LENGTH: 11
<212> TYPE: PRT
<213> ORGANISM: Artificial Sequence
<220> FEATURE:
<223> OTHER INFORMATION: P,R,S 103-class Nanobody FW4 sequence

<400> SEQUENCE: 120

Arg Gly Gln Gly Thr Gln Val Thr Val Ser Ser
1               5                   10

<210> SEQ ID NO 121
<211> LENGTH: 11
<212> TYPE: PRT
<213> ORGANISM: Artificial Sequence
<220> FEATURE:
<223> OTHER INFORMATION: P,R,S 103-class Nanobody FW4 sequence

<400> SEQUENCE: 121

Leu Arg Gly Gly Thr Gln Val Thr Val Ser Ser
1               5                   10

<210> SEQ ID NO 122
<211> LENGTH: 11
<212> TYPE: PRT
<213> ORGANISM: Artificial Sequence
<220> FEATURE:
<223> OTHER INFORMATION: P,R,S 103-class Nanobody FW4 sequence

<400> SEQUENCE: 122

Gly Asn Lys Gly Thr Leu Val Thr Val Ser Ser
1               5                   10

<210> SEQ ID NO 123
<211> LENGTH: 11
<212> TYPE: PRT
<213> ORGANISM: Artificial Sequence
<220> FEATURE:
<223> OTHER INFORMATION: P,R,S 103-class Nanobody FW4 sequence

<400> SEQUENCE: 123

Ser Ser Pro Gly Thr Gln Val Thr Val Ser Ser
1               5                   10

<210> SEQ ID NO 124
<211> LENGTH: 11
<212> TYPE: PRT
<213> ORGANISM: Artificial Sequence
<220> FEATURE:
<223> OTHER INFORMATION: P,R,S 103-class Nanobody FW4 sequence

<400> SEQUENCE: 124

Ser Ser Gln Gly Thr Leu Val Thr Val Ser Ser
1               5                   10

<210> SEQ ID NO 125
<211> LENGTH: 11
<212> TYPE: PRT
<213> ORGANISM: Artificial Sequence
<220> FEATURE:
<223> OTHER INFORMATION: P,R,S 103-class Nanobody FW4 sequence

<400> SEQUENCE: 125

Arg Ser Arg Gly Ile Gln Val Thr Val Ser Ser
1               5                   10

<210> SEQ ID NO 126
<211> LENGTH: 30
<212> TYPE: PRT
<213> ORGANISM: Artificial Sequence
<220> FEATURE:
<223> OTHER INFORMATION: Framework sequence

<400> SEQUENCE: 126

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg

```
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Framework sequence

<400> SEQUENCE: 127

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Ser Phe Ser
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Framework sequence

<400> SEQUENCE: 128

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Framework sequence

<400> SEQUENCE: 129

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Framework sequence

<400> SEQUENCE: 130

Glu Val Gln Leu Val Glu Ser Gly Gly Gly Leu Val Gln Ala Gly Gly
1               5                   10                  15

Ser Leu Arg Leu Ser Cys Ala Ala Ser Arg Asn Ile Leu Ser
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Framework sequence

<400> SEQUENCE: 131

Glu Val Gln Leu Val Glu Ser Gly Gly Gly Leu Val Gln Ala Gly Gly
1               5                   10                  15
```

```
Ser Leu Arg Leu Ser Cys Ala Ala Ser Gly Phe Thr Leu Asp
        20                  25                  30
```

<210> SEQ ID NO 132
<211> LENGTH: 30
<212> TYPE: PRT
<213> ORGANISM: Artificial Sequence
<220> FEATURE:
<223> OTHER INFORMATION: Framework sequence

<400> SEQUENCE: 132

```
Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Arg Phe Ile
        20                  25                  30
```

<210> SEQ ID NO 133
<211> LENGTH: 5
<212> TYPE: PRT
<213> ORGANISM: Artificial Sequence
<220> FEATURE:
<223> OTHER INFORMATION: CDR sequence

<400> SEQUENCE: 133

```
Leu Asp Arg Met Gly
1               5
```

<210> SEQ ID NO 134
<211> LENGTH: 5
<212> TYPE: PRT
<213> ORGANISM: Artificial Sequence
<220> FEATURE:
<223> OTHER INFORMATION: CDR sequence

<400> SEQUENCE: 134

```
Thr Tyr Ile Met Gly
1               5
```

<210> SEQ ID NO 135
<211> LENGTH: 6
<212> TYPE: PRT
<213> ORGANISM: Artificial Sequence
<220> FEATURE:
<223> OTHER INFORMATION: CDR sequence

<400> SEQUENCE: 135

```
Ser Ile Tyr Ala Lys Gly
1               5
```

<210> SEQ ID NO 136
<211> LENGTH: 5
<212> TYPE: PRT
<213> ORGANISM: Artificial Sequence
<220> FEATURE:
<223> OTHER INFORMATION: CDR sequence

<400> SEQUENCE: 136

```
Ser Phe Ala Met Gly
1               5
```

<210> SEQ ID NO 137
<211> LENGTH: 5
<212> TYPE: PRT
<213> ORGANISM: Artificial Sequence
<220> FEATURE:
<223> OTHER INFORMATION: CDR sequence

```
<400> SEQUENCE: 137

Leu Asn Thr Met Gly
1               5

<210> SEQ ID NO 138
<211> LENGTH: 5
<212> TYPE: PRT
<213> ORGANISM: Artificial Sequence
<220> FEATURE:
<223> OTHER INFORMATION: CDR sequence

<400> SEQUENCE: 138

Asp Tyr Ala Ile Ala
1               5

<210> SEQ ID NO 139
<211> LENGTH: 6
<212> TYPE: PRT
<213> ORGANISM: Artificial Sequence
<220> FEATURE:
<223> OTHER INFORMATION: CDR sequence

<400> SEQUENCE: 139

Ser Asn Tyr Ala Met Gly
1               5

<210> SEQ ID NO 140
<211> LENGTH: 14
<212> TYPE: PRT
<213> ORGANISM: Artificial Sequence
<220> FEATURE:
<223> OTHER INFORMATION: Framework sequence

<400> SEQUENCE: 140

Trp Tyr Arg His Arg Thr Gly Glu Pro Arg Glu Leu Val Ala
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Framework sequence

<400> SEQUENCE: 141

Trp Phe Arg Gln Ala Pro Gly Lys Glu Arg Glu Phe Val Ala
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Framework sequence

<400> SEQUENCE: 142

Trp Phe Arg Gln Ala Pro Gly Lys Glu Arg Glu Phe Val Ala
1               5                   10

<210> SEQ ID NO 143
<211> LENGTH: 14
<212> TYPE: PRT
<213> ORGANISM: Artificial Sequence
<220> FEATURE:
<223> OTHER INFORMATION: Framework sequence

<400> SEQUENCE: 143
```

```
Trp Phe Arg Gln Ala Pro Gly Lys Glu Arg Glu Phe Val Ala
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Framework sequence

<400> SEQUENCE: 144

Trp Tyr Arg His Ala Pro Gly Lys Pro Arg Glu Leu Val Ala
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Framework sequence

<400> SEQUENCE: 145

Trp Phe Arg Gln Ala Pro Gly Lys Glu Arg Glu Gly Val Ser
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Framework sequence

<400> SEQUENCE: 146

Trp Phe Arg Gln Ala Pro Gly Gln Glu Arg Ala Phe Val Ala
1               5                   10

<210> SEQ ID NO 147
<211> LENGTH: 16
<212> TYPE: PRT
<213> ORGANISM: Artificial Sequence
<220> FEATURE:
<223> OTHER INFORMATION: CDR sequence

<400> SEQUENCE: 147

Thr Ile Thr Gly Gly Ser Ser Ile Asn Tyr Gly Asp Phe Val Lys Gly
1               5                   10                  15

<210> SEQ ID NO 148
<211> LENGTH: 17
<212> TYPE: PRT
<213> ORGANISM: Artificial Sequence
<220> FEATURE:
<223> OTHER INFORMATION: CDR sequence

<400> SEQUENCE: 148

Thr Ile Ser Arg Ser Gly Ile Thr Thr Arg Ser Ala Asp Ser Val Lys
1               5                   10                  15
Gly

<210> SEQ ID NO 149
<211> LENGTH: 17
<212> TYPE: PRT
<213> ORGANISM: Artificial Sequence
<220> FEATURE:
<223> OTHER INFORMATION: CDR sequence
```

```
<400> SEQUENCE: 149

Ala Ile Ser Arg Ser Gly Arg Ser Thr Ser Tyr Ala Asp Ser Val Lys
1               5                   10                  15

Gly

<210> SEQ ID NO 150
<211> LENGTH: 17
<212> TYPE: PRT
<213> ORGANISM: Artificial Sequence
<220> FEATURE:
<223> OTHER INFORMATION: CDR sequence

<400> SEQUENCE: 150

Ala Ile Ser Arg Ser Gly Tyr Gly Thr Ser Glu Ala Asp Ser Val Arg
1               5                   10                  15

Asp

<210> SEQ ID NO 151
<211> LENGTH: 16
<212> TYPE: PRT
<213> ORGANISM: Artificial Sequence
<220> FEATURE:
<223> OTHER INFORMATION: CDR sequence

<400> SEQUENCE: 151

Arg Ile Ser Ser Asn Ser Lys Thr Asp Tyr Ala Asp Ser Val Lys Gly
1               5                   10                  15

<210> SEQ ID NO 152
<211> LENGTH: 17
<212> TYPE: PRT
<213> ORGANISM: Artificial Sequence
<220> FEATURE:
<223> OTHER INFORMATION: CDR sequence

<400> SEQUENCE: 152

Arg Ile Lys Ile Ser Asn Gly Arg Thr Thr Tyr Ala Gly Ser Val Lys
1               5                   10                  15

Gly

<210> SEQ ID NO 153
<211> LENGTH: 17
<212> TYPE: PRT
<213> ORGANISM: Artificial Sequence
<220> FEATURE:
<223> OTHER INFORMATION: CDR sequence

<400> SEQUENCE: 153

Ala Ile Ser Arg Ser Gly Ser Ile Thr Tyr Tyr Thr Asp Ser Val Lys
1               5                   10                  15

Gly

<210> SEQ ID NO 154
<211> LENGTH: 32
<212> TYPE: PRT
<213> ORGANISM: Artificial Sequence
<220> FEATURE:
<223> OTHER INFORMATION: Framework sequence

<400> SEQUENCE: 154

Arg Phe Thr Ile Ser Ile Asp Asn Ala Lys Asn Thr Val Tyr Leu Gln
1               5                   10                  15

Met Asn Asn Leu Lys Pro Glu Asp Thr Ala Val Tyr Tyr Cys Asn Phe
```

```
            20                  25                  30
```

<210> SEQ ID NO 155
<211> LENGTH: 32
<212> TYPE: PRT
<213> ORGANISM: Artificial Sequence
<220> FEATURE:
<223> OTHER INFORMATION: Framework sequence

<400> SEQUENCE: 155

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30
```

<210> SEQ ID NO 156
<211> LENGTH: 32
<212> TYPE: PRT
<213> ORGANISM: Artificial Sequence
<220> FEATURE:
<223> OTHER INFORMATION: Framework sequence

<400> SEQUENCE: 156

```
Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30
```

<210> SEQ ID NO 157
<211> LENGTH: 32
<212> TYPE: PRT
<213> ORGANISM: Artificial Sequence
<220> FEATURE:
<223> OTHER INFORMATION: Framework sequence

<400> SEQUENCE: 157

```
Arg Phe Ile Ile Ser Arg Asp Asn Ala Lys Asn Thr Val Thr Leu His
1               5                   10                  15

Leu Ser Arg Leu Lys Pro Glu Asp Thr Ala Val Tyr Tyr Cys Ala Ala
            20                  25                  30
```

<210> SEQ ID NO 158
<211> LENGTH: 32
<212> TYPE: PRT
<213> ORGANISM: Artificial Sequence
<220> FEATURE:
<223> OTHER INFORMATION: Framework sequence

<400> SEQUENCE: 158

```
Arg Phe Thr Ile Ser Arg Asp Asn Ala Lys Asn Thr Val Leu Leu Gln
1               5                   10                  15

Met Asn Ser Leu Lys Pro Glu Asp Thr Gly Val Tyr Tyr Cys Asn Leu
            20                  25                  30
```

<210> SEQ ID NO 159
<211> LENGTH: 32
<212> TYPE: PRT
<213> ORGANISM: Artificial Sequence
<220> FEATURE:
<223> OTHER INFORMATION: Framework sequence

<400> SEQUENCE: 159

```
Arg Phe Thr Ile Ser Ser Asp Asn Ala Lys Asn Thr Val Tyr Leu Gln
1               5                   10                  15
```

Met Asn Ser Leu Asn Ala Glu Asp Thr Ala Val Tyr Tyr Cys Ala Ala
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Framework sequence

<400> SEQUENCE: 160

Arg Phe Ser Ile Ser Arg Asp Tyr Ala Lys Ser Thr Val Tyr Leu Gln
1               5                   10                  15

Met Asp Asn Leu Lys Pro Glu Asp Thr Ala Val Tyr Tyr Cys Ala Ala
            20                  25                  30

<210> SEQ ID NO 161
<211> LENGTH: 9
<212> TYPE: PRT
<213> ORGANISM: Artificial Sequence
<220> FEATURE:
<223> OTHER INFORMATION: CDR sequence

<400> SEQUENCE: 161

Asn Lys Tyr Val Thr Ser Arg Asp Thr
1               5

<210> SEQ ID NO 162
<211> LENGTH: 19
<212> TYPE: PRT
<213> ORGANISM: Artificial Sequence
<220> FEATURE:
<223> OTHER INFORMATION: CDR sequence

<400> SEQUENCE: 162

Gly Pro Tyr Val Glu Gln Thr Leu Gly Leu Tyr Gln Thr Leu Gly Pro
1               5                   10                  15

Trp Asp Tyr

<210> SEQ ID NO 163
<211> LENGTH: 14
<212> TYPE: PRT
<213> ORGANISM: Artificial Sequence
<220> FEATURE:
<223> OTHER INFORMATION: CDR sequence

<400> SEQUENCE: 163

Val Gly Gly Ala Thr Thr Val Thr Ala Ser Glu Trp Asp Tyr
1               5                   10

<210> SEQ ID NO 164
<211> LENGTH: 16
<212> TYPE: PRT
<213> ORGANISM: Artificial Sequence
<220> FEATURE:
<223> OTHER INFORMATION: CDR sequence

<400> SEQUENCE: 164

Glu His Thr Leu Gly Arg Pro Ser Arg Ser Gln Ile Asn Tyr Leu Tyr
1               5                   10                  15

<210> SEQ ID NO 165
<211> LENGTH: 9
<212> TYPE: PRT
<213> ORGANISM: Artificial Sequence
<220> FEATURE:

```
<223> OTHER INFORMATION: CDR sequence

<400> SEQUENCE: 165

Asn Val Trp Arg Thr Ser Ser Asp Tyr
1               5

<210> SEQ ID NO 166
<211> LENGTH: 19
<212> TYPE: PRT
<213> ORGANISM: Artificial Sequence
<220> FEATURE:
<223> OTHER INFORMATION: CDR sequence

<400> SEQUENCE: 166

Asp Arg Ser Ser Leu Leu Phe Gly Ser Asn Trp Asp Arg Lys Ala Arg
1               5                   10                  15

Tyr Asp Tyr

<210> SEQ ID NO 167
<211> LENGTH: 15
<212> TYPE: PRT
<213> ORGANISM: Artificial Sequence
<220> FEATURE:
<223> OTHER INFORMATION: CDR sequence

<400> SEQUENCE: 167

Asp Gly Gly Ala Val Arg Asp Leu Thr Thr Asn Leu Pro Asp Tyr
1               5                   10                  15

<210> SEQ ID NO 168
<211> LENGTH: 11
<212> TYPE: PRT
<213> ORGANISM: Artificial Sequence
<220> FEATURE:
<223> OTHER INFORMATION: Framework sequence

<400> SEQUENCE: 168

Trp Gly Gln Gly Thr Gln Val Thr Val Ser Ser
1               5                   10

<210> SEQ ID NO 169
<211> LENGTH: 11
<212> TYPE: PRT
<213> ORGANISM: Artificial Sequence
<220> FEATURE:
<223> OTHER INFORMATION: Framework sequence

<400> SEQUENCE: 169

Trp Gly Gln Gly Thr Gln Val Thr Val Ser Ser
1               5                   10

<210> SEQ ID NO 170
<211> LENGTH: 11
<212> TYPE: PRT
<213> ORGANISM: Artificial Sequence
<220> FEATURE:
<223> OTHER INFORMATION: Framework sequence

<400> SEQUENCE: 170

Trp Gly Leu Gly Thr Gln Val Thr Val Ser Ser
1               5                   10

<210> SEQ ID NO 171
<211> LENGTH: 11
<212> TYPE: PRT
<213> ORGANISM: Artificial Sequence
```

```
<220> FEATURE:
<223> OTHER INFORMATION: Framework sequence

<400> SEQUENCE: 171

Trp Gly Gln Gly Thr Gln Val Thr Val Ser Ser
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Framework sequence

<400> SEQUENCE: 172

Trp Gly Gln Gly Thr Gln Val Thr Val Ser Ser
1               5                   10

<210> SEQ ID NO 173
<211> LENGTH: 11
<212> TYPE: PRT
<213> ORGANISM: Artificial Sequence
<220> FEATURE:
<223> OTHER INFORMATION: Framework sequence

<400> SEQUENCE: 173

Trp Gly Gln Gly Thr Gln Val Thr Val Ser Ser
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Framework sequence

<400> SEQUENCE: 174

Trp Gly Arg Gly Thr Gln Val Thr Val Ser Ser
1               5                   10

<210> SEQ ID NO 175
<211> LENGTH: 183
<212> TYPE: PRT
<213> ORGANISM: Homo sapiens

<400> SEQUENCE: 175

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
                20                  25                  30

Gly Leu Gly Leu Leu Leu Cys Phe Thr Tyr Ile Cys Leu His Phe Ser
            35                  40                  45

Ala Leu Gln Val Ser His Arg Tyr Pro Arg Ile Gln Ser Ile Lys Val
        50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
                100                 105                 110

Val Asn Ile Ser Leu His Tyr Gln Lys Asp Glu Glu Pro Leu Phe Gln
            115                 120                 125
```

```
Leu Lys Lys Val Arg Ser Val Asn Ser Leu Met Val Ala Ser Leu Thr
        130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 176
<211> LENGTH: 183
<212> TYPE: PRT
<213> ORGANISM: Macaca fascicularis

<400> SEQUENCE: 176

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Gln Tyr Pro Arg Ile Gln Ser Ile Lys Val
    50                  55                  60

Gln Phe Thr Glu Tyr Lys Lys Glu Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 177
<211> LENGTH: 450
<212> TYPE: PRT
<213> ORGANISM: Artificial Sequence
<220> FEATURE:
<223> OTHER INFORMATION: Antibody heavy chain

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Ile Ile Ser Gly Ser Gly Gly Phe Thr Tyr Tyr Ala Asp Ser Val
    50                  55                  60

Lys Gly Arg Phe Thr Ile Ser Arg Asp Asn Ser Arg Thr Thr Leu Tyr
```

```
              65                  70                  75                  80
Leu Gln Met Asn Ser Leu Arg Ala Glu Asp Thr Ala Val Tyr Tyr Cys
                    85                  90                  95
Ala Lys Asp Arg Leu Val Ala Pro Gly Thr Phe Asp Tyr Trp Gly Gln
                100                 105                 110
Gly Ala Leu Val Thr Val Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 178
<211> LENGTH: 214
<212> TYPE: PRT
<213> ORGANISM: Artificial Sequence
```

```
<220> FEATURE:
<223> OTHER INFORMATION: Antibody light chain

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 179
<211> LENGTH: 117
<212> TYPE: PRT
<213> ORGANISM: Artificial Sequence
<220> FEATURE:
<223> OTHER INFORMATION: Nanobody sequence

<400> SEQUENCE: 179

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Gln
            100                 105                 110

Val Thr Val Ser Ser
```

<210> SEQ ID NO 180
<211> LENGTH: 128
<212> TYPE: PRT
<213> ORGANISM: Artificial Sequence
<220> FEATURE:
<223> OTHER INFORMATION: Nanobody sequence

<400> SEQUENCE: 180

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Ser Phe Ser Thr Tyr
            20                  25                  30

Ile Met Gly Trp Phe Arg Gln Ala Pro Gly Lys Glu Arg Glu Phe Val
        35                  40                  45

Ala Thr Ile Ser Arg Ser Gly Ile Thr Thr Arg Ser Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Pro Tyr Val Glu Gln Thr Leu Gly Leu Tyr Gln Thr Leu
            100                 105                 110

Gly Pro Trp Asp Tyr Trp Gly Gln Gly Thr Gln Val Thr Val Ser Ser
        115                 120                 125

<210> SEQ ID NO 181
<211> LENGTH: 124
<212> TYPE: PRT
<213> ORGANISM: Artificial Sequence
<220> FEATURE:
<223> OTHER INFORMATION: Nanobody sequence

<400> SEQUENCE: 181

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Leu Gly Thr Gln Val Thr Val Ser Ser
        115                 120

<210> SEQ ID NO 182
<211> LENGTH: 125
<212> TYPE: PRT
<213> ORGANISM: Artificial Sequence
<220> FEATURE:
<223> OTHER INFORMATION: Nanobody sequence

<400> SEQUENCE: 182

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Ser Phe
            20                  25                  30

Ala Met Gly Trp Phe Arg Gln Ala Pro Gly Lys Glu Arg Glu Phe Val
        35                  40                  45

Ala Ala Ile Ser Arg Ser Gly Tyr Gly Thr Ser Glu Ala Asp Ser Val
    50                  55                  60

Arg Asp Arg Phe Ile Ile Ser Arg Asp Asn Ala Lys Asn Thr Val Thr
65                  70                  75                  80

Leu His Leu Ser Arg Leu Lys Pro Glu Asp Thr Ala Val Tyr Tyr Cys
                85                  90                  95

Ala Ala Glu His Thr Leu Gly Arg Pro Ser Arg Ser Gln Ile Asn Tyr
            100                 105                 110

Leu Tyr Trp Gly Gln Gly Thr Gln Val Thr Val Ser Ser
        115                 120                 125

<210> SEQ ID NO 183
<211> LENGTH: 117
<212> TYPE: PRT
<213> ORGANISM: Artificial Sequence
<220> FEATURE:
<223> OTHER INFORMATION: Nanobody sequence

<400> SEQUENCE: 183

Glu Val Gln Leu Val Glu Ser Gly Gly Gly Leu Val Gln Ala Gly Gly
1               5                   10                  15

Ser Leu Arg Leu Ser Cys Ala Ala Ser Arg Asn Ile Leu Ser Leu Asn
            20                  25                  30

Thr Met Gly Trp Tyr Arg His Ala Pro Gly Lys Pro Arg Glu Leu Val
        35                  40                  45

Ala Arg Ile Ser Ser Asn Ser Lys Thr Asp Tyr Ala Asp Ser Val Lys
    50                  55                  60

Gly Arg Phe Thr Ile Ser Arg Asp Asn Ala Lys Asn Thr Val Leu Leu
65                  70                  75                  80

Gln Met Asn Ser Leu Lys Pro Glu Asp Thr Gly Val Tyr Tyr Cys Asn
                85                  90                  95

Leu Asn Val Trp Arg Thr Ser Ser Asp Tyr Trp Gly Gln Gly Thr Gln
            100                 105                 110

Val Thr Val Ser Ser
        115

<210> SEQ ID NO 184
<211> LENGTH: 128
<212> TYPE: PRT
<213> ORGANISM: Artificial Sequence
<220> FEATURE:
<223> OTHER INFORMATION: Nanobody sequence

<400> SEQUENCE: 184

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Asp Tyr
            20                  25                  30

Ala Ile Ala Trp Phe Arg Gln Ala Pro Gly Lys Glu Arg Glu Gly Val
        35                  40                  45

Ser Arg Ile Lys Ile Ser Asn Gly Arg Thr Thr Tyr Ala Gly Ser Val

```
            50                  55                  60
Lys Gly Arg Phe Thr Ile Ser Ser Asp Asn Ala Lys Asn Thr Val Tyr
 65                  70                  75                  80

Leu Gln Met Asn Ser Leu Asn Ala Glu Asp Thr Ala Val Tyr Tyr Cys
                     85                  90                  95

Ala Ala Asp Arg Ser Ser Leu Leu Phe Gly Ser Asn Trp Asp Arg Lys
                    100                 105                 110

Ala Arg Tyr Asp Tyr Trp Gly Gln Gly Thr Gln Val Thr Val Ser Ser
                    115                 120                 125

<210> SEQ ID NO 185
<211> LENGTH: 125
<212> TYPE: PRT
<213> ORGANISM: Artificial Sequence
<220> FEATURE:
<223> OTHER INFORMATION: Nanobody sequence

<400> SEQUENCE: 185

Glu Val Gln Leu Val Glu Ser Gly Gly Gly Leu Val Gln Ala Gly Ala
 1                   5                  10                  15

Ser Leu Arg Leu Ser Cys Ala Ala Ser Gly Arg Arg Phe Ile Ser Asn
                    20                  25                  30

Tyr Ala Met Gly Trp Phe Arg Gln Ala Pro Gly Gln Glu Arg Ala Phe
                    35                  40                  45

Val Ala Ala Ile Ser Arg Ser Gly Ser Ile Thr Tyr Tyr Thr Asp Ser
                    50                  55                  60

Val Lys Gly Arg Phe Ser Ile Ser Arg Asp Tyr Ala Lys Ser Thr Val
 65                  70                  75                  80

Tyr Leu Gln Met Asp Asn Leu Lys Pro Glu Asp Thr Ala Val Tyr Tyr
                    85                  90                  95

Cys Ala Ala Asp Gly Gly Ala Val Arg Asp Leu Thr Thr Asn Leu Pro
                    100                 105                 110

Asp Tyr Trp Gly Arg Gly Thr Gln Val Thr Val Ser Ser
                    115                 120                 125

<210> SEQ ID NO 186
<211> LENGTH: 381
<212> TYPE: PRT
<213> ORGANISM: Artificial Sequence
<220> FEATURE:
<223> OTHER INFORMATION: Nanobody sequence

<400> SEQUENCE: 186

Glu Val Gln Leu Val Glu Ser Gly Gly Gly Leu Val Gln Ala Gly Gly
 1                   5                  10                  15

Ser Leu Arg Leu Ser Cys Ala Ala Ser Gly Arg Thr Phe Ser Ser Ile
                    20                  25                  30

Tyr Ala Lys Gly Trp Phe Arg Gln Ala Pro Gly Lys Glu Arg Glu Phe
                    35                  40                  45

Val Ala Ala Ile Ser Arg Ser Gly Arg Ser Thr Ser Tyr Ala Asp Ser
                    50                  55                  60

Val Lys Gly Arg Phe Thr Ile Ser Arg Asp Asn Ala Lys Asn Thr Val
 65                  70                  75                  80

Tyr Leu Gln Met Asn Ser Leu Lys Pro Glu Asp Thr Ala Val Tyr Tyr
                    85                  90                  95

Cys Ala Ala Val Gly Gly Ala Thr Thr Val Thr Ala Ser Glu Trp Asp
                    100                 105                 110
```

Tyr Trp Gly Leu Gly Thr Gln Val Thr Val Ser Ser Gly Gly Gly
            115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Gly Ser Gly Ser Asp Thr Leu
                180                 185                 190

Tyr Ala Asp Ser Val Lys Gly Arg Phe Thr Ile Ser Arg Asp Asn Ala
                195                 200                 205

Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Gly Gly Gly Gly Ser Gly Gly Gly
                245                 250                 255

Ser Glu Val Gln Leu Val Glu Ser Gly Gly Gly Leu Val Gln Ala Gly
                260                 265                 270

Gly Ser Leu Arg Leu Ser Cys Ala Ala Ser Gly Arg Thr Phe Ser Ser
                275                 280                 285

Ile Tyr Ala Lys Gly Trp Phe Arg Gln Ala Pro Gly Lys Glu Arg Glu
                290                 295                 300

Phe Val Ala Ala Ile Ser Arg Ser Gly Arg Ser Thr Ser Tyr Ala Asp
305                 310                 315                 320

Ser Val Lys Gly Arg Phe Thr Ile Ser Arg Asp Asn Ala Lys Asn Thr
                325                 330                 335

Val Tyr Leu Gln Met Asn Ser Leu Lys Pro Glu Asp Thr Ala Val Tyr
                340                 345                 350

Tyr Cys Ala Ala Val Gly Gly Ala Thr Thr Val Thr Ala Ser Glu Trp
                355                 360                 365

Asp Tyr Trp Gly Leu Gly Thr Gln Val Thr Val Ser Ser
                370                 375                 380

<210> SEQ ID NO 187
<211> LENGTH: 367
<212> TYPE: PRT
<213> ORGANISM: Artificial Sequence
<220> FEATURE:
<223> OTHER INFORMATION: Nanobody sequence

<400> SEQUENCE: 187

Glu Val Gln Leu Val Glu Ser Gly Gly Gly Leu Val Gln Ala Gly Gly
1               5                   10                  15

Ser Leu Arg Leu Ser Cys Ala Ala Ser Arg Asn Ile Leu Ser Leu Asn
            20                  25                  30

Thr Met Gly Trp Tyr Arg His Ala Pro Gly Lys Pro Arg Glu Leu Val
        35                  40                  45

Ala Arg Ile Ser Ser Asn Ser Lys Thr Asp Tyr Ala Asp Ser Val Lys
    50                  55                  60

Gly Arg Phe Thr Ile Ser Arg Asp Asn Ala Lys Asn Thr Val Leu Leu
65                  70                  75                  80

Gln Met Asn Ser Leu Lys Pro Glu Asp Thr Gly Val Tyr Tyr Cys Asn
                85                  90                  95

Leu Asn Val Trp Arg Thr Ser Ser Asp Tyr Trp Gly Gln Gly Thr Gln
            100                 105                 110

Val Thr Val Ser Ser Gly Gly Gly Gly Ser Gly Gly Gly Ser Glu Val
            115                 120                 125

Gln Leu Val Glu Ser Gly Gly Gly Leu Val Gln Pro Gly Asn Ser Leu
            130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
            165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
            195                 200                 205

Met Asn Ser Leu Arg Pro Glu Asp Thr Ala Val Tyr Tyr Cys Thr Ile
            210                 215                 220

Gly Gly Ser Leu Ser Arg Ser Ser Gln Gly Thr Leu Val Thr Val Ser
225                 230                 235                 240

Ser Gly Gly Gly Gly Ser Gly Gly Gly Ser Glu Val Gln Leu Val Glu
            245                 250                 255

Ser Gly Gly Gly Leu Val Gln Ala Gly Gly Ser Leu Arg Leu Ser Cys
            260                 265                 270

Ala Ala Ser Arg Asn Ile Leu Ser Leu Asn Thr Met Gly Trp Tyr Arg
            275                 280                 285

His Ala Pro Gly Lys Pro Arg Glu Leu Val Ala Arg Ile Ser Ser Asn
            290                 295                 300

Ser Lys Thr Asp Tyr Ala Asp Ser Val Lys Gly Arg Phe Thr Ile Ser
305                 310                 315                 320

Arg Asp Asn Ala Lys Asn Thr Val Leu Leu Gln Met Asn Ser Leu Lys
            325                 330                 335

Pro Glu Asp Thr Gly Val Tyr Tyr Cys Asn Leu Asn Val Trp Arg Thr
            340                 345                 350

Ser Ser Asp Tyr Trp Gly Gln Gly Thr Gln Val Thr Val Ser Ser
            355                 360                 365

<210> SEQ ID NO 188
<211> LENGTH: 383
<212> TYPE: PRT
<213> ORGANISM: Artificial Sequence
<220> FEATURE:
<223> OTHER INFORMATION: Nanobody sequence

<400> SEQUENCE: 188

Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Arg Phe Ile Ser Asn
            20                  25                  30

Tyr Ala Met Gly Trp Phe Arg Gln Ala Pro Gly Gln Glu Arg Ala Phe
            35                  40                  45

Val Ala Ala Ile Ser Arg Ser Gly Ser Ile Thr Tyr Tyr Thr Asp Ser
50                  55                  60

Val Lys Gly Arg Phe Ser Ile Ser Arg Asp Tyr Ala Lys Ser Thr Val
65                  70                  75                  80

Tyr Leu Gln Met Asp Asn Leu Lys Pro Glu Asp Thr Ala Val Tyr Tyr
            85                  90                  95

-continued

```
Cys Ala Ala Asp Gly Gly Ala Val Arg Asp Leu Thr Thr Asn Leu Pro
                100                 105                 110
Asp Tyr Trp Gly Arg Gly Thr Gln Val Thr Val Ser Ser Gly Gly Gly
        115                 120                 125
Gly Ser Gly Gly Gly Ser Glu Val Gln Leu Val Glu Ser Gly Gly Gly
    130                 135                 140
Leu Val Gln Pro Gly Asn Ser Leu Arg Leu Ser Cys Ala Ala Ser Gly
145                 150                 155                 160
Phe Thr Phe Ser Ser Phe Gly Met Ser Trp Val Arg Gln Ala Pro Gly
                165                 170                 175
Lys Gly Leu Glu Trp Val Ser Ser Ile Ser Gly Ser Gly Ser Asp Thr
        180                 185                 190
Leu Tyr Ala Asp Ser Val Lys Gly Arg Phe Thr Ile Ser Arg Asp Asn
    195                 200                 205
Ala Lys Thr Thr Leu Tyr Leu Gln Met Asn Ser Leu Arg Pro Glu Asp
210                 215                 220
Thr Ala Val Tyr Tyr Cys Thr Ile Gly Gly Ser Leu Ser Arg Ser Ser
225                 230                 235                 240
Gln Gly Thr Leu Val Thr Val Ser Ser Gly Gly Gly Ser Gly Gly
                245                 250                 255
Gly Ser Glu Val Gln Leu Val Glu Ser Gly Gly Gly Leu Val Gln Ala
    260                 265                 270
Gly Ala Ser Leu Arg Leu Ser Cys Ala Ala Ser Gly Arg Phe Ile
    275                 280                 285
Ser Asn Tyr Ala Met Gly Trp Phe Arg Gln Ala Pro Gly Gln Glu Arg
    290                 295                 300
Ala Phe Val Ala Ala Ile Ser Arg Ser Gly Ser Ile Thr Tyr Tyr Thr
305                 310                 315                 320
Asp Ser Val Lys Gly Arg Phe Ser Ile Ser Arg Asp Tyr Ala Lys Ser
                325                 330                 335
Thr Val Tyr Leu Gln Met Asp Asn Leu Lys Pro Glu Asp Thr Ala Val
        340                 345                 350
Tyr Tyr Cys Ala Ala Asp Gly Gly Ala Val Arg Asp Leu Thr Thr Asn
    355                 360                 365
Leu Pro Asp Tyr Trp Gly Arg Gly Thr Gln Val Thr Val Ser Ser
370                 375                 380

<210> SEQ ID NO 189
<211> LENGTH: 383
<212> TYPE: PRT
<213> ORGANISM: Artificial Sequence
<220> FEATURE:
<223> OTHER INFORMATION: Nanobody sequence

<400> SEQUENCE: 189

Glu Val Gln Leu Val Glu Ser Gly Gly Gly Leu Val Gln Ala Gly Asp
1               5                   10                  15
Ser Leu Arg Leu Ser Cys Ala Ala Ser Gly Leu Thr Phe Ser Ser Phe
            20                  25                  30
Ala Met Gly Trp Phe Arg Gln Ala Pro Gly Lys Glu Arg Glu Phe Val
        35                  40                  45
Ala Ala Ile Ser Arg Ser Gly Tyr Gly Thr Ser Glu Ala Asp Ser Val
    50                  55                  60
Arg Asp Arg Phe Ile Ile Ser Arg Asp Asn Ala Lys Asn Thr Val Thr
65                  70                  75                  80
```

Leu His Leu Ser Arg Leu Lys Pro Glu Asp Thr Ala Val Tyr Tyr Cys
                85                  90                  95

Ala Ala Glu His Thr Leu Gly Arg Pro Ser Arg Ser Gln Ile Asn Tyr
            100                 105                 110

Leu Tyr Trp Gly Gln Gly Thr Gln Val Thr Val Ser Ser Gly Gly Gly
            115                 120                 125

Gly Ser Gly Gly Gly Ser Glu Val Gln Leu Val Glu Ser Gly Gly Gly
            130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
            195                 200                 205

Ala Lys Thr Thr Leu Tyr Leu Gln Met Asn Ser Leu Arg Pro Glu Asp
            210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
            245                 250                 255

Gly Ser Glu Val Gln Leu Val Glu Ser Gly Gly Gly Leu Val Gln Ala
            260                 265                 270

Gly Asp Ser Leu Arg Leu Ser Cys Ala Ala Ser Gly Leu Thr Phe Ser
            275                 280                 285

Ser Phe Ala Met Gly Trp Phe Arg Gln Ala Pro Gly Lys Glu Arg Glu
            290                 295                 300

Phe Val Ala Ala Ile Ser Arg Ser Gly Tyr Gly Thr Ser Glu Ala Asp
305                 310                 315                 320

Ser Val Arg Asp Arg Phe Ile Ile Ser Arg Asp Asn Ala Lys Asn Thr
            325                 330                 335

Val Thr Leu His Leu Ser Arg Leu Lys Pro Glu Asp Thr Ala Val Tyr
            340                 345                 350

Tyr Cys Ala Ala Glu His Thr Leu Gly Arg Pro Ser Arg Ser Gln Ile
            355                 360                 365

Asn Tyr Leu Tyr Trp Gly Gln Gly Thr Gln Val Thr Val Ser Ser
            370                 375                 380

<210> SEQ ID NO 190
<211> LENGTH: 367
<212> TYPE: PRT
<213> ORGANISM: Artificial Sequence
<220> FEATURE:
<223> OTHER INFORMATION: Nanobody sequence

<400> SEQUENCE: 190

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
            35                  40                  45

Ala Thr Ile Thr Gly Gly Ser Ser Ile Asn Tyr Gly Asp Phe Val Lys
50                  55                  60

```
Gly Arg Phe Thr Ile Ser Ile Asp Asn Ala Lys Asn Thr Val Tyr Leu
65                  70                  75                  80

Gln Met Asn Asn Leu Lys Pro Glu Asp Thr Ala Val Tyr Tyr Cys Asn
            85                  90                  95

Phe Asn Lys Tyr Val Thr Ser Arg Asp Thr Trp Gly Gln Gly Thr Gln
            100                 105                 110

Val Thr Val Ser Ser Gly Gly Gly Ser Gly Gly Gly Ser Glu Val
            115                 120                 125

Gln Leu Val Glu Ser Gly Gly Gly Leu Val Gln Pro Gly Asn Ser Leu
            130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
            165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
            195                 200                 205

Met Asn Ser Leu Arg Pro Glu Asp Thr Ala Val Tyr Tyr Cys Thr Ile
            210                 215                 220

Gly Gly Ser Leu Ser Arg Ser Ser Gln Gly Thr Leu Val Thr Val Ser
225                 230                 235                 240

Ser Gly Gly Gly Gly Ser Gly Gly Gly Ser Glu Val Gln Leu Val Glu
            245                 250                 255

Ser Gly Gly Gly Leu Val Gln Ala Gly Gly Ser Leu Arg Leu Ser Cys
            260                 265                 270

Ala Ala Ser Arg Ser Ile Gly Arg Leu Asp Arg Met Gly Trp Tyr Arg
            275                 280                 285

His Arg Thr Gly Glu Pro Arg Glu Leu Val Ala Thr Ile Thr Gly Gly
            290                 295                 300

Ser Ser Ile Asn Tyr Gly Asp Phe Val Lys Gly Arg Phe Thr Ile Ser
305                 310                 315                 320

Ile Asp Asn Ala Lys Asn Thr Val Tyr Leu Gln Met Asn Asn Leu Lys
            325                 330                 335

Pro Glu Asp Thr Ala Val Tyr Tyr Cys Asn Phe Asn Lys Tyr Val Thr
            340                 345                 350

Ser Arg Asp Thr Trp Gly Gln Gly Thr Gln Val Thr Val Ser Ser
            355                 360                 365

<210> SEQ ID NO 191
<211> LENGTH: 389
<212> TYPE: PRT
<213> ORGANISM: Artificial Sequence
<220> FEATURE:
<223> OTHER INFORMATION: Nanobody sequence

<400> SEQUENCE: 191

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Asp Tyr
            20                  25                  30

Ala Ile Ala Trp Phe Arg Gln Ala Pro Gly Lys Glu Arg Glu Gly Val
            35                  40                  45

Ser Arg Ile Lys Ile Ser Asn Gly Arg Thr Thr Tyr Ala Gly Ser Val
            50                  55                  60
```

Lys Gly Arg Phe Thr Ile Ser Ser Asp Asn Ala Lys Asn Thr Val Tyr
65                  70                  75                  80

Leu Gln Met Asn Ser Leu Asn Ala Glu Asp Thr Ala Val Tyr Tyr Cys
            85                  90                  95

Ala Ala Asp Arg Ser Ser Leu Leu Phe Gly Ser Asn Trp Asp Arg Lys
            100                 105                 110

Ala Arg Tyr Asp Tyr Trp Gly Gln Gly Thr Gln Val Thr Val Ser Ser
            115                 120                 125

Gly Gly Gly Gly Ser Gly Gly Gly Ser Glu Val Gln Leu Val Glu Ser
        130                 135                 140

Gly Gly Gly Leu Val Gln Pro Gly Asn Ser Leu Arg Leu Ser Cys Ala
145                 150                 155                 160

Ala Ser Gly Phe Thr Phe Ser Ser Phe Gly Met Ser Trp Val Arg Gln
            165                 170                 175

Ala Pro Gly Lys Gly Leu Glu Trp Val Ser Ser Ile Ser Gly Ser Gly
            180                 185                 190

Ser Asp Thr Leu Tyr Ala Asp Ser Val Lys Gly Arg Phe Thr Ile Ser
        195                 200                 205

Arg Asp Asn Ala Lys Thr Thr Leu Tyr Leu Gln Met Asn Ser Leu Arg
210                 215                 220

Pro Glu Asp Thr Ala Val Tyr Tyr Cys Thr Ile Gly Ser Leu Ser
225                 230                 235                 240

Arg Ser Ser Gln Gly Thr Leu Val Thr Val Ser Ser Gly Gly Gly Gly
            245                 250                 255

Ser Gly Gly Gly Ser Glu Val Gln Leu Val Glu Ser Gly Gly Gly Leu
        260                 265                 270

Val Gln Ala Gly Gly Ser Leu Arg Leu Ser Cys Ala Ala Ser Gly Phe
        275                 280                 285

Thr Leu Asp Asp Tyr Ala Ile Ala Trp Phe Arg Gln Ala Pro Gly Lys
        290                 295                 300

Glu Arg Glu Gly Val Ser Arg Ile Lys Ile Ser Asn Gly Arg Thr Thr
305                 310                 315                 320

Tyr Ala Gly Ser Val Lys Gly Arg Phe Thr Ile Ser Ser Asp Asn Ala
            325                 330                 335

Lys Asn Thr Val Tyr Leu Gln Met Asn Ser Leu Asn Ala Glu Asp Thr
            340                 345                 350

Ala Val Tyr Tyr Cys Ala Ala Asp Arg Ser Ser Leu Leu Phe Gly Ser
            355                 360                 365

Asn Trp Asp Arg Lys Ala Arg Tyr Asp Tyr Trp Gly Gln Gly Thr Gln
        370                 375                 380

Val Thr Val Ser Ser
385

<210> SEQ ID NO 192
<211> LENGTH: 389
<212> TYPE: PRT
<213> ORGANISM: Artificial Sequence
<220> FEATURE:
<223> OTHER INFORMATION: Nanobody sequence

<400> SEQUENCE: 192

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Asp Tyr
            20                  25                  30

-continued

Ala Ile Ala Trp Phe Arg Gln Ala Pro Gly Lys Glu Arg Glu Gly Val
         35                  40                  45

Ser Arg Ile Lys Ile Ser Asn Gly Arg Thr Thr Tyr Ala Gly Ser Val
 50                  55                  60

Lys Gly Arg Phe Thr Ile Ser Ser Asp Asn Ala Lys Asn Thr Val Tyr
 65                  70                  75                  80

Leu Gln Met Asn Ser Leu Asn Ala Glu Asp Thr Ala Val Tyr Tyr Cys
                 85                  90                  95

Ala Ala Asp Arg Ser Ser Leu Leu Phe Gly Ser Asn Trp Asp Arg Lys
             100                 105                 110

Ala Arg Tyr Asp Tyr Trp Gly Gln Gly Thr Gln Val Thr Val Ser Ser
         115                 120                 125

Gly Gly Gly Gly Ser Gly Gly Ser Glu Val Gln Leu Val Glu Ser
         130                 135                 140

Gly Gly Gly Leu Val Gln Pro Gly Asn Ser Leu Arg Leu Ser Cys Ala
145                 150                 155                 160

Ala Ser Gly Phe Thr Phe Ser Ser Phe Gly Met Ser Trp Val Arg Gln
             165                 170                 175

Ala Pro Gly Lys Gly Leu Glu Trp Val Ser Ser Ile Ser Gly Ser Gly
         180                 185                 190

Ser Asp Thr Leu Tyr Ala Asp Ser Val Lys Gly Arg Phe Thr Ile Ser
     195                 200                 205

Arg Asp Asn Ala Lys Thr Thr Leu Tyr Leu Gln Met Asn Ser Leu Arg
210                 215                 220

Pro Glu Asp Thr Ala Val Tyr Tyr Cys Thr Ile Gly Gly Ser Leu Ser
225                 230                 235                 240

Arg Ser Ser Gln Gly Thr Leu Val Thr Val Ser Ser Gly Gly Gly Gly
             245                 250                 255

Ser Gly Gly Gly Ser Glu Val Gln Leu Val Glu Ser Gly Gly Gly Leu
         260                 265                 270

Val Gln Ala Gly Gly Ser Leu Arg Leu Ser Cys Ala Ala Ser Gly Phe
     275                 280                 285

Thr Leu Asp Asp Tyr Ala Ile Ala Trp Phe Arg Gln Ala Pro Gly Lys
290                 295                 300

Glu Arg Glu Gly Val Ser Arg Ile Lys Ile Ser Asn Gly Arg Thr Thr
305                 310                 315                 320

Tyr Ala Gly Ser Val Lys Gly Arg Phe Thr Ile Ser Ser Asp Asn Ala
             325                 330                 335

Lys Asn Thr Val Tyr Leu Gln Met Asn Ser Leu Asn Ala Glu Asp Thr
         340                 345                 350

Ala Val Tyr Tyr Cys Ala Ala Asp Arg Ser Ser Leu Leu Phe Gly Ser
     355                 360                 365

Asn Trp Asp Arg Lys Ala Arg Tyr Asp Tyr Trp Gly Gln Gly Thr Gln
370                 375                 380

Val Thr Val Ser Ser
385

<210> SEQ ID NO 193
<211> LENGTH: 407
<212> TYPE: PRT
<213> ORGANISM: Artificial Sequence
<220> FEATURE:
<223> OTHER INFORMATION: Nanobody sequence

<400> SEQUENCE: 193

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
50                      55                  60

Val Lys Gly Arg Phe Thr Ile Ser Arg Asp Asn Ala Lys Asn Thr Val
65                      70                  75                  80

Tyr Leu Gln Met Asn Ser Leu Lys Pro Glu Asp Thr Ala Val Tyr Tyr
                85                  90                  95

Cys Ala Ala Val Gly Gly Ala Thr Thr Val Thr Ala Ser Glu Trp Asp
                100                 105                 110

Tyr Trp Gly Leu Gly Thr Leu Val Thr Val Ser Ser Gly Gly Gly Gly
            115                 120                 125

Ser Gly Gly Gly Ser Gly Gly Gly Ser Gly Gly Gly Ser
    130                 135                 140

Gly Gly Gly Gly Ser Gly Gly Gly Ser Gly Gly Gly Ser Glu
145                 150                 155                 160

Val Gln Leu Val Glu Ser Gly Gly Leu Val Gln Ala Gly Ser
                165                 170                 175

Leu Arg Leu Ser Cys Ala Ala Ser Gly Arg Thr Phe Ser Ser Ile Tyr
            180                 185                 190

Ala Lys Gly Trp Phe Arg Gln Ala Pro Gly Lys Glu Arg Glu Phe Val
        195                 200                 205

Ala Ala Ile Ser Arg Ser Gly Arg Ser Thr Ser Tyr Ala Asp Ser Val
        210                 215                 220

Lys Gly Arg Phe Thr Ile Ser Arg Asp Asn Ala Lys Asn Thr Val Tyr
225                 230                 235                 240

Leu Gln Met Asn Ser Leu Lys Pro Glu Asp Thr Ala Val Tyr Tyr Cys
                245                 250                 255

Ala Ala Val Gly Gly Ala Thr Thr Val Thr Ala Ser Glu Trp Asp Tyr
                260                 265                 270

Trp Gly Leu Gly Thr Leu Val Thr Val Ser Ser Gly Gly Gly Gly Ser
            275                 280                 285

Gly Gly Gly Ser Glu Val Gln Leu Val Glu Ser Gly Gly Gly Leu Val
        290                 295                 300

Gln Pro Gly Asn Ser Leu Arg Leu Ser Cys Ala Ala Ser Gly Phe Thr
305                 310                 315                 320

Phe Ser Ser Phe Gly Met Ser Trp Val Arg Gln Ala Pro Gly Lys Gly
                325                 330                 335

Leu Glu Trp Val Ser Ser Ile Ser Gly Ser Gly Ser Asp Thr Leu Tyr
            340                 345                 350

Ala Asp Ser Val Lys Gly Arg Phe Thr Ile Ser Arg Asp Asn Ala Lys
        355                 360                 365

Thr Thr Leu Tyr Leu Gln Met Asn Ser Leu Arg Pro Glu Asp Thr Ala
370                 375                 380

Val Tyr Tyr Cys Thr Ile Gly Gly Ser Leu Ser Arg Ser Ser Gln Gly
385                 390                 395                 400

Thr Leu Val Thr Val Ser Ser
                405
```

<210> SEQ ID NO 194
<211> LENGTH: 433
<212> TYPE: PRT
<213> ORGANISM: Artificial Sequence
<220> FEATURE:
<223> OTHER INFORMATION: Nanobody sequence

<400> SEQUENCE: 194

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Leu Gly Thr Leu Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gly Gly Gly Ser Gly Gly Gly Gly Ser Glu
145                 150                 155                 160

Val Gln Leu Val Glu Ser Gly Gly Gly Leu Val Gln Ala Gly Gly Ser
                165                 170                 175

Leu Arg Leu Ser Cys Ala Ala Ser Gly Arg Thr Phe Ser Ser Ile Tyr
            180                 185                 190

Ala Lys Gly Trp Phe Arg Gln Ala Pro Gly Lys Glu Arg Glu Phe Val
        195                 200                 205

Ala Ala Ile Ser Arg Ser Gly Arg Ser Thr Ser Tyr Ala Asp Ser Val
    210                 215                 220

Lys Gly Arg Phe Thr Ile Ser Arg Asp Asn Ala Lys Asn Thr Val Tyr
225                 230                 235                 240

Leu Gln Met Asn Ser Leu Lys Pro Glu Asp Thr Ala Val Tyr Tyr Cys
                245                 250                 255

Ala Ala Val Gly Gly Ala Thr Thr Val Thr Ala Ser Glu Trp Asp Tyr
            260                 265                 270

Trp Gly Leu Gly Thr Leu Val Thr Val Ser Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Ser Gly Gly Gly Ser Gly Gly Gly Ser Glu Val
305                 310                 315                 320

Gln Leu Val Glu Ser Gly Gly Gly Leu Val Gln Pro Gly Asn Ser Leu
                325                 330                 335

Arg Leu Ser Cys Ala Ala Ser Gly Phe Thr Phe Ser Phe Gly Met
            340                 345                 350

Ser Trp Val Arg Gln Ala Pro Gly Lys Gly Leu Glu Trp Val Ser Ser
        355                 360                 365

Ile Ser Gly Ser Gly Ser Asp Thr Leu Tyr Ala Asp Ser Val Lys Gly
```

```
                    370                 375                 380
Arg Phe Thr Ile Ser Arg Asp Asn Ala Lys Thr Thr Leu Tyr Leu Gln
385                 390                 395                 400

Met Asn Ser Leu Arg Pro Glu Asp Thr Ala Val Tyr Tyr Cys Thr Ile
                405                 410                 415

Gly Gly Ser Leu Ser Arg Ser Ser Gln Gly Thr Leu Val Thr Val Ser
                420                 425                 430

Ser

<210> SEQ ID NO 195
<211> LENGTH: 409
<212> TYPE: PRT
<213> ORGANISM: Artificial Sequence
<220> FEATURE:
<223> OTHER INFORMATION: Nanobody sequence

<400> SEQUENCE: 195

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Ser Phe
                20                  25                  30

Ala Met Gly Trp Phe Arg Gln Ala Pro Gly Lys Glu Arg Glu Phe Val
            35                  40                  45

Ala Ala Ile Ser Arg Ser Gly Tyr Gly Thr Ser Glu Ala Asp Ser Val
        50                  55                  60

Arg Asp Arg Phe Ile Ile Ser Arg Asp Asn Ala Lys Asn Thr Val Thr
65                  70                  75                  80

Leu His Leu Ser Arg Leu Lys Pro Glu Asp Thr Ala Val Tyr Tyr Cys
                85                  90                  95

Ala Ala Glu His Thr Leu Gly Arg Pro Ser Arg Ser Gln Ile Asn Tyr
            100                 105                 110

Leu Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Glu Val Gln Leu Val Glu Ser Gly Gly Gly Leu Val Gln Ala Gly Asp
                165                 170                 175

Ser Leu Arg Leu Ser Cys Ala Ala Ser Gly Leu Thr Phe Ser Ser Phe
            180                 185                 190

Ala Met Gly Trp Phe Arg Gln Ala Pro Gly Lys Glu Arg Glu Phe Val
        195                 200                 205

Ala Ala Ile Ser Arg Ser Gly Tyr Gly Thr Ser Glu Ala Asp Ser Val
    210                 215                 220

Arg Asp Arg Phe Ile Ile Ser Arg Asp Asn Ala Lys Asn Thr Val Thr
225                 230                 235                 240

Leu His Leu Ser Arg Leu Lys Pro Glu Asp Thr Ala Val Tyr Tyr Cys
                245                 250                 255

Ala Ala Glu His Thr Leu Gly Arg Pro Ser Arg Ser Gln Ile Asn Tyr
            260                 265                 270

Leu Tyr Trp Gly Gln Gly Thr Leu Val Thr Val Ser Ser Gly Gly Gly
        275                 280                 285

Gly Ser Gly Gly Gly Ser Glu Val Gln Leu Val Glu Ser Gly Gly Gly
    290                 295                 300
```

```
Leu Val Gln Pro Gly Asn Ser Leu Arg Leu Ser Cys Ala Ala Ser Gly
305                 310                 315                 320

Phe Thr Phe Ser Ser Phe Gly Met Ser Trp Val Arg Gln Ala Pro Gly
            325                 330                 335

Lys Gly Leu Glu Trp Val Ser Ser Ile Ser Gly Ser Gly Ser Asp Thr
            340                 345                 350

Leu Tyr Ala Asp Ser Val Lys Gly Arg Phe Thr Ile Ser Arg Asp Asn
        355                 360                 365

Ala Lys Thr Thr Leu Tyr Leu Gln Met Asn Ser Leu Arg Pro Glu Asp
    370                 375                 380

Thr Ala Val Tyr Tyr Cys Thr Ile Gly Gly Ser Leu Ser Arg Ser Ser
385                 390                 395                 400

Gln Gly Thr Leu Val Thr Val Ser Ser
                405
```

<210> SEQ ID NO 196
<211> LENGTH: 435
<212> TYPE: PRT
<213> ORGANISM: Artificial Sequence
<220> FEATURE:
<223> OTHER INFORMATION: Nanobody sequence

<400> SEQUENCE: 196

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Ser Phe
            20                  25                  30

Ala Met Gly Trp Phe Arg Gln Ala Pro Gly Lys Glu Arg Glu Phe Val
        35                  40                  45

Ala Ala Ile Ser Arg Ser Gly Tyr Gly Thr Ser Glu Ala Asp Ser Val
    50                  55                  60

Arg Asp Arg Phe Ile Ile Ser Arg Asp Asn Ala Lys Asn Thr Val Thr
65                  70                  75                  80

Leu His Leu Ser Arg Leu Lys Pro Glu Asp Thr Ala Val Tyr Tyr Cys
            85                  90                  95

Ala Ala Glu His Thr Leu Gly Arg Pro Ser Arg Ser Gln Ile Asn Tyr
        100                 105                 110

Leu Tyr Trp Gly Gln Gly Thr Leu Val Thr Val Ser Ser Gly Gly Gly
    115                 120                 125

Gly Ser Gly Gly Gly Gly Ser Gly Gly Gly Ser Gly Gly Gly Gly
        130                 135                 140

Ser Gly Gly Gly Gly Ser Gly Gly Gly Ser Gly Gly Gly Gly Ser
145                 150                 155                 160

Glu Val Gln Leu Val Glu Ser Gly Gly Gly Leu Val Gln Ala Gly Asp
                165                 170                 175

Ser Leu Arg Leu Ser Cys Ala Ala Ser Gly Leu Thr Phe Ser Ser Phe
            180                 185                 190

Ala Met Gly Trp Phe Arg Gln Ala Pro Gly Lys Glu Arg Glu Phe Val
        195                 200                 205

Ala Ala Ile Ser Arg Ser Gly Tyr Gly Thr Ser Glu Ala Asp Ser Val
    210                 215                 220

Arg Asp Arg Phe Ile Ile Ser Arg Asp Asn Ala Lys Asn Thr Val Thr
225                 230                 235                 240

Leu His Leu Ser Arg Leu Lys Pro Glu Asp Thr Ala Val Tyr Tyr Cys
            245                 250                 255
```

```
Ala Ala Glu His Thr Leu Gly Arg Pro Ser Arg Ser Gln Ile Asn Tyr
            260                 265                 270

Leu Tyr Trp Gly Gln Gly Thr Leu Val Thr Val Ser Gly Gly Gly
        275                 280                 285

Gly Ser Gly Gly Gly Gly Ser Gly Gly Gly Ser Gly Gly Gly Gly
290                 295                 300

Ser Gly Gly Gly Ser Gly Gly Gly Ser Gly Gly Gly Ser
305                 310                 315                 320

Glu Val Gln Leu Val Glu Ser Gly Gly Leu Val Gln Pro Gly Asn
                325                 330                 335

Ser Leu Arg Leu Ser Cys Ala Ala Ser Gly Phe Thr Phe Ser Ser Phe
            340                 345                 350

Gly Met Ser Trp Val Arg Gln Ala Pro Gly Lys Gly Leu Glu Trp Val
            355                 360                 365

Ser Ser Ile Ser Gly Ser Gly Ser Asp Thr Leu Tyr Ala Asp Ser Val
        370                 375                 380

Lys Gly Arg Phe Thr Ile Ser Arg Asp Asn Ala Lys Thr Thr Leu Tyr
385                 390                 395                 400

Leu Gln Met Asn Ser Leu Arg Pro Glu Asp Thr Ala Val Tyr Tyr Cys
                405                 410                 415

Thr Ile Gly Gly Ser Leu Ser Arg Ser Ser Gln Gly Thr Leu Val Thr
            420                 425                 430

Val Ser Ser
        435

<210> SEQ ID NO 197
<211> LENGTH: 393
<212> TYPE: PRT
<213> ORGANISM: Artificial Sequence
<220> FEATURE:
<223> OTHER INFORMATION: Nanobody sequence

<400> SEQUENCE: 197

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser Gly Gly Gly Ser Gly Gly Gly Gly Ser Gly
            115                 120                 125

Gly Gly Ser Gly Gly Gly Ser Gly Gly Gly Ser Gly Gly
130                 135                 140

Gly Gly Ser Gly Gly Gly Ser Glu Val Gln Leu Val Glu Ser Gly
145                 150                 155                 160

Gly Gly Leu Val Gln Ala Gly Gly Ser Leu Arg Leu Ser Cys Ala Ala
                165                 170                 175
```

Ser Arg Ser Ile Gly Arg Leu Asp Arg Met Gly Trp Tyr Arg His Arg
            180                 185                 190

Thr Gly Glu Pro Arg Glu Leu Val Ala Thr Ile Thr Gly Gly Ser Ser
        195                 200                 205

Ile Asn Tyr Gly Asp Phe Val Lys Gly Arg Phe Thr Ile Ser Ile Asp
210                 215                 220

Asn Ala Lys Asn Thr Val Tyr Leu Gln Met Asn Asn Leu Lys Pro Glu
225                 230                 235                 240

Asp Thr Ala Val Tyr Tyr Cys Asn Phe Asn Lys Tyr Val Thr Ser Arg
                245                 250                 255

Asp Thr Trp Gly Gln Gly Thr Leu Val Thr Val Ser Ser Gly Gly Gly
            260                 265                 270

Gly Ser Gly Gly Gly Ser Glu Val Gln Leu Val Glu Ser Gly Gly Gly
        275                 280                 285

Leu Val Gln Pro Gly Asn Ser Leu Arg Leu Ser Cys Ala Ala Ser Gly
        290                 295                 300

Phe Thr Phe Ser Ser Phe Gly Met Ser Trp Val Arg Gln Ala Pro Gly
305                 310                 315                 320

Lys Gly Leu Glu Trp Val Ser Ser Ile Ser Gly Ser Gly Ser Asp Thr
                325                 330                 335

Leu Tyr Ala Asp Ser Val Lys Gly Arg Phe Thr Ile Ser Arg Asp Asn
            340                 345                 350

Ala Lys Thr Thr Leu Tyr Leu Gln Met Asn Ser Leu Arg Pro Glu Asp
        355                 360                 365

Thr Ala Val Tyr Tyr Cys Thr Ile Gly Gly Ser Leu Ser Arg Ser Ser
        370                 375                 380

Gln Gly Thr Leu Val Thr Val Ser Ser
385                 390

<210> SEQ ID NO 198
<211> LENGTH: 419
<212> TYPE: PRT
<213> ORGANISM: Artificial Sequence
<220> FEATURE:
<223> OTHER INFORMATION: Nanobody sequence

<400> SEQUENCE: 198

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
        130                 135                 140

Gly Gly Ser Gly Gly Gly Ser Glu Val Gln Leu Val Glu Ser Gly
145                 150                 155                 160

Gly Gly Leu Val Gln Ala Gly Gly Ser Leu Arg Leu Ser Cys Ala Ala
            165                 170                 175

Ser Arg Ser Ile Gly Arg Leu Asp Arg Met Gly Trp Tyr Arg His Arg
            180                 185                 190

Thr Gly Glu Pro Arg Glu Leu Val Ala Thr Ile Thr Gly Gly Ser Ser
            195                 200                 205

Ile Asn Tyr Gly Asp Phe Val Lys Gly Arg Phe Thr Ile Ser Ile Asp
            210                 215                 220

Asn Ala Lys Asn Thr Val Tyr Leu Gln Met Asn Asn Leu Lys Pro Glu
225                 230                 235                 240

Asp Thr Ala Val Tyr Tyr Cys Asn Phe Asn Lys Tyr Val Thr Ser Arg
            245                 250                 255

Asp Thr Trp Gly Gln Gly Thr Leu Val Thr Val Ser Ser Gly Gly Gly
            260                 265                 270

Gly Ser Gly Gly Gly Gly Ser Gly Gly Gly Ser Gly Gly Gly Gly
            275                 280                 285

Ser Gly Gly Gly Gly Ser Gly Gly Gly Gly Ser Gly Gly Gly Gly Ser
            290                 295                 300

Glu Val Gln Leu Val Glu Ser Gly Gly Gly Leu Val Gln Pro Gly Asn
305                 310                 315                 320

Ser Leu Arg Leu Ser Cys Ala Ala Ser Gly Phe Thr Phe Ser Ser Phe
            325                 330                 335

Gly Met Ser Trp Val Arg Gln Ala Pro Gly Lys Gly Leu Glu Trp Val
            340                 345                 350

Ser Ser Ile Ser Gly Ser Gly Ser Asp Thr Leu Tyr Ala Asp Ser Val
            355                 360                 365

Lys Gly Arg Phe Thr Ile Ser Arg Asp Asn Ala Lys Thr Thr Leu Tyr
            370                 375                 380

Leu Gln Met Asn Ser Leu Arg Pro Glu Asp Thr Ala Val Tyr Tyr Cys
385                 390                 395                 400

Thr Ile Gly Gly Ser Leu Ser Arg Ser Ser Gln Gly Thr Leu Val Thr
            405                 410                 415

Val Ser Ser

<210> SEQ ID NO 199
<211> LENGTH: 128
<212> TYPE: PRT
<213> ORGANISM: Artificial Sequence
<220> FEATURE:
<223> OTHER INFORMATION: Nanobody sequence

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Ser Thr Tyr
            20                  25                  30

Ile Met Gly Trp Phe Arg Gln Ala Pro Gly Lys Glu Arg Glu Phe Val
            35                  40                  45

Ala Thr Ile Ser Arg Ser Gly Ile Thr Thr Arg Ser Ala Asp Ser Val
            50                  55                  60

Lys Gly Arg Phe Thr Ile Ser Arg Asp Asn Ser Lys Asn Thr Val Tyr
65                  70                  75                  80

-continued

```
Leu Gln Met Asn Ser Leu Arg Pro Glu Asp Thr Ala Val Tyr Tyr Cys
                85                  90                  95

Ala Ala Gly Pro Tyr Val Glu Thr Leu Gly Leu Tyr Gln Thr Leu
            100                 105                 110

Gly Pro Trp Asp Tyr Trp Gly Gln Gly Thr Leu Val Thr Val Ser Ser
            115                 120                 125
```

<210> SEQ ID NO 200
<211> LENGTH: 124
<212> TYPE: PRT
<213> ORGANISM: Artificial Sequence
<220> FEATURE:
<223> OTHER INFORMATION: Nanobody sequence

<400> SEQUENCE: 200

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Leu Gly Thr Leu Val Thr Val Ser Ser
        115                 120
```

<210> SEQ ID NO 201
<211> LENGTH: 124
<212> TYPE: PRT
<213> ORGANISM: Artificial Sequence
<220> FEATURE:
<223> OTHER INFORMATION: Nanobody sequence

<400> SEQUENCE: 201

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Leu Gly Thr Leu Val Thr Val Ser Ser
        115                 120
```

<210> SEQ ID NO 202

<211> LENGTH: 124
<212> TYPE: PRT
<213> ORGANISM: Artificial Sequence
<220> FEATURE:
<223> OTHER INFORMATION: Nanobody sequence

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Gln Gly Thr Leu Val Thr Val Ser Ser
        115                 120

<210> SEQ ID NO 203
<211> LENGTH: 124
<212> TYPE: PRT
<213> ORGANISM: Artificial Sequence
<220> FEATURE:
<223> OTHER INFORMATION: Nanobody sequence

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Gln Gly Thr Leu Val Thr Val Ser Ser
        115                 120

<210> SEQ ID NO 204
<211> LENGTH: 124
<212> TYPE: PRT
<213> ORGANISM: Artificial Sequence
<220> FEATURE:
<223> OTHER INFORMATION: Nanobody sequence

<400> SEQUENCE: 204

Asp Val Gln Leu Val Glu Ser Gly Gly Gly Leu Val Gln Pro Gly Gly
1               5                   10                  15

```
Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
                100                 105                 110

Tyr Trp Gly Leu Gly Thr Leu Val Thr Val Ser Ser
        115                 120
```

<210> SEQ ID NO 205
<211> LENGTH: 124
<212> TYPE: PRT
<213> ORGANISM: Artificial Sequence
<220> FEATURE:
<223> OTHER INFORMATION: Nanobody sequence

<400> SEQUENCE: 205

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
                100                 105                 110

Tyr Trp Gly Gln Gly Thr Leu Val Thr Val Ser Ser
        115                 120
```

<210> SEQ ID NO 206
<211> LENGTH: 117
<212> TYPE: PRT
<213> ORGANISM: Artificial Sequence
<220> FEATURE:
<223> OTHER INFORMATION: Nanobody sequence

<400> SEQUENCE: 206

```
Asp Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ala Lys Asn Thr Val Tyr Leu
65                  70                  75                  80
```

Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Gln
            100                 105                 110

Val Thr Val Ser Ser
        115

<210> SEQ ID NO 207
<211> LENGTH: 117
<212> TYPE: PRT
<213> ORGANISM: Artificial Sequence
<220> FEATURE:
<223> OTHER INFORMATION: Nanobody sequence

<400> SEQUENCE: 207

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 208
<211> LENGTH: 117
<212> TYPE: PRT
<213> ORGANISM: Artificial Sequence
<220> FEATURE:
<223> OTHER INFORMATION: Nanobody sequence

<400> SEQUENCE: 208

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Ala Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

```
<210> SEQ ID NO 209
<211> LENGTH: 117
<212> TYPE: PRT
<213> ORGANISM: Artificial Sequence
<220> FEATURE:
<223> OTHER INFORMATION: Nanobody sequence

<400> SEQUENCE: 209
```

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

```
<210> SEQ ID NO 210
<211> LENGTH: 117
<212> TYPE: PRT
<213> ORGANISM: Artificial Sequence
<220> FEATURE:
<223> OTHER INFORMATION: Nanobody sequence

<400> SEQUENCE: 210
```

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Lys Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

```
<210> SEQ ID NO 211
<211> LENGTH: 117
<212> TYPE: PRT
<213> ORGANISM: Artificial Sequence
<220> FEATURE:
<223> OTHER INFORMATION: Nanobody sequence

<400> SEQUENCE: 211
```

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Ala Pro Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
            115

<210> SEQ ID NO 212
<211> LENGTH: 117
<212> TYPE: PRT
<213> ORGANISM: Artificial Sequence
<220> FEATURE:
<223> OTHER INFORMATION: Nanobody sequence

<400> SEQUENCE: 212

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Ala Thr Gly Lys Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
            115

<210> SEQ ID NO 213
<211> LENGTH: 117
<212> TYPE: PRT
<213> ORGANISM: Artificial Sequence
<220> FEATURE:
<223> OTHER INFORMATION: Nanobody sequence

<400> SEQUENCE: 213

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu

```
                65                  70                  75                  80
Gln Met Asn Ser Leu Arg Pro Glu Asp Thr Ala Val Tyr Tyr Cys Asn
                    85                  90                  95

Phe Asn Lys Tyr Val Thr Ser Arg Asp Thr Trp Gly Gln Gly Thr Leu
                100                 105                 110

Val Thr Val Ser Ser
            115

<210> SEQ ID NO 214
<211> LENGTH: 117
<212> TYPE: PRT
<213> ORGANISM: Artificial Sequence
<220> FEATURE:
<223> OTHER INFORMATION: Nanobody sequence

<400> SEQUENCE: 214

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
                20                  25                  30

Arg Met Gly Trp Tyr Arg His Ala Pro Gly Lys Pro Arg Glu Leu Val
                35                  40                  45

Ala Thr Ile Thr Gly Gly Ser Ser Ile Asn Tyr Gly Asp Phe Val Lys
            50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                    85                  90                  95

Phe Asn Lys Tyr Val Thr Ser Arg Asp Thr Trp Gly Gln Gly Thr Leu
                100                 105                 110

Val Thr Val Ser Ser
            115

<210> SEQ ID NO 215
<211> LENGTH: 117
<212> TYPE: PRT
<213> ORGANISM: Artificial Sequence
<220> FEATURE:
<223> OTHER INFORMATION: Nanobody sequence

<400> SEQUENCE: 215

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
                20                  25                  30

Arg Met Gly Trp Tyr Arg His Arg Thr Gly Glu Pro Arg Glu Leu Val
                35                  40                  45

Ala Thr Ile Thr Gly Gly Ser Ser Ile Asn Tyr Ala Asp Phe Val Lys
            50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                    85                  90                  95

Phe Asn Lys Tyr Val Thr Ser Arg Asp Thr Trp Gly Gln Gly Thr Leu
                100                 105                 110

Val Thr Val Ser Ser
            115
```

<210> SEQ ID NO 216
<211> LENGTH: 117
<212> TYPE: PRT
<213> ORGANISM: Artificial Sequence
<220> FEATURE:
<223> OTHER INFORMATION: Nanobody sequence

<400> SEQUENCE: 216

```
Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115
```

<210> SEQ ID NO 217
<211> LENGTH: 117
<212> TYPE: PRT
<213> ORGANISM: Artificial Sequence
<220> FEATURE:
<223> OTHER INFORMATION: Nanobody sequence

<400> SEQUENCE: 217

```
Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115
```

<210> SEQ ID NO 218
<211> LENGTH: 117
<212> TYPE: PRT
<213> ORGANISM: Artificial Sequence
<220> FEATURE:
<223> OTHER INFORMATION: Nanobody sequence

<400> SEQUENCE: 218

```
Asp Val Gln Leu Val Glu Ser Gly Gly Gly Leu Val Gln Pro Gly Gly
```

```
1               5                   10                  15
Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser
            115

<210> SEQ ID NO 219
<211> LENGTH: 117
<212> TYPE: PRT
<213> ORGANISM: Artificial Sequence
<220> FEATURE:
<223> OTHER INFORMATION: Nanobody sequence

<400> SEQUENCE: 219

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser
            115

<210> SEQ ID NO 220
<211> LENGTH: 117
<212> TYPE: PRT
<213> ORGANISM: Artificial Sequence
<220> FEATURE:
<223> OTHER INFORMATION: Nanobody sequence

<400> SEQUENCE: 220

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60
```

```
Gly Arg Phe Thr Ile Ser Arg Asp Asn Ser Lys Asn Thr Val Tyr Leu
65                  70                  75                  80

Gln Met Asn Asn Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 221
<211> LENGTH: 117
<212> TYPE: PRT
<213> ORGANISM: Artificial Sequence
<220> FEATURE:
<223> OTHER INFORMATION: Nanobody sequence

<400> SEQUENCE: 221

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val
        35                  40                  45

Ala Thr Ile Thr Gly Gly Ser Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 222
<211> LENGTH: 117
<212> TYPE: PRT
<213> ORGANISM: Artificial Sequence
<220> FEATURE:
<223> OTHER INFORMATION: Nanobody sequence

<400> SEQUENCE: 222

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val
        35                  40                  45

Ala Thr Ile Thr Gly Gly Ser Ser Ile Asn Tyr Ala Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115
```

<210> SEQ ID NO 223
<211> LENGTH: 117
<212> TYPE: PRT
<213> ORGANISM: Artificial Sequence
<220> FEATURE:
<223> OTHER INFORMATION: Nanobody sequence

<400> SEQUENCE: 223

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val
        35                  40                  45

Ala Thr Ile Thr Gly Gly Ser Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Asn Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 224
<211> LENGTH: 117
<212> TYPE: PRT
<213> ORGANISM: Artificial Sequence
<220> FEATURE:
<223> OTHER INFORMATION: Nanobody sequence

<400> SEQUENCE: 224

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val
        35                  40                  45

Ala Thr Ile Thr Gly Gly Ser Ser Ile Asn Tyr Ala Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Asn Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 225
<211> LENGTH: 117
<212> TYPE: PRT
<213> ORGANISM: Artificial Sequence
<220> FEATURE:
<223> OTHER INFORMATION: Nanobody sequence

<400> SEQUENCE: 225

-continued

Glu Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Glu Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser
            115

<210> SEQ ID NO 226
<211> LENGTH: 117
<212> TYPE: PRT
<213> ORGANISM: Artificial Sequence
<220> FEATURE:
<223> OTHER INFORMATION: Nanobody sequence

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser
            115

<210> SEQ ID NO 227
<211> LENGTH: 441
<212> TYPE: PRT
<213> ORGANISM: Artificial Sequence
<220> FEATURE:
<223> OTHER INFORMATION: Nanobody sequence

<400> SEQUENCE: 227

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Ser Thr Tyr
            20                  25                  30

Ile Met Gly Trp Phe Arg Gln Ala Pro Gly Lys Glu Arg Glu Phe Val
        35                  40                  45

Ala Thr Ile Ser Arg Ser Gly Ile Thr Thr Arg Ser Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Ala Gly Pro Tyr Val Glu Gln Thr Leu Gly Leu Tyr Gln Thr Leu
            100                 105                 110

Gly Pro Trp Asp Tyr Trp Gly Gln Gly Thr Leu Val Thr Val Ser Ser
            115                 120                 125

Gly Gly Gly Gly Ser Gly Gly Gly Ser Gly Gly Gly Ser Gly
            130                 135                 140

Gly Gly Gly Ser Gly Gly Gly Ser Gly Gly Gly Ser Gly Gly
145                 150                 155                 160

Gly Gly Ser Glu Val Gln Leu Val Glu Ser Gly Gly Leu Val Gln
            165                 170                 175

Pro Gly Gly Ser Leu Arg Leu Ser Cys Ala Ala Ser Gly Arg Ser Phe
            180                 185                 190

Ser Thr Tyr Ile Met Gly Trp Phe Arg Gln Ala Pro Gly Lys Glu Arg
            195                 200                 205

Glu Phe Val Ala Thr Ile Ser Arg Ser Gly Ile Thr Thr Arg Ser Ala
210                 215                 220

Asp Ser Val Lys Gly Arg Phe Thr Ile Ser Arg Asp Asn Ser Lys Asn
225                 230                 235                 240

Thr Val Tyr Leu Gln Met Asn Ser Leu Arg Pro Glu Asp Thr Ala Val
            245                 250                 255

Tyr Tyr Cys Ala Ala Gly Pro Tyr Val Glu Gln Thr Leu Gly Leu Tyr
            260                 265                 270

Gln Thr Leu Gly Pro Trp Asp Tyr Trp Gly Gln Gly Thr Leu Val Thr
            275                 280                 285

Val Ser Ser Gly Gly Gly Gly Ser Gly Gly Gly Gly Ser Gly Gly Gly
290                 295                 300

Gly Ser Gly Gly Gly Gly Ser Gly Gly Gly Gly Ser Gly Gly Gly Gly
305                 310                 315                 320

Ser Gly Gly Gly Gly Ser Glu Val Gln Leu Val Glu Ser Gly Gly Gly
            325                 330                 335

Leu Val Gln Pro Gly Asn Ser Leu Arg Leu Ser Cys Ala Ala Ser Gly
            340                 345                 350

Phe Thr Phe Ser Ser Phe Gly Met Ser Trp Val Arg Gln Ala Pro Gly
            355                 360                 365

Lys Gly Leu Glu Trp Val Ser Ser Ile Ser Gly Ser Gly Ser Asp Thr
            370                 375                 380

Leu Tyr Ala Asp Ser Val Lys Gly Arg Phe Thr Ile Ser Arg Asp Asn
385                 390                 395                 400

Ala Lys Thr Thr Leu Tyr Leu Gln Met Asn Ser Leu Arg Pro Glu Asp
            405                 410                 415

Thr Ala Val Tyr Tyr Cys Thr Ile Gly Gly Ser Leu Ser Arg Ser Ser
            420                 425                 430

Gln Gly Thr Leu Val Thr Val Ser Ser
            435                 440

<210> SEQ ID NO 228
<211> LENGTH: 441
<212> TYPE: PRT
<213> ORGANISM: Artificial Sequence
<220> FEATURE:

<223> OTHER INFORMATION: Nanobody sequence

<400> SEQUENCE: 228

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Ser Thr Tyr
            20                  25                  30

Ile Met Gly Trp Phe Arg Gln Ala Pro Gly Lys Glu Arg Glu Phe Val
        35                  40                  45

Ala Thr Ile Ser Arg Ser Gly Ile Thr Thr Arg Ser Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gly Pro Tyr Val Glu Gln Thr Leu Gly Leu Tyr Gln Thr Leu
            100                 105                 110

Gly Pro Trp Asp Tyr Trp Gly Gln Gly Thr Leu Val Thr Val Ser Ser
        115                 120                 125

Gly Gly Gly Gly Ser Gly Gly Gly Ser Gly Gly Gly Ser
130                 135                 140

Gly Gly Gly Ser Gly Gly Gly Ser Gly Gly Gly Ser Gly Gly Gly Gly
145                 150                 155                 160

Gly Gly Ser Glu Val Gln Leu Val Glu Ser Gly Gly Gly Leu Val Gln
        165                 170                 175

Pro Gly Asn Ser Leu Arg Leu Ser Cys Ala Ala Ser Gly Phe Thr Phe
            180                 185                 190

Ser Ser Phe Gly Met Ser Trp Val Arg Gln Ala Pro Gly Lys Gly Leu
        195                 200                 205

Glu Trp Val Ser Ser Ile Ser Gly Ser Gly Ser Asp Thr Leu Tyr Ala
    210                 215                 220

Asp Ser Val Lys Gly Arg Phe Thr Ile Ser Arg Asp Asn Ala Lys Thr
225                 230                 235                 240

Thr Leu Tyr Leu Gln Met Asn Ser Leu Arg Pro Glu Asp Thr Ala Val
                245                 250                 255

Tyr Tyr Cys Thr Ile Gly Gly Ser Leu Ser Arg Ser Ser Gln Gly Thr
            260                 265                 270

Leu Val Thr Val Ser Ser Gly Gly Gly Gly Ser Gly Gly Gly Gly Ser
        275                 280                 285

Gly Gly Gly Gly Ser Gly Gly Gly Gly Ser Gly Gly Gly Gly Ser Gly
            290                 295                 300

Gly Gly Ser Gly Gly Gly Ser Glu Val Gln Leu Val Glu Ser
305                 310                 315                 320

Gly Gly Gly Leu Val Gln Pro Gly Gly Ser Leu Arg Leu Ser Cys Ala
                325                 330                 335

Ala Ser Gly Arg Ser Phe Ser Thr Tyr Ile Met Gly Trp Phe Arg Gln
            340                 345                 350

Ala Pro Gly Lys Glu Arg Glu Phe Val Ala Thr Ile Ser Arg Ser Gly
        355                 360                 365

Ile Thr Thr Arg Ser Ala Asp Ser Val Lys Gly Arg Phe Thr Ile Ser
    370                 375                 380

Arg Asp Asn Ser Lys Asn Thr Val Tyr Leu Gln Met Asn Ser Leu Arg
385                 390                 395                 400

```
Pro Glu Asp Thr Ala Val Tyr Tyr Cys Ala Ala Gly Pro Tyr Val Glu
                405                 410                 415

Gln Thr Leu Gly Leu Tyr Gln Thr Leu Gly Pro Trp Asp Tyr Trp Gly
            420                 425                 430

Gln Gly Thr Leu Val Thr Val Ser Ser
        435                 440

<210> SEQ ID NO 229
<211> LENGTH: 433
<212> TYPE: PRT
<213> ORGANISM: Artificial Sequence
<220> FEATURE:
<223> OTHER INFORMATION: Nanobody sequence

<400> SEQUENCE: 229

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Ala Ala Ser Gly Arg Thr Phe Ser Ser Ile Tyr
            180                 185                 190

Ala Lys Gly Trp Phe Arg Gln Ala Pro Gly Lys Glu Arg Glu Phe Val
        195                 200                 205

Ala Ala Ile Ser Arg Ser Gly Arg Ser Thr Ser Tyr Ala Asp Ser Val
    210                 215                 220

Lys Gly Arg Phe Thr Ile Ser Arg Asp Asn Ser Lys Asn Thr Val Tyr
225                 230                 235                 240

Leu Gln Met Asn Ser Leu Arg Pro Glu Asp Thr Ala Val Tyr Tyr Cys
                245                 250                 255

Ala Ala Val Gly Gly Ala Thr Thr Val Thr Ala Ser Glu Trp Asp Tyr
            260                 265                 270

Trp Gly Gln Gly Thr Leu Val Thr Val Ser Ser Gly Gly Gly Gly Ser
        275                 280                 285

Gly Gly Gly Gly Ser Gly Gly Gly Gly Ser Gly Gly Gly Gly Ser Gly
    290                 295                 300

Gly Gly Gly Ser Gly Gly Gly Gly Ser Gly Gly Gly Gly Ser Glu Val
305                 310                 315                 320
```

```
Gln Leu Val Glu Ser Gly Gly Gly Leu Val Gln Pro Gly Asn Ser Leu
                325                 330                 335

Arg Leu Ser Cys Ala Ala Ser Gly Phe Thr Phe Ser Ser Phe Gly Met
            340                 345                 350

Ser Trp Val Arg Gln Ala Pro Gly Lys Gly Leu Glu Trp Val Ser Ser
        355                 360                 365

Ile Ser Gly Ser Gly Ser Asp Thr Leu Tyr Ala Asp Ser Val Lys Gly
    370                 375                 380

Arg Phe Thr Ile Ser Arg Asp Asn Ala Lys Thr Thr Leu Tyr Leu Gln
385                 390                 395                 400

Met Asn Ser Leu Arg Pro Glu Asp Thr Ala Val Tyr Tyr Cys Thr Ile
                405                 410                 415

Gly Gly Ser Leu Ser Arg Ser Ser Gln Gly Thr Leu Val Thr Val Ser
            420                 425                 430

Ser
```

<210> SEQ ID NO 230
<211> LENGTH: 433
<212> TYPE: PRT
<213> ORGANISM: Artificial Sequence
<220> FEATURE:
<223> OTHER INFORMATION: Nanobody sequence

<400> SEQUENCE: 230

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
                100                 105                 110

Tyr Trp Gly Gln Gly Thr Leu Val Thr Val Ser Ser Gly Gly Gly Gly
            115                 120                 125

Ser Gly Gly Gly Gly Ser Gly Gly Gly Gly Ser Gly Gly Gly Gly Ser
    130                 135                 140

Gly Gly Gly Gly Ser Gly Gly Gly Gly Ser Gly Gly Gly Gly Ser Glu
145                 150                 155                 160

Val Gln Leu Val Glu Ser Gly Gly Leu Val Gln Pro Gly Asn Ser
                165                 170                 175

Leu Arg Leu Ser Cys Ala Ala Ser Gly Phe Thr Phe Ser Ser Phe Gly
            180                 185                 190

Met Ser Trp Val Arg Gln Ala Pro Gly Lys Gly Leu Glu Trp Val Ser
        195                 200                 205

Ser Ile Ser Gly Ser Gly Ser Asp Thr Leu Tyr Ala Asp Ser Val Lys
    210                 215                 220

Gly Arg Phe Thr Ile Ser Arg Asp Asn Ala Lys Thr Thr Leu Tyr Leu
225                 230                 235                 240

Gln Met Asn Ser Leu Arg Pro Glu Asp Thr Ala Val Tyr Tyr Cys Thr
```

```
                   245                 250                 255
Ile Gly Gly Ser Leu Ser Arg Ser Ser Gln Gly Thr Leu Val Thr Val
            260                 265                 270

Ser Ser Gly Gly Gly Ser Gly Gly Gly Ser Gly Gly Gly Gly
        275                 280                 285

Ser Gly Gly Gly Ser Gly Gly Gly Ser Gly Gly Gly Ser
        290                 295                 300

Gly Gly Gly Gly Ser Glu Val Gln Leu Val Glu Ser Gly Gly Gly Leu
305                 310                 315                 320

Val Gln Pro Gly Gly Ser Leu Arg Leu Ser Cys Ala Ala Ser Gly Arg
                325                 330                 335

Thr Phe Ser Ser Ile Tyr Ala Lys Gly Trp Phe Arg Gln Ala Pro Gly
            340                 345                 350

Lys Glu Arg Glu Phe Val Ala Ala Ile Ser Arg Ser Gly Arg Ser Thr
                355                 360                 365

Ser Tyr Ala Asp Ser Val Lys Gly Arg Phe Thr Ile Ser Arg Asp Asn
        370                 375                 380

Ser Lys Asn Thr Val Tyr Leu Gln Met Asn Ser Leu Arg Pro Glu Asp
385                 390                 395                 400

Thr Ala Val Tyr Tyr Cys Ala Ala Val Gly Ala Thr Thr Val Thr
                405                 410                 415

Ala Ser Glu Trp Asp Tyr Trp Gly Gln Gly Thr Leu Val Thr Val Ser
                420                 425                 430

Ser

<210> SEQ ID NO 231
<211> LENGTH: 367
<212> TYPE: PRT
<213> ORGANISM: Artificial Sequence
<220> FEATURE:
<223> OTHER INFORMATION: Nanobody sequence

<400> SEQUENCE: 231

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Glu Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser Gly Gly Gly Gly Ser Gly Gly Gly Ser Glu Val
        115                 120                 125

Gln Leu Val Glu Ser Gly Gly Gly Leu Val Gln Pro Gly Asn Ser Leu
    130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
                165                 170                 175
```

```
Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
            195                 200                 205

Met Asn Ser Leu Arg Pro Glu Asp Thr Ala Val Tyr Tyr Cys Thr Ile
210                 215                 220

Gly Gly Ser Leu Ser Arg Ser Ser Gln Gly Thr Leu Val Thr Val Ser
225                 230                 235                 240

Ser Gly Gly Gly Gly Ser Gly Gly Ser Glu Val Gln Leu Val Glu
            245                 250                 255

Ser Gly Gly Gly Leu Val Gln Pro Gly Gly Ser Leu Arg Leu Ser Cys
            260                 265                 270

Ala Ala Ser Arg Ser Ile Gly Arg Leu Asp Arg Met Gly Trp Tyr Arg
            275                 280                 285

His Arg Pro Gly Glu Pro Arg Glu Leu Val Ala Thr Ile Thr Gly Gly
            290                 295                 300

Ser Ser Ile Asn Tyr Gly Asp Ser Val Lys Gly Arg Phe Thr Ile Ser
305                 310                 315                 320

Ile Asp Asn Ser Lys Asn Thr Val Tyr Leu Gln Met Asn Ser Leu Arg
                325                 330                 335

Pro Glu Asp Thr Ala Val Tyr Tyr Cys Asn Phe Asn Lys Tyr Val Thr
            340                 345                 350

Ser Arg Asp Thr Trp Gly Gln Gly Thr Leu Val Thr Val Ser Ser
            355                 360                 365

<210> SEQ ID NO 232
<211> LENGTH: 367
<212> TYPE: PRT
<213> ORGANISM: Artificial Sequence
<220> FEATURE:
<223> OTHER INFORMATION: Nanobody sequence

<400> SEQUENCE: 232

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser Gly Gly Gly Ser Gly Gly Ser Glu Val
        115                 120                 125

Gln Leu Val Glu Ser Gly Gly Gly Leu Val Gln Pro Gly Asn Ser Leu
    130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
                165                 170                 175
```

```
Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
        195                 200                 205

Met Asn Ser Leu Arg Pro Glu Asp Thr Ala Val Tyr Tyr Cys Thr Ile
    210                 215                 220

Gly Gly Ser Leu Ser Arg Ser Ser Gln Gly Thr Leu Val Thr Val Ser
225                 230                 235                 240

Ser Gly Gly Gly Gly Ser Gly Gly Ser Glu Val Gln Leu Val Glu
            245                 250                 255

Ser Gly Gly Gly Leu Val Gln Pro Gly Gly Ser Leu Arg Leu Ser Cys
            260                 265                 270

Ala Ala Ser Arg Ser Ile Gly Arg Leu Asp Arg Met Gly Trp Tyr Arg
            275                 280                 285

His Arg Pro Gly Lys Pro Arg Glu Leu Val Ala Thr Ile Thr Gly Gly
            290                 295                 300

Ser Ser Ile Asn Tyr Gly Asp Ser Val Lys Gly Arg Phe Thr Ile Ser
305                 310                 315                 320

Ile Asp Asn Ser Lys Asn Thr Val Tyr Leu Gln Met Asn Ser Leu Arg
                325                 330                 335

Pro Glu Asp Thr Ala Val Tyr Tyr Cys Asn Phe Asn Lys Tyr Val Thr
            340                 345                 350

Ser Arg Asp Thr Trp Gly Gln Gly Thr Leu Val Thr Val Ser Ser
            355                 360                 365

<210> SEQ ID NO 233
<211> LENGTH: 441
<212> TYPE: PRT
<213> ORGANISM: Artificial Sequence
<220> FEATURE:
<223> OTHER INFORMATION: Nanobody sequence

<400> SEQUENCE: 233

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Ser Thr Tyr
            20                  25                  30

Ile Met Gly Trp Phe Arg Gln Ala Pro Gly Lys Glu Arg Glu Phe Val
        35                  40                  45

Ala Thr Ile Ser Arg Ser Gly Ile Thr Thr Arg Ser Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gly Pro Tyr Val Glu Gln Thr Leu Gly Leu Tyr Gln Thr Leu
            100                 105                 110

Gly Pro Trp Asp Tyr Trp Gly Gln Gly Thr Leu Val Thr Val Ser Ser
            115                 120                 125

Gly Gly Gly Gly Ser Gly Gly Gly Ser Gly Gly Gly Ser
            130                 135                 140

Gly Gly Gly Ser Gly Gly Gly Ser Gly Gly Gly Ser Gly Gly
145                 150                 155                 160

Gly Gly Ser Glu Val Gln Leu Val Glu Ser Gly Gly Gly Leu Val Gln
                165                 170                 175
```

```
Pro Gly Asn Ser Leu Arg Leu Ser Cys Ala Ala Ser Gly Phe Thr Phe
            180                 185                 190

Ser Ser Phe Gly Met Ser Trp Val Arg Gln Ala Pro Gly Lys Gly Leu
        195                 200                 205

Glu Trp Val Ser Ser Ile Ser Gly Ser Gly Ser Asp Thr Leu Tyr Ala
    210                 215                 220

Asp Ser Val Lys Gly Arg Phe Thr Ile Ser Arg Asp Asn Ala Lys Thr
225                 230                 235                 240

Thr Leu Tyr Leu Gln Met Asn Ser Leu Arg Pro Glu Asp Thr Ala Val
            245                 250                 255

Tyr Tyr Cys Thr Ile Gly Gly Ser Leu Ser Arg Ser Ser Gln Gly Thr
        260                 265                 270

Leu Val Thr Val Ser Ser Gly Gly Gly Ser Gly Gly Gly Gly Ser
            275                 280                 285

Gly Gly Gly Gly Ser Gly Gly Gly Ser Gly Gly Gly Ser Gly
        290                 295                 300

Gly Gly Ser Gly Gly Gly Ser Glu Val Gln Leu Val Glu Ser
305                 310                 315                 320

Gly Gly Gly Leu Val Gln Pro Gly Gly Ser Leu Arg Leu Ser Cys Ala
            325                 330                 335

Ala Ser Gly Arg Ser Phe Ser Thr Tyr Ile Met Gly Trp Phe Arg Gln
        340                 345                 350

Ala Pro Gly Lys Glu Arg Glu Phe Val Ala Thr Ile Ser Arg Ser Gly
        355                 360                 365

Ile Thr Thr Arg Ser Ala Asp Ser Val Lys Gly Arg Phe Thr Ile Ser
    370                 375                 380

Arg Asp Asn Ser Lys Asn Thr Val Tyr Leu Gln Met Asn Ser Leu Arg
385                 390                 395                 400

Pro Glu Asp Thr Ala Val Tyr Tyr Cys Ala Ala Gly Pro Tyr Val Glu
            405                 410                 415

Gln Thr Leu Gly Leu Tyr Gln Thr Leu Gly Pro Trp Asp Tyr Trp Gly
            420                 425                 430

Gln Gly Thr Leu Val Thr Val Ser Ser
            435                 440

<210> SEQ ID NO 234
<211> LENGTH: 389
<212> TYPE: PRT
<213> ORGANISM: Artificial Sequence
<220> FEATURE:
<223> OTHER INFORMATION: Nanobody sequence

<400> SEQUENCE: 234

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Ser Thr Tyr
            20                  25                  30

Ile Met Gly Trp Phe Arg Gln Ala Pro Gly Lys Glu Arg Glu Phe Val
        35                  40                  45

Ala Thr Ile Ser Arg Ser Gly Ile Thr Thr Arg Ser Ala Asp Ser Val
    50                  55                  60
```

```
Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                 85                  90                  95

Ala Ala Gly Pro Tyr Val Glu Gln Thr Leu Gly Leu Tyr Gln Thr Leu
            100                 105                 110

Gly Pro Trp Asp Tyr Trp Gly Gln Gly Thr Leu Val Thr Val Ser Ser
            115                 120                 125

Gly Gly Gly Gly Ser Gly Gly Ser Glu Val Gln Leu Val Glu Ser
130                 135                 140

Gly Gly Gly Leu Val Gln Pro Gly Asn Ser Leu Arg Leu Ser Cys Ala
145                 150                 155                 160

Ala Ser Gly Phe Thr Phe Ser Ser Phe Gly Met Ser Trp Val Arg Gln
            165                 170                 175

Ala Pro Gly Lys Gly Leu Glu Trp Val Ser Ser Ile Ser Gly Ser Gly
            180                 185                 190

Ser Asp Thr Leu Tyr Ala Asp Ser Val Lys Gly Arg Phe Thr Ile Ser
            195                 200                 205

Arg Asp Asn Ala Lys Thr Thr Leu Tyr Leu Gln Met Asn Ser Leu Arg
210                 215                 220

Pro Glu Asp Thr Ala Val Tyr Tyr Cys Thr Ile Gly Gly Ser Leu Ser
225                 230                 235                 240

Arg Ser Ser Gln Gly Thr Leu Val Thr Val Ser Ser Gly Gly Gly Gly
            245                 250                 255

Ser Gly Gly Gly Ser Glu Val Gln Leu Val Glu Ser Gly Gly Gly Leu
            260                 265                 270

Val Gln Pro Gly Gly Ser Leu Arg Leu Ser Cys Ala Ala Ser Gly Arg
            275                 280                 285

Ser Phe Ser Thr Tyr Ile Met Gly Trp Phe Arg Gln Ala Pro Gly Lys
            290                 295                 300

Glu Arg Glu Phe Val Ala Thr Ile Ser Arg Ser Gly Ile Thr Thr Arg
305                 310                 315                 320

Ser Ala Asp Ser Val Lys Gly Arg Phe Thr Ile Ser Arg Asp Asn Ser
            325                 330                 335

Lys Asn Thr Val Tyr Leu Gln Met Asn Ser Leu Arg Pro Glu Asp Thr
            340                 345                 350

Ala Val Tyr Tyr Cys Ala Ala Gly Pro Tyr Val Glu Gln Thr Leu Gly
            355                 360                 365

Leu Tyr Gln Thr Leu Gly Pro Trp Asp Tyr Trp Gly Gln Gly Thr Leu
            370                 375                 380

Val Thr Val Ser Ser
385
```

SINGLE VARIABLE DOMAIN ANTIBODIES AGAINST OX40L, CONSTRUCTS AND THERAPEUTIC USE

RELATED APPLICATIONS

This application is a continuation of U.S. patent application Ser. No. 14/587,042, which is a continuation of U.S. patent application Ser. No. 13/515,876, filed Sep. 25, 2012 and now issued as U.S. Pat. No. 8,962,807, which is a national stage filing under 35 U.S.C. § 371 of international application PCT/EP2010/069606, filed Dec. 14, 2010, which claims the benefit under 35 U.S.C. § 119(e) of U.S. provisional application Ser. No. 61/286,163, filed Dec. 14, 2009, the disclosures of which are incorporated by reference herein in their entireties.

FIELD OF THE INVENTION

The present invention relates to amino acid sequences that are directed against (as defined herein) OX40L, as well as to compounds or constructs, and in particular proteins and polypeptides, that comprise or essentially consist of one or more such amino acid sequences (also referred to herein as "amino acid sequences of the invention", "compounds of the invention", and "polypeptides of the invention", respectively).

The invention also relates to nucleic acids encoding such amino acid sequences and polypeptides (also referred to herein as "nucleic acids of the invention" or "nucleotide sequences of the invention"); to methods for preparing such amino acid sequences and polypeptides; to host cells expressing or capable of expressing such amino acid sequences or polypeptides; to compositions, and in particular to pharmaceutical compositions, that comprise such amino acid sequences, polypeptides, nucleic acids and/or host cells; and to uses of such amino acid sequences or polypeptides, nucleic acids, host cells and/or compositions, in particular for prophylactic, therapeutic or diagnostic purposes, such as the prophylactic, therapeutic or diagnostic purposes mentioned herein.

BACKGROUND OF THE INVENTION

Allergic diseases have reached epidemic proportions worldwide and are generally accepted to be increasing. Allergy symptoms are treated efficiently with cheap small molecule drugs in most patients, but none are curative. However, there is a clear unmet medical need for patients suffering persistent asthma. Current standard treatment for inflammatory diseases include immunosuppressing or immunomodulating medications such as (but not limited to) corticosteroids, non-steroidal anti inflammatory drugs, TNF-alpha antagonists, cytokine (receptor) agonists or antagonists. Current standard treatment for allergic asthma include inhaled or systemically administered corticosteroids in combination with inhaled (long or short acting) Beta-2 agonists, possibly combined with medications such as (but not limited to) Leukotriene receptor antagonists, theophylline, cromolyn, nedocromyl.

The introduction of monoclonal antibodies and soluble cytokine receptors is revolutionizing approaches to the treatment of asthma and allergy. The successful introduction of omalizumab (anti IgE) for severe allergic asthma has stimulated great interest in this approach, but even with this humanised monoclonal antibody, cost effectiveness analyses are restricting its use even though it has passed scrutiny by such agents as the National Institute of Health & Clinical Excellence in the UK. Also, substantial portions of the potential patient population in asthma have IgE levels higher than can successfully be neutralized with the current molecule. A more potent inhibitor is required for these, and attempts have been made to produce such a molecule.

Understanding the underlying mechanisms of allergic disease has stimulated the further development of a series of biologics targeted towards critical cells and molecules. Because of the sentinel roles of Th2 cells and their products, Th2 cytokines, in orchestrating allergic inflammation, they and their receptors are key therapeutic targets. One of these is the TNF family member "OX40L" (Review: Michael J. Gough et al., Therapeutic Targets of the TNF superfamily, edited by Iqbal S. Grewal, 2007). OX40L and antibodies against OX40L which are able to disrupt binding of OX40L to its receptor OX40 (and thus inhibit the relevant signaling cascade) are mentioned in e.g. WO95/12673, WO95/21915, WO99/15200, WO2006/029879, WO2005/094879 and WO2007/133290.

SUMMARY OF THE INVENTION

Single variable domains, such as Nanobodies and dAbs and antigen binding fragments derived therefrom are widely used to specifically target their respective antigens in research and therapeutic applications. However, Nanobodies and dAbs lack the Fc part and will not induce effector function mediated depletion of OX40L-expressing cells and thus potential toxicity associated with effector function mediated depletion is not of relevance. However, in order to compensate for the efficacy increase by the effector function of the full length monoclonal antibody (lacking in the single variable domains such as Nanobodies), there is then a need for an ultrapotent OX40L binding Nanobody or construct thereof. Furthermore, the patient group with severe persistent allergic asthma who remain symptomatic despite optimized standard treatment, require significant use of health services and are at risk of severe exacerbations including morbidity. Thus, new therapies to address these clear and unmet needs need to be developed.

The invention has overcome the disadvantages of the prior art and addresses the unmet medical needs.

The polypeptides and compositions of the present invention can generally be used to modulate, and in particular inhibit and/or prevent, binding of OX40L to OX40, and thus to modulate, and in particular inhibit or prevent, the signalling that is mediated by OX40L and/or OX40, to modulate the biological pathways in which OX40L and/or OX40 are involved, and/or to modulate the biological mechanisms, responses and effects associated with such signalling or these pathways.

As such, the polypeptides and compositions of the present invention can be used for the prevention and treatment (as defined herein) of inflammatory disorders such as e.g. asthma and/or allergic asthma. Generally, "inflammatory disorders such as e.g. asthma" can be defined as diseases and disorders that can be prevented and/or treated, respectively, by suitably administering to a subject in need thereof (i.e. having the disease or disorder or at least one symptom thereof and/or at risk of attracting or developing the disease or disorder) of either a polypeptide or composition of the invention (and in particular, of a pharmaceutically active amount thereof) and/or of a known active principle active against OX40L or a biological pathway or mechanism in which OX40L is involved (and in particular, of a pharmaceutically active amount thereof). Examples of such inflammatory disorders such as e.g. asthma and/or allergic asthma, will be clear to the skilled person based on the disclosure herein, and for example include the following diseases and disorders: rheumatoid arthritis, asthma, allergic asthma including moderate to severe asthma such as e.g. severe persistent asthma whose symptoms are not adequately controlled with inhaled corticosteroids.

In particular, the polypeptides and compositions of the present invention can be used for the prevention and treatment of inflammatory disorders such as e.g. asthma and/or allergic asthma which are characterized by excessive and/or unwanted signaling mediated by OX40L or by the pathway (s) in which OX40L is involved. Examples of such inflammatory disorders such as e.g. asthma and/or allergic asthma (Gough, supra), chronic colitis such as Crohn's disease (Tostuka et al., 2003, Am J Physiol Gastrointest. Liver Physiol. 284, G595-G603), inflammatory bowel disease (Souza H S et al., 1999, Gut, 45, 856-863), and/or atherosclerosis (Olofsson P. S., 2008, Circulation, 117, 1291-1301) will again be clear to the skilled person. Without being limiting, other diseases and/or disorders associated with OX40L includean immune disorder and/or an autoimmune disorder (such as asthma, allergic asthma, atopic dermatitis, allergic rhinitis, inflammatory bowel disease, multiple sclerosis, graft verses host disease (GVHD), and/or systemic lupus erythematosus); a disorder associated with virus, bacteria or other infectious agent, for example virus-induced immunopathology, e.g., pathology induced by infection with influenze or RSV or related viruses, e.g., in the lung; arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis); autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, auto-immune asthma, allergic asthma, and pediatric asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, antiglomerular basement membrane disease, anti-phospholipid antibody syndrome, motoneuritis, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressier's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis. Other examples, which in some cases encompass those listed above, include but are not limited to autoimmune rheumatologic disorders (such as, for example, rheumatoid arthritis, Sjogren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant. GVHD, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)).

Thus, without being limited thereto, the amino acid sequences and polypeptides of the invention can for example be used to prevent and/or to treat all diseases and disorders that are currently being prevented or treated with active principles that can modulate OX40L-mediated signalling, such as those mentioned in the prior art cited above. It is also envisaged that the polypeptides of the invention can be used to prevent and/or to treat all diseases and disorders for which treatment with such active principles is currently being developed, has been proposed, or will be proposed or developed in future. In addition, it is envisaged that, because of their favourable properties as further described herein, the polypeptides of the present invention may be used for the prevention and treatment of other diseases and disorders than those for which these known active principles are being used or will be proposed or developed; and/or that the polypeptides of the present invention may provide new methods and regimens for treating the diseases and disorders described herein.

Other applications and uses of the amino acid sequences and polypeptides of the invention will become clear to the skilled person from the further disclosure herein.

Generally, it is an object of the invention to provide pharmacologically active agents, as well as compositions comprising the same, that can be used in the diagnosis, prevention and/or treatment of inflammatory disorders such as e.g. asthma and/or allergic asthma and of the further diseases and disorders mentioned herein; and to provide methods for the diagnosis, prevention and/or treatment of such diseases and disorders that involve the administration and/or use of such agents and compositions.

In particular, it is an object of the invention to provide such pharmacologically active agents, compositions and/or methods that have certain advantages compared to the agents, compositions and/or methods that are currently used and/or known in the art. These advantages will become clear from the further description below.

More in particular, it is an object of the invention to provide therapeutic proteins that can be used as pharmacologically active agents, as well as compositions comprising the same, for the diagnosis, prevention and/or treatment of inflammatory disorders such as e.g. asthma and/or allergic asthma and of the further diseases and disorders mentioned herein; and to provide methods for the diagnosis, prevention and/or treatment of such diseases and disorders that involve the administration and/or the use of such therapeutic proteins and compositions.

Accordingly, it is a specific object of the present invention to provide amino acid sequences that are directed against (as defined herein) OX40L, in particular against OX40L from a warm-blooded animal, more in particular against OX40L from a mammal such as e.g. cynomolgus OX40L (SEQ ID NO: 176), and especially against human OX40L (SEQ ID NO: 175); and to provide proteins and polypeptides comprising or essentially consisting of at least one such amino acid sequence.

In particular, it is a specific object of the present invention to provide such amino acid sequences and such proteins and/or polypeptides that are suitable for prophylactic, therapeutic and/or diagnostic use in a warm-blooded animal, and in particular in a mammal, and more in particular in a human being.

More in particular, it is a specific object of the present invention to provide such amino acid sequences and such proteins and/or polypeptides that can be used for the prevention, treatment, alleviation and/or diagnosis of one or more diseases, disorders or conditions associated with OX40L and/or mediated by OX40L (such as the diseases, disorders and conditions mentioned herein) in a warm-blooded animal, in particular in a mammal, and more in particular in a human being.

It is also a specific object of the invention to provide such amino acid sequences and such proteins and/or polypeptides that can be used in the preparation of pharmaceutical or veterinary compositions for the prevention and/or treatment of one or more diseases, disorders or conditions associated with and/or mediated by OX40L (such as the diseases, disorders and conditions mentioned herein) in a warm-blooded animal, in particular in a mammal, and more in particular in a human being.

In the invention, generally, these objects are achieved by the use of the amino acid sequences, proteins, polypeptides and compositions that are described herein.

In general, the invention provides amino acid sequences that are directed against (as defined herein) and/or can specifically bind (as defined herein) to OX40L; as well as compounds and constructs, and in particular proteins and polypeptides, that comprise at least one such amino acid sequence.

More in particular, the invention provides amino acid sequences that can bind to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; as well as compounds and constructs, and in particular proteins and polypeptides, that comprise at least one such amino acid sequence.

In particular, amino acid sequences and polypeptides of the invention are preferably such that they:

bind to OX40L with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to OX40L with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between 10 $M^{-1}s^{-1}$ and $10^7$ $M^{-1}s^{-1}$;

and/or such that they:

bind to OX40L with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a monovalent amino acid sequence of the invention (or a polypeptide that contains only one amino acid sequence of the invention) is preferably such that it will bind to OX40L with an affinity less than 500 nM, preferably less than 200 nM, more preferably less than 10 nM, such as less than 500 pM.

Some preferred IC50 values for binding of the amino acid sequences or polypeptides of the invention to OX40L will become clear from the further description and examples herein.

For binding to OX40L, an amino acid sequence of the invention will usually contain within its amino acid sequence one or more amino acid residues or one or more stretches of amino acid residues (i.e. with each "stretch" comprising two or amino acid residues that are adjacent to each other or in close proximity to each other, i.e. in the primary or tertiary structure of the amino acid sequence) via which the amino acid sequence of the invention can bind to OX40L, which amino acid residues or stretches of amino acid residues thus form the "site" for binding to OX40L (also referred to herein as the "antigen binding site").

The amino acid sequences provided by the invention are preferably in essentially isolated form (as defined herein), or form part of a protein or polypeptide of the invention (as defined herein), which may comprise or essentially consist of one or more amino acid sequences of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than OX40L), so as to provide a monovalent, multivalent or multispecific polypeptide of the invention, respectively, all as described herein. Such a protein or polypeptide may also be in essentially isolated form (as defined herein).

The amino acid sequences and polypeptides of the invention as such preferably essentially consist of a single amino acid chain that is not linked via disulphide bridges to any other amino acid sequence or chain (but that may or may not contain one or more intramolecular disulphide bridges. For example, it is known that Nanobodies—as described herein—may sometimes contain a disulphide bridge between CDR3 and CDR1 or FR2). However, it should be noted that one or more amino acid sequences of the invention may be linked to each other and/or to other amino acid sequences (e.g. via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat Biotechnol. 2005 September; 23(9):1126-36).

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, in essentially isolated form (as defined herein).

It will also be clear to the skilled person that for pharmaceutical use, the amino acid sequences of the invention (as well as compounds, constructs and polypeptides comprising the same) are preferably directed against human OX40L; whereas for veterinary purposes, the amino acid sequences and polypeptides of the invention are preferably directed against OX40L from the species to be treated, or at least cross-reactive with OX40L from the species to be treated.

Furthermore, an amino acid sequence of the invention may optionally, and in addition to the at least one binding site for binding against OX40L, contain one or more further binding sites for binding against other antigens, proteins or targets.

The efficacy of the amino acid sequences and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include *Ascaris suum* model for asthma in monkey, as well as the assays and animal models used in the experimental part below and in the prior art cited herein.

Also, according to the invention, amino acid sequences and polypeptides that are directed against OX40L from a first species of warm-blooded animal may or may not show cross-reactivity with OX40L from one or more other species of warm-blooded animal. For example, amino acid sequences and polypeptides directed against human OX40L may or may not show cross reactivity with OX40L from one or more other species of primates (such as, without limitation, monkeys from the genus *Macaca* (such as, and in particular, cynomolgus monkeys (*Macaca fascicularis*) and/or rhesus monkeys (*Macaca mulatta*)) and baboon (*Popio ursinus*)) and/or with OX40L from one or more species of animals that are often used in animal models for diseases (for example mouse, rat, rabbit, pig or dog), and in particular in animal models for diseases and disorders associated with OX40L (such as the species and animal models mentioned herein). In this respect, it will be clear to the skilled person that such cross-reactivity, when present, may have advantages from a drug development point of view, since it allows the amino acid sequences and polypeptides against human OX40L to be tested in such disease models.

More generally, amino acid sequences and polypeptides of the invention that are cross-reactive with OX40L from multiple species of mammal will usually be advantageous for use in veterinary applications, since it will allow the same amino acid sequence or polypeptide to be used across multiple species. Thus, it is also encompassed within the scope of the invention that amino acid sequences and polypeptides directed against OX40L from one species of animal (such as amino acid sequences and polypeptides against human OX40L) can be used in the treatment of another species of animal, as long as the use of the amino acid sequences and/or polypeptides provide the desired effects in the species to be treated.

The present invention is in its broadest sense also not particularly limited to or defined by a specific antigenic determinant, epitope, part, domain, subunit or confirmation (where applicable) of OX40L against which the amino acid sequences and polypeptides of the invention are directed. For example, the amino acid sequences and polypeptides may or may not be directed against an "interaction site" (as defined herein). However, it is generally assumed and preferred that the amino acid sequences and polypeptides of the invention are preferably directed against an interaction site (as defined herein), and in particular against one or more epitopes of Nanobodies as described herein, e.g. one or more epitopes of Nanobody 01B11 (SEQ ID NO: 179), 18E09 (SEQ ID NO: 183) and 15B07 (SEQ ID NO: 182). Thus, in one preferred, but non-limiting aspect, the amino acid sequences and polypeptides of the invention are directed against one or more epitopes of Nanobody 01B11 (SEQ ID NO: 179), 18E09 (SEQ ID NO: 183) and 15B07 (SEQ ID NO: 182) and are as further defined herein.

As further described herein, a polypeptide of the invention may contain two or more amino acid sequences of the invention that are directed against OX40L Generally, such polypeptides will bind to OX40L with increased avidity compared to a single amino acid sequence of the invention. Such a polypeptide may for example comprise two amino acid sequences of the invention that are directed against the same antigenic determinant, epitope, part, domain, subunit or confirmation (where applicable) of OX40L (which may or may not be an interaction site); or comprise at least one "first" amino acid sequence of the invention that is directed against a first antigenic determinant, epitope, part, domain, subunit or confirmation (where applicable) of OX40L (which may or may not be an interaction site); and at least one "second" amino acid sequence of the invention that is directed against a second antigenic determinant, epitope, part, domain, subunit or confirmation (where applicable) different from the first (and which again may or may not be an interaction site). Preferably, in such "biparatopic" polypeptides of the invention, at least one amino acid sequence of the invention is directed against an interaction site (as defined herein), although the invention in its broadest sense is not limited thereto.

Also, when the target is part of a binding pair (for example, a receptor-ligand binding pair), the amino acid sequences and polypeptides may be such that they compete with the cognate binding partner (e.g. the ligand, receptor or other binding partner, as applicable) for binding to the target, and/or such that they (fully or partially) neutralize binding of the binding partner to the target.

It is also within the scope of the invention that, where applicable, an amino acid sequence of the invention can bind to two or more antigenic determinants, epitopes, parts, domains, subunits or confirmations of OX40L. In such a case, the antigenic determinants, epitopes, parts, domains or subunits of OX40L to which the amino acid sequences and/or polypeptides of the invention bind may be essentially the same (for example, if OX40L contains repeated structural motifs or occurs in a multimeric form) or may be different (and in the latter case, the amino acid sequences and polypeptides of the invention may bind to such different antigenic determinants, epitopes, parts, domains, subunits of OX40L with an affinity and/or specificity which may be the same or different). Also, for example, when OX40L exists in an activated conformation and in an inactive conformation, the amino acid sequences and polypeptides of the invention may bind to either one of these confirmation, or may bind to both these confirmations (i.e. with an affinity and/or specificity which may be the same or different). Also, for example, the amino acid sequences and polypeptides of the invention may bind to a conformation of OX40L in which it is bound to a pertinent ligand, may bind to a conformation of OX40L in which it not bound to a pertinent ligand, or may bind to both such conformations (again with an affinity and/or specificity which may be the same or different).

It is also expected that the amino acid sequences and polypeptides of the invention will generally bind to all naturally occurring or synthetic analogs, variants, mutants, alleles, parts and fragments of OX40L; or at least to those analogs, variants, mutants, alleles, parts and fragments of OX40L that contain one or more antigenic determinants or epitopes that are essentially the same as the antigenic determinant(s) or epitope(s) to which the amino acid sequences and polypeptides of the invention bind in OX40L (e.g. in wild-type OX40L). Again, in such a case, the amino acid sequences and polypeptides of the invention may bind to such analogs, variants, mutants, alleles, parts and fragments with an affinity and/or specificity that are the same as, or that are different from (i.e. higher than or lower than), the affinity and specificity with which the amino acid sequences of the invention bind to (wild-type) OX40L. It is also included within the scope of the invention that the amino acid sequences and polypeptides of the invention bind to some analogs, variants, mutants, alleles, parts and fragments of OX40L, but not to others.

When OX40L exists in a monomeric form and in one or more multimeric forms, it is within the scope of the invention that the amino acid sequences and polypeptides of the invention only bind to OX40L in monomeric form, only bind to OX40L in multimeric form, or bind to both the monomeric and the multimeric form. Again, in such a case, the amino acid sequences and polypeptides of the invention may bind to the monomeric form with an affinity and/or specificity that are the same as, or that are different from (i.e. higher than or lower than), the affinity and specificity with which the amino acid sequences of the invention bind to the multimeric form.

Also, when OX40L can associate with other proteins or polypeptides to form protein complexes (e.g. with multiple subunits), it is within the scope of the invention that the amino acid sequences and polypeptides of the invention bind to OX40L in its non-associated state, bind to OX40L in its associated state, or bind to both. In all these cases, the amino acid sequences and polypeptides of the invention may bind to such multimers or associated protein complexes with an affinity and/or specificity that may be the same as or different from (i.e. higher than or lower than) the affinity and/or specificity with which the amino acid sequences and polypeptides of the invention bind to OX40L in its monomeric and non-associated state.

Also, as will be clear to the skilled person, proteins or polypeptides that contain two or more amino acid sequences directed against OX40L may bind with higher avidity to OX40L than the corresponding monomeric amino acid sequence(s). For example, and without limitation, proteins or polypeptides that contain two or more amino acid sequences directed against different epitopes of OX40L may (and usually will) bind with higher avidity than each of the different monomers, and proteins or polypeptides that contain two or more amino acid sequences directed against OX40L may (and usually will) bind also with higher avidity to a multimer of OX40L.

Generally, amino acid sequences and polypeptides of the invention will at least bind to those forms of OX40L (including monomeric, multimeric and associated forms) that are the most relevant from a biological and/or therapeutic point of view, as will be clear to the skilled person.

It is also within the scope of the invention to use parts, fragments, analogs, mutants, variants, alleles and/or derivatives of the amino acid sequences and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against OX40L; and more preferably will be capable of specific binding to OX40L, and even more preferably capable of binding to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

In one specific, but non-limiting aspect of the invention, which will be further described herein, such analogs, mutants, variants, alleles, derivatives have an increased half-life in serum (as further described herein) compared to the amino acid sequence from which they have been derived. For example, an amino acid sequence of the invention may be linked (chemically or otherwise) to one or more groups or moieties that extend the half-life (such as PEG), so as to provide a derivative of an amino acid sequence of the invention with increased half-life.

In one specific, but non-limiting aspect, the amino acid sequence of the invention may be an amino acid sequence that comprises an immunoglobulin fold or may be an amino acid sequence that, under suitable conditions (such as physiological conditions) is capable of forming an immunoglobulin fold (i.e. by folding). Reference is inter alia made to the review by Halaby et al., J. (1999) Protein Eng. 12, 563-71. Preferably, when properly folded so as to form an immunoglobulin fold, such an amino acid sequence is capable of specific binding (as defined herein) to OX40L; and more preferably capable of binding to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Also, parts, fragments, analogs, mutants, variants, alleles and/or derivatives of such amino acid sequences are preferably such that they comprise an immunoglobulin fold or are capable for forming, under suitable conditions, an immunoglobulin fold.

In particular, but without limitation, the amino acid sequences of the invention may be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein).

The amino acid sequences of the invention may in particular be an immunoglobulin sequence or a suitable fragment thereof, and more in particular be an immunoglobulin variable domain sequence, immunoglobulin single variable domain sequences or a suitable fragment thereof, such as light chain variable domain sequence (e.g. a $V_L$-sequence) or a suitable fragment thereof; or a heavy chain variable domain sequence (e.g. a $V_H$-sequence) or a suitable fragment thereof. When the amino acid sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein).

However, it should be noted that the invention is not limited as to the origin of the amino acid sequence of the invention (or of the nucleotide sequence of the invention used to express it), nor as to the way that the amino acid sequence or nucleotide sequence of the invention is (or has been) generated or obtained. Thus, the amino acid sequences of the invention may be naturally occurring amino acid sequences (from any suitable species) or synthetic or semi-synthetic amino acid sequences. In a specific but non-limiting aspect of the invention, the amino acid sequence is a naturally occurring immunoglobulin sequence (from any suitable species) or a synthetic or semi-synthetic immunoglobulin sequence, including but not limited to "humanized" (as defined herein) immunoglobulin sequences (such as partially or fully humanized mouse or rabbit immunoglobulin sequences, and in particular partially or fully humanized $V_{HH}$ sequences or Nanobodies), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Reference is for example made to the standard handbooks, as well as to the further description and prior art mentioned herein.

Similarly, the nucleotide sequences of the invention may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

The amino acid sequence of the invention may in particular be an immunoglobulin single variable domain sequence such as a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody (as defined herein, and including but not limited to a $V_{HH}$ sequence); other single variable domains, or any suitable fragment of any one thereof. For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may be a Nanobody® (as defined herein) or a suitable fragment thereof. [Note: Nanobody®, Nanobodies® and Nonoclone® ore registered trademarks of Ablynx N.V.] Such Nanobodies directed against OX40L will also be referred to herein as "Nonobodies of the invention".

For a general description of Nanobodies, reference is made to the further description below, as well as to the prior art cited herein. In this respect, it should however be noted that this description and the prior art mainly described Nanobodies of the so-called "$V_H3$ class" (i.e. Nanobodies with a high degree of sequence homology to human germline sequences of the $V_H3$ class such as DP-47, DP-51 or DP-29), which Nanobodies form a preferred aspect of this invention. It should however be noted that the invention in its broadest sense generally covers any type of Nanobody directed against OX40L, and for example also covers the Nanobodies belonging to the so-called "$V_H4$ class" (i.e. Nanobodies with a high degree of sequence homology to human germline sequences of the $V_H4$ class such as DP-78), as for example described in WO 07/118670.

Generally, Nanobodies (in particular $V_{HH}$ sequences and partially humanized Nanobodies) can in particular be characterized by the presence of one or more "Hollmark residues" (as described herein) in one or more of the framework sequences (again as further described herein).

Thus, generally, a Nanobody can be defined as an amino acid sequence with the (general) structure

FR1-CDR1-FR2-CDR2-FR3-CDR-3-FR4 in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a Nanobody can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a Nanobody can be an amino acid sequence with the (general) structure

FR1-CDR1-FR2-CDR2-FR3-CDR-3-FR4 in which FR1 to FR4 refer to framework regions 1 to 4, respectively, and in which CDR1 to CDR3 refer to the complementarity determining regions 1 to 3, respectively, and in which:
i) preferably one or more of the amino acid residues at positions 11, 37, 44, 45, 47, 83, 84, 103, 104 and 108 according to the Kabat numbering are chosen from the Hallmark residues mentioned in Table B-2 below;
and in which:
ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded.

In these Nanobodies, the CDR sequences are generally as further defined herein.

Thus, the invention also relates to such Nanobodies that can bind to (as defined herein) and/or are directed against OX40L, to suitable fragments thereof, as well as to polypeptides that comprise or essentially consist of one or more of such Nanobodies and/or suitable fragments.

SEQ ID NO's: 179 to 185 (see Table A-1) give the amino acid sequences of a number of $V_{HH}$ sequences that have been raised against OX40L.

In particular, the invention in some specific aspects provides:
amino acid sequences that are directed against (as defined herein) OX40L and that have at least 80%, preferably at least 85%, such as 90% or 95% or more sequence identity with at least one of the amino acid sequences of SEQ ID NO's: 179 to 185 (see Table A-1). These amino acid sequences may further be such that they neutralize binding of the cognate ligand or receptor to OX40L; and/or compete with the cognate ligand or receptor for binding to OX40L; and/or are directed against an interaction site (as defined herein) on OX40L (such as the ligand or receptor binding site);
amino acid sequences that cross-block (as defined herein) the binding of at least one of the amino acid sequences of SEQ ID NO's: 179 to 185 (see Table A-1) to OX40L and/or that compete with at least one of the amino acid sequences of SEQ ID NO's: 179 to 185 (see Table A-1) for binding to OX40L. Again, these amino acid sequences may further be such that they neutralize binding of the cognate ligand or receptor to OX40L; and/or compete with the cognate ligand or receptor for binding to OX40L; and/or are directed against an interaction site (as defined herein) on OX40L (such as the ligand or receptor binding site); which amino acid sequences may be as further described herein (and may for example be Nanobodies); as well as polypeptides of the invention that comprise one or more of such amino acid sequences (which may be as further described herein, and may for example be bispecific and/or biparatopic polypeptides as described herein), and nucleic acid sequences that encode such amino acid sequences and polypeptides. Such amino acid sequences and polypeptides do not include any naturally occurring ligands.

In some other specific aspects, the invention provides:
amino acid sequences of the invention that are specific for OX40L compared to other members of the TNF family; which amino acid sequences of the invention may be as further described herein (and may for example be Nanobodies); as well as polypeptides of the invention that comprise one or more of such amino acid sequences (which may be as further described herein, and may for example be bispecific and/or biparatopic polypeptides as described herein), and nucleic acid sequences that encode such amino acid sequences and polypeptides. Such amino acid sequences and polypeptides do not include any naturally occurring ligands.

Accordingly, some particularly preferred Nanobodies of the invention are Nanobodies which can bind (as further defined herein) to and/or are directed against to OX40L and which:
i) have at least 80% amino acid identity with at least one of the amino acid sequences of SEQ ID NO's: 179 to 185 (see Table A-1), in which for the purposes of determining the degree of amino acid identity, the amino acid residues that form the CDR sequences are disregarded. In this respect, reference is also made to Table B-1, which lists the framework 1 sequences (SEQ ID NO's: 126 to 132), framework 2 sequences (SEQ ID NO's: 140 to 146), framework 3 sequences (SEQ ID NO's: 154 to 160) and framework 4 sequences (SEQ ID NO's: 168 to 174) of the Nanobodies of SEQ ID NO's: 179 to 185 (see Table A-1) (with respect to the amino acid residues at positions 1 to 4 and 27 to 30 of the framework 1 sequences, reference is also made to the comments made below. Thus, for determining the degree of amino acid identity, these residues are preferably disregarded);

and in which:
ii) preferably one or more of the amino acid residues at positions 11, 37, 44, 45, 47, 83, 84, 103, 104 and 108 according to the Kabat numbering are chosen from the Hallmark residues mentioned in Table B-2 below.

In these Nanobodies, the CDR sequences are generally as further defined herein.

Again, such Nanobodies may be derived in any suitable manner and from any suitable source, and may for example be naturally occurring $V_{HH}$ sequences (i.e. from a suitable species of Camelid) or synthetic or semi-synthetic amino acid sequences, including but not limited to "humanized" (as defined herein) Nanobodies, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when a Nanobody comprises a $V_{HH}$ sequence, said Nanobody may be suitably humanized, as further described herein, so as to provide one or more further (partially or fully) humanized Nanobodies of the invention. Similarly, when a Nanobody comprises a synthetic or semi-synthetic sequence (such as a partially humanized sequence), said Nanobody may optionally be further suitably humanized, again as described herein, again so as to provide one or more further (partially or fully) humanized Nanobodies of the invention.

In particular, humanized Nanobodies may be amino acid sequences that are as generally defined for Nanobodies in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Some particularly preferred humanized Nanobodies of the invention are humanized variants of the Nanobodies of SEQ ID NO's: 179 to 185 (see Table A-1), of which the amino acid sequences of SEQ ID NO's: 199 to 226 (see Table A-2) are some especially preferred examples.

According to another specific aspect of the invention, the invention provides a number of stretches of amino acid residues (i.e. small peptides) that are particularly suited for binding to OX40L. These stretches of amino acid residues may be present in, and/or may be incorporated into, an amino acid sequence of the invention, in particular in such a way that they form (part of) the antigen binding site of an amino acid sequence of the invention. As these stretches of amino acid residues were first generated as CDR sequences of heavy chain antibodies or $V_{HH}$ sequences that were raised against OX40L (or may be based on and/or derived from such CDR sequences, as further described herein), they will also generally be referred to herein as "CDR sequences" (i.e. as CDR1 sequences, CDR2 sequences and CDR3 sequences, respectively). It should however be noted that the invention in its broadest sense is not limited to a specific structural role or function that these stretches of amino acid residues may have in an amino acid sequence of the invention, as long as these stretches of amino acid residues allow the amino acid sequence of the invention to bind to OX40L. Thus, generally, the invention in its broadest sense comprises any amino acid sequence that is capable of binding to OX40L and that comprises one or more CDR sequences as described herein, and in particular a suitable combination of two or more such CDR sequences, that are suitably linked to each other via one or more further amino acid sequences, such that the entire amino acid sequence forms a binding domain and/or binding unit that is capable of binding to OX40L. It should however also be noted that the presence of only one such CDR sequence in an amino acid sequence of the invention may by itself already be sufficient to provide an amino acid sequence of the invention that is capable of binding to OX40L; reference is for example again made to the so-called "Expedite fragments" described in WO 03/050531 or WO2009/127691.

Thus, in another specific, but non-limiting aspect, the amino acid sequence of the invention may be an amino acid sequence that comprises at least one amino acid sequence that is chosen from the group consisting of the CDR1 sequences, CDR2 sequences and CDR3 sequences that are described herein (or any suitable combination thereof). In particular, an amino acid sequence of the invention may be an amino acid sequence that comprises at least one antigen binding site, wherein said antigen binding site comprises at least one amino acid sequence that is chosen from the group consisting of the CDR1 sequences, CDR2 sequences and CDR3 sequences that are described herein (or any suitable combination thereof).

Generally, in this aspect of the invention, the amino acid sequence of the invention may be any amino acid sequence that comprises at least one stretch of amino acid residues, in which said stretch of amino acid residues has an amino acid sequence that corresponds to the sequence of at least one of the CDR sequences described herein. Such an amino acid sequence may or may not comprise an immunoglobulin fold. For example, and without limitation, such an amino acid sequence may be a suitable fragment of an immunoglobulin sequence that comprises at least one such CDR sequence, but that is not large enough to form a (complete) immunoglobulin fold (reference is for example again made to the "Expedite fragments" described in WO03/050531 or WO2009/127691). Alternatively, such an amino acid sequence may be a suitable "protein scaffold" that comprises at least one stretch of amino acid residues that corresponds to such a CDR sequence (i.e. as part of its antigen binding site). Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al., Comb Chem High Throughput Screen 2006 9(8):619-32).

Again, any amino acid sequence of the invention that comprises one or more of these CDR sequences is preferably such that it can specifically bind (as defined herein) to OX40L, and more in particular such that it can bind to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), that is as defined herein.

More in particular, the amino acid sequences according to this aspect of the invention may be any amino acid sequence that comprises at least one antigen binding site, wherein said antigen binding site comprises at least two amino acid sequences that are chosen from the group consisting of the CDR1 sequences described herein, the CDR2 sequences described herein and the CDR3 sequences described herein, such that (i) when the first amino acid sequence is chosen from the CDR1 sequences described herein, the second amino acid sequence is chosen from the CDR2 sequences described herein or the CDR3 sequences described herein; (ii) when the first amino acid sequence is chosen from the CDR2 sequences described herein, the second amino acid sequence is chosen from the CDR1 sequences described herein or the CDR3 sequences described herein; or (iii) when the first amino acid sequence is chosen from the CDR3 sequences described herein, the second amino acid sequence is chosen from the CDR1 sequences described herein or the CDR3 sequences described herein.

Even more in particular, the amino acid sequences of the invention may be amino acid sequences that comprise at least one antigen binding site, wherein said antigen binding site comprises at least three amino acid sequences that are chosen from the group consisting of the CDR1 sequences described herein, the CDR2 sequences described herein and the CDR3 sequences described herein, such that the first amino acid sequence is chosen from the CDR1 sequences described herein, the second amino acid sequence is chosen from the CDR2 sequences described herein, and the third amino acid sequence is chosen from the CDR3 sequences described herein. Preferred combinations of CDR1, CDR2 and CDR3 sequences will become clear from the further description herein. As will be clear to the skilled person, such an amino acid sequence is preferably an immunoglobulin sequence (as further described herein), but it may for example also be any other amino acid sequence that comprises a suitable scaffold for presenting said CDR sequences.

Thus, in one specific, but non-limiting aspect, the invention relates to an amino acid sequence directed against OX40L, that comprises one or more stretches of amino acid residues chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;
d) the amino acid sequences of SEQ ID NO's: 147 to 153;

e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167;
or any suitable combination thereof.

When an amino acid sequence of the invention contains one or more amino acid sequences according to b) and/or c):
i) any amino acid substitution in such an amino acid sequence according to b) and/or c) is preferably, and compared to the corresponding amino acid sequence according to a), a conservative amino acid substitution, (as defined herein);
and/or
ii) the amino acid sequence according to b) and/or c) preferably only contains amino acid substitutions, and no amino acid deletions or insertions, compared to the corresponding amino acid sequence according to a);
and/or
iii) the amino acid sequence according to b) and/or c) may be an amino acid sequence that is derived from an amino acid sequence according to a) by means of affinity maturation using one or more techniques of affinity maturation known per se.

Similarly, when an amino acid sequence of the invention contains one or more amino acid sequences according to e) and/or f):
i) any amino acid substitution in such an amino acid sequence according to e) and/or f) is preferably, and compared to the corresponding amino acid sequence according to d), a conservative amino acid substitution, (as defined herein);
and/or
ii) the amino acid sequence according to e) and/or f) preferably only contains amino acid substitutions, and no amino acid deletions or insertions, compared to the corresponding amino acid sequence according to d);
and/or
iii) the amino acid sequence according to e) and/or f) may be an amino acid sequence that is derived from an amino acid sequence according to d) by means of affinity maturation using one or more techniques of affinity maturation known per se.

Also, similarly, when an amino acid sequence of the invention contains one or more amino acid sequences according to h) and/or i):
i) any amino acid substitution in such an amino acid sequence according to h) and/or i) is preferably, and compared to the corresponding amino acid sequence according to g), a conservative amino acid substitution, (as defined herein);
and/or
ii) the amino acid sequence according to h) and/or i) preferably only contains amino acid substitutions, and no amino acid deletions or insertions, compared to the corresponding amino acid sequence according to g);
and/or
iii) the amino acid sequence according to h) and/or i) may be an amino acid sequence that is derived from an amino acid sequence according to g) by means of affinity maturation using one or more techniques of affinity maturation known per se.

It should be understood that the last preceding paragraphs also generally apply to any amino acid sequences of the invention that comprise one or more amino acid sequences according to b), c), e), f), h) or i), respectively.

In this specific aspect, the amino acid sequence preferably comprises one or more stretches of amino acid residues chosen from the group consisting of:
i) the amino acid sequences of SEQ ID NO's: 133 to 139;
ii) the amino acid sequences of SEQ ID NO's: 147 to 153; and
iii) the amino acid sequences of SEQ ID NO's: 161 to 167;
or any suitable combination thereof.

Also, preferably, in such an amino acid sequence, at least one of said stretches of amino acid residues forms part of the antigen binding site for binding against OX40L.

In a more specific, but again non-limiting aspect, the invention relates to an amino acid sequence directed against OX40L, that comprises two or more stretches of amino acid residues chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;
d) the amino acid sequences of SEQ ID NO's: 147 to 153;
e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167;
such that (i) when the first stretch of amino acid residues corresponds to one of the amino acid sequences according to a), b) or c), the second stretch of amino acid residues corresponds to one of the amino acid sequences according to d), e), f), g), h) or i); (ii) when the first stretch of amino acid residues corresponds to one of the amino acid sequences according to d), e) or f), the second stretch of amino acid residues corresponds to one of the amino acid sequences according to a), b), c), g), h) or i); or (iii) when the first stretch of amino acid residues corresponds to one of the amino acid sequences according to g), h) or i), the second stretch of amino acid residues corresponds to one of the amino acid sequences according to a), b), c), d), e) or f).

In this specific aspect, the amino acid sequence preferably comprises two or more stretches of amino acid residues chosen from the group consisting of:
i) the amino acid sequences of SEQ ID NO's: 133 to 139;
ii) the amino acid sequences of SEQ ID NO's: 147 to 153; and
iii) the amino acid sequences of SEQ ID NO's: 161 to 167;
such that, (i) when the first stretch of amino acid residues corresponds to one of the amino acid sequences of SEQ ID NO's: 133 to 139, the second stretch of amino acid residues corresponds to one of the amino acid sequences of SEQ ID NO's: 147 to 153 or of SEQ ID NO's: 161 to 167; (ii) when the first stretch of amino acid residues corresponds to one of the amino acid sequences of SEQ ID NO's: 147 to 153, the second stretch of amino acid residues corresponds to one of the amino acid sequences of SEQ ID NO's: 133 to 139 or of SEQ ID NO's: 161 to 167; or (iii) when the first stretch of amino acid residues corresponds to one of the amino acid sequences of SEQ ID NO's: 161 to 167, the second stretch of amino acid residues corresponds to one of the amino acid sequences of SEQ ID NO's: 133 to 139 or of SEQ ID NO's: 147 to 153.

Also, in such an amino acid sequence, the at least two stretches of amino acid residues again preferably form part of the antigen binding site for binding against OX40L.

In an even more specific, but non-limiting aspect, the invention relates to an amino acid sequence directed against OX40L, that comprises three or more stretches of amino acid residues, in which the first stretch of amino acid residues is chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;
the second stretch of amino acid residues is chosen from the group consisting of:
d) the amino acid sequences of SEQ ID NO's: 147 to 153;
e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
and the third stretch of amino acid residues is chosen from the group consisting of:
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167.

Preferably, in this specific aspect, the first stretch of amino acid residues is chosen from the group consisting of the amino acid sequences of SEQ ID NO's: 133 to 139; the second stretch of amino acid residues is chosen from the group consisting of the amino acid sequences of SEQ ID NO's: 147 to 153; and the third stretch of amino acid residues is chosen from the group consisting of the amino acid sequences of SEQ ID NO's: 161 to 167.

Again, preferably, in such an amino acid sequence, the at least three stretches of amino acid residues forms part of the antigen binding site for binding against OX40L.

Preferred combinations of such stretches of amino acid sequences will become clear from the further disclosure herein.

Preferably, in such amino acid sequences the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 179 to 185 (see Table A-1). This degree of amino acid identity can for example be determined by determining the degree of amino acid identity (in a manner described herein) between said amino acid sequence and one or more of the sequences of SEQ ID NO's: 179 to 185 (see Table A-1), in which the amino acid residues that form the framework regions are disregarded. Also, such amino acid sequences of the invention can be as further described herein.

Also, such amino acid sequences are preferably such that they can specifically bind (as defined herein) to OX40L; and more in particular bind to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

When the amino acid sequence of the invention essentially consists of 4 framework regions (FR1 to FR4, respectively) and 3 complementarity determining regions (CDR1 to CDR3, respectively), the amino acid sequence of the invention is preferably such that:
CDR1 is chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;
and/or
CDR2 is chosen from the group consisting of:
d) the amino acid sequences of SEQ ID NO's: 147 to 153;
e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
and/or
CDR3 is chosen from the group consisting of:
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167.

In particular, such an amino acid sequence of the invention may be such that CDR1 is chosen from the group consisting of the amino acid sequences of SEQ ID NO's: 133 to 139; and/or CDR2 is chosen from the group consisting of the amino acid sequences of SEQ ID NO's: 147 to 153; and/or CDR3 is chosen from the group consisting of the amino acid sequences of SEQ ID NO's: 161 to 167.

In particular, when the amino acid sequence of the invention essentially consists of 4 framework regions (FR1 to FR4, respectively) and 3 complementarity determining regions (CDR1 to CDR3, respectively), the amino acid sequence of the invention is preferably such that:
CDR1 is chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;
and
CDR2 is chosen from the group consisting of:
d) the amino acid sequences of SEQ ID NO's: 147 to 153;

e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
and
CDR3 is chosen from the group consisting of:
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167; or any suitable fragment of such an amino acid sequence In particular, such an amino acid sequence of the invention may be such that CDR1 is chosen from the group consisting of the amino acid sequences of SEQ ID NO's: 133 to 139; and CDR2 is chosen from the group consisting of the amino acid sequences of SEQ ID NO's: 147 to 153; and CDR3 is chosen from the group consisting of the amino acid sequences of SEQ ID NO's: 161 to 167.

Again, preferred combinations of CDR sequences will become clear from the further description herein.

Also, such amino acid sequences are preferably such that they can specifically bind (as defined herein) to OX40L; and more in particular bind to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In one preferred, but non-limiting aspect, the invention relates to an amino acid sequence that essentially consists of 4 framework regions (FR1 to FR4, respectively) and 3 complementarity determining regions (CDR1 to CDR3, respectively), in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 179 to 185 (see Table A-1). This degree of amino acid identity can for example be determined by determining the degree of amino acid identity (in a manner described herein) between said amino acid sequence and one or more of the sequences of SEQ ID NO's: 179 to 185 (see Table A-1), in which the amino acid residues that form the framework regions are disregarded. Such amino acid sequences of the invention can be as further described herein.

In such an amino acid sequence of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences are preferably such that the amino acid sequence of the invention is a domain antibody (or an amino acid sequence that is suitable for use as a domain antibody); is a single domain antibody (or an amino acid sequence that is suitable for use as a single domain antibody); is a "dAb" (or an amino acid sequence that is suitable for use as a dAb); or is a Nanobody (including but not limited to $V_{HH}$ sequence). Again, suitable framework sequences will be clear to the skilled person, for example on the basis the standard handbooks and the further disclosure and prior art mentioned herein.

In particular, the framework sequences present in the amino acid sequences of the invention may contain one or more of Hallmark residues (as defined herein), such that the amino acid sequence of the invention is a Nanobody. Some preferred, but non-limiting examples of (suitable combinations of) such framework sequences will become clear from the further disclosure herein.

Again, as generally described herein for the amino acid sequences of the invention, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived). Such fragments may also again be such that they comprise or can form an immunoglobulin fold, or alternatively be such that they do not comprise or cannot form an immunoglobulin fold.

In one specific aspect, such a fragment comprises a single CDR sequence as described herein (and in particular a CDR3 sequence), that is flanked on each side by (part of) a framework sequence (and in particular, part of the framework sequence(s) that, in the immunoglobulin sequence from which the fragment is derived, are adjacent to said CDR sequence. For example, a CDR3 sequence may be preceded by (part of) a FR3 sequence and followed by (part of) a FR4 sequence). Such a fragment may also contain a disulphide bridge, and in particular a disulphide bridge that links the two framework regions that precede and follow the CDR sequence, respectively (for the purpose of forming such a disulphide bridge, cysteine residues that naturally occur in said framework regions may be used, or alternatively cysteine residues may be synthetically added to or introduced into said framework regions). For a further description of these "Expedite fragments", reference is again made to WO 03/050531, as well as to the US provisional application of Ablynx N.V. entitled "Peptides capable of binding to serum proteins" of Ablynx N.V. (inventors: Revets, Hilde Adi Pierrette; Kolkman, Joost Alexander; and Hoogenboom, Hendricus Renerus Jacobus Mattheus) filed on Dec. 5, 2006 (see also PCT/EP2007/063348).

In another aspect, the invention relates to a compound or construct, and in particular a protein or polypeptide (also referred to herein as a "compound of the invention" or "polypeptide of the invention", respectively) that comprises or essentially consists of one or more amino acid sequences of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence of the invention (and/or to the compound or construct in which it is present) and may or may not modify the properties of the amino acid sequence of the invention.

For example, such further groups, residues, moieties or binding units may be one or more additional amino acid sequences, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more amino acid sequences of the invention so as to provide a "derivative" of an amino acid sequence or polypeptide of the invention, as further described herein.

Also within the scope of the present invention are compounds or constructs, that comprises or essentially consists of one or more derivatives as described herein, and optionally further comprises one or more other groups, residues, moieties or binding units, optionally linked via one or more linkers. Preferably, said one or more other groups, residues, moieties or binding units are amino acid sequences.

In the compounds or constructs described above, the one or more amino acid sequences of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound or construct is a fusion (protein) or fusion (polypeptide).

As will be clear from the further description above and herein, this means that the amino acid sequences of the invention can be used as "building blocks" to form polypeptides of the invention, i.e. by suitably combining them with other groups, residues, moieties or binding units, in order to form compounds or constructs as described herein (such as, without limitations, the biparatopic. bi/multivalent and bi/multispecific polypeptides of the invention described herein) which combine within one molecule one or more desired properties or biological functions.

The compounds or polypeptides of the invention can generally be prepared by a method which comprises at least one step of suitably linking the one or more amino acid sequences of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted amino acid sequences form a further aspect of the invention.

In one specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein, and for example comprise amino acid sequences or polypeptides of the invention that have been chemically modified to increase the half-life thereof (for example, by means of pegylation); amino acid sequences of the invention that comprise at least one additional binding site for binding to a serum protein (such as serum albumin); or polypeptides of the invention that comprise at least one amino acid sequence of the invention that is linked to at least one moiety (and in particular at least one amino acid sequence) that increases the half-life of the amino acid sequence of the invention. Examples of polypeptides of the invention that comprise such half-life extending moieties or amino acid sequences will become clear to the skilled person based on the further disclosure herein; and for example include, without limitation, polypeptides in which the one or more amino acid sequences of the invention are suitable linked to one or more serum proteins or fragments thereof (such as (human) serum albumin or suitable fragments thereof) or to one or more binding units that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more amino acid sequences of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006 (see also PCT/EP2007/063348).

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another aspect, the invention relates to a nucleic acid that encodes an amino acid sequence of the invention or a polypeptide of the invention (or a suitable fragment thereof). Such a nucleic acid will also be referred to herein as a "nucleic acid of the invention" and may for example be in the form of a genetic construct, as further described herein.

In another aspect, the invention relates to a host or host cell that expresses (or that under suitable circumstances is capable of expressing) an amino acid sequence of the invention and/or a polypeptide of the invention; and/or that contains a nucleic acid of the invention. Some preferred but non-limiting examples of such hosts or host cells will become clear from the further description herein.

The invention further relates to a product or composition containing or comprising at least one amino acid sequence of the invention, at least one polypeptide of the invention (or a suitable fragment thereof) and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention also relates to the use of an amino acid sequence, Nanobody or polypeptide of the invention, or of a composition comprising the same, in (methods or compositions for) modulating OX40L, either in vitro (e.g. in an in vitro or cellular assay) or in vivo (e.g. in an a single cell or in a multicellular organism, and in particular in a mammal, and more in particular in a human being, such as in a human being that is at risk of or suffers from an inflammatory disorder such as e.g. asthma and/or allergic asthma).

The invention also relates to methods for modulating OX40L, either in vitro (e.g. in an in vitro or cellular assay) or in vivo (e.g. in an a single cell or multicellular organism, and in particular in a mammal, and more in particular in a human being, such as in a human being that is at risk of or suffers from an inflammatory disorder such as e.g. asthma and/or allergic asthma), which method comprises at least the step of contacting OX40L with at least one amino acid sequence, Nanobody or polypeptide of the invention, or with a composition comprising the same, in a manner and in an amount suitable to modulate OX40L with at least one amino acid sequence, Nanobody or polypeptide of the invention.

The invention also relates to the use of an amino acid sequence, Nanobody or polypeptide of the invention in the preparation of a composition (such as, without limitation, a pharmaceutical composition or preparation as further described herein) for modulating OX40L, either in vitro (e.g. in an in vitro or cellular assay) or in vivo (e.g. in an a single cell or multicellular organism, and in particular in a mammal, and more in particular in a human being, such as in a human being that is at risk of or suffers from an inflammatory disorder such as e.g. asthma and/or allergic asthma).

In the context of the present invention, "modulating" or "to modulate" generally means either reducing or inhibiting the activity of, or alternatively increasing the activity of OX40L, as measured using a suitable in vitro, cellular or in vivo assay (such as those mentioned herein). In particular, "modulating" or "to modulate" may mean either reducing or inhibiting the activity of, or alternatively increasing the activity of OX40L, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of OX40L in the same assay under the same conditions but without the presence of the amino acid sequence, Nanobody or polypeptide of the invention.

As will be clear to the skilled person, "modulating" may also involve effecting a change (which may either be an increase or a decrease) in affinity, avidity, specificity and/or selectivity of OX40L for one or more of its targets, ligands or substrates; and/or effecting a change (which may either be an increase or a decrease) in the sensitivity of OX40L for one or more conditions in the medium or surroundings in which OX40L is present (such as pH, ion strength, the presence of co-factors, etc.), compared to the same conditions but without the presence of the amino acid sequence, Nanobody or polypeptide of the invention. As will be clear to the skilled person, this may again be determined in any suitable manner and/or using any suitable assay known per se, such as the assays described herein or in the prior art cited herein.

"Modulating" may also mean effecting a change (i.e. an activity as an agonist or as an antagonist, respectively) with respect to one or more biological or physiological mechanisms, effects, responses, functions, pathways or activities in which OX40L (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, such as the assays described herein or in the prior art cited herein. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the amino acid sequence, Nanobody or polypeptide of the invention.

Modulating may for example involve reducing or inhibiting the binding of OX40L to one of its substrates or ligands and/or competing with a natural ligand, substrate for binding to OX40L Modulating may also involve activating OX40L or the mechanism or pathway in which it is involved. Modulating may be reversible or irreversible, but for pharmaceutical and pharmacological purposes will usually be in a reversible manner.

The invention further relates to methods for preparing or generating the amino acid sequences, polypeptides, nucleic acids, host cells, products and compositions described herein. Some preferred but non-limiting examples of such methods will become clear from the further description herein.

Generally, these methods may comprise the steps of:
a) providing a set, collection or library of amino acid sequences; and
b) screening said set, collection or library of amino acid sequences for amino acid sequences that can bind to and/or have affinity for OX40L; and
c) isolating the amino acid sequence(s) that can bind to and/or have affinity for OX40L.

In such a method, the set, collection or library of amino acid sequences may be any suitable set, collection or library of amino acid sequences. For example, the set, collection or library of amino acid sequences may be a set, collection or library of immunoglobulin sequences (as described herein), such as a naïve set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of amino acid sequences may be a set, collection or library of heavy chain variable domains (such as $V_H$ domains or $V_{HH}$ domains) or of light chain variable domains. For example, the set, collection or library of amino acid sequences may be a set, collection or library of domain antibodies or single domain antibodies, or may be a set, collection or library of amino acid sequences that are capable of functioning as a domain antibody or single domain antibody.

In a preferred aspect of this method, the set, collection or library of amino acid sequences may be an immune set, collection or library of immunoglobulin sequences, for example derived from a mammal that has been suitably immunized with OX40L or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In another aspect, the method for generating amino acid sequences comprises at least the steps of:
a) providing a collection or sample of cells expressing amino acid sequences;
b) screening said collection or sample of cells for cells that express an amino acid sequence that can bind to and/or has affinity for OX40L; and
c) either (i) isolating said amino acid sequence; or (ii) isolating from said cell a nucleic acid sequence that encodes said amino acid sequence, followed by expressing said amino acid sequence.

For example, when the desired amino acid sequence is an immunoglobulin sequence, the collection or sample of cells may for example be a collection or sample of B-cells. Also, in this method, the sample of cells may be derived from a mammal that has been suitably immunized with OX40L or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820 (2001).

In another aspect, the method for generating an amino acid sequence directed against OX40L may comprise at least the steps of:
a) providing a set, collection or library of nucleic acid sequences encoding amino acid sequences;
b) screening said set, collection or library of nucleic acid sequences for nucleic acid sequences that encode an amino acid sequence that can bind to and/or has affinity for OX40L; and
c) isolating said nucleic acid sequence, followed by expressing said amino acid sequence.

In such a method, the set, collection or library of nucleic acid sequences encoding amino acid sequences may for example be a set, collection or library of nucleic acid sequences encoding a naïve set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

Also, in such a method, the set, collection or library of nucleic acid sequences may encode a set, collection or library of heavy chain variable domains (such as $V_H$ domains or $V_{HH}$ domains) or of light chain variable domains. For example, the set, collection or library of nucleic acid sequences may encode a set, collection or library of domain antibodies or single domain antibodies, or a set, collection or library of amino acid sequences that are capable of functioning as a domain antibody or single domain antibody.

In a preferred aspect of this method, the set, collection or library of nucleic acid sequences may be an immune set, collection or library of nucleic acid sequences, for example derived from a mammal that has been suitably immunized with OX40L or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The set, collection or library of nucleic acid sequences may for example encode an immune set, collection or library of heavy chain variable domains or of light chain variable domains. In one specific aspect, the set, collection or library of nucleotide sequences may encode a set, collection or library of $V_{HH}$ sequences.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

In another aspect, the method for generating an amino acid sequence directed against OX40L may comprise at least the steps of:
a) providing a set, collection or library of nucleic acid sequences encoding amino acid sequences;
b) screening said set, collection or library of nucleic acid sequences for nucleic acid sequences that encode an amino acid sequence that can bind to and/or has affinity for OX40L and that is cross-blocked or is cross blocking a Nanobody of the invention, e.g. one of SEQ ID NO's: 179 to 185 (Table A-1), or a humanized or sequence optimized Nanobody of the invention such as e.g. one of SEQ ID NO's: 199 to 226 (Table A-2), or a polypeptide or construct of the invention, e.g. one of SEQ ID NO's: 186 to 198 and 227 to 234 (see Table A-3 and Table A-4); and
c) isolating said nucleic acid sequence, followed by expressing said amino acid sequence.

The invention also relates to amino acid sequences that are obtained by the above methods, or alternatively by a method that comprises the one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Also, following the steps above, one or more amino acid sequences of the invention may be suitably humanized (or alternatively camelized); and/or the amino acid sequence(s) thus obtained may be linked to each other or to one or more other suitable amino acid sequences (optionally via one or more suitable linkers) so as to provide a polypeptide of the invention. Also, a nucleic acid sequence encoding an amino acid sequence of the invention may be suitably humanized (or alternatively camelized) and suitably expressed; and/or one or more nucleic acid sequences encoding an amino acid sequence of the invention may be linked to each other or to one or more nucleic acid sequences that encode other suitable amino acid sequences (optionally via nucleotide sequences that encode one or more suitable linkers), after which the nucleotide sequence thus obtained may be suitably expressed so as to provide a polypeptide of the invention.

The invention further relates to applications and uses of the amino acid sequences, compounds, constructs, polypeptides, nucleic acids, host cells, products and compositions described herein, as well as to methods for the prevention and/or treatment for diseases and disorders associated with OX40L Some preferred but non-limiting applications and uses will become clear from the further description herein.

The invention also relates to the amino acid sequences, compounds, constructs, polypeptides, nucleic acids, host cells, products and compositions described herein for use in therapy.

In particular, the invention also relates to the amino acid sequences, compounds, constructs, polypeptides, nucleic acids, host cells, products and compositions described herein for use in therapy of a disease or disorder that can be prevented or treated by administering, to a subject in need thereof, of (a pharmaceutically effective amount of) an amino acid sequence, compound, construct or polypeptide as described herein.

More in particular, the invention relates to the amino acid sequences, compounds, constructs, polypeptides, nucleic acids, host cells, products and compositions described herein for use in therapy of inflammatory disorders such as e.g. asthma and/or allergic asthma.

Other aspects, embodiments, advantages and applications of the invention will also become clear from the further description herein, in which the invention will be described and discussed in more detail with reference to the Nanobodies of the invention and polypeptides of the invention comprising the same, which form some of the preferred aspects of the invention.

As will become clear from the further description herein, Nanobodies generally offer certain advantages (outlined herein) compared to "dAb's" or similar (single) domain antibodies or immunoglobulin sequences, which advantages are also provided by the Nanobodies of the invention. However, it will be clear to the skilled person that the more general aspects of the teaching below can also be applied (either directly or analogously) to other amino acid sequences of the invention.

DETAILED DESCRIPTION OF THE INVENTION

Figure 1:
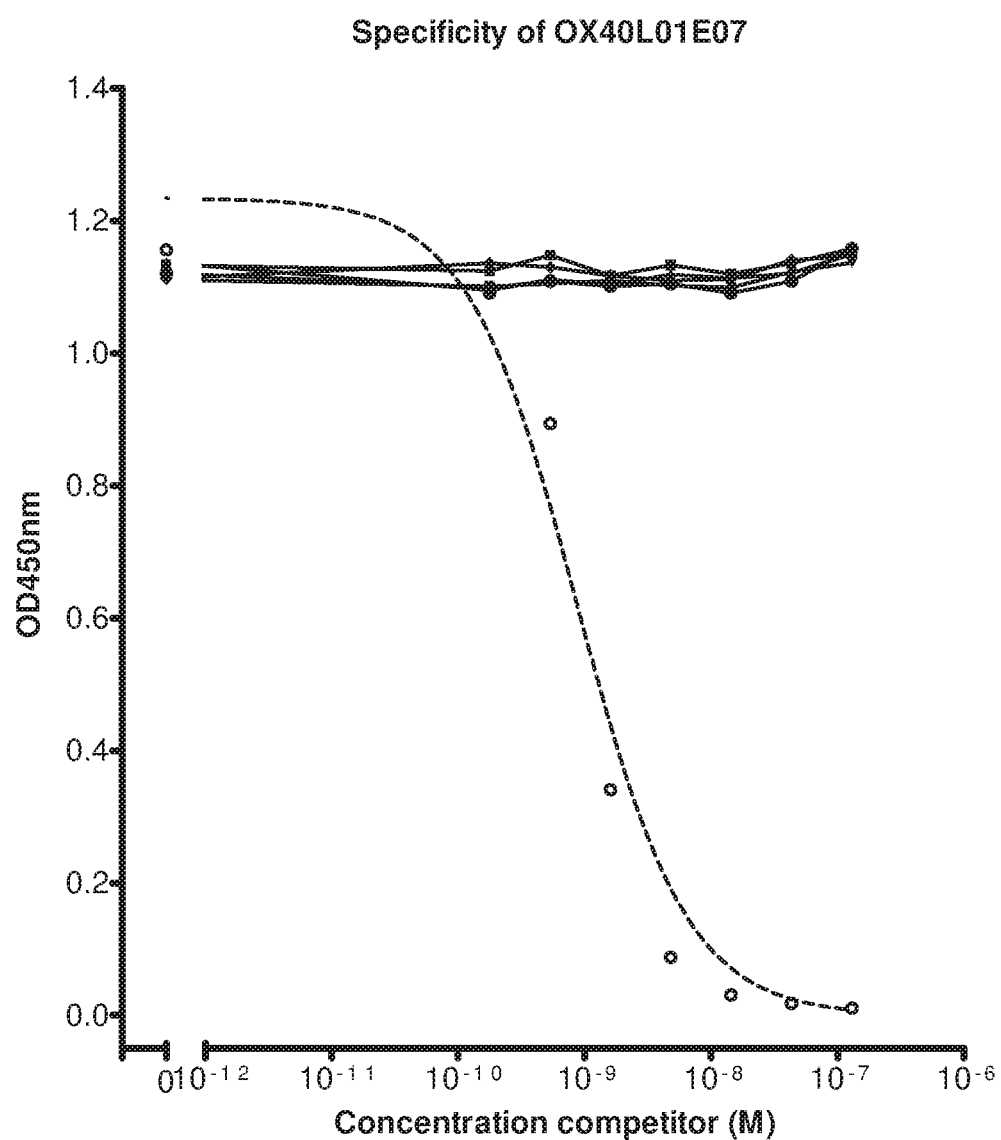
FIG. 1: Specificity of OX40L blocking Nanobody OX40L01E07. Binding of the OX40L01E07 to hOX40L captured on neutravidin was only inhibited by exogenously added hOX40L (o, dashed line) and was not affected by the addition of the other TNF superfamily members, i.e. hRANKL (a), hCD30L (▲), hCD40L (▼), hTRAIL (¯) or hTNFa (•).

In the present description, examples and claims:
a) Unless indicated or defined otherwise, all terms used have their usual meaning in the art, which will be clear to the skilled person. Reference is for example made to the standard handbooks mentioned in paragraph a) on page 46 of WO 08/020079.
b) Unless indicated otherwise, the terms "immunoglobulin sequence", "sequence", "nucleotide sequence" and "nucleic acid" are as described in paragraph b) on page 46 of WO 08/020079.
c) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.
d) Amino acid residues will be indicated according to the standard three-letter or one-letter amino acid code. Reference is made to Table A-2 on page 48 of the International application WO 08/020079 of Ablynx N.V. entitled "Amino acid sequences directed against IL-6R and polypeptides comprising the some for the treatment of diseases and disorders associated with 11-6 mediated signalling".
e) For the purposes of comparing two or more nucleotide sequences, the percentage of "sequence identity" between a first nucleotide sequence and a second nucleotide sequence may be calculated or determined as described in paragraph e) on page 49 of WO 08/020079 (incorporated herein by reference), such as by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique, again as described in paragraph e) on pages 49 of WO 08/020079 (incorporated herein by reference).
f) For the purposes of comparing two or more amino acid sequences, the percentage of "sequence identity" between a first amino acid sequence and a second amino acid sequence (also referred to herein as "amino acid identity") may be calculated or determined as described in paragraph f) on pages 49 and 50 of WO 08/020079 (incorporated herein by reference), such as by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein; or using a suitable computer algorithm or technique, again as described in paragraph f) on pages 49 and 50 of WO 08/020079 (incorporated herein by reference).

Also, in determining the degree of sequence identity between two amino acid sequences, the skilled person may take into account so-called "conservative" amino acid substitutions, as described on page 50 of WO 08/020079.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J Molec. Biol. 157: 105-132, 198 1, and Goldman et al., Ann. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_H$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

g) Amino acid sequences and nucleic acid sequences are said to be "exactly the same" if they have 100% sequence identity (as defined herein) over their entire length.
h) When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences.
i) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020079.
j) The term "in essentially isolated form" has the meaning given to it in paragraph j) on pages 52 and 53 of WO 08/020079.
k) The terms "domain" and "binding domain" have the meanings given to it in paragraph k) on page 53 of WO 08/020079.
l) The term "variable domain" refers to the part or domain of an immunoglobulin molecule or antibody which is partially or fully responsible for antigen binding.
m) The term "single variable domain" or "immunoglobulin single variable domain", defines molecules wherein the antigen binding site is present on, and formed by, a single immunoglobulin domain. This sets single variable domains apart from "conventional" immunoglobulins or their fragments, wherein two immunoglobulin domains, in particular two "variable domains" interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs. The term "immunoglobulin single variable domain" does comprise fragments of conventional immunoglobulins wherein the antigen binding site is formed by a single variable domain.

Generally, immunoglobulin single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's). Such immunoglobulin single variable domains and fragments are most preferably such that they comprise an immunoglobulin fold or are capable for forming, under suitable conditions, an immunoglobulin fold. As such, the immunoglobulin single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the immunoglobulin single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

In one aspect of the invention, the immunoglobulin single variable domains are light chain variable domain sequences (e.g. a $V_L$-sequence), or heavy chain variable domain sequences (e.g. a $V_H$-sequence); more specifically, the single variable domains can be heavy chain variable domain sequences that are derived from a conventional four-chain antibody or heavy chain variable domain sequences that are derived from a heavy chain antibody.

The immunoglobulin single variable domain may be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody® (as defined herein, and including but not limited to a $V_{HH}$ sequence) [Note: Nanobody® and Nanobodies® are registered trademarks of Ablynx N.V.]; other immunoglobulin single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341: 544-546), to Holt et al. 2003 (Trends Biotechnol. 21: 484-490); as well as to for example WO 04/068820, WO 06/030220, WO 06/003388 and other published patent applications of Domantis Ltd. It should also be noted that, although less preferred in the context of the present invention because they are not of mammalian origin, immunoglobulin single variable domains can be derived from certain species of shark (for example, the so-called "IgNAR domains", see for example WO 05/18629).

n) The terms "antigenic determinant" and "epitope", which may also be used interchangeably herein, have the meanings given to it in paragraph l) on page 53 of WO 08/020079.

o) As further described in paragraph m) on page 53 of WO 08/020079, an amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

p) The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as a Nanobody or a polypeptide of the invention) molecule can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as a Nanobody or polypeptide of the invention) and the pertinent antigen. Typically, antigen-binding proteins (such as the amino acid sequences, Nanobodies and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^5$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

q) The half-life of an amino acid sequence, compound or polypeptide of the invention can generally be defined as described in paragraph o) on page 57 of WO 08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t½-alpha, t½-beta and the area under the curve (AUC). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" as also as defined in paragraph o) on page 57 of WO 08/020079 and in particular refer to an increase in the t1/2-beta, either with or without an increase in the t1/2-alpha and/or the AUC or both.

r) In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention.

Modulating may for example also involve allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may for example also involve effecting a change in respect of the folding or confirmation of the target or antigen, or in respect of the ability of the target or antigen to fold, to change its confirmation (for example, upon binding of a ligand), to associate with other (sub)units, or to disassociate. Modulating may for example also involve effecting a change in the ability of the target or antigen to transport other compounds or to serve as a channel for other compounds (such as ions).

Modulating may be reversible or irreversible, but for pharmaceutical and pharmacological purposes will usually be in a reversible manner.

s) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

t) An amino acid sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10.000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or polypeptide. Preferably, when an amino acid sequence or polypeptide is "specific for" a first target or antigen compared to a second target or antigen, it is directed against (as defined herein) said first target or antigen, but not directed against said second target or antigen.

u) The terms "cross-block", "cross-blocked" and "cross-blocking" are used interchangeably herein to mean the ability of an amino acid sequence or other binding agents (such as a Nanobody, polypeptide or compound or construct of the invention) to interfere with the binding of other amino acid sequences or binding agents of the invention to a given target. The extend to which an amino acid sequence or other binding agents of the invention is able to interfere with the binding of another to the target, and therefore whether it can be said to cross-block according to the invention, can be determined using competition binding assays. One particularly suitable quantitative cross-blocking assay uses a Biacore machine which can measure the extent of interactions using surface plasmon resonance technology. Another suitable quantitative cross-blocking assay uses an ELISA-based approach to measure competition between amino acid sequences or other binding agents in terms of their binding to the target. The following generally describes a suitable Biacore assay for determining whether an amino acid sequence or other binding agent cross-blocks or is capable of cross-blocking according to the invention. It will be appreciated that the assay can be used with any of the amino acid sequences or other binding agents described herein. The Biacore machine (for example the Biacore 3000) is operated in line with the manufacturer's recommendations. Thus in one cross-blocking assay, the target protein is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound amino acid sequences without damaging the chip-bound target. Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or other binding agent according to the invention is one which will bind to the target in the above Biacore cross-blocking assay such that, during the assay and in the presence of a second amino acid sequence or other binding agent of the invention, the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination. The Biacore assay described above is a primary assay used to determine if amino acid sequences or other binding agents cross-block each other according to the invention. On rare occasions particular amino acid sequences or other binding agents may not bind to target coupled via amine chemistry to a CM5 Biacore chip (this usually occurs when the relevant binding site on target is masked or destroyed by the coupling to the chip). In such cases cross-blocking can be determined using a tagged version of the target, for example a N-terminal His-tagged version. In this particular format, an anti-His amino acid sequence would be coupled to the Biacore chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged target, C-terminal His-tagged target could alternatively be used.

Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an amino acid sequence or other binding agent directed against a target cross-blocks or is capable of cross-blocking as defined herein. It will be appreciated that the assay can be used with any of the amino acid sequences (or other binding agents such as polypeptides of the invention) described herein. The general principal of the assay is to have an amino acid sequence or binding agent that is directed against the target coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target amino acid sequence (in this case Ab-X). The background signal for the assay is defined as the signal obtained in wells with the coated amino acid sequence (in this case Ab-X), second solution phase amino acid sequence (in this case Ab-Y), target buffer only (i.e. without target) and target detection reagents. The positive control signal for the assay is defined as the signal obtained in wells with the coated amino acid sequence (in this case Ab-X), second solution phase amino acid sequence buffer only (i.e. without second solution phase amino acid sequence), target and target detection reagents. The ELISA assay may be run in such a manner so as to have the positive control signal be at least 6 times the background signal. To avoid any artefacts (e.g. significantly different affinities between Ab-X and Ab-Y for the target) resulting from the choice of which amino acid sequence to use as the coating amino acid sequence and which to use as the second (competitor) amino acid sequence, the cross-blocking assay may be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal (i.e. the amount of target bound by the coated amino acid sequence) as compared to the target detection signal obtained in the absence of the solution phase anti-target amino acid sequence (i.e. the positive control wells).

v) An amino acid sequence is said to be "cross-reactive" for two different antigens or antigenic determinants (such as serum albumin from two different species of mammal, such as human serum albumin and cyno serum albumin) if it is specific for (as defined herein) both these different antigens or antigenic determinants.

w) By binding that is "essentially independent of the pH" is generally meant herein that the association constant ($K_A$) of the amino acid sequence with respect to the serum protein (such as serum albumin) at the pH value(s) that occur in a cell of an animal or human body (as further described herein) is at least 5%, such as at least 10%, preferably at least 25%, more preferably at least 50%, even more preferably at least 60%, such as even more preferably at least 70%, such as at least 80% or 90% or more (or even more than 100%, such as more than 110%, more than 120% or even 130% or more, or even more than 150%, or even more than 200%) of the association constant ($K_A$) of the amino acid sequence with respect to the same serum protein at the pH value(s) that occur outside said cell. Alternatively, by binding that is "essentially independent of the pH" is generally meant herein that the $k_{off}$ rate (measured by Biacore) of the amino acid sequence with respect to the serum protein (such as serum albumin) at the pH value(s) that occur in a cell of an animal or human body (as e.g. further described herein, e.g. pH around 5.5, e.g. 5.3 to 5.7) is at least 5%, such as at least 10%, preferably at least 25%, more preferably at least 50%, even more preferably at least 60%, such as even more preferably at least 70%, such as at least 80% or 90% or more (or even more than 100%, such as more than 110%, more than 120% or even 130% or more, or even more than 150%, or even more than 200%) of the $k_{off}$ rate of the amino acid sequence with respect to the same serum protein at the pH value(s) that occur outside said cell, e.g. pH 7.2 to 7.4. By "the pH value(s) that occur in a cell of an animal or human body" is meant the pH value(s) that may occur inside a cell, and in particular inside a cell that is involved in the recycling of the serum protein. In particular, by "the pH value(s) that occur in a cell of an animal or human body" is meant the pH value(s) that may occur inside a (sub)cellular compartment or vesicle that is involved in recycling of the serum protein (e.g. as a result of pinocytosis, endocytosis, transcytosis, exocytosis and phagocytosis or a similar mechanism of uptake or internalization into said cell), such as an endosome, lysosome or pinosome.

x) As further described herein, the total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein;

y) As further described in paragraph q) on pages 58 and 59 of WO 08/020079 (incorporated herein by reference), the amino acid residues of a Nanobody are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication), and accordingly FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113.

z) The Figures, Sequence Listing and the Experimental Part/Examples are only given to further illustrate the invention and should not be interpreted or construed as limiting the scope of the invention and/or of the appended claims in any way, unless explicitly indicated otherwise herein.

For a general description of heavy chain antibodies and the variable domains thereof, reference is inter alia made to the prior art cited herein, as well as to the prior art mentioned on page 59 of WO 08/020079 and to the list of references mentioned on pages 41-43 of the International application WO 06/040153, which prior art and references are incorporated herein by reference.

In accordance with the terminology used in the art (see the above references), the variable domains present in naturally occurring heavy chain antibodies will also be referred to as "$V_{HH}$ domains", in order to distinguish them from the heavy chain variable domains that are present in conventional 4-chain antibodies (which will be referred to hereinbelow as "$V_H$ domains") and from the light chain variable domains that are present in conventional 4-chain antibodies (which will be referred to hereinbelow as "$V_L$ domains").

As mentioned in the prior art referred to above, $V_{HH}$ domains have a number of unique structural characteristics and functional properties which make isolated $V_{HH}$ domains (as well as Nanobodies based thereon, which share these structural characteristics and functional properties with the naturally occurring $V_{HH}$ domains) and proteins containing the same highly advantageous for use as functional antigen-binding domains or proteins. In particular, and without being limited thereto, $V_{HH}$ domains (which have been "designed" by nature to functionally bind to an antigen without the presence of, and without any interaction with, a light chain variable domain) and Nanobodies can function as a single, relatively small, functional antigen-binding structural unit, domain or protein. This distinguishes the $V_{HH}$ domains from the $V_H$ and $V_L$ domains of conventional 4-chain antibodies, which by themselves are generally not suited for practical application as single antigen-binding proteins or domains, but need to be combined in some form or another to provide a functional antigen-binding unit (as in for example conventional antibody fragments such as Fab fragments; in ScFv's fragments, which consist of a $V_H$ domain covalently linked to a $V_L$ domain).

Because of these unique properties, the use of $V_{HH}$ domains and Nanobodies as single antigen-binding proteins or as antigen-binding domains (i.e. as part of a larger protein or polypeptide) offers a number of significant advantages over the use of conventional $V_H$ and $V_L$ domains, scFv's or conventional antibody fragments (such as Fab- or F(ab')$_2$-fragments), including the advantages that are listed on pages 60 and 61 of WO 08/020079.

In a specific and preferred aspect, the invention provides Nanobodies against OX40L, and in particular Nanobodies against OX40L from a warm-blooded animal, and more in particular Nanobodies against OX40L from a mammal, and especially Nanobodies against human OX40L; as well as proteins and/or polypeptides comprising at least one such Nanobody.

In particular, the invention provides Nanobodies against OX40L, and proteins and/or polypeptides comprising the same, that have improved therapeutic and/or pharmacological properties and/or other advantageous properties (such as, for example, improved ease of preparation and/or reduced costs of goods), compared to conventional antibodies against OX40L or fragments thereof, compared to constructs that could be based on such conventional antibodies or antibody fragments (such as Fab' fragments, F(ab')$_2$ fragments, ScFv constructs, "diabodies" and other multispecific constructs (see for example the review by Holliger and Hudson, Nat Biotechnol. 2005 September; 23(9):1126-36)), and also compared to the so-called "dAb's" or similar (single) domain antibodies that may be derived from variable domains of conventional antibodies. These improved and advantageous properties will become clear from the further description herein, and for example include, without limitation, one or more of:

increased affinity and/or avidity for OX40L, either in a monovalent format, in a multivalent format (for example in a bivalent format) and/or in a multispecific format (for example one of the multispecific formats described hereinbelow);

better suitability for formatting in a multivalent format (for example in a bivalent format); better suitability for formatting in a multispecific format (for example one of the multispecific formats described hereinbelow);

improved suitability or susceptibility for "humanizing" substitutions (as defined herein);

less immunogenicity, either in a monovalent format, in a multivalent format (for example in a bivalent format) and/or in a multispecific format (for example one of the multispecific formats described hereinbelow);

increased stability, either in a monovalent format, in a multivalent format (for example in a bivalent format) and/or in a multispecific format (for example one of the multispecific formats described hereinbelow);

increased specificity towards OX40L, either in a monovalent format, in a multivalent format (for example in a bivalent format) and/or in a multispecific format (for example one of the multispecific formats described hereinbelow);

decreased or where desired increased cross-reactivity with OX40L from different species; and/or one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described hereinbelow).

As generally described herein for the amino acid sequences of the invention, the Nanobodies of the invention are preferably in essentially isolated form (as defined herein), or form part of a protein or polypeptide of the invention (as defined herein), which may comprise or essentially consist of one or more Nanobodies of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than OX40L), so as to provide a monovalent, multivalent or multispecific polypeptide of the invention, respectively, all as described herein. In particular, such a protein or polypeptide may comprise or essentially consist of one or more Nanobodies of the invention and optionally one or more (other) Nanobodies (i.e. directed against other targets than OX40L), all optionally linked via one or more suitable linkers, so as to provide a monovalent, multivalent or multispecific Nanobody construct, respectively, as further described herein. Such proteins or polypeptides may also be in essentially isolated form (as defined herein).

In a Nanobody of the invention, the binding site for binding against OX40L is preferably formed by the CDR sequences. Optionally, a Nanobody of the invention may also, and in addition to the at least one binding site for binding against OX40L, contain one or more further binding sites for binding against other antigens, proteins or targets. For methods and positions for introducing such second binding sites, reference is for example made to Keck and Huston, Biophysical Journal, 71, October 1996, 2002-2011; EP 0 640 130; and WO 06/07260.

As generally described herein for the amino acid sequences of the invention, when a Nanobody of the invention (or a polypeptide of the invention comprising the same) is intended for administration to a subject (for example for therapeutic and/or diagnostic purposes as described herein), it is preferably directed against human OX40L; whereas for veterinary purposes, it is preferably directed against OX40L from the species to be treated. Also, as with the amino acid sequences of the invention, a Nanobody of the invention may or may not be cross-reactive (i.e. directed against OX40L from two or more species of mammal, such as against human OX40L and OX40L from at least one of the species of mammal mentioned herein).

Also, again as generally described herein for the amino acid sequences of the invention, the Nanobodies of the invention may generally be directed against any antigenic determinant, epitope, part, domain, subunit or confirmation (where applicable) of OX40L.

As already described herein, the amino acid sequence and structure of a Nanobody can be considered—without however being limited thereto—to be comprised of four framework regions or "FR's" (or sometimes also referred to as "FW's"), which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. Some preferred framework sequences and CDR's (and combinations thereof) that are present in the Nanobodies of the invention are as described herein. Other suitable CDR sequences can be obtained by the methods described herein.

According to a non-limiting but preferred aspect of the invention, (the CDR sequences present in) the Nanobodies of the invention are such that:

the Nanobodies can bind to OX40L with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that:

the Nanobodies can bind to OX40L with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

the Nanobodies can bind to OX40L with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^4$ $s^{-1}$ and $10^{-6}$ $s^{-1}$.

Preferably, (the CDR sequences present in) the Nanobodies of the invention are such that: a monovalent Nanobody of the invention (or a polypeptide that contains only one Nanobody of the invention) is preferably such that it will bind to OX40L with an affinity less than 500 nM, preferably less than 200 nM, more preferably less than 10 nM, such as less than 500 pM.

The affinity of the Nanobody of the invention against OX40L can be determined in a manner known per se, for example using the general techniques for measuring $K_D$, $K_A$, $k_{off}$ or $k_{on}$ mentioned herein, as well as some of the specific assays described herein.

Some preferred IC50 values for binding of the Nanobodies of the invention (and of polypeptides comprising the same) to OX40L will become clear from the further description and examples herein.

In a preferred but non-limiting aspect, the invention relates to a Nanobody (as defined herein) against OX40L, which consists of 4 framework regions (FR1 to FR4 respectively) and 3 complementarity determining regions (CDR1 to CDR3 respectively), in which:

CDR1 is chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;

and/or

CDR2 is chosen from the group consisting of:
d) the amino acid sequences of SEQ ID NO's: 147 to 153;
e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;

and/or
CDR3 is chosen from the group consisting of:
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167;
or any suitable fragment of such an amino acid sequence.

In particular, according to this preferred but non-limiting aspect, the invention relates to a Nanobody (as defined herein) against OX40L, which consists of 4 framework regions (FR1 to FR4 respectively) and 3 complementarity determining regions (CDR1 to CDR3 respectively), in which:

CDR1 is chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;
and
CDR2 is chosen from the group consisting of:
d) the amino acid sequences of SEQ ID NO's: 147 to 153;
e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
and
CDR3 is chosen from the group consisting of:
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167;
or any suitable fragment of such an amino acid sequences.

As generally mentioned herein for the amino acid sequences of the invention, when a Nanobody of the invention contains one or more CDR1 sequences according to b) and/or c):
i) any amino acid substitution in such a CDR according to b) and/or c) is preferably, and compared to the corresponding CDR according to a), a conservative amino acid substitution (as defined herein);
and/or
ii) the CDR according to b) and/or c) preferably only contains amino acid substitutions, and no amino acid deletions or insertions, compared to the corresponding CDR according to a);
and/or
iii) the CDR according to b) and/or c) may be a CDR that is derived from a CDR according to a) by means of affinity maturation using one or more techniques of affinity maturation known per se.

Similarly, when a Nanobody of the invention contains one or more CDR2 sequences according to e) and/or f):
i) any amino acid substitution in such a CDR according to e) and/or f) is preferably, and compared to the corresponding CDR according to d), a conservative amino acid substitution (as defined herein);
and/or
ii) the CDR according to e) and/or f) preferably only contains amino acid substitutions, and no amino acid deletions or insertions, compared to the corresponding CDR according to d);
and/or
iii) the CDR according to e) and/or f) may be a CDR that is derived from a CDR according to d) by means of affinity maturation using one or more techniques of affinity maturation known per se.

Also, similarly, when a Nanobody of the invention contains one or more CDR3 sequences according to h) and/or i):
i) any amino acid substitution in such a CDR according to h) and/or i) is preferably, and compared to the corresponding CDR according to g), a conservative amino acid substitution (as defined herein);
and/or
ii) the CDR according to h) and/or i) preferably only contains amino acid substitutions, and no amino acid deletions or insertions, compared to the corresponding CDR according to g);
and/or
iii) the CDR according to h) and/or i) may be a CDR that is derived from a CDR according to g) by means of affinity maturation using one or more techniques of affinity maturation known per se.

It should be understood that the last three paragraphs generally apply to any Nanobody of the invention that comprises one or more CDR1 sequences, CDR2 sequences and/or CDR3 sequences according to b), c), e), f), h) or i), respectively.

Of the Nanobodies of the invention, Nanobodies comprising one or more of the CDR's explicitly listed above are particularly preferred; Nanobodies comprising two or more of the CDR's explicitly listed above are more particularly preferred; and Nanobodies comprising three of the CDR's explicitly listed above are most particularly preferred.

Some particularly preferred, but non-limiting combinations of CDR sequences, as well as preferred combinations of CDR sequences and framework sequences, are mentioned in Table B-1 below, which lists the CDR sequences and framework sequences that are present in a number of preferred (but non-limiting) Nanobodies of the invention. As will be clear to the skilled person, a combination of CDR1, CDR2 and CDR3 sequences that occur in the same clone (i.e. CDR1, CDR2 and CDR3 sequences that are mentioned on the same line in Table B-1) will usually be preferred (although the invention in its broadest sense is not limited thereto, and also comprises other suitable combinations of the CDR sequences mentioned in Table B-1). Also, a combination of CDR sequences and framework sequences that occur in the same clone (i.e. CDR sequences and framework sequences that are mentioned on the same line in Table B-1) will usually be preferred (although the invention in its broadest sense is not limited thereto, and also comprises other suitable combinations of the CDR sequences and framework sequences mentioned in Table B-1, as well as combinations of such CDR sequences and other suitable framework sequences, e.g. as further described herein).

Also, in the Nanobodies of the invention that comprise the combinations of CDR's mentioned in Table B-1, each CDR can be replaced by a CDR chosen from the group consisting of amino acid sequences that have at least 80%, preferably at least 90%, more preferably at least 95%, even more preferably at least 99% sequence identity (as defined herein) with the mentioned CDR's; in which:

i) any amino acid substitution in such a CDR is preferably, and compared to the corresponding CDR sequence mentioned in Table B-1, a conservative amino acid substitution (as defined herein);

and/or ii) any such CDR sequence preferably only contains amino acid substitutions, and no amino acid deletions or insertions, compared to the corresponding CDR sequence mentioned in Table B-1;

and/or iii) any such CDR sequence is a CDR that is derived by means of a technique for affinity maturation known per se, and in particular starting from the corresponding CDR sequence mentioned in Table B-1.

However, as will be clear to the skilled person, the (combinations of) CDR sequences, as well as (the combinations of) CDR sequences and framework sequences mentioned in Table B-1 will generally be preferred.

TABLE B4

Preferred combinations of CDR sequences, preferred combinations of framework sequences, and preferred combinations of framework and CDR sequences. ("ID" refers to the SEQ ID NO as used herein

| ID | FR1 | ID | CDR1 | ID | FR2 | ID | CDR2 | ID | FR3 | ID | CDR3 | ID | FR4 |
|---|---|---|---|---|---|---|---|---|---|---|---|---|---|
| 126 | EVQLVESGGGLVQAGG SLRLSCAASRSIGR | 133 | LDRMG | 140 | WYRHRTGE PRELVA | 147 | TITGGSSINYG DFVKG | 154 | RFTISIDNAKNTV YLQMNNLKPEDT AVYYCNF | 161 | NKYVTSRD T | 168 | WGQGTQ VTVSS |
| 127 | EVQLVESGGGLVQAGG SLRLSCVASGRSFS | 134 | TYIMG | 141 | WFRQAPG KEREFVA | 148 | TISRSGITTRS ADSVKG | 155 | RFTISRDNAKNT VVLQMNSLKPED TAVYYCAA | 162 | GPYVEQTL GLYQTLGP WDY | 169 | WGQGTQ VTVSS |
| 128 | EVQLVESGGGLVQAGG SLRLSCAASGRTFS | 135 | SIYAKG | 142 | WFRQAPG KEREFVA | 149 | AISRSGRSTSY ADSVKG | 156 | RFTISRDNAKNT VVLQMNSLKPED TAVYYCAA | 163 | VGGATTV TASEWDY | 170 | WGLGTQV TVSS |
| 129 | EVQLVESGGGLVQAGD SLRLSCAASGLTFS | 136 | SFAMG | 143 | WFRQAPG KEREFVA | 150 | AISRSGYGTSE ADSVRD | 157 | RFIISRDNAKNTV TLHLSRLKPEDTA VYYCAA | 164 | EHTLGRPS RSQINYLY | 171 | WGQGTQ VTVSS |
| 130 | EVQLVESGGGLVQAGG SLRLSCAASRNILS | 137 | LNTMG | 144 | WYRHAPG KPRELVA | 151 | RISSNSKTDYA DSVKG | 158 | RFTISRDNAKNT VILQMNSLKPED TGVYYCNL | 165 | NVWRTSS DY | 172 | WGQGTQ VTVSS |
| 131 | EVQLVESGGGLVQAGG SLRLSCAASGFTLD | 138 | DYAIA | 145 | WFRQAPG KEREGVS | 152 | RIKISNGRTTY AGSVKG | 159 | RFTISSDNAKNTV YLQMNLNAEDT AVYYCAA | 166 | DRSSLLFG SNWDRKA RYDY | 173 | WGQGTQ VTVSS |
| 132 | EVQLVESGGGLVQAGA SLRLSCAASGRRFI | 139 | SNYAM G | 146 | WFRQAPG QERAFVA | 153 | AISRSGSITYY TDSVKG | 160 | RFSISRDYAKSTV YLQMDNLKPEDT AVYYCAA | 167 | DGGAVRD LTTNLPDY | 174 | WGRGTQ VTVSS |

Thus, in the Nanobodies of the invention, at least one of the CDR1, CDR2 and CDR3 sequences present is suitably chosen from the group consisting of the CDR1, CDR2 and CDR3 sequences, respectively, listed in Table B-1; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table B-1; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table B-1.

In this context, by "suitably chosen" is meant that, as applicable, a CDR1 sequence is chosen from suitable CDR1 sequences (i.e. as defined herein), a CDR2 sequence is chosen from suitable CDR2 sequences (i.e. as defined herein), and a CDR3 sequence is chosen from suitable CDR3 sequence (i.e. as defined herein), respectively. More in particular, the CDR sequences are preferably chosen such that the Nanobodies of the invention bind to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein.

In particular, in the Nanobodies of the invention, at least the CDR3 sequence present is suitably chosen from the group consisting of the CDR3 sequences listed in Table B-1 or from the group of CDR3 sequences that have at least 80%, preferably at least 90%, more preferably at least 95%, even more preferably at least 99% sequence identity with at least one of the CDR3 sequences listed in Table B-1; and/or from the group consisting of the CDR3 sequences that have 3, 2 or only 1 amino acid difference(s) with at least one of the CDR3 sequences listed in Table B-1.

Preferably, in the Nanobodies of the invention, at least two of the CDR1, CDR2 and CDR3 sequences present are suitably chosen from the group consisting of the CDR1, CDR2 and CDR3 sequences, respectively, listed in Table B-1 or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-1; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table B-1.

In particular, in the Nanobodies of the invention, at least the CDR3 sequence present is suitably chosen from the group consisting of the CDR3 sequences listed in Table B-1 or from the group of CDR3 sequences that have at least 80%, preferably at least 90%, more preferably at least 95%, even more preferably at least 99% sequence identity with at least one of the CDR3 sequences listed in Table B-1, respectively; and at least one of the CDR1 and CDR2 sequences present is suitably chosen from the group consisting of the CDR1 and CDR2 sequences, respectively, listed in Table B-1 or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table B-1; and/or from the group consisting of the CDR1 and CDR2 sequences, respectively, that have 3, 2 or only 1 amino acid difference(s) with at least one of the CDR1 and CDR2 sequences, respectively, listed in Table B-1.

Most preferably, in the Nanobodies of the invention, all three CDR1, CDR2 and CDR3 sequences present are suitably chosen from the group consisting of the CDR1, CDR2 and CDR3 sequences, respectively, listed in Table B-1 or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-1; and/or from the group consisting of the CDR1, CDR2 and CDR3 sequences, respectively, that have 3, 2 or only 1 amino acid difference(s) with at least one of the CDR1, CDR2 and CDR3 sequences, respectively, listed in Table B-1.

Even more preferably, in the Nanobodies of the invention, at least one of the CDR1, CDR2 and CDR3 sequences present is suitably chosen from the group consisting of the CDR1, CDR2 and CDR3 sequences, respectively, listed in Table B-1. Preferably, in this aspect, at least one or preferably both of the other two CDR sequences present are suitably chosen from CDR sequences that have at least 80%, preferably at least 90%, more preferably at least 95%, even more preferably at least 99% sequence identity with at least one of the corresponding CDR sequences, respectively, listed in Table B-1; and/or from the group consisting of the CDR sequences that have 3, 2 or only 1 amino acid difference(s) with at least one of the corresponding sequences, respectively, listed in Table B-1.

In particular, in the Nanobodies of the invention, at least the CDR3 sequence present is suitably chosen from the group consisting of the CDR3 listed in Table B-1. Preferably, in this aspect, at least one and preferably both of the CDR1 and CDR2 sequences present are suitably chosen from the groups of CDR1 and CDR2 sequences, respectively, that have at least 80%, preferably at least 90%, more preferably at least 95%, even more preferably at least 99% sequence identity with the CDR1 and CDR2 sequences, respectively, listed in Table B-1; and/or from the group consisting of the CDR1 and CDR2 sequences, respectively, that have 3, 2 or only 1 amino acid difference(s) with at least one of the CDR1 and CDR2 sequences, respectively, listed in Table B-1.

Even more preferably, in the Nanobodies of the invention, at least two of the CDR1, CDR2 and CDR3 sequences present are suitably chosen from the group consisting of the CDR1, CDR2 and CDR3 sequences, respectively, listed in Table B-1. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-1; and/or from the group consisting of CDR sequences that have 3, 2 or only 1 amino acid difference(s) with at least one of the corresponding sequences listed in Table B-1.

In particular, in the Nanobodies of the invention, at least the CDR3 sequence is suitably chosen from the group consisting of the CDR3 sequences listed in Table B-1, and either the CDR1 sequence or the CDR2 sequence is suitably chosen from the group consisting of the CDR1 and CDR2 sequences, respectively, listed in Table B-1. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-1; and/or from the group consisting of CDR sequences that have 3, 2 or only 1 amino acid difference(s) with the corresponding CDR sequences listed in Table B-1.

Even more preferably, in the Nanobodies of the invention, all three CDR1, CDR2 and CDR3 sequences present are suitably chosen from the group consisting of the CDR1, CDR2 and CDR3 sequences, respectively, listed in Table B-1.

Also, generally, the combinations of CDR's listed in Table B-1 (i.e. those mentioned on the same line in Table B-1) are preferred. Thus, it is generally preferred that, when a CDR in a Nanobody of the invention is a CDR sequence mentioned in Table B-1 or is suitably chosen from the group of CDR sequences that have at least 80%, preferably at least 90%, more preferably at least 95%, even more preferably at least 99% sequence identity with a CDR sequence listed in Table B-1; and/or from the group consisting of CDR sequences that have 3, 2 or only 1 amino acid difference(s) with a CDR sequence listed in Table B-1, that at least one and preferably both of the other CDR's are suitably chosen from the CDR sequences that belong to the same combination in Table B-1 (i.e. mentioned on the same line in Table B-1) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table B-1.

Thus, by means of non-limiting examples, a Nanobody of the invention can for example comprise a CDR1 sequence that has more than 80% sequence identity with one of the CDR1 sequences mentioned in Table B-1, a CDR2 sequence that has 3, 2 or 1 amino acid difference with one of the CDR2 sequences mentioned in Table B-1 (but belonging to a different combination), and a CDR3 sequence.

Some preferred Nanobodies of the invention may for example comprise: (1) a CDR1 sequence that has more than 80% sequence identity with one of the CDR1 sequences mentioned in Table B-1; a CDR2 sequence that has 3, 2 or 1 amino acid difference with one of the CDR2 sequences mentioned in Table B-1 (but belonging to a different combination); and a CDR3 sequence that has more than 80% sequence identity with one of the CDR3 sequences mentioned in Table B-1 (but belonging to a different combination); or (2) a CDR1 sequence that has more than 80% sequence identity with one of the CDR1 sequences mentioned in Table B-1; a CDR2 sequence, and one of the CDR3 sequences listed in Table B-1; or (3) a CDR1 sequence; a CDR2 sequence that has more than 80% sequence identity with one of the CDR2 sequence listed in Table B-1; and a CDR3 sequence that has 3, 2 or 1 amino acid differences with the CDR3 sequence mentioned in Table B-1 that belongs to the same combination as the CDR2 sequence.

Some particularly preferred Nanobodies of the invention may for example comprise: (1) a CDR1 sequence that has more than 80% sequence identity with one of the CDR1 sequences mentioned in Table B-1; a CDR2 sequence that has 3, 2 or 1 amino acid difference with the CDR2 sequence mentioned in Table B-1 that belongs to the same combination; and a CDR3 sequence that has more than 80% sequence identity with the CDR3 sequence mentioned in Table B-1 that belongs to the same combination; (2) a CDR1 sequence; a CDR 2 listed in Table B-1 and a CDR3 sequence listed in Table B-1 (in which the CDR2 sequence and CDR3 sequence may belong to different combinations).

Some even more preferred Nanobodies of the invention may for example comprise: (1) a CDR1 sequence that has more than 80% sequence identity with one of the CDR1 sequences mentioned in Table B-1; the CDR2 sequence listed in Table B-1 that belongs to the same combination; and a CDR3 sequence mentioned in Table B-1 that belongs to a different combination; or (2) a CDR1 sequence mentioned in Table B-1; a CDR2 sequence that has 3, 2 or 1 amino acid differences with the CDR2 sequence mentioned in Table B-1 that belongs to the same combination; and a CDR3 sequence that has more than 80% sequence identity with the CDR3 sequence listed in Table B-1 that belongs to the same or a different combination.

Particularly preferred Nanobodies of the invention may for example comprise a CDR1 sequence mentioned in Table B-1, a CDR2 sequence that has more than 80% sequence identity with the CDR2 sequence mentioned in Table B-1 that belongs to the same combination; and the CDR3 sequence mentioned in Table B-1 that belongs to the same combination.

In the most preferred Nanobodies of the invention, the CDR1, CDR2 and CDR3 sequences present are suitably chosen from one of the combinations of CDR1, CDR2 and CDR3 sequences, respectively, listed in Table B-1.

According to another preferred, but non-limiting aspect of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In another preferred, but non-limiting aspect, the invention relates to a Nanobody in which the CDR sequences (as defined herein) have more than 80%, preferably more than 90%, more preferably more than 95%, such as 99% or more sequence identity (as defined herein) with the CDR sequences of at least one of the amino acid sequences of SEQ ID NO's: 179 to 185 (see Table A-1).

Generally, Nanobodies with the above CDR sequences may be as further described herein, and preferably have framework sequences that are also as further described herein. Thus, for example and as mentioned herein, such Nanobodies may be naturally occurring Nanobodies (from any suitable species), naturally occurring $V_{HH}$ sequences (i.e. from a suitable species of Camelid) or synthetic or semi-synthetic amino acid sequences or Nanobodies, including but not limited to partially humanized Nanobodies or $V_{HH}$ sequences, fully humanized Nanobodies or $V_{HH}$ sequences, camelized heavy chain variable domain sequences, as well as Nanobodies that have been obtained by the techniques mentioned herein.

Thus, in one specific, but non-limiting aspect, the invention relates to a humanized Nanobody, which consists of 4 framework regions (FR1 to FR4 respectively) and 3 complementarity determining regions (CDR1 to CDR3 respectively), in which CDR1 to CDR3 are as defined herein and in which said humanized Nanobody comprises at least one humanizing substitution (as defined herein), and in particular at least one humanizing substitution in at least one of its framework sequences (as defined herein).

In another preferred, but non-limiting aspect, the invention relates to a Nanobody in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 179 to 185 (see Table A-1). This degree of amino acid identity can for example be determined by determining the degree of amino acid identity (in a manner described herein) between said Nanobody and one or more of the sequences of SEQ ID NO's: 179 to 185 (see Table A-1), in which the amino acid residues that form the framework regions are disregarded. Such Nanobodies can be as further described herein.

In another preferred, but non-limiting aspect, the invention relates to a Nanobody with an amino acid sequence that is chosen from the group consisting of SEQ ID NO's: 179 to 185 (see Table A-1) or from the group consisting of from amino acid sequences that have more than 80%, preferably more than 90%, more preferably more than 95%, such as 99% or more sequence identity (as defined herein) with at least one of the amino acid sequences of SEQ ID NO's: 179 to 185 (see Table A-1).

Another preferred, but non-limiting aspect of the invention relates to humanized and/or sequence optimized variants of the Nanobodies of SEQ ID NO's: 179 to 185 (see Table A-1), that comprise, compared to the corresponding native $V_{HH}$ sequence, at least one humanizing and/or sequence optimizing substitution (as defined herein), and in particular at least one humanizing and/or sequence optimizing substitution in at least one of its framework sequences (as defined herein). Some preferred, but non-limiting examples of such humanized and/or sequence optimized variants are the humanized and/or sequence optimized Nanobodies of SEQ ID NO's: 199 to 226 (see Table A-2). Thus, the invention also relates to a humanized and/or sequence optimized Nanobody with an amino acid sequence that is chosen from the group consisting of SEQ ID NO's: 199 to 226 (see Table A-2) or from the group consisting of from amino acid sequences that have more than 80%, preferably more than 90%, more preferably more than 95%, such as 99% or more sequence identity (as defined herein) with at least one of the amino acid sequences of SEQ ID NO's: 199 to 226 (see Table A-2) (in which amino acid sequences that are chosen from the latter group of amino acid sequences may contain a greater number or a smaller number of humanizing and/or sequence optimizing substitutions compared to the corresponding sequence of SEQ ID NO's: 199 to 226 (see Table A-2), as long as they retain at least one of the humanizing and/or sequence optimizing substitutions present in the corresponding sequence of SEQ ID NO's: 199 to 226 (see Table A-2)).

The polypeptides of the invention comprise or essentially consist of at least one Nanobody of the invention. Some preferred, but non-limiting examples of polypeptides of the invention are given in SEQ ID NO's: 186 to 198 (see Table A-3) and SEQ ID NO's: 227 to 234 (see Table A-4).

It will be clear to the skilled person that the Nanobodies that are mentioned herein as "preferred" (or "more preferred", "even more preferred", etc.) are also preferred (or more preferred, or even more preferred, etc.) for use in the polypeptides described herein. Thus, polypeptides that comprise or essentially consist of one or more "preferred" Nanobodies of the invention will generally be preferred, and polypeptides that comprise or essentially consist of one or more "more preferred" Nanobodies of the invention will generally be more preferred, etc.

Generally, proteins or polypeptides that comprise or essentially consist of a single Nanobody (such as a single Nanobody of the invention) will be referred to herein as "monovalent" proteins or polypeptides or as "monovalent constructs". Proteins and polypeptides that comprise or essentially consist of two or more Nanobodies (such as at least two Nanobodies of the invention or at least one Nanobody of the invention and at least one other Nanobody) will be referred to herein as "multivalent" proteins or polypeptides or as "multivalent constructs", and these may provide certain advantages compared to the corresponding monovalent Nanobodies of the invention. Some non-limiting examples of such multivalent constructs will become clear from the further description herein.

According to one specific, but non-limiting aspect, a polypeptide of the invention comprises or essentially consists of at least two Nanobodies of the invention, such as two or three Nanobodies of the invention. As further described herein, such multivalent constructs can provide certain advantages compared to a protein or polypeptide comprising or essentially consisting of a single Nanobody of the invention, such as a much improved avidity for OX40L. Such multivalent constructs will be clear to the skilled person based on the disclosure herein; some preferred, but non-limiting examples of such multivalent Nanobody constructs are the constructs of SEQ ID NO's: 186 to 198 and 227 to 234, more preferably constructs of SEQ ID NO's: 186, 187, 189, 190, 227, 228, 229, 230, 231, 233; most preferred construct of SEQ ID NO's: 190, 227, 228, 231 and 233.

According to another specific, but non-limiting aspect, a polypeptide of the invention comprises or essentially consists of at least one Nanobody of the invention and at least one other binding unit (i.e. directed against another epitope, antigen, target, protein or polypeptide), which is preferably also a Nanobody. Such proteins or polypeptides are also referred to herein as "multispecific" proteins or polypeptides or as "multispecific constructs", and these may provide certain advantages compared to the corresponding monovalent Nanobodies of the invention (as will become clear from the further discussion herein of some preferred, but-nonlimiting multispecific constructs). Such multispecific constructs will be clear to the skilled person based on the disclosure herein; some preferred, but non-limiting examples of such multispecific Nanobody constructs are the constructs of SEQ ID NO's: 186 to 198 and 227 to 234, more preferably constructs of SEQ ID NO's: 186, 187, 189, 190, 227, 228, 229, 230, 231, 233; most preferred construct of SEQ ID NO's: 190, 227, 228, 231 and 233.

According to yet another specific, but non-limiting aspect, a polypeptide of the invention comprises or essentially consists of at least one Nanobody of the invention, optionally one or more further Nanobodies, and at least one other amino acid sequence (such as a protein or polypeptide) that confers at least one desired property to the Nanobody of the invention and/or to the resulting fusion protein. Again, such fusion proteins may provide certain advantages compared to the corresponding monovalent Nanobodies of the invention. Some non-limiting examples of such amino acid sequences and of such fusion constructs will become clear from the further description herein.

It is also possible to combine two or more of the above aspects, for example to provide a trivalent bispecific construct comprising two Nanobodies of the invention and one other Nanobody, and optionally one or more other amino acid sequences. Further non-limiting examples of such constructs, as well as some constructs that are particularly preferred within the context of the present invention, will become clear from the further description herein.

In the above constructs, the one or more Nanobodies and/or other amino acid sequences may be directly linked to each other and/or suitably linked to each other via one or more linker sequences. Some suitable but non-limiting examples of such linkers will become clear from the further description herein.

In one specific aspect of the invention, a Nanobody of the invention or a compound, construct or polypeptide of the invention comprising at least one Nanobody of the invention may have an increased half-life, compared to the corresponding amino acid sequence of the invention. Some preferred, but non-limiting examples of such Nanobodies, compounds and polypeptides will become clear to the skilled person based on the further disclosure herein, and for example comprise Nanobodies sequences or polypeptides of the invention that have been chemically modified to increase the half-life thereof (for example, by means of pegylation); amino acid sequences of the invention that comprise at least one additional binding site for binding to a serum protein (such as serum albumin, see for example EP 0 368 684 B1, page 4); or polypeptides of the invention that comprise at least one Nanobody of the invention that is linked to at least one moiety (and in particular at least one amino acid sequence) that increases the half-life of the Nanobody of the invention. Examples of polypeptides of the invention that comprise such half-life extending moieties or amino acid sequences will become clear to the skilled person based on the further disclosure herein; and for example include, without limitation, polypeptides in which the one or more Nanobodies of the invention are suitable linked to one or more serum proteins or fragments thereof (such as serum albumin or suitable fragments thereof) or to one or more binding units that can bind to serum proteins (such as, for example, Nanobodies or (single) domain antibodies that can bind to serum proteins such as serum albumin, serum immunoglobulins such as IgG, or transferrin); polypeptides in which a Nanobody of the invention is linked to an Fc portion (such as a human Fc) or a suitable part or fragment thereof; or polypeptides in which the one or more Nanobodies of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006 (see also PCT/EP/2007/063348).

Again, as will be clear to the skilled person, such Nanobodies, compounds, constructs or polypeptides may contain one or more additional groups, residues, moieties or binding units, such as one or more further amino acid sequences and in particular one or more additional Nanobodies (i.e. not directed against OX40L), so as to provide a tri- of multi-specific Nanobody construct.

Generally, the Nanobodies of the invention (or compounds, constructs or polypeptides comprising the same) with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the Nanobodies, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such Nanobodies, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another one aspect of the invention, a polypeptide of the invention comprises one or more (such as two or preferably one) Nanobodies of the invention linked (optionally via one or more suitable linker sequences) to one or more (such as two and preferably one) amino acid sequences that allow the resulting polypeptide of the invention to cross the blood brain barrier. In particular, said one or more amino acid sequences that allow the resulting polypeptides of the invention to cross the blood brain barrier may be one or more (such as two and preferably one) Nanobodies, such as the Nanobodies described in WO 02/057445, of which FC44 (SEQ ID NO: 189 of WO 06/040153) and FC5 (SEQ ID NO: 190 of WO 06/040154) are preferred examples.

In particular, polypeptides comprising one or more Nanobodies of the invention are preferably such that they:

bind to OX40L with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:

bind to OX40L with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;

and/or such that they:

bind to OX40L with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a polypeptide that contains only one amino acid sequence of the invention is preferably such that it will bind to OX40L with an affinity less than 500 nM, preferably less than 200 nM, more preferably less than 10 nM, such as less than 500 pM. In this respect, it will be clear to the skilled person that a polypeptide that contains two or more Nanobodies of the invention may bind to OX40L with an increased avidity, compared to a polypeptide that contains only one amino acid sequence of the invention.

Some preferred $IC_{50}$ values for binding of the amino acid sequences or polypeptides of the invention to OX40L will become clear from the further description and examples herein.

Other polypeptides according to this preferred aspect of the invention may for example be chosen from the group consisting of amino acid sequences that have more than 80%, preferably more than 90%, more preferably more than 95%, such as 99% or more "sequence identity" (as defined herein) with one or more of the amino acid sequences of SEQ ID NO's: 186 to 198 (see Table A-3) and SEQ ID NO's: 227 to 234 (Table A-4), in which the Nanobodies comprised within said amino acid sequences are preferably as further defined herein.

Another aspect of this invention relates to a nucleic acid that encodes an amino acid sequence of the invention (such as a Nanobody of the invention) or a polypeptide of the invention comprising the same. Again, as generally described herein for the nucleic acids of the invention, such a nucleic acid may be in the form of a genetic construct, as defined herein.

In another aspect, the invention relates to host or host cell that expresses or that is capable of expressing an amino acid sequence (such as a Nanobody) of the invention and/or a polypeptide of the invention comprising the same; and/or that contains a nucleic acid of the invention. Some preferred but non-limiting examples of such hosts or host cells will become clear from the further description herein.

Another aspect of the invention relates to a product or composition containing or comprising at least one amino acid sequence of the invention, at least one polypeptide of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention further relates to methods for preparing or generating the amino acid sequences, compounds, constructs, polypeptides, nucleic acids, host cells, products and compositions described herein. Some preferred but non-limiting examples of such methods will become clear from the further description herein.

The invention further relates to applications and uses of the amino acid sequences, compounds, constructs, polypeptides, nucleic acids, host cells, products and compositions described herein, as well as to methods for the prevention and/or treatment for diseases and disorders associated with OX40L Some preferred but non-limiting applications and uses will become clear from the further description herein.

Other aspects, embodiments, advantages and applications of the invention will also become clear from the further description hereinbelow.

Generally, it should be noted that the term Nanobody as used herein in its broadest sense is not limited to a specific biological source or to a specific method of preparation. For example, as will be discussed in more detail below, the Nanobodies of the invention can generally be obtained by any of the techniques (1) to (8) mentioned on pages 61 and 62 of WO 08/020079, or any other suitable technique known per se. One preferred class of Nanobodies corresponds to the $V_H$ domains of naturally occurring heavy chain antibodies directed against OX40L. As further described herein, such $V_{HH}$ sequences can generally be generated or obtained by suitably immunizing a species of Camelid with OX40L (i.e. so as to raise an immune response and/or heavy chain antibodies directed against OX40L), by obtaining a suitable biological sample from said Camelid (such as a blood sample, serum sample or sample of B-cells), and by generating $V_{HH}$ sequences directed against OX40L, starting from said sample, using any suitable technique known per se. Such techniques will be clear to the skilled person and/or are further described herein.

Alternatively, such naturally occurring $V_{HH}$ domains against OX40L, can be obtained from naïve libraries of Camelid $V_{HH}$ sequences, for example by screening such a library using OX40L, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from naïve $V_{HH}$ libraries may be used, such as $V_{HH}$ libraries obtained from naïve $V_{HH}$ libraries by techniques such as random mutagenesis and/or CDR shuffling, as for example described in WO 00/43507.

Thus, in another aspect, the invention relates to a method for generating Nanobodies that are directed against OX40L. In one aspect, said method at least comprises the steps of:
a) providing a set, collection or library of Nanobody sequences; and
b) screening said set, collection or library of Nanobody sequences for Nanobody sequences that can bind to and/or have affinity for OX40L; and
c) isolating the Nanobody or Nanobodies that can bind to and/or have affinity for OX40L.

In such a method, the set, collection or library of Nanobody sequences may be a naïve set, collection or library of Nanobody sequences; a synthetic or semi-synthetic set, collection or library of Nanobody sequences; and/or a set, collection or library of Nanobody sequences that have been subjected to affinity maturation.

In a preferred aspect of this method, the set, collection or library of Nanobody sequences may be an immune set, collection or library of Nanobody sequences, and in particular an immune set, collection or library of $V_{HH}$ sequences, that have been derived from a species of Camelid that has been suitably immunized with OX40L or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of Nanobody or $V_{HH}$ sequences may be displayed on a phage, phagemid, ribosome or suitable micro-organism (such as yeast), such as to facilitate screening. Suitable methods, techniques and host organisms for displaying and screening (a set, collection or library of) Nanobody sequences will be clear to the person skilled in the art, for example on the basis of the further disclosure herein. Reference is also made to WO 03/054016 and to the review by Hoogenboom in Nature Biotechnology, 23, 9, 1105-1116 (2005).

In another aspect, the method for generating Nanobody sequences comprises at least the steps of:
a) providing a collection or sample of cells derived from a species of Camelid that express immunoglobulin sequences;
b) screening said collection or sample of cells for (i) cells that express an immunoglobulin sequence that can bind to and/or have affinity for OX40L; and (ii) cells that express heavy chain antibodies, in which substeps (i) and (ii) can be performed essentially as a single screening step or in any suitable order as two separate screening steps, so as to provide at least one cell that expresses a heavy chain antibody that can bind to and/or has affinity for OX40L;

and
c) either (i) isolating from said cell the $V_{HH}$ sequence present in said heavy chain antibody; or (ii) isolating from said cell a nucleic acid sequence that encodes the $V_{HH}$ sequence present in said heavy chain antibody, followed by expressing said $V_{HH}$ domain.

In the method according to this aspect, the collection or sample of cells may for example be a collection or sample of B-cells. Also, in this method, the sample of cells may be derived from a Camelid that has been suitably immunized with OX40L or a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820. Particular reference is made to the so-called "Nanoclone™" technique described in International application WO 06/079372 by Ablynx N.V.

In another aspect, the method for generating an amino acid sequence directed against OX40L may comprise at least the steps of:
a) providing a set, collection or library of nucleic acid sequences encoding heavy chain antibodies or Nanobody sequences;
b) screening said set, collection or library of nucleic acid sequences for nucleic acid sequences that encode a heavy chain antibody or a Nanobody sequence that can bind to and/or has affinity for OX40L;
and
c) isolating said nucleic acid sequence, followed by expressing the $V_{HH}$ sequence present in said heavy chain antibody or by expressing said Nanobody sequence, respectively.

In such a method, the set, collection or library of nucleic acid sequences encoding heavy chain antibodies or Nanobody sequences may for example be a set, collection or library of nucleic acid sequences encoding a naïve set, collection or library of heavy chain antibodies or $V_{HH}$ sequences; a set, collection or library of nucleic acid sequences encoding a synthetic or semi-synthetic set, collection or library of Nanobody sequences; and/or a set, collection or library of nucleic acid sequences encoding a set, collection or library of Nanobody sequences that have been subjected to affinity maturation.

In a preferred aspect of this method, the set, collection or library of nucleic acid sequences may be an immune set, collection or library of nucleic acid sequences encoding heavy chain antibodies or $V_{HH}$ sequences derived from a Camelid that has been suitably immunized with OX40L or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of nucleotide sequences may be displayed on a phage, phagemid, ribosome or suitable micro-organism (such as yeast), so as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to WO 03/054016 and to the review by Hoogenboom in Nature Biotechnology, 23, 9, 1105-1116 (2005).

As will be clear to the skilled person, the screening step of the methods described herein can also be performed as a selection step. Accordingly the term "screening" as used in the present description can comprise selection, screening or any suitable combination of selection and/or screening techniques. Also, when a set, collection or library of sequences is used, it may contain any suitable number of sequences, such as 1, 2, 3 or about 5, 10, 50, 100, 500, 1000, 5000, $10^4$, $10^5$, $10^6$, $10^7$, $10^8$ or more sequences.

Also, one or more or all of the sequences in the above set, collection or library of amino acid sequences may be obtained or defined by rational, or semi-empirical approaches such as computer modelling techniques or biostatics or datamining techniques.

Furthermore, such a set, collection or library can comprise one, two or more sequences that are variants from one another (e.g. with designed point mutations or with randomized positions), compromise multiple sequences derived from a diverse set of naturally diversified sequences (e.g. an immune library)), or any other source of diverse sequences (as described for example in Hoogenboom et al, Nat Biotechnol 23:1105, 2005 and Binz et al, Nat Biotechnol 2005, 23:1247). Such set, collection or library of sequences can be displayed on the surface of a phage particle, a ribosome, a bacterium, a yeast cell, a mammalian cell, and linked to the nucleotide sequence encoding the amino acid sequence within these carriers. This makes such set, collection or library amenable to selection procedures to isolate the desired amino acid sequences of the invention. More generally, when a sequence is displayed on a suitable host or host cell, it is also possible (and customary) to first isolate from said host or host cell a nucleotide sequence that encodes the desired sequence, and then to obtain the desired sequence by suitably expressing said nucleotide sequence in a suitable host organism. Again, this can be performed in any suitable manner known per se, as will be clear to the skilled person.

Yet another technique for obtaining $V_{HH}$ sequences or Nanobody sequences directed against OX40L involves suitably immunizing a transgenic mammal that is capable of expressing heavy chain antibodies (i.e. so as to raise an immune response and/or heavy chain antibodies directed against OX40L), obtaining a suitable biological sample from said transgenic mammal that contains (nucleic acid sequences encoding) said $V_{HH}$ sequences or Nanobody sequences (such as a blood sample, serum sample or sample of B-cells), and then generating $V_{HH}$ sequences directed against OX40L, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

The invention also relates to the $V_{HH}$ sequences or Nanobody sequences that are obtained by the above methods, or alternatively by a method that comprises the one of the above methods and in addition at least the steps of determining the nucleotide sequence or amino acid sequence of said $V_{HH}$ sequence or Nanobody sequence; and of expressing or synthesizing said $V_{HH}$ sequence or Nanobody sequence in a manner known per se, such as by expression in a suitable host cell or host organism or by chemical synthesis.

As mentioned herein, a particularly preferred class of Nanobodies of the invention comprises Nanobodies with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above), as further described on, and using the techniques mentioned on, page 63 of WO 08/020079. Another particularly preferred class of Nanobodies of the invention comprises Nanobodies with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody, as further described on, and using the techniques mentioned on, page 63 of WO 08/020079.

Other suitable methods and techniques for obtaining the Nanobodies of the invention and/or nucleic acids encoding the same, starting from naturally occurring $V_H$ sequences or preferably $V_{HH}$ sequences, will be clear from the skilled person, and may for example include the techniques that are mentioned on page 64 of WO 08/00279. As mentioned herein, Nanobodies may in particular be characterized by the presence of one or more "Hallmark residues" (as described herein) in one or more of the framework sequences.

Thus, according to one preferred, but non-limiting aspect of the invention, a Nanobody in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 45 according to the Kabat numbering is a charged amino acid (as defined herein) or a cysteine residue, and position 44 is preferably an E;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a Nanobody of the invention may have the structure
    FR1-CDR1-FR2-CDR2-FDR3-CDR3-FR4
in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q;
and/or in which:
b) the amino acid residue at position 45 according to the Kabat numbering is a charged amino acid or a cysteine and the amino acid residue at position 44 according to the Kabat numbering is preferably E;
and/or in which:
c) the amino acid residue at position 103 according to the Kabat numbering is chosen from the group consisting of P, R and S, and is in particular chosen from the group consisting of R and S; and in which:
d) CDR1, CDR2 and CDR3 are as defined herein, and are preferably as defined according to one of the preferred aspects herein, and are more preferably as defined according to one of the more preferred aspects herein.

In particular, a Nanobody in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and 5, and is in particular chosen from the group consisting of R and S.

Thus, according to a preferred, but non-limiting aspect, a Nanobody of the invention may have the structure
    FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q;
and/or in which:
b) the amino acid residue at position 44 according to the Kabat numbering is E and in which the amino acid residue at position 45 according to the Kabat numbering is an R;
and/or in which:
c) the amino acid residue at position 103 according to the Kabat numbering is chosen from the group consisting of P, R and S, and is in particular chosen from the group consisting of R and S;

and in which:
d) CDR1, CDR2 and CDR3 are as defined herein, and are preferably as defined according to one of the preferred aspects herein, and are more preferably as defined according to one of the more preferred aspects herein.

In particular, a Nanobody against OX40L according to the invention may have the structure:

FR1-CDR1-FR2-CDR2-FR3-CDR-3-FR4 in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q;
and/or in which:
b) the amino acid residue at position 44 according to the Kabat numbering is E and in which the amino acid residue at position 45 according to the Kabat numbering is an R;
and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, according to one preferred, but non-limiting aspect of the invention, a Nanobody can generally be defined as a polypeptide comprising an amino acid sequence that is comprised of four framework regions/sequences interrupted by three complementarity determining regions/sequences, in which;
a-1) the amino acid residue at position 44 according to the Kabat numbering is chosen from the group consisting of A, G, E, D, G, Q, R, S, L; and is preferably chosen from the group consisting of G, E or Q; and
a-2) the amino acid residue at position 45 according to the Kabat numbering is chosen from the group consisting of L, R or C; and is preferably chosen from the group consisting of L or R; and
a-3) the amino acid residue at position 103 according to the Kabat numbering is chosen from the group consisting of W, R or S; and is preferably W or R, and is most preferably W;
a-4) the amino acid residue at position 108 according to the Kabat numbering is Q;
or in which:
b-1) the amino acid residue at position 44 according to the Kabat numbering is chosen from the group consisting of E and Q; and
b-2) the amino acid residue at position 45 according to the Kabat numbering is R; and
b-3) the amino acid residue at position 103 according to the Kabat numbering is chosen from the group consisting of W, R and S; and is preferably W;
b-4) the amino acid residue at position 108 according to the Kabat numbering is chosen from the group consisting of Q and L; and is preferably Q;
or in which:
c-1) the amino acid residue at position 44 according to the Kabat numbering is chosen from the group consisting of A, G, E, D, Q, R, S and L; and is preferably chosen from the group consisting of G, E and Q; and c-2) the amino acid residue at position 45 according to the Kabat numbering is chosen from the group consisting of L, R and C; and is preferably chosen from the group consisting of L and R; and
c-3) the amino acid residue at position 103 according to the Kabat numbering is chosen from the group consisting of P, R and S; and is in particular chosen from the group consisting of R and S; and
c-4) the amino acid residue at position 108 according to the Kabat numbering is chosen from the group consisting of Q and L; is preferably Q;
and in which
d) CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
a-1) the amino acid residue at position 44 according to the Kabat numbering is chosen from the group consisting of A, G, E, D, G, CQ R, S, L; and is preferably chosen from the group consisting of G, E or Q;
and in which:
a-2) the amino acid residue at position 45 according to the Kabat numbering is chosen from the group consisting of L, R or C; and is preferably chosen from the group consisting of L or R;
and in which:
a-3) the amino acid residue at position 103 according to the Kabat numbering is chosen from the group consisting of W, R or S; and is preferably W or R, and is most preferably W;
and in which
a-4) the amino acid residue at position 108 according to the Kabat numbering is Q;
and in which:
d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:
b-1) the amino acid residue at position 44 according to the Kabat numbering is chosen from the group consisting of E and Q;
and in which:
b-2) the amino acid residue at position 45 according to the Kabat numbering is R;
and in which:
b-3) the amino acid residue at position 103 according to the Kabat numbering is chosen from the group consisting of W, R and S; and is preferably W;
and in which:
b-4) the amino acid residue at position 108 according to the Kabat numbering is chosen from the group consisting of Q and L; and is preferably Q;

and in which:

d) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR-3-FR4 in which FR1 to FR4 refer to framework regions 1 to 4, respectively, and in which CDR1 to CDR3 refer to the complementarity determining regions 1 to 3, respectively, and in which:

c-1) the amino acid residue at position 44 according to the Kabat numbering is chosen from the group consisting of A, G, E, D, Q, R, S and L; and is preferably chosen from the group consisting of G, E and Q;

and in which:

c-2) the amino acid residue at position 45 according to the Kabat numbering is chosen from the group consisting of L, R and C; and is preferably chosen from the group consisting of L and R;

and in which:

c-3) the amino acid residue at position 103 according to the Kabat numbering is chosen from the group consisting of P, R and 5; and is in particular chosen from the group consisting of R and S;

and in which:

c-4) the amino acid residue at position 108 according to the Kabat numbering is chosen from the group consisting of Q and L; is preferably Q;

and in which:

d) CDR1, CDR2 and CDR3 are as defined herein, and are preferably as defined according to one of the preferred aspects herein, and are more preferably as defined according to one of the more preferred aspects herein.

Two particularly preferred, but non-limiting groups of the Nanobodies of the invention are those according to a) above; according to (a-1) to (a-4) above; according to b) above; according to (b-1) to (b-4) above; according to (c) above; and/or according to (c-1) to (c-4) above, in which either:

i) the amino acid residues at positions 44-47 according to the Kabat numbering form the sequence GLEW (or a GLEW-like sequence as described herein) and the amino acid residue at position 108 is Q;

or in which:

ii) the amino acid residues at positions 43-46 according to the Kabat numbering form the sequence KERE or KQRE (or a KERE-like sequence as described) and the amino acid residue at position 108 is Q or L, and is preferably Q.

Thus, in another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 44-47 according to the Kabat numbering form the sequence GLEW (or a GLEW-like sequence as defined herein) and the amino acid residue at position 108 is Q;

and in which:

ii) CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) the amino acid residues at positions 43-46 according to the Kabat numbering form the sequence KERE or KQRE (or a KERE-like sequence) and the amino acid residue at position 108 is Q or L, and is preferably Q;

and in which:

ii) CDR1, CDR2 and CDR3 are as defined herein, and are preferably as defined according to one of the preferred aspects herein, and are more preferably as defined according to one of the more preferred aspects herein.

In the Nanobodies of the invention in which the amino acid residues at positions 43-46 according to the Kabat numbering form the sequence KERE or KQRE, the amino acid residue at position 37 is most preferably F. In the Nanobodies of the invention in which the amino acid residues at positions 44-47 according to the Kabat numbering form the sequence GLEW, the amino acid residue at position 37 is chosen from the group consisting of Y, H, I, L, V or F, and is most preferably V.

Thus, without being limited hereto in any way, on the basis of the amino acid residues present on the positions mentioned above, the Nanobodies of the invention can generally be classified on the basis of the following three groups:

i) The "GLEW-group": Nanobodies with the amino acid sequence GLEW at positions 44-47 according to the Kabat numbering and Q at position 108 according to the Kabat numbering. As further described herein, Nanobodies within this group usually have a V at position 37, and can have a W, P, R or S at position 103, and preferably have a W at position 103. The GLEW group also comprises some GLEW-like sequences such as those mentioned in Table B-2 below. More generally, and without limitation, Nanobodies belonging to the GLEW-group can be defined as Nanobodies with a G at position 44 and/or with a W at position 47, in which position 46 is usually E and in which preferably position 45 is not a charged amino acid residue and not cysteine;

ii) The "KERE-group": Nanobodies with the amino acid sequence KERE or KQRE (or another KERE-like sequence) at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103. More generally, and without limitation, Nanobodies belonging to the KERE-group can be defined as Nanobodies with a K, Q or R at position 44 (usually K) in which position 45 is a charged amino acid residue or cysteine, and position 47 is as further defined herein;

iii) The "103 P, R, S-group": Nanobodies with a P, R or S at position 103. These Nanobodies can have either the amino acid sequence GLEW at positions 44-47 according to the Kabat numbering or the amino acid sequence KERE or KQRE at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Also, where appropriate, Nanobodies may belong to (i.e. have characteristics of) two or more of these classes. For example, one specifically preferred group of Nanobodies has GLEW or a GLEW-like sequence at positions 44-47; P, R or S (and in particular R) at position 103; and Q at position 108 (which may be humanized to L).

More generally, it should be noted that the definitions referred to above describe and apply to Nanobodies in the form of a native (i.e. non-humanized) $V_{HH}$ sequence, and that humanized variants of these Nanobodies may contain other amino acid residues than those indicated above (i.e. one or more humanizing substitutions as defined herein). For example, and without limitation, in some humanized Nanobodies of the GLEW-group or the 103 P, R, S-group, Q at position 108 may be humanized to 108L As already mentioned herein, other humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a Nanobody may be partially humanized or fully humanized.

Thus, in another preferred, but non-limiting aspect, a Nanobody of the invention may be a Nanobody belonging to the GLEW-group (as defined herein), and in which CDR1, CDR2 and CDR3 are as defined herein, and are preferably as defined according to one of the preferred aspects herein, and are more preferably as defined according to one of the more preferred aspects herein.

In another preferred, but non-limiting aspect, a Nanobody of the invention may be a Nanobody belonging to the KERE-group (as defined herein), and CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a Nanobody of the invention may be a Nanobody belonging to the 103 P, R, S-group (as defined herein), and in which CDR1, CDR2 and CDR3 are as defined herein, and are preferably as defined according to one of the preferred aspects herein, and are more preferably as defined according to one of the more preferred aspects herein.

Also, more generally and in addition to the 108Q, 43E/44R and 103 P,R,S residues mentioned above, the Nanobodies of the invention can contain, at one or more positions that in a conventional $V_H$ domain would form (part of) the $V_H/V_L$ interface, one or more amino acid residues that are more highly charged than the amino acid residues that naturally occur at the same position(s) in the corresponding naturally occurring $V_H$ sequence, and in particular one or more charged amino acid residues (as mentioned in Table A-2 on page 48 of the International application WO 08/020079). Such substitutions include, but are not limited to, the GLEW-like sequences mentioned in Table B-2 below; as well as the substitutions that are described in the International Application WO 00/29004 for so-called "microbodies", e.g. so as to obtain a Nanobody with Q at position 108 in combination with KLEW at positions 44-47. Other possible substitutions at these positions will be clear to the skilled person based upon the disclosure herein.

In one aspect of the Nanobodies of the invention, the amino acid residue at position 83 is chosen from the group consisting of L, M, S, V and W; and is preferably L.

Also, in one aspect of the Nanobodies of the invention, the amino acid residue at position 83 is chosen from the group consisting of R, K, N, E, G, I, T and Q; and is most preferably either K or E (for Nanobodies corresponding to naturally occurring $V_{HH}$ domains) or R (for "humanized" Nanobodies, as described herein). The amino acid residue at position 84 is chosen from the group consisting of P, A, R, S, D T, and V in one aspect, and is most preferably P (for Nanobodies corresponding to naturally occurring $V_{HH}$ domains) or R (for "humanized" Nanobodies, as described herein).

Furthermore, in one aspect of the Nanobodies of the invention, the amino acid residue at position 104 is chosen from the group consisting of G and D; and is most preferably G.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human $V_H$ domain, $V_H3$, are summarized in Table B-2.

Some especially preferred but non-limiting combinations of these Hallmark Residues as occur in naturally occurring $V_{HH}$ domains are mentioned in Table B-3. For comparison, the corresponding amino acid residues of the human $V_H3$ called DP-47 have been indicated in italics.

TABLE B-2

Hallmark Residues in Nanobodies

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | $F^{(1)}$, Y, V, L, A, H, S, I, W, C, N, G, D, T, P, preferably $F^{(1)}$ or Y |
| 44[8] | G | $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$ |
| 45[8] | L | $L^{(2)}$, $R^{(3)}$, P, H, F, G, Q, S, E, T, Y, C, I, D, V; preferably $L^{(2)}$ or $R^{(3)}$ |
| 47[8] | W, Y | $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ |

TABLE B-2-continued

Hallmark Residues in Nanobodies

| Position | Human $V_H3$ | Hallmark Residues |
|---|---|---|
| 83 | R or K; usually R | R, K[(5)], T, E[(5)], Q, N, S, I, V, G, M, L, A, D, Y, H; preferably K or R; most preferably K |
| 84 | A, T, D; predominantly A | P[(5)], S, H, L, A, V, I, T, F, D, R, Y, N, Q, G, E; preferably P |
| 103 | W | W[(4)], R[(6)], G, S, K, A, M, Y, L, F, T, N, V, Q, P[(6)], E, C; preferably W |
| 104 | G | G, A, S, T, D, P, N, E, C, L; preferably G |
| 108 | L, M or T; predominantly L | Q, L[(7)], R, P, E, K, S, T, M, A, H; preferably Q or L[(7)] |

Notes:
[(1)]In particular, but not exclusively, in combination with KERE or KQRE at positions 43-46.
[(2)]Usually as GLEW at positions 44-47.
[(3)]Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
[(4)]With both GLEW at positions 44-47 and KERE or KQRE at positions 43-46.
[(5)]Often as KP or EP at positions 83-84 of naturally occurring $V_{HH}$ domains.
[(6)]In particular, but not exclusively, in combination with GLEW at positions 44-47.
[(7)]With the proviso that when positions 44-47 are GLEW, position 108 is always Q in (non-humanized) $V_{HH}$ sequences that also contain a W at 103.
[(8)]The GLEW group also contains GLEW-like sequences at positions 44-47, such as for example GVEW, EPEW, GLER, DQEW, DLEW, GIEW, ELEW, GPEW, EWLP, GPER, GLER and ELEW.

TABLE B-3

Some preferred but non-limiting combinations of Hallmark Residues in naturally occurring Nanobodies. For humanization of these combinations, reference is made to the specification.

|  | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
|  | L | F | E | R | F | E | P | W | G | Q |
|  | L | F | E | R | F | K | P | W | G | Q |
|  | L | Y | Q | R | L | K | P | W | G | Q |
|  | L | F | L | R | V | K | P | Q | G | Q |
|  | L | F | Q | R | L | K | P | W | G | Q |
|  | L | F | E | R | F | K | P | W | G | Q |
| "GLEW" group | L | V | G | L | W | K | S | W | G | Q |
|  | M | V | G | L | W | K | P | R | G | Q |

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables B-4 to B-7 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a Nanobody) is indicated in bold; and other preferred amino acid residues for each position have been underlined (note: the number of amino acid residues that are found at positions 26-30 of naturally occurring $V_{HH}$ domains supports the hypothesis underlying the numbering by Chothia (supra) that the residues at these positions already form part of CDR1).

In Tables B-4-B-7, some of the non-limiting residues that can be present at each position of a human $V_H3$ domain have also been mentioned. Again, for each position, the amino acid residue that most frequently occurs at each position of a naturally occurring human $V_H3$ domain is indicated in bold; and other preferred amino acid residues have been underlined.

For reference only, Tables B-4-B-7 also contain data on the $V_{HH}$ entropy ("$V_{HH}$ Ent.") and $V_{HH}$ variability ("$V_{HH}$ Var.") at each amino acid position for a representative sample of 7732 $V_{HH}$ sequences (including a.o. data kindly provided by David Lutje Hulsing and Prof. Theo Verrips of Utrecht University). The values for the $V_{HH}$ entropy and the $V_{HH}$ variability provide a measure for the variability and degree of conservation of amino acid residues between the 7732 $V_{HH}$ sequences analyzed: low values (i.e. <1, such as <0.5) indicate that an amino acid residue is highly conserved between the $V_{HH}$ sequences (i.e. little variability). For example, the G at position 9 and the W at position 36 have values for the $V_{HH}$ entropy of 0.01 and 0 respectively, indicating that these residues are highly conserved and have little variability (and in case of position 36 is W in all 7732 sequences analysed), whereas for residues that form part of the CDR's generally values of 1.5 or more are found (data not shown). Note that the data represented below support the hypothesis that the amino acid residues at positions 27-30 and maybe even also at positions 93 and 94 already form part of the CDR's (although the invention is not limited to any specific hypothesis or explanation, and as mentioned above, herein the numbering according to Kabat is used). For a general explanation of sequence entropy, sequence variability and the methodology for determining the same, see Oliveira et al., PROTEINS:Structure, Function and Genetics, 52: 544-552 (2003).

TABLE B-4

Non-limiting examples of amino acid residues in FR1 (for the footnotes, see the footnotes to Table B-2)

| | | Amino acid residue(s): | | |
|---|---|---|---|---|
| Pos. | Human $V_H3$ | Camelid $V_{HH}$'s | $V_{HH}$ Ent. | $V_{HH}$ Var. |
| 1 | E, Q | E, Q, K, D, A, G, R | 0.47 | 5 |
| 2 | V | V, M, A, E, L | 0.04 | 1 |
| 3 | Q | Q, K, P, H, F, R | 0.04 | 1 |

TABLE B-4-continued

Non-limiting examples of amino acid residues in FR1
(for the footnotes, see the footnotes to Table B-2)

Amino acid residue(s):

| Pos. | Human $V_H3$ | Camelid $V_{HH}$'s | $V_{HH}$ Ent. | $V_{HH}$ Var. |
|---|---|---|---|---|
| 4 | L | L, M, Q, P, R, F, V | 0.02 | 1 |
| 5 | V, L | V, Q, M, E, A, L, P, K, R | 0.35 | 3 |
| 6 | E | E, A, Q, D, K, H | 0.21 | 5 |
| 7 | S, T | S, F, L, W, T | 0.05 | 2 |
| 8 | G, R | G, R, E, V | 0.04 | 1 |
| 9 | G | G, R, V, A | 0.01 | 1 |
| 10 | G, V | G, D, R, S, K, E, A, Q, N, T, V | 0.22 | 4 |
| 11 | | Hallmark residue: L, S, V, M, W, F, T, Q, E, A, R, G, K, Y, N, P, I; preferably L | 0.35 | 4 |
| 12 | V, I | V, A, L, M, E, G, T | 0.11 | 2 |
| 13 | Q, K, R | Q, L, R, H, P, E, K, T, S, V, D, G, A, N, M | 0.46 | 3 |
| 14 | P | A, P, T, V, S, D, F, N, I, E, L, R, G, Y, Q, H | 0.92 | 5 |
| 15 | G | G, E | 0 | 1 |
| 16 | G, R | G, D, E, A, S, N, V, R, K, T, P, C, L | 0.47 | 4 |
| 17 | S | S, F, P, Y, T, A, C, R, N | 0.14 | 2 |
| 18 | L | L, V, R, M, P, Q, S, A, T, K, H | 0.06 | 1 |
| 19 | R, K | R, T, K, S, N, G, A, I, L, Q, F, E, V, M | 0.36 | 4 |
| 20 | L | L, F, V, I, P, H, S | 0.18 | 3 |
| 21 | S | S, A, T, P, F, V, H, D, R, L, I, G | 0.13 | 3 |
| 22 | C | C, W | 0 | 1 |
| 23 | A, T | A, V, T, E, S, L, G, I, K, Q, R, D, F, N, P, M | 0.88 | 5 |
| 24 | A | A, D, V, T, H, Y, P, G, S, F, L, I, N, Q, E, R | 0.78 | 9 |
| 25 | S | S, P, T, A, F, L, N, Y, R, H, D, V, I, W, G, K, Q, C | 0.2 | 2 |
| 26 | G | G, E, R, V, T, A, S, K, D, L, I, Q, N, F, Y, M, W, P, H | 0.45 | 6 |
| 27 | F | R, F, S, P, L, G, I, N, T, D, H, V, E, A, Y, K, M, Q, W, C | 1.89 | 12 |
| 28 | T | T, I, S, A, P, F, D, N, V, R, M, L, G, Y, K, E, H, W, Q | 1.29 | 12 |
| 29 | F, V | F, L, S, V, I, A, W, Y, G, D, R, T, P, N, E, M, H, Q, K, C | 1.23 | 11 |
| 30 | S, D, G | S, D, N, G, R, T, A, E, I, Y, K, V, H, L, F, W, M, P, C, Q | 1.55 | 12 |

TABLE B-5

Non-limiting examples of amino acid residues in FR2
(for the footnotes, see the footnotes to Table B-2)

Amino acid residue(s):

| Pos. | Human $V_H3$ | Camelid $V_{HH}$'s | $V_{HH}$ Ent. | $V_{HH}$ Var. |
|---|---|---|---|---|
| 36 | W | W | 0 | 1 |
| 37 | | Hallmark residue: F(1), Y, V, L, A, H, S, I, W, C, N, G, D, T, P, preferably F(1) or Y | 1.1 | 7 |
| 38 | R | R, H, C, P, Y, L, V | 0.01 | 1 |
| 39 | Q | Q, E, R, H, L, A, S, K, P, V, T, D | 0.22 | 3 |
| 40 | A | A, V, T, P, G, S, D, I, L, R, N, F, Y, C, E, H | 0.55 | 6 |
| 41 | P, S, T | P, S, A, L, T, Q, R, V, D, G, I, H | 0.18 | 3 |
| 42 | G | G, E, A, R, D, V, W, T, Q, K, L, N, H, M | 0.1 | 2 |
| 43 | K | K, N, Q, E, R, T, L, S, M, D, G, A, V, H, I, F, P | 0.45 | 7 |
| 44 | | Hallmark residue: E(3), Q(3), G(2), D, A, K, R, L, P, S, V, H, T, N, W, M, I; preferably G(2), E(3) or Q(3); most preferably G(2) or Q(3). | 1.11 | 4 |
| 45 | | Hallmark residue: L(2), R(3), P, H, F, G, Q, S, E, T, Y, C, I, D, V; preferably L(2) or R(3) | 0.56 | 3 |
| 46 | E, V | E, D, A, Q, V, M, K, T, G, R, S, N, I, L, F | 0.42 | 4 |

TABLE B-5-continued

Non-limiting examples of amino acid residues in FR2
(for the footnotes, see the footnotes to Table B-2)

Amino acid residue(s):

| Pos. | Human $V_H3$ | Camelid $V_{HH}$'s | $V_{HH}$ Ent. | $V_{HH}$ Var. |
|---|---|---|---|---|
| 47 | | Hallmark residue: F(1), L(1) or W(2) G, I, S, A, V, M, R, Y, E, P, T, C, H, K, Q, N, D; preferably W(2), L(1) or F(1) | 1.64 | 11 |
| 48 | V | V, I, L, A, T, Q, F, M, G, E, R | 0.35 | 5 |
| 49 | S, A, G | A, S, G, T, V, L, C, I, F, P, E, Y, M, D, R | 0.89 | 5 |

TABLE B-6

Non-limiting examples of amino acid residues in FR3
(for the footnotes, see the footnotes to Table B-2)

Amino acid residue(s):

| Pos. | Human $V_H3$ | Camelid $V_{HH}$'s | $V_{HH}$ Ent. | $V_{HH}$ Var. |
|---|---|---|---|---|
| 66 | R | R | 0 | 1 |
| 67 | F | F, S, L, V, I, C, A, Y, M, G | 0.1 | 1 |
| 68 | T | T, A, S, I, F, V, P, N, G, R, K, M, D, L, W, Q | 0.34 | 4 |
| 69 | I | I, V, M, T, L, A, F, P, S, G, N | 0.5 | 5 |
| 70 | S | S, T, A, F, P, V, Y, L, D, G, N, H, W, E, C | 0.22 | 4 |
| 71 | R | R, S, K, G, T, I, W, A, N, V, E, L, M, F, D, Q, C | 0.61 | 7 |
| 72 | D, E | D, N, E, G, V, A, H, L, S, T, I, Q, F, P, Y, R | 0.34 | 4 |
| 73 | N, D, G | N, D, S, K, I, Y, G, T, H, R, A, V, F, L, E, M, P, C | 0.65 | 9 |
| 74 | A, S | A, T, V, S, F, G, D, P, N, I, R, L, Y, H, E, Q, K, W, M | 0.8 | 8 |
| 75 | K | K, N, E, R, Q, A, G, T, M, S, L, D, V, W, Y, I | 0.71 | 6 |
| 76 | N, S | N, K, S, R, D, T, H, G, E, A, Y, I, M, Q, L, W, P, F, V | 0.66 | 7 |
| 77 | S, T, I | T, A, M, S, R, I, V, L, P, E, N, K, G, W, Q | 0.72 | 7 |
| 78 | L, A | V, L, A, M, I, G, T, F, W, Q, S, E, N, H | 1.11 | 6 |
| 79 | Y, H | Y, F, D, S, H, N, T, A, L, W, V, C, G, E, I, P, R | 0.68 | 8 |
| 80 | L | L, M, V, P, F | 0.05 | 2 |
| 81 | Q | Q, E, R, H, L, D, T, G, K, P, A, I, S, N, Y, V, M | 0.38 | 4 |
| 82 | M | M, I, L, V, A, T, S, K | 0.12 | 3 |
| 82a | N, G | N, S, D, T, E, H, K, I, A, G, R, Y, L, V, F, Q | 0.77 | 5 |
| 82b | S | S, N, T, G, H, D, R, A, K, I, M, V, F, E, P, Y, C, L | 0.72 | 8 |
| 82c | L | L, V, M, P, A, T, G | 0.08 | 2 |
| 83 | | Hallmark residue: R, K(5), T, E(5), Q, N, S, I, V, G, M, L, A, D, Y, H; preferably K or R; most preferably K | 0.66 | 6 |
| 84 | | Hallmark residue: P(5), S, H, L, A, V, I, T, F, D, R, Y, N, Q, G, E; preferably P | 0.85 | 7 |
| 85 | E, G | E, D, G, A, Q, V, S, N, K, T, R, L | 0.27 | 3 |
| 86 | D | D, E, G, N | 0.02 | 1 |
| 87 | T, M | T, S, A, M, R, P, K, E | 0.15 | 3 |
| 88 | A | A, G, S, D, N, T, P, V | 0.23 | 2 |
| 89 | V, L | V, I, L, E, A, R, T, D, F, M, N, S, K, G, Q, H | 0.71 | 7 |
| 90 | Y | Y, H, F, N | 0 | 1 |
| 91 | Y, H | Y, F, R, S, H, T, I, V, L, N, D, C, Q, W, A, E, M | 0.6 | 7 |
| 92 | C | C, R, P | 0 | 1 |
| 93 | A, K, T | A, N, T, K, G, V, R, Y, S, H, W, L, F, Q, M, I, E, C, D | 1.33 | 10 |

TABLE B-6-continued

Non-limiting examples of amino acid residues in FR3
(for the footnotes, see the footnotes to Table B-2)

| Pos. | Human $V_H3$ | Camelid $V_{HH}$'s | Amino acid residue(s): | $V_{HH}$ Ent. | $V_{HH}$ Var. |
|---|---|---|---|---|---|
| 94 | K, R, T | A, K, V, T, R, L, G, S, D, Q, I, M, F, Y, N, E, H, P, C, W | | 1.55 | 12 |

TABLE B-7

Non-limiting examples of amino acid residues in FR4
(for the footnotes, see the footnotes to Table B-2)

| Pos. | Human $V_H3$ | Camelid $V_{HH}$'s Amino acid residue(s): | $V_{HH}$ Ent. | $V_{HH}$ Var. |
|---|---|---|---|---|
| 103 | | Hallmark residue: W[(4)], R[(6)], G, S, K, A, M, Y, L, F, T, N, V, Q, P[(6)], E, C; preferably W | 0.54 | 6 |
| 104 | | Hallmark residue: G, A, S, T, D, P, N, E, C, L; preferably G | 0.13 | 3 |
| 105 | Q, R | Q, K, H, R, P, E, L, T, N, S, V, A, M, G | 0.52 | 5 |
| 106 | G | G, R, E | 0 | 1 |
| 107 | T | T, Q, I, A, S, N, R, V, D | 0.24 | 3 |
| 108 | | Hallmark residue: Q, L[(7)], R, P, E, K, S, T, M, A, H; preferably Q or L[(7)] | 0.3 | 4 |
| 109 | V | V, I, L | 0 | 1 |
| 110 | T | T, S, N, A, I, F | 0.01 | 1 |
| 111 | V | V, I, A | 0.01 | 1 |
| 112 | S | S, T, P, F, A | 0.01 | 1 |
| 113 | S | S, T, A, L, P, F, E, V | 0.04 | |

Thus, in another preferred, but not limiting aspect, a Nanobody of the invention can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to complementarity determining regions 1 to 3, respectively, and in which:

i) one or more of the amino acid residues at positions 11, 37, 44, 45, 47, 83, 84, 103, 104 and 108 according to the Kabat numbering are chosen from the Hallmark residues mentioned in Table B-2;

and in which:

ii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

In particular, a Nanobody of the invention can be an amino acid sequence with the (general) structure

FR1-CDR1-FR2-CDR2-FR3-CDR-3-FR4 in which FR1 to FR4 refer to framework regions 1 to 4, respectively, and in which CDR1 to CDR3 refer to the complementarity determining regions 1 to 3, respectively, and in which:

i) (preferably) one or more of the amino acid residues at positions 11, 37, 44, 45, 47, 83, 84, 103, 104 and 108 according to the Kabat numbering are chosen from the Hallmark residues mentioned in Table B-2 (it being understood that $V_{HH}$ sequences will contain one or more Hallmark residues; and that partially humanized Nanobodies will usually, and preferably, [still] contain one or more Hallmark residues [although it is also within the scope of the invention to provide—where suitable in accordance with the invention—partially humanized Nanobodies in which all Hallmark residues, but not one or more of the other amino acid residues, have been humanized]; and that in fully humanized Nanobodies, where suitable in accordance with the invention, all amino acid residues at the positions of the Hallmark residues will be amino acid residues that occur in a human $V_H3$ sequence. As will be clear to the skilled person based on the disclosure herein that such $V_{HH}$ sequences, such partially humanized Nanobodies with at least one Hallmark residue, such partially humanized Nanobodies without Hallmark residues and such fully humanized Nanobodies all form aspects of this invention);

and in which:

ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded;

and in which:

iii) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

TABLE B-8

Representative amino acid sequences for Nanobodies of the KERE, GLEW and P, R, S 103 group.
The CDR's are indicated with XXXXX

| KERE sequence no. 1 | SEQ ID NO: 1 | EVQLVESGGGLVQPGGSLRLSCAASGIPFSXXXXXXWFRQAPGKQRDSVAXXXXXXRFTISR DNAKNTVYLQMNSLKPEDTAVYRCYFXXXXXWGQGTQVTVSS |
|---|---|---|
| KERE sequence no. 2 | SEQ ID NO: 2 | QVKLEESGGGLVQAGGSLRLSCVGSGRTFSXXXXXWERLAPGKEREEVAXXXXXXRFTISR DTASNRGYLHMNNLTPEDTAVYYCAAXXXXXXWGQGTQVTVSS |
| KERE sequence no. 3 | SEQ ID NO: 3 | AVQLVDSGGGLVQAGDSLKLSCALIGGAFTXXXXXWERQTPGREREFVAXXXXXXRFTIS RDNAKNMVYLRMNSLIPEDAAVYSCAAXXXXXXWGQGTLVTVSS |

TABLE B-8-continued

Representative amino acid sequences for Nanobodies of the KERE, GLEW and P, R, S 103 group.
The CDR's are indicated with XXXXX

| | | |
|---|---|---|
| KERE sequence no. 4 | SEQ ID NO: 4 | QVQLVESGGGLVEAGGSLRLSCTASESPERXXXXXWFRQTSGQEREFVAXXXXXRFTISR DDAKNTVWLHGSTLKPEDTAVYYCAAXXXXXWGQGTQVTVSS |
| KERE sequence no. 5 | SEQ ID NO: 5 | AVQLVESGGGLVQGGGSLRLACAASERIFDXXXXXWYRQGPGNERELVAXXXXXRFTIS MDYTKQTVYLHMNSLRPEDIGLYYCKIXXXXXWGQGIQVTVSS |
| KERE sequence no. 6 | SEQ ID NO: 6 | DVKFVESGGGLVQAGGSLRLSCVASGFNFDXXXXXWFRQAPGKEREEVAXXXXXRFTIS SEKDKNSVYLQMNSLKPEDTALYICAGXXXXXWGRGTQVTVSS |
| KERE sequence no. 7 | SEQ ID NO: 7 | QVRLAESGGGLVQSGGSLRLSCVASGSTYTXXXXXWYRQYPGKQRALVAXXXXXRFTIA RDSTKDTFCLQMNNLKPEDTAVYYCYAXXXXXWGQGTQVTVSS |
| KERE sequence no. 8 | SEQ ID NO: 8 | EVQLVESGGGLVQAGGSLRLSCAASGFTSDXXXXXWFRQAPGKPREGVSXXXXXRFTIST DNAKNTVHLLMNRVNAEDTALYYCAVXXXXXWGRGTRVTVSS |
| KERE sequence no. 9 | SEQ ID NO: 9 | QVQLVESGGGLVQPGGSLRLSCQASGDISTXXXXXWYRQVPGKLREFVAXXXXXRFTISG DNAKRAIYLQMNNLKPDDTAVYYCNRXXXXXWGQGTQVTVSP |
| KERE sequence no. 10 | SEQ ID NO: 10 | QVPVVESGGGLVQAGDSLRLFCAVPSFTSTXXXXXWFRQAPGKEREFVAXXXXXRFTISR NATKNTLTLRMDSLKPEDTAVYYCAAXXXXXWGQGTQVTVSS |
| KERE sequence no. 11 | SEQ ID NO: 11 | EVQLVESGGGLVQAGDSLRLFCTVSGGTASXXXXXWFRQAPGEKREFVAXXXXXRFTIA RENAGNMVYLQMNNLKPDDTALYTCAAXXXXXWGRGTQVTVSS |
| KERE sequence no. 12 | SEQ ID NO: 12 | AVQLVESGGDSVQPGDSQTLSCAASGRTNSXXXXXWFRQAPGKERVFLAXXXXXRFTIS RDSAKNMMYLQMNNLKPQDTAVYYCAAXXXXXWGQGTQVTVSS |
| KERE sequence no. 13 | SEQ ID NO: 13 | AVQLVESGGGLVQAGGSLRLSCVVSGLTSSXXXXXWFRQTPWQERDFVAXXXXXRFTIS RDNYKDTVLLEMNFLKPEDTAIYYCAAXXXXXWGQGTQVTVSS |
| KERE sequence no. 14 | SEQ ID NO: 14 | AVQLVESGGGLVQAGASLRLSCATSTRTLDXXXXXWFRQAPGRDREFVAXXXXXRFTVS RDSAENTVALQMNSLKPEDTAVYYCAAXXXXXWGQGTRVTVSS |
| KERE sequence no. 15 | SEQ ID NO: 15 | QVQLVESGGGLVQPGGSLRLSCTVSRLTAHXXXXXWFRQAPGKEREAVSXXXXXRFTISR DYAGNTAFLQMDSLKPEDTGVYYCATXXXXXWGQGTQVTVSS |
| KERE sequence no. 16 | SEQ ID NO: 16 | EVQLVESGGELVQAGGSLKLSCTASGRNFVXXXXXWFRRAPGKEREFVAXXXXXRFTVS RDNGKNTAYLRMNSLKPEDTADYYCAVXXXXXLGSGTQVTVSS |
| GLEW sequence no. 1 | SEQ ID NO: 17 | AVQLVESGGGLVQPGGSLRLSCAASGFTESXXXXXWVRQAPGKVLEWVSXXXXXRFTIS RDNAKNTLYLQMNSLKPEDTAVYYCVKXXXXXGSQGTQVTVSS |
| GLEW sequence no. 2 | SEQ ID NO: 18 | EVQLVESGGGLVQPGGSLRLSCVCVSSGCTXXXXXWVRQAPGKAEEWVSXXXXXRFKIS RDNAKKTLYLQMNSLPEDTAMYYCQRXXXXXRGQGTQVTVSS |
| GLEW sequence no. 3 | SEQ ID NO: 19 | EVQLVESGGGLALPGGSLTLSCVFSGSTFSXXXXXWVRHTPGKAEEWVSXXXXXRFTISR DNAKNTLYLEMNSLSPEDTAMYYCGRXXXXXRSKGIQVTVSS |
| P, R, S 103 sequence no. 1 | SEQ ID NO: 20 | AVQLVESGGGLVQAGGSLRLSCAASGRTFSXXXXXWFRQAPGKEREFVAXXXXXRFTISR DNAKNTVYLQMNSLKPEDTAVYYCAAXXXXXRGQGTQVTVSS |
| P, R, S 103 sequence no. 2 | SEQ ID NO: 21 | DVQLVESGGDLVQPGGSLRLSCAASGFSFDXXXXXWLRQTPGKGLEWVGXXXXXRFTIS RDNAKNMLYLHLNNLKSEDTAVYYCRRXXXXXLGQGTQVTVSS |
| P, R, S 103 sequence no. 3 | SEQ ID NO: 22 | EVQLVESGGGLVQPGGSLRLSCVCVSSGCTXXXXXWVRQAPGKAEEWVSXXXXXRFKIS RDNAKKTLYLQMNSLGPEDTAMYYCQRXXXXXRGQGTQVTVSS |

In particular, a Nanobody of the invention of the KERE group can be an amino acid sequence with the (general) structure
FR1-CDR1-FR2-CDR2-FR3-CDR3-FR4
in which:
i) the amino acid residue at position 45 according to the Kabat numbering is a charged amino acid (as defined herein) or a cysteine residue, and position 44 is preferably an E;

and in which:

ii) FR1 is an amino acid sequence that has at least 80% amino acid identity with at least one of the following amino acid sequences:

TABLE B-9

Representative FW1 sequences for Nanobodies of the KERE-group.

| | | |
|---|---|---|
| KERE FW1 sequence no. 1 | SEQ ID NO: 23 | QVQRVESGGGLVQAGGSLRLSCAASGRTSS |
| KERE FW1 sequence no. 2 | SEQ ID NO: 24 | QVQLVESGGGLVQTGDSLSLSCSASGRTFS |
| KERE FW1 sequence no. 3 | SEQ ID NO: 25 | QVKLEESGGGLVQAGDSLRLSCAATGRAFG |
| KERE FW1 sequence no. 4 | SEQ ID NO: 26 | AVQLVESGGGLVQPGFSLGLSCVASGRDFV |
| KERE FW1 sequence no. 5 | SEQ ID NO: 27 | EVQLVESGGGLVQAGGSLRLSCEVLGRTAG |
| KERE FW1 sequence no. 6 | SEQ ID NO: 28 | QVQLVESGGGWVQPGGSLRLSCAASETILS |
| KERE FW1 sequence no. 7 | SEQ ID NO: 29 | QVQLVESGGGTVQPGGSLNLSCVASGNTFN |
| KERE FW1 sequence no. 8 | SEQ ID NO: 30 | EVQLVESGGGLAQPGGSLQLSCSAPGFTLD |
| KERE FW1 sequence no. 9 | SEQ ID NO: 31 | AQELEESGGGLVQAGGSLRLSCAASGRTFN | and in which:
iii) FR2 is an amino acid sequence that has at least 80% amino acid identity with at least one of the following amino acid sequences:

TABLE B-10

Representative FW2 sequences for Nanobodies of the KERE-group.

| | | |
|---|---|---|
| KERE FW2 sequence no. 1 | SEQ ID NO: 41 | WFRQAPGKEREFVA |
| KERE FW2 sequence no. 2 | SEQ ID NO: 42 | WFRQTPGREREFVA |
| KERE FW2 sequence no. 3 | SEQ ID NO: 43 | WYRQAPGKQREMVA |
| KERE FW2 sequence no. 4 | SEQ ID NO: 44 | WYRQGPGKQRELVA |
| KERE FW2 sequence no. 5 | SEQ ID NO: 45 | WIRQAPGKEREGVS |
| KERE FW2 sequence no. 6 | SEQ ID NO: 46 | WFREAPGKEREGIS |
| KERE FW2 sequence no. 7 | SEQ ID NO: 47 | WYRQAPGKERDLVA |
| KERE FW2 sequence no. 8 | SEQ ID NO: 48 | WFRQAPGKQREEVS |
| KERE FW2 sequence no. 9 | SEQ ID NO: 49 | WFRQPPGKVREFVG | and in which:
iv) FR3 is an amino acid sequence that has at least 80% amino acid identity with at least one of the following amino acid sequences:

TABLE B-11

Representative FW3 sequences for Nanobodies of the KERE-group.

| | | |
|---|---|---|
| KERE FW3 sequence no. 1. | SEQ ID NO: 50 | RFTISRDNAKNTVYLQMNSLKPEDTAVYRCYF |
| KERE FW3 sequence no. 2 | SEQ ID NO: 51 | RFAISRDNNKNTGYLQMNSLEPEDTAVYYCAA |
| KERE FW3 sequence no. 3 | SEQ ID NO: 52 | RFTVARNNAKNTVNLEMNSLKPEDTAVYYCAA |
| KERE FW3 sequence no. 4 | SEQ ID NO: 53 | RFTISRDIAKNTVDLLMNNLEPEDTAVYYCAA |

TABLE B-11-continued

Representative FW3 sequences for Nanobodies of the KERE-group.

| | | |
|---|---|---|
| KERE FW3 sequence no. 5 | SEQ ID NO: 54 | RLTISRDNAVDTMYLQMNSLKPEDTAVYYCAA |
| KERE FW3 sequence no. 6 | SEQ ID NO: 55 | RFTISRDNAKNTVYLQMDNVKPEDTAIYYCAA |
| KERE FW3 sequence no. 7 | SEQ ID NO: 56 | RFTISKDSGKNTVYLQMTSLKPEDTAVYYCAT |
| KERE FW3 sequence no. 8 | SEQ ID NO: 57 | RFTISRDSAKNMMYLQMNNLKPQDTAVYYCAA |
| KERE FW3 sequence no. 9 | SEQ ID NO: 58 | RFTISRENDKSTVYLQLNSLKPEDTAVYYCAA |
| KERE FW3 sequence no. 10 | SEQ ID NO: 59 | RFTISRDYAGNTAYLQMNSLKPEDTGVYYCAT | and in which:
v) FR4 is an amino acid sequence that has at least 80% amino acid identity with at least one of the following amino acid sequences:

TABLE B-12

Representative FW4 sequences for Nanabodies of the KERE-group.

| | | |
|---|---|---|
| KERE FW4 sequence no. 1 | SEQ ID NO: 60 | WGQGTQVTVSS |
| KERE FW4 sequence no. 2 | SEQ ID NO: 61 | WGKGTLVTVSS |
| KERE FW4 sequence no. 3 | SEQ ID NO: 62 | RGQGTRVTVSS |
| KERE FW4 sequence no. 4 | SEQ ID NO: 63 | WGLGTQVTISS | and in which:
vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

Also, the above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

With regard to framework 1, it will be clear to the skilled person that, when an amino acid sequence as outlined above is generated by expression of a nucleotide sequence, the first four amino acid sequences (i.e. amino acid residues 1-4 according to the Kabat numbering) may often be determined by the primer(s) that have been used to generate said nucleic acid. Thus, for determining the degree of amino acid identity, the first four amino acid residues are preferably disregarded.

Also, with regard to framework 1, and although amino acid positions 27 to 30 are according to the Kabat numbering considered to be part of the framework regions (and not the CDR's), it has been found by analysis of a database of more than 1000 $V_{HH}$ sequences that the positions 27 to 30 have a variability (expressed in terms of $V_{HH}$ entropy and $V_{HH}$ variability—see Tables B-4 to B-7) that is much greater than the variability on positions 1 to 26. Because of this, for determining the degree of amino acid identity, the amino acid residues at positions 27 to 30 are preferably also disregarded.

In view of this, a Nanobody of the KERE class may be an amino acid sequence that is comprised of four framework regions/sequences interrupted by three complementarity determining regions/sequences, in which:
i) the amino acid residue at position 45 according to the Kabat numbering is a charged amino acid (as defined herein) or a cysteine residue, and position 44 is preferably an E;
and in which:
ii) FR1 is an amino acid sequence that, on positions 5 to 26 of the Kabat numbering, has at least 80% amino acid identity with at least one of the following amino acid sequences:

TABLE B-13

Representative FW1 sequences (amino acid residues 5 to 26) for Nanobodies of the KERE-group.

| | | |
|---|---|---|
| KERE FW1 sequence no. 10 | SEQ ID NO: 32 | VESGGGLVQPGGSLRLSCAASG |
| KERE FW1 sequence no. 11 | SEQ ID NO: 33 | VDSGGGLVQAGDSLKLSCALTG |
| KERE FW1 sequence no. 12 | SEQ ID NO: 34 | VDSGGGLVQAGDSLRLSCAASG |

TABLE B-13-continued

Representative FW1 sequences (amino acid residues 5 to 26) for Nanobodies of the KERE-group.

| | | |
|---|---|---|
| KERE FW1 sequence no. 13 | SEQ ID NO: 35 | VDSGGGLVEAGGSLRLSCQVSE |
| KERE FW1 sequence no. 14 | SEQ ID NO: 36 | QDSGGGSVQAGGSLKLSCAASG |
| KERE FW1 sequence no. 15 | SEQ ID NO: 37 | VQSGGRLVQAGDSLRLSCAASE |
| KERE FW1 sequence no. 16 | SEQ ID NO: 38 | VESGGTLVQSGDSLKLSCASST |
| KERE FW1 sequence no. 17 | SEQ ID NO: 39 | MESGGDSVQSGGSLTLSCVASG |
| KERE FW1 sequence no. 18 | SEQ ID NO: 40 | QASGGGLVQAGGSLRLSCSASV | and in which:

iii) FR2, FR3 and FR4 are as mentioned herein for FR2, FR3 and FR4 of Nanobodies of the KERE-class;

and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

A Nanobody of the GLEW class may be an amino acid sequence that is comprised of four framework regions/sequences interrupted by three complementarity determining regions/sequences, in which i) preferably, when the Nanobody of the GLEW-class is a non-humanized Nanobody, the amino acid residue in position 108 is Q;

ii) FR1 is an amino acid sequence that has at least 80% amino acid identity with at least one of the following amino acid sequences:

TABLE B-14

Representative FW1 sequences for Nanobodies of the GLEW-group.

| | | |
|---|---|---|
| GLEW FW1 sequence no. 1 | SEQ ID NO: 64 | QVQLVESGGGLVQPGGSLRLSCAASGFTFS |
| GLEW FW1 sequence no. 2 | SEQ ID NO: 65 | EVHLVESGGGLVRPGGSLRLSCAAFGFIFK |
| GLEW FW1 sequence no. 3 | SEQ ID NO: 66 | QVKLEESGGGLAQPGGSLRLSCVASGFTFS |
| GLEW FW1 sequence no. 4 | SEQ ID NO: 67 | EVQLVESGGGLVQPGGSLRLSCVCVSSGCT |
| GLEW FW1 sequence no. 5 | SEQ ID NO: 68 | EVQLVESGGGLALPGGSLTLSCVFSGSTFS | and in which:

iii) FR2 is an amino acid sequence that has at least 80% amino acid identity with at least one of the following amino acid sequences:

TABLE B-15

Representative FW2 sequences for Nanobodies of the GLEW-group.

| | | |
|---|---|---|
| GLEW FW2 sequence no. 1 | SEQ ID NO: 72 | WVRQAPGKVLEWVS |
| GLEW FW2 sequence no. 2 | SEQ ID NO: 73 | WVRRPPGKGLEWVS |
| GLEW FW2 sequence no. 3 | SEQ ID NO: 74 | WVRQAPGMGLEWVS |
| GLEW FW2 sequence no. 4 | SEQ ID NO: 75 | WVRQAPGKEPEWVS |
| GLEW FW2 sequence no. 5 | SEQ ID NO: 76 | WVRQAPGKDQEWVS |
| GLEW FW2 sequence no. 6 | SEQ ID NO: 77 | WVRQAPGKAEEWVS |
| GLEW FW2 sequence no. 7 | SEQ ID NO: 78 | WVRQAPGKGLEWVA |
| GLEW FW2 sequence no. 8 | SEQ ID NO: 79 | WVRQAPGRATEWVS | and in which:
iv) FR3 is an amino acid sequence that has at least 80% amino acid identity with at least one of the following amino acid sequences:

TABLE B-16

Representative FW3 sequences for Nanobodies of the GLEW-group.

| | | |
|---|---|---|
| GLEW FW3 sequence no. 1 | SEQ ID NO: 80 | RFTISRDNAKNTLYLQMNSLKPEDTAVYYCVK |
| GLEW FW3 sequence no. 2 | SEQ ID NO: 81 | RFTISRDNARNTLYLQMDSLIPEDTALYYCAR |
| GLEW FW3 sequence no. 3 | SEQ ID NO: 82 | RFTSSRDNAKSTLYLQMNDLKPEDTALYYCAR |
| GLEW FW3 sequence no. 4 | SEQ ID NO: 83 | RFIISRDNAKNILYLQMNSLGPEDTAMYYCQR |
| GLEW FW3 sequence no. 5 | SEQ ID NO: 84 | RFTASRDNAKNTLYLQMNSLKSEDTARYYCAR |
| GLEW FW3 sequence no. 6 | SEQ ID NO: 85 | RFTISRDNAKNTLYLQMDDLQSEDTAMYYCGR | and in which:
v) FR4 is an amino acid sequence that has at least 80% amino acid identity with at least one of the following amino acid sequences:

TABLE B-17

Representative FW4 sequences for Nanobodies of the GLEW-group.

| | | |
|---|---|---|
| GLEW FW4 sequence no. 1 | SEQ ID NO: 86 | GSQGTQVTVSS |
| GLEW FW4 sequence no. 2 | SEQ ID NO: 87 | LRGGTQVTVSS |
| GLEW FW4 sequence no. 3 | SEQ ID NO: 88 | RGQGTLVTVSS |
| GLEW FW4 sequence no. 4 | SEQ ID NO: 89 | RSRGIQVTVSS |
| GLEW FW4 sequence no. 5 | SEQ ID NO: 90 | WGKGTQVTVSS |
| GLEW FW4 sequence no. 6 | SEQ ID NO: 91 | WGQGTQVTVSS | and in which:
vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a Nanobody of the GLEW class may be an amino acid sequence that is comprised of four framework regions/sequences interrupted by three complementarity determining regions/sequences, in which:

i) preferably, when the Nanobody of the GLEW-class is a non-humanized Nanobody, the amino acid residue in position 108 is Q;

and in which:
ii) FR1 is an amino acid sequence that, on positions 5 to 26 of the Kabat numbering, has at least 80% amino acid identity with at least one of the following amino acid sequences:

TABLE B-18

Representative FW1 sequences (amino acid residues 5 to 26) for Nanobodies of the KERE-group.

| | | |
|---|---|---|
| GLEW FW1 sequence no. 6 | SEQ ID NO: 69 | VESGGGLVQPGGSLRLSCAASG |
| GLEW FW1 sequence no. 7 | SEQ ID NO: 70 | EESGGGLAQPGGSLRLSCVASG |
| GLEW FW1 sequence no. 8 | SEQ ID NO: 71 | VESGGGLALPGGSLTLSCVFSG | and in which:

iii) FR2, FR3 and FR4 are as mentioned herein for FR2, FR3 and FR4 of Nanobodies of the GLEW-class;

and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein. In the above Nanobodies, one or more of the further Hallmark residues are preferably as described herein (for example, when they are $V_{HH}$ sequences or partially humanized Nanobodies).

A Nanobody of the P, R, S 103 class may be an amino acid sequence that is comprised of four framework regions/sequences interrupted by three complementarity determining regions/sequences, in which i) the amino acid residue at position 103 according to the Kabat numbering is different from W;

and in which:

ii) preferably the amino acid residue at position 103 according to the Kabat numbering is P, R or 5, and more preferably R;

and in which:

iii) FR1 is an amino acid sequence that has at least 80% amino acid identity with at least one of the following amino acid sequences:

TABLE B-19

Representative FW1 sequences for Nanobodies of the P, R, S 103-group.

| | | |
|---|---|---|
| P, R, S 103 FW1 sequence no. 1 | SEQ ID NO: 92 | AVQLVESGGGLVQAGGSLRLSCAASGRTFS |
| P, R, S 103 FW1 sequence no. 2 | SEQ ID NO: 93 | QVQLQESGGGMVQPGGSLRLSCAASGFDFG |
| P, R, S 103 FW1 sequence no. 3 | SEQ ID NO: 94 | EVHLVESGGGLVRPGGSLRLSCAAFGFIFK |
| P, R, S 103 FW1 sequence no. 4 | SEQ ID NO: 95 | QVQLAESGGGLVQPGGSLKLSCAASRTIVS |
| P, R, S 103 FW1 sequence no. 5 | SEQ ID NO: 96 | QEHLVESGGGLVDIGGSLRLSCAASERIFS |
| P, R, S 103 FW1 sequence no. 6 | SEQ ID NO: 97 | QVKLEESGGGLAQPGGSLRLSCVASGFTFS |
| P, R, S 103 FW1 sequence no. 7 | SEQ ID NO: 98 | EVQLVESGGGLVQPGGSLRLSCVCVSSGCT |
| P, R, S 103 FW1 sequence no. 8 | SEQ ID NO: 99 | EVQLVESGGGLALPGGSLTLSCVFSGSTFS | and in which iv) FR2 is an amino acid sequence that has at least 80% amino acid identity with at least one of the following amino acid sequences:

TABLE B-20

Representative FW2 sequences for Nanobodies of the P, R, S 103-group.

| | | |
|---|---|---|
| P, R, S 103 FW2 sequence no. 1 | SEQ ID NO: 102 | WFRQAPGKEREFVA |
| P, R, S 103 FW2 sequence no. 2 | SEQ ID NO: 103 | WVRQAPGKVLEWVS |
| P, R, S 103 FW2 sequence no. 3 | SEQ ID NO: 104 | WVRRPPGKGLEWVS |
| P, R, S 103 FW2 sequence no. 4 | SEQ ID NO: 105 | WIRQAPGKEREGVS |
| P, R, S 103 FW2 sequence no. 5 | SEQ ID NO: 106 | WVRQYPGKEPEWVS |
| P, R, S 103 FW2 sequence no. 6 | SEQ ID NO: 107 | WFRQPPGKEHEFVA |
| P, R, S 103 FW2 sequence no. 7 | SEQ ID NO: 108 | WYRQAPGKRTELVA |
| P, R, S 103 FW2 sequence no. 8 | SEQ ID NO: 109 | WLRQAPGQGLEWVS |
| P, R, S 103 FW2 sequence no. 9 | SEQ ID NO: 110 | WLRQTPGKGLEWVG |
| P, R, S 103 FW2 sequence no. 10 | SEQ ID NO: 111 | WVRQAPGKAEEFVS | and in which:
v) FR3 is an amino acid sequence that has at least 80% amino acid identity with at least one of the following amino acid sequences:

TABLE B-21

Representative FW3 sequences for Nanobodies of the P, R, S 103-group.

| | | |
|---|---|---|
| P, R, S 103 FW3 sequence no. 1 | SEQ ID NO: 112 | RFTISRDNAKNTVYLQMNSLKPEDTAVYYCAA |
| P, R, S 103 FW3 sequence no. 2 | SEQ ID NO: 113 | RFTISRDNARNTLYLQMDSLIPEDTALYYCAR |
| P, R, S 103 FW3 sequence no. 3 | SEQ ID NO: 114 | RFTISRDNAKNEMYLQMNNLKTEDTGVYWCGA |
| P, R, S 103 FW3 sequence no. 4 | SEQ ID NO: 115 | RFTISSDSNRNMIYLQMNNLKPEDTAVYYCAA |
| P, R, S 103 FW3 sequence no. 5 | SEQ ID NO: 116 | RFTISRDNAKNMLYLHLNNLKSEDTAVYYCRR |
| P, R, S 103 FW3 sequence no. 6 | SEQ ID NO: 117 | RFTISRDNAKKTVYLRLNSLNPEDTAVYSCNL |
| P, R, S 103 FW3 sequence no. 7 | SEQ ID NO: 118 | RFKISRDNAKKTLYLQMNSLGPEDTAMYYCQR |
| P, R, S 103 FW3 sequence no. 8 | SEQ ID NO: 119 | RFTVSRDNGKNTAYLRMNSLKPEDTADYYCAV | and in which:
vi) FR4 is an amino acid sequence that has at least 80% amino acid identity with at least one of the following amino acid sequences:

TABLE B-22

Representative FW4 sequences for Nanobodies of the P, R, S 103-group.

| | | |
|---|---|---|
| P, R, S 103 FW4 sequence no. 1 | SEQ ID NO: 120 | RGQGTQVTVSS |
| P, R, S 103 FW4 sequence no. 2 | SEQ ID NO: 121 | LRGGTQVTVSS |
| P, R, S 103 FW4 sequence no. 3 | SEQ ID NO: 122 | GNKGTLVTVSS |
| P, R, S 103 FW4 sequence no. 4 | SEQ ID NO: 123 | SSPGTQVTVSS |
| P, R, S 103 FW4 sequence no. 5 | SEQ ID NO: 124 | SSQGTLVTVSS |
| P, R, S 103 FW4 sequence no. 6 | SEQ ID NO: 125 | RSRGIQVTVSS | and in which:
vii) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are V$_{HH}$ sequences or partially humanized Nanobodies).

regions/sequences interrupted by three complementarity determining regions/sequences, in which:
i) the amino acid residue at position 103 according to the Kabat numbering is different from W;

and in which:
ii) preferably the amino acid residue at position 103 according to the Kabat numbering is P, R or S, and more preferably R;

and in which:
iii) FR1 is an amino acid sequence that, on positions 5 to 26 of the Kabat numbering, has at least 80% amino acid identity with at least one of the following amino acid sequences:

TABLE B-23

Representative FW1 sequences (amino acid residues 5 to 26) for Nanobodies of the P, R, S 103-group.

| | | |
|---|---|---|
| P, R, S 103 FW1 sequence no. 9 | SEQ ID NO: 100 | VESGGGLVQAGGSLRLSCAASG |
| P, R, S 103 FW1 sequence no. 10 | SEQ ID NO: 101 | AESGGGLVQPGGSLKLSCAASR |

With regard to framework 1, it will again be clear to the skilled person that, for determining the degree of amino acid identity, the amino acid residues on positions 1 to 4 and 27 to 30 are preferably disregarded.

In view of this, a Nanobody of the P,R,S 103 class may be an amino acid sequence that is comprised of four framework and in which:
iv) FR2, FR3 and FR4 are as mentioned herein for FR2, FR3 and FR4 of Nanobodies of the P,R,S 103 class;

and in which:
v) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above Nanobody sequences are $V_{HH}$ sequences, they may be suitably humanized, as further described herein. When the Nanobodies are partially humanized Nanobodies, they may optionally be further suitably humanized, again as described herein.

In the above Nanobodies, one or more of the further Hallmark residues are preferably as described herein (for example, when they are $V_{HH}$ sequences or partially humanized Nanobodies).

In another preferred, but non-limiting aspect, the invention relates to a Nanobody as described above, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 179 to 185 (see Table A-1). This degree of amino acid identity can for example be determined by determining the degree of amino acid identity (in a manner described herein) between said Nanobody and one or more of the sequences of SEQ ID NO's: 179 to 185 (see Table A-1), in which the amino acid residues that form the framework regions are disregarded. Such Nanobodies can be as further described herein.

As already mentioned herein, another preferred but non-limiting aspect of the invention relates to a Nanobody with an amino acid sequence that is chosen from the group consisting of SEQ ID NO's: 179 to 185 (see Table A-1) or from the group consisting of from amino acid sequences that have more than 80%, preferably more than 90%, more preferably more than 95%, such as 99% or more sequence identity (as defined herein) with at least one of the amino acid sequences of SEQ ID NO's: 179 to 185 (see Table A-1).

Also, in the above Nanobodies:
i) any amino acid substitution (when it is not a humanizing substitution as defined herein) is preferably, and compared to the corresponding amino acid sequence of SEQ ID NO's: 179 to 185 (see Table A-1), a conservative amino acid substitution, (as defined herein);
and/or:
ii) its amino acid sequence preferably contains either only amino acid substitutions, or otherwise preferably no more than 5, preferably no more than 3, and more preferably only 1 or 2 amino acid deletions or insertions, compared to the corresponding amino acid sequence of SEQ ID NO's: 179 to 185 (see Table A-1);
and/or
iii) the CDR's may be CDR's that are derived by means of affinity maturation, for example starting from the CDR's of to the corresponding amino acid sequence of SEQ ID NO's: 179 to 185 (see Table A-1).

Preferably, the CDR sequences and FR sequences in the Nanobodies of the invention are such that the Nanobodies of the invention (and polypeptides of the invention comprising the same):
bind to OX40L with a dissociation constant ($K_D$) of $10^{-5}$ to $10^{12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:
bind to OX40L with a $k_{on}$-rate of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$;
and/or such that they:
bind to OX40L with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, CDR sequences and FR sequences present in the Nanobodies of the invention are such that the Nanobodies of the invention will bind to OX40L with an affinity less than 500 nM, preferably less than 200 nM, more preferably less than 10 nM, such as less than 500 pM.

According to one non-limiting aspect of the invention, a Nanobody may be as defined herein, but with the proviso that it has at least "one amino acid difference" (as defined herein) in at least one of the framework regions compared to the corresponding framework region of a naturally occurring human $V_H$ domain, and in particular compared to the corresponding framework region of DP-47. More specifically, according to one non-limiting aspect of the invention, a Nanobody may be as defined herein, but with the proviso that it has at least "one amino acid difference" (as defined herein) at at least one of the Hallmark residues (including those at positions 108, 103 and/or 45) compared to the corresponding framework region of a naturally occurring human $V_H$ domain, and in particular compared to the corresponding framework region of DP-47. Usually, a Nanobody will have at least one such amino acid difference with a naturally occurring $V_H$ domain in at least one of FR2 and/or FR4, and in particular at at least one of the Hallmark residues in FR2 and/or FR4 (again, including those at positions 108, 103 and/or 45).

Also, a humanized Nanobody of the invention may be as defined herein, but with the proviso that it has at least "one amino acid difference" (as defined herein) in at least one of the framework regions compared to the corresponding framework region of a naturally occurring $V_{HH}$ domain. More specifically, according to one non-limiting aspect of the invention, a humanized Nanobody may be as defined herein, but with the proviso that it has at least "one amino acid difference" (as defined herein) at at least one of the Hallmark residues (including those at positions 108, 103 and/or 45) compared to the corresponding framework region of a naturally occurring $V_{HH}$ domain. Usually, a humanized Nanobody will have at least one such amino acid difference with a naturally occurring $V_{HH}$ domain in at least one of FR2 and/or FR4, and in particular at at least one of the Hallmark residues in FR2 and/or FR4 (again, including those at positions 108, 103 and/or 45).

As will be clear from the disclosure herein, it is also within the scope of the invention to use natural or synthetic analogs, mutants, variants, alleles, homologs and orthologs (herein collectively referred to as "onologs") of the Nanobodies of the invention as defined herein, and in particular analogs of the Nanobodies of SEQ ID NO's 179 to 185 (see Table A-1). Thus, according to one aspect of the invention, the term "Nanobody of the invention" in its broadest sense also covers such analogs.

Generally, in such analogs, one or more amino acid residues may have been replaced, deleted and/or added, compared to the Nanobodies of the invention as defined herein. Such substitutions, insertions or deletions may be made in one or more of the framework regions and/or in one or more of the CDR's. When such substitutions, insertions or deletions are made in one or more of the framework regions, they may be made at one or more of the Hallmark residues and/or at one or more of the other positions in the framework residues, although substitutions, insertions or deletions at the Hallmark residues are generally less preferred (unless these are suitable humanizing substitutions as described herein).

By means of non-limiting examples, a substitution may for example be a conservative substitution (as described herein) and/or an amino acid residue may be replaced by another amino acid residue that naturally occurs at the same position in another $V_{HH}$ domain (see Tables B-4 to B-7 for some non-limiting examples of such substitutions), although the invention is generally not limited thereto. Thus, any one or more substitutions, deletions or insertions, or any combination thereof, that either improve the properties of the Nanobody of the invention or that at least do not detract too much from the desired properties or from the balance or combination of desired properties of the Nanobody of the invention (i.e. to the extent that the Nanobody is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the Nanobodies thus obtained.

For example, and depending on the host organism used to express the Nanobody or polypeptide of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables B-4 to B-7 above, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions.

The analogs are preferably such that they can bind to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

The analogs are preferably also such that they retain the favourable properties the Nanobodies, as described herein.

Also, according to one preferred aspect, the analogs have a degree of sequence identity of at least 70%, preferably at least 80%, more preferably at least 90%, such as at least 95% or 99% or more; and/or preferably have at most 20, preferably at most 10, even more preferably at most 5, such as 4, 3, 2 or only 1 amino acid difference (as defined herein), with one of the Nanobodies of SEQ ID NOs: 179 to 185 (see Table A-1).

Also, the framework sequences and CDR's of the analogs are preferably such that they are in accordance with the preferred aspects defined herein. More generally, as described herein, the analogs will have (a) a Q at position 108; and/or (b) a charged amino acid or a cysteine residue at position 45 and preferably an E at position 44, and more preferably E at position 44 and R at position 45; and/or (c) P, R or S at position 103.

One preferred class of analogs of the Nanobodies of the invention comprise Nanobodies that have been humanized (i.e. compared to the sequence of a naturally occurring Nanobody of the invention). As mentioned in the background art cited herein, such humanization generally involves replacing one or more amino acid residues in the sequence of a naturally occurring $V_{HH}$ with the amino acid residues that occur at the same position in a human $V_H$ domain, such as a human $V_H3$ domain. Examples of possible humanizing substitutions or combinations of humanizing substitutions will be clear to the skilled person, for example from the Tables herein, from the possible humanizing substitutions mentioned in the background art cited herein, and/or from a comparison between the sequence of a Nanobody and the sequence of a naturally occurring human $V_H$ domain.

The humanizing substitutions should be chosen such that the resulting humanized Nanobodies still retain the favourable properties of Nanobodies as defined herein, and more preferably such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies thus obtained.

Generally, as a result of humanization, the Nanobodies of the invention may become more "human-like", while still retaining the favorable properties of the Nanobodies of the invention as described herein. As a result, such humanized Nanobodies may have several advantages, such as a reduced immunogenicity, compared to the corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favourable properties provided by the humanizing substitutions on the one hand and the favourable properties of naturally occurring $V_H$ domains on the other hand.

The Nanobodies of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies of the "P,R,S-103 group" or the "KERE group" is Q108 into L108. Nanobodies of the "GLEW class" may also be humanized by a Q108 into L108 substitution, provided at least one of the other Hallmark residues contains a camelid (camelizing) substitution (as defined herein). For example, as mentioned above, one particularly preferred class of humanized Nanobodies has GLEW or a GLEW-like sequence at positions 44-47; P, R or S (and in particular R) at position 103, and an L at position 108.

The humanized and other analogs, and nucleic acid sequences encoding the same, can be provided in any manner known per se, for example using one or more of the techniques mentioned on pages 103 and 104 of WO 08/020079.

Also, in addition to humanizing substitutions as described herein, the amino acid sequences of the invention may contain one or more other/further substitutions. Again, some preferred, but non-limiting examples of such other/further substitutions will become clear from the further description herein, and for example may include (and preferably essentially consist of) one or more of the following substitutions:
(a) one or more conservative amino acid substitutions; and/or
(b) one or more substitutions in which a "camelid" amino acid residue at a certain position is replaced by a different "camelid" amino acid residue that occurs at said position, for which reference is for example made to Tables A-6 to A-9 from PCT/EP2008/066365 (published on Jun. 4, 2009 as WO 09/068627), which mention the various Camelid residues that occur as each amino acid position in wild-type $V_{HH}$'s. Such substitutions may even comprise suitable substitutions of an amino acid residue that occurs at a Hallmark position with another amino acid residue that occurring at a Hallmark position in a wild-type $V_{HH}$ (for which reference is for example made to Tables A-6 to A-9 from PCT/EP2008/066365); and/or
(c) one or more substitutions that improve the (other) properties of the protein, such as substitutions that improve the long-term stability and/or properties under storage of the protein. These may for example and without limitation be substitutions that prevent or reduce oxidation events (for example, of methionine residues); that prevent or reduce pyroglutamate formation; and/or that prevent or reduce isomerisation or deamidation of aspartic acids or asparagines (for example, of DG, DS, NG or NS motifs). For such substitutions, reference is for example made to the International application WO 09/095235, which is generally directed to methods for stabilizing single immunoglobulin variable domains by means of such substitutions, and also gives some specific example of suitable substitutions (see for example pages 4 and 5 and pages 10 to 15). One example of such substitution may be to replace an NS motif at positions 82a and 82b with an NN motif.

As mentioned there, it will be also be clear to the skilled person that the Nanobodies of the invention (including their analogs) can be designed and/or prepared starting from human $V_H$ sequences (i.e. amino acid sequences or the corresponding nucleotide sequences), such as for example from human $V_H3$ sequences such as DP-47, DP-51 or DP-29, i.e. by introducing one or more camelizing substitutions (i.e. changing one or more amino acid residues in the amino acid sequence of said human $V_H$ domain into the amino acid residues that occur at the corresponding position in a $V_{HH}$ domain), so as to provide the sequence of a Nanobody of the invention and/or so as to confer the favourable properties of a Nanobody to the sequence thus obtained. Again, this can generally be performed using the various methods and techniques referred to in the previous paragraph, using an amino acid sequence and/or nucleotide sequence for a human $V_H$ domain as a starting point.

Some preferred, but non-limiting camelizing substitutions can be derived from Tables B-4-B-7. It will also be clear that camelizing substitutions at one or more of the Hallmark residues will generally have a greater influence on the desired properties than substitutions at one or more of the other amino acid positions, although both and any suitable combination thereof are included within the scope of the invention. For example, it is possible to introduce one or more camelizing substitutions that already confer at least some the desired properties, and then to introduce further camelizing substitutions that either further improve said properties and/or confer additional favourable properties. Again, the skilled person will generally be able to determine and select suitable camelizing substitutions or suitable combinations of camelizing substitutions, based on the disclosure herein and optionally after a limited degree of routine experimentation, which may for example involve introducing a limited number of possible camelizing substitutions and determining whether the favourable properties of Nanobodies are obtained or improved (i.e. compared to the original $V_H$ domain).

Generally, however, such camelizing substitutions are preferably such that the resulting an amino acid sequence at least contains (a) a Q at position 108; and/or (b) a charged amino acid or a cysteine residue at position 45 and preferably also an E at position 44, and more preferably E at position 44 and R at position 45; and/or (c) P, R or S at position 103; and optionally one or more further camelizing substitutions. More preferably, the camelizing substitutions are such that they result in a Nanobody of the invention and/or in an analog thereof (as defined herein), such as in a humanized analog and/or preferably in an analog that is as defined in the preceding paragraphs.

Nanobodies can also be derived from $V_H$ domains by the incorporation of substitutions that are rare in nature, but nonetheless, structurally compatible with the VH domain fold. For example, but without being limiting, these substitutions may include on or more of the following: Gly at position 35, Ser, Val or Thr at position 37, Ser, Thr, Arg, Lys, His, Asp or Glu at position 39, Glu or His at position 45, Trp, Leu, Val, Ala, Thr, or Glu at position 47, S or R at position 50. (Barthelemy et al. J Biol Chem. 2008 Feb. 8; 283(6): 3639-54. Epub 2007 Nov. 28)

As will also be clear from the disclosure herein, it is also within the scope of the invention to use parts or fragments, or combinations of two or more parts or fragments, of the Nanobodies of the invention as defined herein, and in particular parts or fragments of the Nanobodies of SEQ ID NO's: 179 to 185 (see Table A-1). Thus, according to one aspect of the invention, the term "Nanobody of the invention" in its broadest sense also covers such parts or fragments.

Generally, such parts or fragments of the Nanobodies of the invention (including analogs thereof) have amino acid sequences in which, compared to the amino acid sequence of the corresponding full length Nanobody of the invention (or analog thereof), one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length Nanobody of the invention.

Also, any part or fragment is such preferably that it comprises at least one of CDR1, CDR2 and/or CDR3 or at least part thereof (and in particular at least CDR3 or at least part thereof). More preferably, any part or fragment is such that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting aspect, such a part or fragment comprises at least CDR3, such as FR3, CDR3 and FR4 of the corresponding full length Nanobody of the invention, i.e. as for example described in the International application WO 03/050531 (Lasters et al.).

As already mentioned above, it is also possible to combine two or more of such parts or fragments (i.e. from the same or different Nanobodies of the invention), i.e. to provide an analog (as defined herein) and/or to provide further parts or fragments (as defined herein) of a Nanobody of the invention. It is for example also possible to combine one or more parts or fragments of a Nanobody of the invention with one or more parts or fragments of a human $V_H$ domain.

According to one preferred aspect, the parts or fragments have a degree of sequence identity of at least 50%, preferably at least 60%, more preferably at least 70%, even more preferably at least 80%, such as at least 90%, 95% or 99% or more with one of the Nanobodies of SEQ ID NOs 179 to 185 (see Table A-1).

The parts and fragments, and nucleic acid sequences encoding the same, can be provided and optionally combined in any manner known per se. For example, such parts or fragments can be obtained by inserting a stop codon in a nucleic acid that encodes a full-sized Nanobody of the invention, and then expressing the nucleic acid thus obtained in a manner known per se (e.g. as described herein). Alternatively, nucleic acids encoding such parts or fragments can be obtained by suitably restricting a nucleic acid that encodes a full-sized Nanobody of the invention or by synthesizing such a nucleic acid in a manner known per se. Parts or fragments may also be provided using techniques for peptide synthesis known per se.

The invention in its broadest sense also comprises derivatives of the Nanobodies of the invention. Such derivatives can generally be obtained by modification, and in particular by chemical and/or biological (e.g. enzymatical) modification, of the Nanobodies of the invention and/or of one or more of the amino acid residues that form the Nanobodies of the invention.

Examples of such modifications, as well as examples of amino acid residues within the Nanobody sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the Nanobody of the invention, and in particular of one or more functional groups, residues or moieties that confer one or more desired properties or functionalities to the Nanobody of the invention. Example of such functional groups will be clear to the skilled person.

For example, such modification may comprise the introduction (e.g. by covalent binding or in any other suitable manner) of one or more functional groups that increase the half-life, the solubility and/or the absorption of the Nanobody of the invention, that reduce the immunogenicity and/or the toxicity of the Nanobody of the invention, that eliminate or attenuate any undesirable side effects of the Nanobody of the invention, and/or that confer other advantageous properties to and/or reduce the undesired properties of the Nanobodies and/or polypeptides of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a Nanobody of the invention, a Nanobody of the invention may be modified so as to suitably introduce one or more cysteine residues for attachment of PEG, or an amino acid sequence comprising one or more cysteine residues for attachment of PEG may be fused to the N- and/or C-terminus of a Nanobody of the invention, all using techniques of protein engineering known per se to the skilled person.

Preferably, for the Nanobodies and proteins of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the Nanobody or polypeptide of the invention.

Yet another modification may comprise the introduction of one or more detectable labels or other signal-generating groups or moieties, depending on the intended use of the labelled Nanobody. Suitable labels and techniques for attaching, using and detecting them will be clear to the skilled person, and for example include, but are not limited to, the fluorescent labels, phosphorescent labels, chemiluminescent labels, bioluminescent labels, radio-isotopes, metals, metal chelates, metallic cations, chromophores and enzymes, such as those mentioned on page 109 of WO 08/020079. Other suitable labels will be clear to the skilled person, and for example include moieties that can be detected using NMR or ESR spectroscopy.

Such labelled Nanobodies and polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the Nanobody of the invention to another protein, polypeptide or chemical compound that is bound to the other half of the binding pair, i.e. through formation of the binding pair. For example, a Nanobody of the invention may be conjugated to biotin, and linked to another protein, polypeptide, compound or carrier conjugated to avidin or streptavidin. For example, such a conjugated Nanobody may be used as a reporter, for example in a diagnostic system where a detectable signal-producing agent is conjugated to avidin or streptavidin. Such binding pairs may for example also be used to bind the Nanobody of the invention to a carrier, including carriers suitable for pharmaceutical purposes. One non-limiting example are the liposomal formulations described by Cao and Suresh, Journal of Drug Targetting, 8, 4, 257 (2000). Such binding pairs may also be used to link a therapeutically active agent to the Nanobody of the invention.

For some applications, in particular for those applications in which it is intended to kill a cell that expresses the target against which the Nanobodies of the invention are directed (e.g. in the treatment of cancer), or to reduce or slow the growth and/or proliferation such a cell, the Nanobodies of the invention may also be linked to a toxin or to a toxic residue or moiety. Examples of toxic moieties, compounds or residues which can be linked to a Nanobody of the invention to provide—for example—a cytotoxic compound will be clear to the skilled person and can for example be found in the prior art cited above and/or in the further description herein. One example is the so-called ADEPT™ technology described in WO 03/055527.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

Preferably, the derivatives are such that they bind to OX40L with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

As mentioned above, the invention also relates to proteins or polypeptides that essentially consist of or comprise at least one Nanobody of the invention. By "essentially consist of" is meant that the amino acid sequence of the polypeptide of the invention either is exactly the same as the amino acid sequence of a Nanobody of the invention or corresponds to the amino acid sequence of a Nanobody of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence of the Nanobody.

Said amino acid residues may or may not change, alter or otherwise influence the (biological) properties of the Nanobody and may or may not add further functionality to the Nanobody. For example, such amino acid residues:

can comprise an N-terminal Met residue, for example as result of expression in a heterologous host cell or host organism.

may form a signal sequence or leader sequence that directs secretion of the Nanobody from a host cell upon synthesis. Suitable secretory leader peptides will be clear to the skilled person, and may be as further described herein. Usually, such a leader sequence will be linked to the N-terminus of the Nanobody, although the invention in its broadest sense is not limited thereto;

may form a sequence or signal that allows the Nanobody to be directed towards and/or to penetrate or enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such amino acid sequences will be clear to the skilled person and include those mentioned in paragraph c) on page 112 of WO 08/020079.

may form a "tag", for example an amino acid sequence or residue that allows or facilitates the purification of the Nanobody, for example using affinity techniques directed against said sequence or residue. Thereafter, said sequence or residue may be removed (e.g. by chemical or enzymatical cleavage) to provide the Nanobody sequence (for this purpose, the tag may optionally be linked to the Nanobody sequence via a cleavable linker sequence or contain a cleavable motif). Some preferred, but non-limiting examples of such residues are multiple histidine residues, glutathione residues and a myc-tag (see for example SEQ ID NO:31 of WO 06/12282).

may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the Nanobodies of the invention.

According to another aspect, a polypeptide of the invention comprises a Nanobody of the invention, which is fused at its amino terminal end, at its carboxy terminal end, or both at its amino terminal end and at its carboxy terminal end to at least one further amino acid sequence, i.e. so as to provide a fusion protein comprising said Nanobody of the invention and the one or more further amino acid sequences. Such a fusion will also be referred to herein as a "Nanobody fusion".

The one or more further amino acid sequence may be any suitable and/or desired amino acid sequences. The further amino acid sequences may or may not change, alter or otherwise influence the (biological) properties of the Nanobody, and may or may not add further functionality to the Nanobody or the polypeptide of the invention. Preferably, the further amino acid sequence is such that it confers one or more desired properties or functionalities to the Nanobody or the polypeptide of the invention.

For example, the further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the Nanobody of the invention is directed, or a different protein, polypeptide, antigen, antigenic determinant or epitope).

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005).

For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the Nanobody of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In particular, it has been described in the art that linking fragments of immunoglobulins (such as $V_H$ domains) to serum albumin or to fragments thereof can be used to increase the half-life. Reference is for made to WO 00/27435 and WO 01/077137). According to the invention, the Nanobody of the invention is preferably either directly linked to serum albumin (or to a suitable fragment thereof) or via a suitable linker, and in particular via a suitable peptide linked so that the polypeptide of the invention can be expressed as a genetic fusion (protein). According to one specific aspect, the Nanobody of the invention may be linked to a fragment of serum albumin that at least comprises the domain III of serum albumin or part thereof. Reference is for example made to WO 07/112940 of Ablynx N.V.

Alternatively, the further amino acid sequence may provide a second binding site or binding unit that is directed against a serum protein (such as, for example, human serum albumin or another serum protein such as IgG), so as to provide increased half-life in serum. Such amino acid sequences for example include the Nanobodies described below, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, as well as to WO 08/028977, WO 08/043821, WO 08/043822 by Ablynx N.V. and US provisional application of Ablynx N.V. entitled "Peptides capable of binding to serum proteins" filed on Dec. 5, 2006 ((see also PCT/EP2007/063348).

Such amino acid sequences may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see for example WO 06/0122787) and/or amino acid sequences that are capable of binding to amino acid residues on serum albumin that do not form part of domain III of serum albumin (see again for example WO 06/0122787); amino acid sequences that have or can provide an increased half-life (see for example WO 08/028977 by Ablynx N.V.); amino acid sequences against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*), reference is again made to WO 08/028977; amino acid sequences that can bind to serum albumin in a pH independent manner (see for example WO 08/043821 by Ablynx N.V. entitled "Amino acid sequences that bind to serum proteins in a manner that is essentially independent of the pH, compounds comprising the same, and uses thereof") and/or amino acid sequences that are conditional binders (see for example WO 08/043822 by Ablynx N.V. entitled "Amino acid sequences that bind to a desired molecule in a conditional manner").

According to another aspect, the one or more further amino acid sequences may comprise one or more parts, fragments or domains of conventional 4-chain antibodies (and in particular human antibodies) and/or of heavy chain antibodies. For example, although usually less preferred, a Nanobody of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

The at least one Nanobody may also be linked to one or more (preferably human) $C_H1$, $C_H2$ and/or $C_H3$ domains, optionally via a linker sequence. For instance, a Nanobody linked to a suitable $C_H1$ domain could for example be used—together with suitable light chains—to generate antibody fragments/structures analogous to conventional Fab fragments or F(ab')$_2$ fragments, but in which one or (in case of an F(ab')$_2$ fragment) one or both of the conventional $V_H$ domains have been replaced by a Nanobody of the invention. Also, two Nanobodies could be linked to a $C_H3$ domain (optionally via a linker) to provide a construct with increased half-life in vivo.

According to one specific aspect of a polypeptide of the invention, one or more Nanobodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a Nanobody), in which the Camelidae $C_H2$ and/or $C_H3$ domain have been replaced by human $C_H2$ and $C_H3$ domains, so as to provide an immunoglobulin that consists of 2 heavy chains each comprising a Nanobody and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the Nanobodies of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and to the non-prepublished US provisional application by Ablynx N.V. entitled "Constructs comprising single variable domains and an Fc portion derived from IgE" which has a filing date of Dec. 4, 2007. Coupling of a Nanobody of the invention to an Fc portion may also lead to an increased half-life, compared to the corresponding Nanobody of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more Nanobodies and one or more constant domains with increased half-life in vivo will be clear to the skilled person, and may for example comprise two Nanobodies linked to a $C_H3$ domain, optionally via a linker sequence. Generally, any fusion protein or derivatives with increased half-life will preferably have a molecular weight of more than 50 kD, the cut-off value for renal absorption.

In another one specific, but non-limiting, aspect, in order to form a polypeptide of the invention, one or more amino acid sequences of the invention may be linked (optionally via a suitable linker or hinge region) to naturally occurring, synthetic or semisynthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al., J Biol Chem 1996 271 7494, describe monomeric Fc chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Bivalent/multivalent, bispecific/multispecific or biparatopic/multiparatopic polypeptides of the invention may also be linked to Fc portions, in order to provide polypeptide constructs of the type that is described in the non-prepublished US provisional application U.S. 61/005, 331 entitled "immunoglobulin constructs" filed on Dec. 4, 2007.

The further amino acid sequences may also form a signal sequence or leader sequence that directs secretion of the Nanobody or the polypeptide of the invention from a host cell upon synthesis (for example to provide a pre-, pro- or prepro-form of the polypeptide of the invention, depending on the host cell used to express the polypeptide of the invention).

The further amino acid sequence may also form a sequence or signal that allows the Nanobody or polypeptide of the invention to be directed towards and/or to penetrate or enter into specific organs, tissues, cells, or parts or compartments of cells, and/or that allows the Nanobody or polypeptide of the invention to penetrate or cross a biological barrier such as a cell membrane, a cell layer such as a layer of epithelial cells, a tumor including solid tumors, or the blood-brain-barrier. Suitable examples of such amino acid sequences will be clear to the skilled person, and for example include, but are not limited to, those mentioned on page 118 of WO 08/020079. For some applications, in particular for those applications in which it is intended to kill a cell that expresses the target against which the Nanobodies of the invention are directed (e.g. in the treatment of cancer), or to reduce or slow the growth and/or proliferation of such a cell, the Nanobodies of the invention may also be linked to a (cyto)toxic protein or polypeptide. Examples of such toxic proteins and polypeptides which can be linked to a Nanobody of the invention to provide—for example—a cytotoxic polypeptide of the invention will be clear to the skilled person and can for example be found in the prior art cited above and/or in the further description herein. One example is the so-called ADEPT™ technology described in WO 03/055527.

According to one preferred, but non-limiting aspect, said one or more further amino acid sequences comprise at least one further Nanobody, so as to provide a polypeptide of the invention that comprises at least two, such as three, four, five or more Nanobodies, in which said Nanobodies may optionally be linked via one or more linker sequences (as defined herein). As described on pages 119 and 120 of WO 08/020079, polypeptides of the invention that comprise two or more Nanobodies, of which at least one is a Nanobody of the invention, will also be referred to herein as "multivalent" polypeptides of the invention, and the Nanobodies present in such polypeptides will also be referred to herein as being in a "multivalent format". For example, "bivalent" and "trivalent" polypeptides of the invention may be as further described on pages 119 and 120 of WO 08/020079.

Polypeptides of the invention that contain at least two Nanobodies, in which at least one Nanobody is directed against a first antigen (i.e. against OX40L,) and at least one Nanobody is directed against a second antigen (i.e. different from OX40L), will also be referred to as "multispecific" polypeptides of the invention, and the Nanobodies present in such polypeptides will also be referred to herein as being in a "multispecific format". Thus, for example, a "bispecific" polypeptide of the invention is a polypeptide that comprises at least one Nanobody directed against a first antigen (i.e. OX40L,) and at least one further Nanobody directed against a second antigen (i.e. different from OX40L), whereas a "trispecific" polypeptide of the invention is a polypeptide that comprises at least one Nanobody directed against a first antigen (i.e. OX40L), at least one further Nanobody directed against a second antigen (i.e. different from OX40L,) and at least one further Nanobody directed against a third antigen (i.e. different from both OX40L, and the second antigen); etc.

Accordingly, in its simplest form, a bispecific polypeptide of the invention is a bivalent polypeptide of the invention (as defined herein), comprising a first Nanobody directed against OX40L, and a second Nanobody directed against a second antigen, in which said first and second Nanobody may optionally be linked via a linker sequence (as defined herein); whereas a trispecific polypeptide of the invention in its simplest form is a trivalent polypeptide of the invention (as defined herein), comprising a first Nanobody directed against OX40L, a second Nanobody directed against a second antigen and a third Nanobody directed against a third antigen, in which said first, second and third Nanobody may optionally be linked via one or more, and in particular one and more, in particular two, linker sequences.

However, as will be clear from the description hereinabove, the invention is not limited thereto, in the sense that a multispecific polypeptide of the invention may comprise at least one Nanobody against OX40L, and any number of Nanobodies directed against one or more antigens different from OX40L.

Furthermore, although it is encompassed within the scope of the invention that the specific order or arrangement of the various Nanobodies in the polypeptides of the invention may have some influence on the properties of the final polypeptide of the invention (including but not limited to the affinity, specificity or avidity for OX40L, or against the one or more other antigens), said order or arrangement is usually not critical and may be suitably chosen by the skilled person, optionally after some limited routine experiments based on the disclosure herein. Thus, when reference is made to a specific multivalent or multispecific polypeptide of the invention, it should be noted that this encompasses any order or arrangements of the relevant Nanobodies, unless explicitly indicated otherwise.

Finally, it is also within the scope of the invention that the polypeptides of the invention contain two or more Nanobodies and one or more further amino acid sequences (as mentioned herein).

For multivalent and multispecific polypeptides containing one or more V domains and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103 and WO 99/23221. Some other examples of some specific multispecific and/or multivalent polypeptide of the invention can be found in the applications by Ablynx N.V. referred to herein.

One preferred, but non-limiting example of a multispecific polypeptide of the invention comprises at least one Nanobody of the invention and at least one Nanobody that provides for an increased half-life. Such Nanobodies may for example be Nanobodies that are directed against a serum protein, and in particular a human serum protein, such as human serum albumin, thyroxine-binding protein, (human) transferrin, fibrinogen, an immunoglobulin such as IgG, IgE or IgM, or against one of the serum proteins listed in WO 04/003019. Of these, Nanobodies that can bind to serum albumin (and in particular human serum albumin) or to IgG (and in particular human IgG, see for example Nanobody VH-1 described in the review by Muyldermans, supra) are particularly preferred (although for example, for experiments in mice or primates, Nanobodies against or cross-reactive with mouse serum albumin (MSA) or serum albumin from said primate, respectively, can be used. However, for pharmaceutical use, Nanobodies against human serum albumin or human IgG will usually be preferred). Nanobodies that provide for increased half-life and that can be used in the polypeptides of the invention include the Nanobodies directed against serum albumin that are described in WO 04/041865, in WO 06/122787 and in the further patent applications by Ablynx N.V., such as those mentioned above.

For example, the some preferred Nanobodies that provide for increased half-life for use in the present invention include Nanobodies that can bind to amino acid residues on (human) serum albumin that are not involved in binding of serum albumin to FcRn (see for example WO 06/0122787); Nanobodies that are capable of binding to amino acid residues on serum albumin that do not form part of domain III of serum albumin (see for example WO 06/0122787); Nanobodies that have or can provide an increased half-life (see for example WO 08/028977 by Ablynx N.V mentioned herein); Nanobodies against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Popio ursinus*)) (see for example WO 08/028977 by Ablynx N.V)); Nanobodies that can bind to serum albumin in a pH independent manner (see for example WO2008/043821 by Ablynx N.V. mentioned herein) and/or Nanobodies that are conditional binders (see for example WO 08/043822 by Ablynx N.V.).

Some particularly preferred Nanobodies that provide for increased half-life and that can be used in the polypeptides of the invention include the Nanobodies ALB-1 to ALB-10 disclosed in WO 06/122787 (see Tables II and III) of which ALB-8 (SEQ ID NO: 62 in WO 06/122787) is particularly preferred.

Some preferred, but non-limiting examples of polypeptides of the invention that comprise at least one Nanobody of the invention and at least one Nanobody that provides for increased half-life are given in SEQ ID NO's 186 to 198 and 227 to 234.

According to a specific, but non-limiting aspect of the invention, the polypeptides of the invention contain, besides the one or more Nanobodies of the invention, at least one Nanobody against human serum albumin.

Generally, any polypeptides of the invention with increased half-life that contain one or more Nanobodies of the invention, and any derivatives of Nanobodies of the invention or of such polypeptides that have an increased half-life, preferably have a half-life that is at least 1.5 times, preferably at least 2 times, such as at least 5 times, for example at least 10 times or more than 20 times, greater than the half-life of the corresponding Nanobody of the invention per se. For example, such a derivative or polypeptides with increased half-life may have a half-life that is increased with more than 1 hours, preferably more than 2 hours, more preferably more than 6 hours, such as more than 12 hours, or even more than 24, 48 or 72 hours, compared to the corresponding Nanobody of the invention per se.

In a preferred, but non-limiting aspect of the invention, such derivatives or polypeptides may exhibit a serum half-life in human of at least about 12 hours, preferably at least 24 hours, more preferably at least 48 hours, even more preferably at least 72 hours or more. For example, such derivatives or polypeptides may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

According to one aspect of the invention the polypeptides are capable of binding to one or more molecules which can increase the half-life of the polypeptide in vivo.

The polypeptides of the invention are stabilised in vivo and their half-life increased by binding to molecules which resist degradation and/or clearance or sequestration. Typically, such molecules are naturally occurring proteins which themselves have a long half-life in vivo.

Another preferred, but non-limiting example of a multi-specific polypeptide of the invention comprises at least one Nanobody of the invention and at least one Nanobody that directs the polypeptide of the invention towards, and/or that allows the polypeptide of the invention to penetrate or to enter into specific organs, tissues, cells, or parts or compartments of cells, and/or that allows the Nanobody to penetrate or cross a biological barrier such as a cell membrane, a cell layer such as a layer of epithelial cells, a tumor including solid tumors, or the blood-brain-barrier. Examples of such Nanobodies include Nanobodies that are directed towards specific cell-surface proteins, markers or epitopes of the desired organ, tissue or cell (for example cell-surface markers associated with tumor cells), and the single-domain brain targeting antibody fragments described in WO 02/057445 and WO 06/040153, of which FC44 (SEQ ID NO: 189 of WO 06/040153) and FC5 (SEQ ID NO: 190 of WO 06/040154) are preferred examples.

In the polypeptides of the invention, the one or more Nanobodies and the one or more polypeptides may be directly linked to each other (as for example described in WO 99/23221) and/or may be linked to each other via one or more suitable spacers or linkers, or any combination thereof.

Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each Nanobody by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_xser_y)_z$, such as (for example $(gly_4ser)_3$ or $(gly_3ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678).

Some other particularly preferred linkers are poly-alanine (such as AAA), as well as the linkers GS30 (SEQ ID NO: 85 in WO 06/122825) and GS59 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for OX40L, or for one or more of the other antigens. Based on the disclosure herein, the skilled person will be able to determine the optimal linker(s) for use in a specific polypeptide of the invention, optionally after some limited routine experiments.

For example, in multivalent polypeptides of the invention that comprise Nanobodies directed against a multimeric antigen (such as a multimeric receptor or other protein), the length and flexibility of the linker are preferably such that it allows each Nanobody of the invention present in the polypeptide to bind to the antigenic determinant on each of the subunits of the multimer. Similarly, in a multispecific polypeptide of the invention that comprises Nanobodies directed against two or more different antigenic determinants on the same antigen (for example against different epitopes of an antigen and/or against different subunits of a multimeric receptor, channel or protein), the length and flexibility of the linker are preferably such that it allows each Nanobody to bind to its intended antigenic determinant. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the Nanobodies of the invention). For example, linkers containing one or more charged amino acid residues (see Table A-2 on page 48 of the International application WO 08/020079) can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thereto. For example, when a polypeptide of the invention comprises three of more Nanobodies, it is possible to link them by use of a linker with three or more "arms", which each "arm" being linked to a Nanobody, so as to provide a "star-shaped" construct. It is also possible, although usually less preferred, to use circular constructs.

The invention also comprises derivatives of the polypeptides of the invention, which may be essentially analogous to the derivatives of the Nanobodies of the invention, i.e. as described herein.

The invention also comprises proteins or polypeptides that "essentially consist" of a polypeptide of the invention (in which the wording "essentially consist of" has essentially the same meaning as indicated hereinabove).

According to one aspect of the invention, the polypeptide of the invention is in essentially isolated from, as defined herein.

The amino acid sequences, Nanobodies, polypeptides and nucleic acids of the invention can be prepared in a manner known per se, as will be clear to the skilled person from the further description herein. For example, the Nanobodies and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies, polypeptides and nucleic acids include the methods and techniques described herein.

As will be clear to the skilled person, one particularly useful method for preparing an amino acid sequence, Nanobody and/or a polypeptide of the invention generally comprises the steps of:
i) the expression, in a suitable host cell or host organism (also referred to herein as a "host of the invention") or in another suitable expression system of a nucleic acid that encodes said amino acid sequence, Nanobody or polypeptide of the invention (also referred to herein as a "nucleic acid of the invention"), optionally followed by:
ii) isolating and/or purifying the amino acid sequence, Nanobody or polypeptide of the invention thus obtained.

In particular, such a method may comprise the steps of:
i) cultivating and/or maintaining a host of the invention under conditions that are such that said host of the invention expresses and/or produces at least one amino acid sequence, Nanobody and/or polypeptide of the invention; optionally followed by:
ii) isolating and/or purifying the amino acid sequence, Nanobody or polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences for the polypeptides of the invention given herein, and/or can be isolated from a suitable natural source. To provide analogs, nucleotide sequences encoding naturally occurring V, domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring form of OX40L as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art and as described on pages 131-134 of WO 08/020079 (incorporated herein by reference). Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises
i) at least one nucleic acid of the invention; operably connected to
ii) one or more regulatory elements, such as a promoter and optionally a suitable terminator;
and optionally also
iii) one or more further elements of genetic constructs known per se;
in which the terms "operably connected" and "operably linked" have the meaning given on pages 131-134 of WO 08/020079; and in which the "regulatory elements", "promoter", "terminator" and "further elements" are as described on pages 131-134 of WO 08/020079; and in which the genetic constructs may further be as described on pages 131-134 of WO 08/020079.

The nucleic acids of the invention and/or the genetic constructs of the invention may be used to transform a host cell or host organism, i.e. for expression and/or production of the amino acid sequence, Nanobody or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example those described on pages 134 and 135 of WO 08/020079; as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The amino acid sequences, Nanobodies and polypeptides of the invention can also be introduced and expressed in one or more cells, tissues or organs of a multicellular organism, for example for prophylactic and/or therapeutic purposes (e.g. as a gene therapy), as further described on pages 135 and 136 of in WO 08/020079 and in the further references cited in WO 08/020079.

For expression of the Nanobodies in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The amino acid sequences, Nanobodies and polypeptides of the invention can for example also be produced in the milk of transgenic mammals, for example in the milk of rabbits, cows, goats or sheep (see for example U.S. Pat. Nos. 6,741,957, 6,304,489 and 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori*.

Furthermore, the amino acid sequences, Nanobodies and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person.

As also will be clear to the skilled person, polypeptides of the invention suitable for pharmaceutical use can be prepared using techniques for peptide synthesis.

For production on industrial scale, preferred heterologous hosts for the (industrial) production of Nanobodies or Nanobody-containing protein therapeutics include strains of *E. coli, Pichia postoris, S. cerevisiae* that are suitable for large scale expression/production/fermentation, and in particular for large scale pharmaceutical (i.e. GMP grade) expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a Nanobody-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, Nanobody or polypeptide to be obtained.

Thus, according to one non-limiting aspect of the invention, the amino acid sequence, Nanobody or polypeptide of the invention is glycosylated. According to another non-limiting aspect of the invention, the amino acid sequence, Nanobody or polypeptide of the invention is non-glycosylated.

According to one preferred, but non-limiting aspect of the invention, the amino acid sequence, Nanobody or polypeptide of the invention is produced in a bacterial cell, in particular a bacterial cell suitable for large scale pharmaceutical production, such as cells of the strains mentioned above.

According to another preferred, but non-limiting aspect of the invention, the amino acid sequence, Nanobody or polypeptide of the invention is produced in a yeast cell, in particular a yeast cell suitable for large scale pharmaceutical production, such as cells of the species mentioned above.

According to yet another preferred, but non-limiting aspect of the invention, the amino acid sequence, Nanobody or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

As further described on pages 138 and 139 of WO 08/020079, when expression in a host cell is used to produce the amino acid sequences, Nanobodies and the polypeptides of the invention, the amino acid sequences, Nanobodies and polypeptides of the invention can be produced either intracellullarly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. Thus, according to one non-limiting aspect of the invention, the amino acid sequence, Nanobody or polypeptide of the invention is an amino acid sequence, Nanobody or polypeptide that has been produced intracellularly and that has been isolated from the host cell, and in particular from a bacterial cell or from an inclusion body in a bacterial cell. According to another non-limiting aspect of the invention, the amino acid sequence, Nanobody or polypeptide of the invention is an amino acid sequence, Nanobody or polypeptide that has been produced extracellularly, and that has been isolated from the medium in which the host cell is cultivated.

Some preferred, but non-limiting promoters for use with these host cells include those mentioned on pages 139 and 140 of WO 08/020079.

Some preferred, but non-limiting secretory sequences for use with these host cells include those mentioned on page 140 of WO 08/020079.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence, Nanobody or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences of the invention, the transformed host cell or transformed host organism may generally be kept, maintained and/or cultured under conditions such that the (desired) amino acid sequence, Nanobody or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence, Nanobody or polypeptide of the invention may (first) be generated in an immature form (as mentioned above), which may then be subjected to post-translational modification, depending on the host cell/host organism used. Also, the amino acid sequence, Nanobody or polypeptide of the invention may be glycosylated, again depending on the host cell/host organism used.

The amino acid sequence, Nanobody or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, Nanobody or polypeptide of the invention) and/or preparative immunological techniques (i.e. using antibodies against the amino acid sequence to be isolated).

Generally, for pharmaceutical use, the polypeptides of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one amino acid of the invention, at least one Nanobody of the invention or at least one polypeptide of the invention and at least one suitable carrier, diluent or excipient (i.e. suitable for pharmaceutical use), and optionally one or more further active substances.

Generally, the amino acid sequences, Nanobodies and polypeptides of the invention can be formulated and administered in any suitable manner known per se, for which reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

For example, the amino acid sequences, Nanobodies and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. Usually, aqueous solutions or suspensions will be preferred.

The amino acid sequences, Nanobodies and polypeptides of the invention can also be administered using gene therapy methods of delivery. See, e.g., U.S. Pat. No. 5,399,346, which is incorporated by reference in its entirety. Using a gene therapy method of delivery, primary cells transfected with the gene encoding an amino acid sequence, Nanobody or polypeptide of the invention can additionally be transfected with tissue specific promoters to target specific organs, tissue, grafts, tumors, or cells and can additionally be transfected with signal and stabilization sequences for subcellularly localized expression.

Thus, the amino acid sequences, Nanobodies and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the amino acid sequences, Nanobodies and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, Nanobody or polypeptide of the invention. Their percentage in the compositions and preparations may, of course, be varied and may conveniently be between about 2 to about 60% of the weight of a given unit dosage form. The amount of the amino acid sequence, Nanobody or polypeptide of the invention in such therapeutically useful compositions is such that an effective dosage level will be obtained.

The tablets, troches, pills, capsules, and the like may also contain binders, excipients, disintegrating agents, lubricants and sweetening or flavouring agents, for example those mentioned on pages 143-144 of WO 08/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the amino acid sequences, Nanobodies and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the amino acid sequences, Nanobodies and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The amino acid sequences, Nanobodies and polypeptides of the invention may also be administered intravenously or intraperitoneally by infusion or injection, as further described on pages 144 and 145 of WO 08/020079.

For topical administration, the amino acid sequences, Nanobodies and polypeptides of the invention may be applied in pure form, i.e., when they are liquids. However, it will generally be desirable to administer them to the skin as compositions or formulations, in combination with a dermatologically acceptable carrier, which may be a solid or a liquid, as further described on page 145 of WO 08/020079.

Generally, the concentration of the amino acid sequences, Nanobodies and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the amino acid sequences, Nanobodies and polypeptides of the invention required for use in treatment will vary not only with the particular amino acid sequence, Nanobody or polypeptide selected but also with the route of administration, the nature of the condition being treated and the age and condition of the patient and will be ultimately at the discretion of the attendant physician or clinician. Also the dosage of the amino acid sequences, Nanobodies and polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one inflammatory disease and/or disorder such as e.g. asthma and/or allergic asthma, said method comprising administering, to a subject in need thereof, a pharmaceutically active amount of an amino acid sequence of the invention, of a Nanobody of the invention, of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease and/or disorder that is associated with OX40L, with its biological or pharmacological activity, and/or with the biological pathways or signalling in which OX40L is involved, said method comprising administering, to a subject in need thereof, a pharmaceutically active amount of an amino acid sequence of the invention, of a Nanobody of the invention, of a polypeptide of the invention, and/or of a pharmaceutical composition comprising the same. In particular, the invention relates to a method for the prevention and/or treatment of at least one disease or disorder that can be treated by modulating OX40L, its biological or pharmacological activity, and/or the biological pathways or signalling in which OX40L is involved, said method comprising administering, to a subject in need thereof, a pharmaceutically active amount of an amino acid sequence of the invention, of a Nanobody of the invention, of a polypeptide of the invention, and/or of a pharmaceutical composition comprising the same. In particular, said pharmaceutically effective amount may be an amount that is sufficient to modulate OX40L, its biological or pharmacological activity, and/or the biological pathways or signalling in which OX40L is involved; and/or an amount that provides a level of the amino acid sequence of the invention, of a Nanobody of the invention, of a polypeptide of the invention in the circulation that is sufficient to modulate OX40L, its biological or pharmacological activity, and/or the biological pathways or signalling in which OX40L is involved.

The invention furthermore relates to a method for the prevention and/or treatment of at least one disease or disorder that can be prevented and/or treated by administering an amino acid sequence of the invention, a Nanobody of the invention or a polypeptide of the invention to a patient, said method comprising administering, to a subject in need thereof, a pharmaceutically active amount of an amino acid sequence of the invention, of a Nanobody of the invention, of a polypeptide of the invention, and/or of a pharmaceutical composition comprising the same.

More in particular, the invention relates to a method for the prevention and/or treatment of at least one disease or disorder chosen from the group consisting of the diseases and disorders listed herein, said method comprising administering, to a subject in need thereof, a pharmaceutically active amount of an amino acid sequence of the invention, of a Nanobody of the invention, of a polypeptide of the invention, and/or of a pharmaceutical composition comprising the same.

In another aspect, the invention relates to a method for immunotherapy, and in particular for passive immunotherapy, which method comprises administering, to a subject suffering from or at risk of the diseases and disorders mentioned herein, a pharmaceutically active amount of an amino acid sequence of the invention, of a Nanobody of the invention, of a polypeptide of the invention, and/or of a pharmaceutical composition comprising the same.

In the above methods, the amino acid sequences, Nanobodies and/or polypeptides of the invention and/or the compositions comprising the same can be administered in any suitable manner, depending on the specific pharmaceutical formulation or composition to be used. Thus, the amino acid sequences, Nanobodies and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The amino acid sequences, Nanobodies and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, Nanobody or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, Nanobodies and/or polypeptides of the invention, or of one or more compositions comprising the same, in one or more pharmaceutically effective amounts or doses. The specific amount(s) or doses to administered can be determined by the clinician, again based on the factors cited above.

Generally, for the prevention and/or treatment of the diseases and disorders mentioned herein and depending on the specific disease or disorder to be treated, the potency of the specific amino acid sequence, Nanobody and polypeptide of the invention to be used, the specific route of administration and the specific pharmaceutical formulation or composition used, the amino acid sequences, Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, Nanobody or polypeptide of the invention will be used. It is however within the scope of the invention to use two or more amino acid sequences, Nanobodies and/or polypeptides of the invention in combination.

The Nanobodies, amino acid sequences and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, Nanobodies and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, Nanobody or polypeptide of the invention in the preparation of a pharmaceutical composition for prevention and/or treatment of at least one inflammatory disease and/or disorder such as e.g. asthma and/or allergic asthma; and/or for use in one or more of the methods of treatment mentioned herein.

The subject to be treated may be any warm-blooded animal, but is in particular a mammal, and more in particular a human being. As will be clear to the skilled person, the subject to be treated will in particular be a person suffering from, or at risk of, the diseases and/or disorders mentioned herein.

The invention also relates to the use of an amino acid sequence, Nanobody or polypeptide of the invention in the preparation of a pharmaceutical composition for the prevention and/or treatment of at least one disease and/or disorder that can be prevented and/or treated by administering an amino acid sequence, Nanobody or polypeptide of the invention to a patient.

More in particular, the invention relates to the use of an amino acid sequence, Nanobody or polypeptide of the invention in the preparation of a pharmaceutical composition for the prevention and/or treatment of one or more inflammatory diseases and/or disorders such as e.g. asthma and/or allergic asthma, and in particular for the prevention and treatment of one or more of the diseases and/or disorders listed herein.

Again, in such a pharmaceutical composition, the one or more amino acid sequences, Nanobodies or polypeptides of the invention may also be suitably combined with one or more other active principles, such as those mentioned herein.

Finally, although the use of the Nanobodies of the invention (as defined herein) and of the polypeptides of the invention is much preferred, it will be clear that on the basis of the description herein, the skilled person will also be able to design and/or generate, in an analogous manner, other amino acid sequences and in particular (single) domain antibodies against OX40L, as well as polypeptides comprising such (single) domain antibodies.

For example, it will also be clear to the skilled person that it may be possible to "graft" one or more of the CDR's mentioned above for the Nanobodies of the invention onto such (single) domain antibodies or other protein scaffolds, including but not limited to human scaffolds or non-immunoglobulin scaffolds. Suitable scaffolds and techniques for such CDR grafting will be clear to the skilled person and are well known in the art, see for example those mentioned in WO 08/020079. For example, techniques known per se for grafting mouse or rat CDR's onto human frameworks and scaffolds can be used in an analogous manner to provide chimeric proteins comprising one or more of the CDR's of the Nanobodies of the invention and one or more human framework regions or sequences.

It should also be noted that, when the Nanobodies of the inventions contain one or more other CDR sequences than the preferred CDR sequences mentioned above, these CDR sequences can be obtained in any manner known per se, for example using one or more of the techniques described in WO 08/020079.

Further uses of the amino acid sequences, Nanobodies, polypeptides, nucleic acids, genetic constructs and hosts and host cells of the invention will be clear to the skilled person based on the disclosure herein. For example, and without limitation, the amino acid sequences of the invention can be linked to a suitable carrier or solid support so as to provide a medium than can be used in a manner known per se to purify OX40L from compositions and preparations comprising the same. Derivatives of the amino acid sequences of the invention that comprise a suitable detectable label can also be used as markers to determine (qualitatively or quantitatively) the presence of OX40L in a composition or preparation or as a marker to selectively detect the presence of OX40L on the surface of a cell or tissue (for example, in combination with suitable cell sorting techniques).

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All of the references described herein are incorporated by reference, in particular for the teaching that is referenced hereinabove.

The invention will now be further described by means of the following non-limiting preferred aspects, examples and figures:

Preferred Aspects:

Aspect A-1: An amino acid sequence that is directed against and/or that can specifically bind to OX40L Aspect A-2: An amino acid sequence according to aspect A-1, that is in essentially isolated form.

Aspect A-3: An amino acid sequence according to aspect A-1 or A-2, for administration to a subject, wherein said amino acid sequence does not naturally occur in said subject.

Aspect A-4: An amino acid sequence that can specifically bind to OX40L with a dissociation constant ($K_D$) of $10^{-5}$ to $10^{-12}$ moles/litre or less, and preferably $10^{-7}$ to $10^{-12}$ moles/litre or less and more preferably $10^{-8}$ to $10^{-12}$ moles/litre or less. Such an amino acid sequence may in particular be an amino acid sequence according to any of the preceding aspects.

Aspect A-5: An amino acid sequence that can specifically bind to OX40L with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-}$, such as between $10^5$ $M^{-1}s^{-1}$ and $10^7$ $M^{-1}s^{-1}$. Such an amino acid sequence may in particular be an amino acid sequence according to any of the preceding aspects.

Aspect A-6: An amino acid sequence that can specifically bind to OX40L with a rate of dissociation ($k_{off}$ rate) between 1 $s^{-1}$ and $10^{-6}$ $s^{-1}$, preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}s^{-1}$. Such an amino acid sequence may in particular be an amino acid sequence according to any of the preceding aspects.

Aspect A-7: An amino acid sequence that can specifically bind to OX40L with an affinity less than 500 nM, preferably less than 200 nM, more preferably less than 10 nM, such as less than 500 pM, even more preferably less than 1 nM. Such an amino acid sequence may in particular be an amino acid sequence according to any of the preceding aspects.

Aspect A-8: An amino acid sequence that can specifically bind to OX40L and has an IC50 value in the alphascreen assay (e.g. as defined herein) with 0.12 nM hOX40L and 0.2 nM OX40/Fc of less than 10 nM, preferably less than 1 nM, more preferably less than 500 pM, even more preferably less than 1 nM, most preferred less than 100 pM. Such an amino acid sequence may in particular be an amino acid sequence according to any of the preceding aspects.

Aspect A-9: An amino acid sequence that can specifically bind to OX40L and has an IC50 value in the FACS assay (e.g. as defined herein) of less than 100 nM, preferably less than 50 nM, more preferably less than 20 nM, even more preferably less than 10 nM, most preferred less than 1 nM. Such an amino acid sequence may in particular be an amino acid sequence according to any of the preceding aspects.

Aspect A-10: An amino acid sequence that can specifically bind to OX40L and has an IC50 value in the T-cell activation assay using human donors (e.g. as defined herein) that is less than the IC50 of the benchmark Fab (as defined herein, example section), or that is preferably less than the benchmark IgG (as defined herein, SEQ ID NO: 177 and 178). Such an amino acid sequence may in particular be an amino acid sequence according to any of the preceding aspects.

Aspect A-11: An amino acid sequence according to any of the preceding aspects, that essentially consists of 4 framework regions (FR1 to FR4 respectively) and 3 complementarity determining regions (CDR1 to CDR3 respectively).

Aspect A-12: An amino acid sequence according to any of the preceding aspects that is a naturally occurring immunoglobulin sequence (from any suitable species) or a synthetic or semi-synthetic immunoglobulin sequence.

Aspect A-13: An amino acid sequence according to any of the preceding aspects that is a humanized immunoglobulin sequence, a camelized immunoglobulin sequence or an immunoglobulin sequence that has been obtained by techniques such as affinity maturation.

Aspect A-14: An amino acid sequence according to any of the preceding aspects, that essentially consists of an immunoglobulin single variable domain sequence such as a light chain variable domain sequence (e.g. a VL-sequence); or of a heavy chain variable domain sequence (e.g. a VH-sequence).

Aspect A-15: An amino acid sequence according to any of the preceding aspects, that essentially consists of a heavy chain variable domain sequence that is derived from a conventional four-chain antibody or that essentially consist of a heavy chain variable domain sequence that is derived from heavy chain antibody.

Aspect A-16: An amino acid sequence according to any of the preceding aspects, that essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody (including but not limited to a VHH sequence).

Aspect A-17: An amino acid sequence according to any of the preceding aspects, that essentially consists of a Nanobody.

Aspect A-18: An amino acid sequence according to any of the preceding aspects, that essentially consists of a Nanobody that
i) has at least 80% amino acid identity with at least one of the amino acid sequences of SEQ ID NO's: 1 to 22, in which for the purposes of determining the degree of amino acid identity, the amino acid residues that form the CDR sequences are disregarded;
and in which:

ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect A-19: An amino acid sequence according to any of the preceding aspects, that essentially consists of a polypeptide that
  i) has at least 80% amino acid identity with at least one of the amino acid sequences of SEQ ID NO's: 186 to 198 and 227 to 234, in which for the purposes of determining the degree of amino acid identity, the amino acid residues that form the CDR sequences are disregarded; and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect A-20: An amino acid sequence according to any of the preceding aspects, that essentially consists of a Nanobody that
  i) has at least 80% amino acid identity with at least one of the amino acid sequences of SEQ ID NO's: 179 to 185, in which for the purposes of determining the degree of amino acid identity, the amino acid residues that form the CDR sequences are disregarded; and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect A-21: An amino acid sequence according to any of the preceding aspects, that essentially consists of a humanized Nanobody.

Aspect A-22: An amino acid sequence according to any of the preceding aspects, that in addition to the at least one binding site for binding against OX40L, contains one or more further binding sites for binding against other antigens, proteins or targets.

Aspect B-1: An amino acid sequence that is directed against and/or that can specifically bind OX40L, and that comprises one or more stretches of amino acid residues chosen from the group consisting of:
  a) the amino acid sequences of SEQ ID NO's: 133 to 139;
  b) amino acid sequences that have at least 80% amino acid identity with at least one of the amino acid sequences of SEQ ID NO's: 133 to 139;
  c) amino acid sequences that have 3, 2, or 1 amino acid difference with at least one of the amino acid sequences of SEQ ID NO's: 133 to 139;
  d) the amino acid sequences of SEQ ID NO's: 147 to 153;
  e) amino acid sequences that have at least 80% amino acid identity with at least one of the amino acid sequences of SEQ ID NO's: 147 to 153;
  f) amino acid sequences that have 3, 2, or 1 amino acid difference with at least one of the amino acid sequences of SEQ ID NO's: 147 to 153;
  g) the amino acid sequences of SEQ ID NO's: 161 to 167;
  h) amino acid sequences that have at least 80% amino acid identity with at least one of the amino acid sequences of SEQ ID NO's: 161 to 167;
  i) amino acid sequences that have 3, 2, or 1 amino acid difference with at least one of the amino acid sequences of SEQ ID NO's: 161 to 167;
  or any suitable combination thereof.

Such an amino acid sequence may in particular be an amino acid sequence according to any of the aspects A-1 to A-22.

Aspect B-2: An amino acid sequence according to aspect B-1, in which at least one of said stretches of amino acid residues forms part of the antigen binding site for binding against OX40L.

Aspect B-3: An amino acid sequence that is directed against and/or that can specifically bind OX40L and that comprises two or more stretches of amino acid residues chosen from the group consisting of:
  a) the amino acid sequences of SEQ ID NO's: 133 to 139;
  b) amino acid sequences that have at least 80% amino acid identity with at least one of the amino acid sequences of SEQ ID NO's: 133 to 139;
  c) amino acid sequences that have 3, 2, or 1 amino acid difference with at least one of the amino acid sequences of SEQ ID NO's: 133 to 139;
  d) the amino acid sequences of SEQ ID NO's: 147 to 153;
  e) amino acid sequences that have at least 80% amino acid identity with at least one of the amino acid sequences of SEQ ID NO's: 147 to 153;
  f) amino acid sequences that have 3, 2, or 1 amino acid difference with at least one of the amino acid sequences of SEQ ID NO's: 147 to 153;
  g) the amino acid sequences of SEQ ID NO's: 161 to 167;
  h) amino acid sequences that have at least 80% amino acid identity with at least one of the amino acid sequences of SEQ ID NO's: 161 to 167;
  i) amino acid sequences that have 3, 2, or 1 amino acid difference with at least one of the amino acid sequences of SEQ ID NO's: 161 to 167;
  such that (i) when the first stretch of amino acid residues corresponds to one of the amino acid sequences according to a), b) or c), the second stretch of amino acid residues corresponds to one of the amino acid sequences according to d), e), f), g), h) or i); (ii) when the first stretch of amino acid residues corresponds to one of the amino acid sequences according to d), e) or f), the second stretch of amino acid residues corresponds to one of the amino acid sequences according to a), b), c), g), h) or i); or (iii) when the first stretch of amino acid residues corresponds to one of the amino acid sequences according to g), h) or i), the second stretch of amino acid residues corresponds to one of the amino acid sequences according to a), b), c), d), e) or f).

Such an amino acid sequence may in particular be an amino acid sequence according to any of the aspects A-1 to A-22, B-1 and/or B-2.

Aspect B-4: An amino acid sequence according to aspect B-3, in which the at least two stretches of amino acid residues forms part of the antigen binding site for binding against OX40L.

Aspect B-5: An amino acid sequence that is directed against and/or that can specifically bind OX40L and that comprises three or more stretches of amino acid residues, in which the first stretch of amino acid residues is chosen from the group consisting of:
  a) the amino acid sequences of SEQ ID NO's: 133 to 139;
  b) amino acid sequences that have at least 80% amino acid identity with at least one of the amino acid sequences of SEQ ID NO's: 133 to 139;
  c) amino acid sequences that have 3, 2, or 1 amino acid difference with at least one of the amino acid sequences of SEQ ID NO's: 133 to 139;
  the second stretch of amino acid residues is chosen from the group consisting of:
  d) the amino acid sequences of SEQ ID NO's: 147 to 153;

e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
and the third stretch of amino acid residues is chosen from the group consisting of:
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167.

Such an amino acid sequence may in particular be an amino acid sequence according to any of the aspects A-1 to A-22 and/or B-1 to B-4.

Aspect B-6: An amino acid sequence according to aspect B-5, in which the at least three stretches of amino acid residues forms part of the antigen binding site for binding against OX40L.

Aspect B-7: An amino acid sequence that is directed against and/or that can specifically bind OX40L in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 179 to 185. Such an amino acid sequence may in particular be an amino acid sequence according to any of the aspects A-1 to A-22 and/or B-1 to B-6.

Aspect C-1: An amino acid sequence that is directed against OX40L and that cross-blocks the binding of at least one of the amino acid sequences of SEQ ID NO's: 179 to 185 to OX40L Such an amino acid sequence may in particular be an amino acid sequence according to any of the aspects A-1 to A-22 and/or according to aspects B-1 to B-7. Also, preferably, such an amino acid sequence is able to specifically bind to OX40L.

Aspect C-2: An amino acid sequence that is directed against OX40L and that is cross-blocked from binding to OX40L by at least one of the amino acid sequences of SEQ ID NO's: 179 to 185. Such an amino acid sequence may in particular be an amino acid sequence according to any of the aspects A-1 to A-22 and/or according to aspects B-1 to B-7. Also, preferably, such an amino acid sequence is able to specifically bind to OX40L.

Aspect C-3: An amino acid sequence according to any of aspects C-1 or C-2, wherein the ability of said amino acid sequence to cross-block or to be cross-blocked is detected in a Biacore assay.

Aspect C-4: An amino acid sequence according to any of aspects C-1 to C-3 wherein the ability of said amino acid sequence to cross-block or to be cross-blocked is detected in an ELISA assay.

Aspect D-1: An amino acid sequence according to any of aspects B-1 to B-7 or C-1 to C-4, that is in essentially isolated form.

Aspect D-2: An amino acid sequence according to any of aspects B-1 to B-7, C-1 to C-4, and/or D1 for administration to a subject, wherein said amino acid sequence does not naturally occur in said subject.

Aspect D-3: An amino acid sequence according to any of aspects B-1 to B-7, C-1 to C-4, and/or D1 to D-2 that can specifically bind to OX40L with a dissociation constant ($K_D$) of $10^{-5}$ to $10^{-12}$ moles/litre or less, and preferably $10^{-7}$ to $10^{-2}$ moles/litre or less and more preferably $10^{-8}$ to $10^{-12}$ moles/litre.

Aspect D-4: An amino acid sequence according to any of aspects B-1 to B-7, C-1 to C-4, and/or D-1 to D-3 that can specifically bind to OX40L with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect D-5: An amino acid sequence according to any of aspects B-1 to B-7, C-1 to C-4, and/or D-1 to D-4 that can specifically bind to OX40L with a rate of dissociation ($k_{off}$ rate) between $1$ $s^{-1}$ and $10^{-6}$ $s^{-1}$ preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect D-6: An amino acid sequence according to any of aspects B-1 to B-7, C-1 to C-4, and/or D-1 to D-5 that can specifically bind to OX40L with an affinity less than 500 nM, preferably less than 200 nM, more preferably less than 10 nM, such as less than 500 pM.

The amino acid sequences according to aspects D-1 to D-6 may in particular be an amino acid sequence according to any of the aspects A-1 to A-22.

Aspect E-1: An amino acid sequence according to any of aspects B-1 to B-7, C-1 to C-4 and/or D-1 to D-6, that is a naturally occurring amino acid sequence (from any suitable species) or a synthetic or semi-synthetic amino acid sequence.

Aspect E-2: An amino acid sequence according to any of aspects B-1 to B-7, C-1 to C-4, D-1 to D-6, and/or E-1 that comprises an immunoglobulin fold or that under suitable conditions is capable of forming an immunoglobulin fold.

Aspect E-3: An amino acid sequence according to any of aspects B-1 to B-7, C-1 to C-4, D-1 to D-6, and/or E-1 to E-2, that is an immunoglobulin sequence.

Aspect E-4: An amino acid sequence according to any of aspects B-1 to B-7, C-1 to C-4, D-1 to D-6, and/or E-1 to E-3, that is a naturally occurring immunoglobulin sequence (from any suitable species) or a synthetic or semi-synthetic immunoglobulin sequence.

Aspect E-5: An amino acid sequence according to any of aspects B-1 to B-7, C-1 to C-4, D-1 to D-6, and/or E-1 to E-4 that is a humanized immunoglobulin sequence, a camelized immunoglobulin sequence or an immunoglobulin sequence that has been obtained by techniques such as affinity maturation.

Aspect E-6: An amino acid sequence according to any of aspects B-1 to B-7, C-1 to C-4, D-1 to D-6, and/or E-1 to E-5 that essentially consists of an immunoglobulin single variable domain sequence such as a light chain variable domain sequence (e.g. a $V_L$-sequence); or of a heavy chain variable domain sequence (e.g. a $V_H$-sequence).

Aspect E-7: An amino acid sequence according to any of aspects B-1 to B-7, C-1 to C-4, D-1 to D-6, and/or E-1 to E-6, that essentially consists of a heavy chain variable domain sequence that is derived from a conventional four-chain antibody or that essentially consist of a heavy chain variable domain sequence that is derived from heavy chain antibody.

Aspect E-8: An amino acid sequence according to any of aspects B-1 to B-7, C-1 to C-4, D-1 to D-6, and/or E-1 to E-7, that essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody (including but not limited to a V$_{HH}$ sequence).

Aspect E-9: An amino acid sequence according to any of aspects B-1 to B-7, C-1 to C-4, D-1 to D-6, and/or E-1 to E-8 that essentially consists of a Nanobody.

Aspect E-10: An amino acid sequence according to any of aspects B-1 to B-7, C-1 to C-4, D-1 to D-6, and/or E-1 to E-9 that essentially consists of a Nanobody that
i) has at least 80% amino acid identity with at least one of the amino acid sequences of SEQ ID NO's: 1 to 22, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect E-11: An amino acid sequence according to any of aspects B-1 to B-7, C-1 to C-4, D-1 to D-6, and/or E-1 to E-10, that essentially consists of a Nanobody that
i) has at least 80% amino acid identity with at least one of the An amino acid sequences of SEQ ID NO's: 179 to 185, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect E-12: An amino acid sequence according to any of aspects B-1 to B-7, C-1 to C-4, D-1 to D-6, and/or E-1 to E-11, that essentially consists of a humanized Nanobody.

Aspect E-13: An amino acid sequence according to any of the aspects B-1 to B-7, C-1 to C-4, D-1 to D-6, and/or E-1 to E-12, that in addition to the at least one binding site for binding formed by the CDR sequences, contains one or more further binding sites for binding against other antigens, proteins or targets.

The amino acid sequences according to aspects E-1 to E-13 may in particular be an amino acid sequence according to any of the aspects A-1 to A-22.

Aspect F-1: An amino acid sequence that essentially consists of 4 framework regions (FR1 to FR4, respectively) and 3 complementarity determining regions (CDR1 to CDR3, respectively), in which:
CDR1 is chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;
and/or
CDR2 is chosen from the group consisting of:
d) the amino acid sequences of SEQ ID NO's: 147 to 153;
e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
and/or
CDR3 is chosen from the group consisting of:
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167.

Such an amino acid sequence is preferably directed against OX40L and/or an amino acid sequence that can specifically bind to OX40L. Also, such an amino acid sequence is preferably an amino acid sequence according to any of the aspects A-1 to A-22, C-1 to C-4, D1 to D-6 and/or E-1 to E-13.

Aspect F-2: An amino acid sequence that essentially consists of 4 framework regions (FR1 to FR4, respectively) and 3 complementarity determining regions (CDR1 to CDR3, respectively), in which:
CDR1 is chosen from the group consisting of:
a) the amino acid sequences of SEQ ID NO's: 133 to 139;
b) amino acid sequences that have at least 80% amino acid identity with at least one of the amino acid sequences of SEQ ID NO's: 133 to 139;
c) amino acid sequences that have 3, 2, or 1 amino acid difference with at least one of the amino acid sequences of SEQ ID NO's: 133 to 139;
and
CDR2 is chosen from the group consisting of:
d) the amino acid sequences of SEQ ID NO's: 147 to 153;
e) amino acid sequences that have at least 80% amino acid identity with at least one of the amino acid sequences of SEQ ID NO's: 147 to 153;
f) amino acid sequences that have 3, 2, or 1 amino acid difference with at least one of the amino acid sequences of SEQ ID NO's: 147 to 153;
and
CDR3 is chosen from the group consisting of:
g) the amino acid sequences of SEQ ID NO's: 161 to 167;
h) amino acid sequences that have at least 80% amino acid identity with at least one of the amino acid sequences of SEQ ID NO's: 161 to 167;
i) amino acid sequences that have 3, 2, or 1 amino acid difference with at least one of the amino acid sequences of SEQ ID NO's: 161 to 167.

Such an amino acid sequence is preferably directed against OX40L and/or an amino acid sequence that can specifically bind to OX40L. Also, such an amino acid sequence is preferably an amino acid sequence according to any of the aspects A-1 to A-22, C-1 to C-4, D-1 to D-6 and/or E-1 to E-13.

Aspect F-3: An amino acid sequence according to any of aspects F-1 and F-2, in which the CDR sequences of said amino acid sequence have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 179 to 185.

Such an amino acid sequence is preferably directed against OX40L and/or an amino acid sequence that can specifically bind to OX40L. Also, such an amino acid sequence is preferably an amino acid sequence according to any of the aspects A-1 to A-22, C-1 to C-4, D-1 to D-6 and/or E-1 to E-13.

Aspect F-4: An amino acid sequence according to any of aspects F-1 to F-3 that is directed against OX40L and that cross-blocks the binding to OX40L of at least one of the amino acid sequences of SEQ ID NO's: 179 to 185.

Aspect F-5: An amino acid sequence according to any of aspects F-1 to F-3 that is directed against OX40L and that is cross-blocked from binding to OX40L by at least one of the amino acid sequences of SEQ ID NO's: 179 to 185.

Aspect F-6: Amino acid sequence according to any of aspects F-4 or F-5 wherein the ability of said amino acid sequence to cross-block or to be cross-blocked is detected in a Biacore assay.

Aspect F-7: Amino acid sequence according to any of aspects F4 or F-5 wherein the ability of said amino acid sequence to cross-block or to be cross-blocked is detected in an ELISA assay.

Aspect F-8: An amino acid sequence according to any of aspects F-1 to F-7, that is in essentially isolated form.

Aspect F-9: An amino acid sequence according to any of aspects F-1 to F-8, for administration to a subject, wherein said an amino acid sequence does not naturally occur in said subject.

Aspect F-10: An amino acid sequence according to any of aspects F-1 to F-9, that can specifically bind to OX40L with a dissociation constant ($K_D$) of $10^{-5}$ to $10^{-12}$ moles/litre or less, and preferably $10^{-7}$ to $10^{-12}$ moles/litre or less and more preferably $10^{-8}$ to $10^{-12}$ moles/litre.

Aspect F-11: An amino acid sequence according to any of aspects F-1 to F-10, that can specifically bind to OX40L with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect F-12: An amino acid sequence according to any of aspects F-1 to F-11, that can specifically bind to OX40L with a rate of dissociation ($k_{off}$-rate) between 1 $s^{-1}$ and $10^6$ $s^{-1}$ preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect F-13: An amino acid sequence according to any of aspects F-1 to F-12, that can specifically bind to OX40L with an affinity less than 500 nM, preferably less than 200 nM, more preferably less than 10 nM, such as less than 500 pM.

Aspect F-14: An amino acid sequence according to any of aspects F-1 to F-13, that is a naturally occurring amino acid sequence (from any suitable species) or a synthetic or semi-synthetic amino acid sequence.

Aspect F-15: An amino acid sequence according to any of aspects F-1 to F-14, that comprises an immunoglobulin fold or that under suitable conditions is capable of forming an immunoglobulin fold.

Aspect F-16: An amino acid sequence according to any of aspects F-1 to F-15, that is an immunoglobulin sequence.

Aspect F-17: An amino acid sequence according to any of aspects F-1 to F-16, that is a naturally occurring immunoglobulin sequence (from any suitable species) or a synthetic or semi-synthetic immunoglobulin sequence.

Aspect F-18: An amino acid sequence according to any of aspects F-1 to F-17, that is a humanized immunoglobulin sequence, a camelized immunoglobulin sequence or an immunoglobulin sequence that has been obtained by techniques such as affinity maturation.

Aspect F-19: An amino acid sequence according to any of aspects F-1 to F-18, that essentially consists of an immunoglobulin single variable domain sequence such as a light chain variable domain sequence (e.g. a $V_L$-sequence); or of a heavy chain variable domain sequence (e.g. a $V_H$-sequence).

Aspect F-20: An amino acid sequence according to any of aspects F-1 to F-19, that essentially consists of a heavy chain variable domain sequence that is derived from a conventional four-chain antibody or that essentially consist of a heavy chain variable domain sequence that is derived from heavy chain antibody.

Aspect F-21: An amino acid sequence according to any of aspects F-1 to F-20, that essentially consists of a domain antibody (or an amino acid sequence that is suitable for use as a domain antibody), of a single domain antibody (or an amino acid sequence that is suitable for use as a single domain antibody), of a "dAb" (or an amino acid sequence that is suitable for use as a dAb) or of a Nanobody (including but not limited to a $V_{HH}$ sequence).

Aspect F-22: An amino acid sequence according to any of aspects F-1 to F-21, that essentially consists of a Nanobody.

Aspect F-23: An amino acid sequence according to any of aspects F-1 to F-22, that essentially consists of a Nanobody that
  i) has at least 80% amino acid identity with at least one of the amino acid sequences of SEQ ID NO's: 1 to 22, in which for the purposes of determining the degree of amino acid identity, the amino acid residues that form the CDR sequences are disregarded;
  and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect F-24: An amino acid sequence according to any of aspects F-1 to F-23, that essentially consists of a Nanobody that
  i) has at least 80% amino acid identity with at least one of the amino acid sequences of SEQ ID NO's: 179 to 185, in which for the purposes of determining the degree of amino acid identity, the amino acid residues that form the CDR sequences are disregarded;
  and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect F-25: An amino acid sequence according to any of aspects F-1 to F-24, that essentially consists of a humanized Nanobody.

Aspect G-1: An amino acid sequence according to any of the preceding aspects, that in addition to the at least one binding site for binding formed by the CDR sequences, contains one or more further binding sites for binding against another antigen, protein or target.

Aspect H-1: Nanobody that is directed against and/or that can specifically bind to OX40L.

Aspect H-2: Nanobody according to aspect H-1, that is in essentially isolated form.

Aspect H-3: Nanobody according to any of aspects H-1 to H-2, that can specifically bind to OX40L with a dissociation constant ($K_D$) of $10^{-5}$ to $10^{-12}$ moles/litre or less, and preferably $10^{-7}$ to $10^{-12}$ moles/litre or less and more preferably $10^{-8}$ to $10^{-12}$ moles/litre.

Aspect H-4: Nanobody according to any of aspects H-1 to H-3, that can specifically bind to OX40L with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect H-5: Nanobody according to any of aspects H-1 to H-4, that can specifically bind to OX40L with a rate of dissociation ($k_{off}$ rate) between 1 $s^{-1}$ and $10^{-6}$ $s^{-1}$ preferably between $10^{-2}$ $s^{-1}$ and $10^{-6}s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect H-6: Nanobody according to any of aspects H-1 to H-5, that can specifically bind to OX40L with an affinity less than 500 nM, preferably less than 200 nM, more preferably less than 10 nM, such as less than 500 pM.

Aspect H-7: Nanobody that can specifically bind to OX40L and that has an IC50 value in the alphascreen assay (e.g. as defined herein) with 0.12 nM hOX40L and 0.2 nM OX40/Fc of less than 10 nM, preferably less than 1 nM, more preferably less than 500 pM, even more preferably less than 1 nM, most preferred less than 100 pM. Such a Nanobody may in particular be an amino acid sequence and/or Nanobody according to any of the preceding aspects.

Aspect H-8: Nanobody that can specifically bind to OX40L and that has an IC50 value in the FACS assay (e.g. as defined herein) of less than 100 nM, preferably less than 50 nM, more preferably less than 20 nM, even more preferably less than 10 nM, most preferred less than 1 nM. Such a Nanobody may in particular be a an amino acid sequence and/or Nanobody according to any of the preceding aspects.

Aspect H-9: Nanobody that can specifically bind to OX40L and that has an IC50 value in the T-cell activation assay using human donors (e.g. as defined herein) that is less than the IC50 of the benchmark Fab (as defined herein, example section), or that is preferably less than the benchmark IgG (as defined herein, SEQ ID NO: 177 and 178). Such a Nanobody may in particular be an amino acid sequence and/or Nanobody according to any of the preceding aspects.

Aspect H-10: Nanobody according to any of aspects H-1 to H-9, that
  i) has at least 80% amino acid identity with at least one of the amino acid sequences of SEQ ID NO's: 179 to 185, in which for the purposes of determining the degree of amino acid identity, the amino acid residues that form the CDR sequences are disregarded;
  and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect H-11: Nanobody according to any of aspects H-1 to H-10, in which:
  CDR1 is chosen from the group consisting of:
  a) the amino acid sequences of SEQ ID NO's: 133 to 139;
  b) amino acid sequences that have at least 80% amino acid identity with at least one of the amino acid sequences of SEQ ID NO's: 133 to 139;
  c) amino acid sequences that have 3, 2, or 1 amino acid difference with at least one of the amino acid sequences of SEQ ID NO's: 133 to 139;
  and/or
  CDR2 is chosen from the group consisting of:
  d) the amino acid sequences of SEQ ID NO's: 147 to 153;
  e) amino acid sequences that have at least 80% amino acid identity with at least one of the amino acid sequences of SEQ ID NO's: 147 to 153;
  f) amino acid sequences that have 3, 2, or 1 amino acid difference with at least one of the amino acid sequences of SEQ ID NO's: 147 to 153;
  and/or
  CDR3 is chosen from the group consisting of:
  g) the amino acid sequences of SEQ ID NO's: 161 to 167;
  h) amino acid sequences that have at least 80% amino acid identity with at least one of the amino acid sequences of SEQ ID NO's: 161 to 167;
  i) amino acid sequences that have 3, 2, or 1 amino acid difference with at least one of the amino acid sequences of SEQ ID NO's: 161 to 167.

Aspect H-12: Nanobody according to any of aspects H-1 to H-11, in which:
  CDR1 is chosen from the group consisting of:
  a) the amino acid sequences of SEQ ID NO's: 133 to 139;
  b) amino acid sequences that have at least 80% amino acid identity with at least one of the amino acid sequences of SEQ ID NO's: 133 to 139;
  c) amino acid sequences that have 3, 2, or 1 amino acid difference with at least one of the amino acid sequences of SEQ ID NO's: 133 to 139;
  and
  CDR2 is chosen from the group consisting of:
  d) the amino acid sequences of SEQ ID NO's: 147 to 153;
  e) amino acid sequences that have at least 80% amino acid identity with at least one of the amino acid sequences of SEQ ID NO's: 147 to 153;
  f) amino acid sequences that have 3, 2, or 1 amino acid difference with at least one of the amino acid sequences of SEQ ID NO's: 147 to 153;
  and
  CDR3 is chosen from the group consisting of:
  g) the amino acid sequences of SEQ ID NO's: 161 to 167;
  h) amino acid sequences that have at least 80% amino acid identity with at least one of the amino acid sequences of SEQ ID NO's: 161 to 167;
  i) amino acid sequences that have 3, 2, or 1 amino acid difference with at least one of the amino acid sequences of SEQ ID NO's: 161 to 167.

Aspect H-13: Nanobody according to any of aspects H-1 to H-12, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 179 to 185.

Aspect H-14: Nanobody according to any of aspects H-1 to H-13, which is a partially humanized Nanobody.

Aspect H-15: Nanobody according to any of aspects H-1 to H-14, which is a fully humanized Nanobody.

Aspect H-16: Nanobody according to any of aspects H-1 to H-15, that is chosen from the group consisting of SEQ ID NO's: 179 to 185 or from the group consisting of from amino acid sequences that have more than 80%, preferably more than 90%, more preferably more than 95%, such as 99% or more sequence identity (as defined herein) with at least one of the amino acid sequences of SEQ ID NO's: 179 to 185.

Aspect H-17: Nanobody according to any of aspects H-1 to H-16, which is a humanized Nanobody that is chosen from the group consisting of SEQ ID NO's: 199 to 226 or from the group consisting of amino acid sequences that have more than 80%, preferably more than 90%, more preferably more than 95%, such as 99% or more sequence identity (as defined herein) with at least one of the amino acid sequences of SEQ ID NO's: 199 to 226.

Aspect H-18: Nanobody according to any of aspects H-1 to H-17, that is chosen from the group consisting of SEQ ID NO's: 179 to 185 or from the group consisting of SEQ ID NO's: 199 to 226.

Aspect H-19: Nanobody directed against OX40L that cross-blocks the binding to OX40L of at least one of the amino acid sequences of SEQ ID NO's: 179 to 185 and 199 to 226.

Aspect H-20: Nanobody directed against OX40L that is cross-blocked from binding to OX40L by at least one of the amino acid sequences of SEQ ID NO's: 179 to 185 and 199 to 226.

Aspect H-21: Nanobody according to any of aspects H-19 or H-20 wherein the ability of said Nanobody to cross-block or to be cross-blocked is detected in a Biacore assay.

Aspect H-22: Nanobody according to any of aspects H-19 to H-21 wherein the ability of said Nanobody to cross-block or to be cross-blocked is detected in an ELISA assay.

Aspect K-1: Polypeptide that comprises or essentially consists of one or more amino acid sequences according to any of aspects A-1 to A-22, B-1 to B-7, C-1 to C-4, D-1 to D-6, E-1 to E-13, F-1 to F-25 or G-1 (of the invention) and/or one or more Nanobodies according to any of aspects H-1 to H-22, and optionally further comprises one or more other residues or binding units, optionally linked via one or more peptidic linkers.

Aspect K-2: Polypeptide according to aspect K-1, in which said one or more binding units are immunoglobulin sequences.

Aspect K-3: Polypeptide according to any of aspects K-1 or K-2, in which said one or more other residues or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Aspect K-4: Polypeptide according to any of aspects K-1 to K-3, in which said one or more amino acid sequences of the invention are immunoglobulin sequences.

Aspect K-5: Polypeptide according to any of aspects K-1 to K-4, in which said one or more amino acid sequences of the invention are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Aspect K-6: Polypeptide according to any of aspects K-1 to K-5, that comprises or essentially consists of one or more Nanobodies according to any of aspects H-1 to H-22 and in which said one or more other binding units are Nanobodies.

Aspect K-7: Polypeptide according to any of aspects K-1 to K-6, which is a multivalent construct.

Aspect K-8: Polypeptide according to any of aspects K-1 to K-7, which is a multispecific construct.

Aspect K-9: Polypeptide according to any of aspects K-1 to K-8, which is a multiparatopic construct.

Aspect K-10: Polypeptide according to any of aspects K-1 to K-9, which has an increased half-life, compared to the corresponding amino acid sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect K-11: Polypeptide according to aspect K-10, in which said one or more other binding units provide the polypeptide with increased half-life, compared to the corresponding amino acid sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect K-12: Polypeptide according to aspect K-10 or K-11, in which said one or more other binding units that provide the polypeptide with increased half-life is chosen from the group consisting of serum proteins or fragments thereof, binding units that can bind to serum proteins, an Fc portion, and small proteins or peptides that can bind to serum proteins.

Aspect K-13: Polypeptide according to any of aspects K-10 to K-12, in which said one or more other binding units that provide the polypeptide with increased half-life is chosen from the group consisting of human serum albumin or fragments thereof.

Aspect K-14: Polypeptide according to any of aspect K-10 to K-13, in which said one or more other binding units that provides the polypeptide with increased half-life are chosen from the group consisting of binding units that can bind to serum albumin (such as human serum albumin) or a serum immunoglobulin (such as IgG).

Aspect K-15: Polypeptide according to any of aspects K-10 to K-14, in which said one or more other binding units that provides the polypeptide with increased half-life are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum albumin (such as human serum albumin) or a serum immunoglobulin (such as IgG).

Aspect K-16: Polypeptide according to aspect K-10 to K-15, in which said one or more other binding units that provides the polypeptide with increased half-life is a Nanobody that can bind to serum albumin (such as human serum albumin) or a serum immunoglobulin (such as IgG).

Aspect K-17: Polypeptide according to any of aspects K-10 to K-16, that has a serum half-life that is at least 1.5 times, preferably at least 2 times, such as at least 5 times, for example at least 10 times or more than 20 times, greater than the half-life of the corresponding amino acid sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect K-18: Polypeptide according to any of aspects K-10 to K-17, that has a serum half-life that is increased with more than 1 hours, preferably more than 2 hours, more preferably more than 6 hours, such as more than 12 hours, or even more than 24, 48 or 72 hours, compared to the corresponding amino acid sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect K-19: Polypeptide according to any of aspects K-1 to K-18, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect K-20: Polypeptide according to aspect K-10 or K-11, that is chosen from the group consisting of SEQ ID NO's: 186 to 198 and 227 to 234 or from the group consisting of from amino acid sequences that have more than 80%, preferably more than 90%, more preferably more than 95%, such as 99% or more sequence identity (as defined herein) with at least one of the amino acid sequences of SEQ ID NO's: 186 to 198 and 227 to 234.

Aspect K-21: Polypeptide according to aspect K-10 or K-11, that is chosen from the group consisting of SEQ ID NO's: 186 to 198 and 227 to 234, more preferably one of SEQ ID NO's: 190, 227, 228, 231 and 233.

Aspect L-1: Compound or construct, that comprises or essentially consists of one or more amino acid sequences according to any of aspects A-1 to A-22, B-1 to B-7, C-1 to C-4, D-1 to D-6, E-1 to E-13, F-1 to F-25 or G-1 and/or one or more Nanobodies according to any of aspects H-1 to H-22, and optionally further comprises one or more other groups, residues, moieties or binding units, optionally linked via one or more linkers.

Aspect L-2: Compound or construct according to aspect L-1, in which said one or more other groups, residues, moieties or binding units are amino acid sequences.

Aspect L-3: Compound or construct according to aspect L-1 or L-2, in which said one or more linkers, if present, are one or more amino acid sequences.

Aspect L-4: Compound or construct according to any of aspects L-1 to L-3, in which said one or more other groups, residues, moieties or binding units are immunoglobulin sequences.

Aspect L-5: Compound or construct according to any of aspects L-1 to L-4, in which said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Aspect L-6: Compound or construct according to any of aspects L-1 to L-5, in which said one or more amino acid sequences of the invention are immunoglobulin sequences.

Aspect L-7: Compound or construct according to any of aspects L-1 to L-6, in which said one or more amino acid sequences of the invention are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Aspect L-8: Compound or construct according to any of aspects L-1 to L-7, that comprises or essentially consists of one or more Nanobodies according to any of aspects H-1 to H-22 and in which said one or more other groups, residues, moieties or binding units are Nanobodies.

Aspect L-9: Compound or construct according to any of aspects L-1 to L-8, which is a multivalent construct.

Aspect L-10: Compound or construct according to any of aspects L-1 to L-9, which is a multispecific construct.

Aspect L-11: Compound or construct according to any of aspects L-1 to L-10, which has an increased half-life, compared to the corresponding amino acid sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect L-12: Compound or construct according to aspect L-1 to L-11, in which said one or more other groups, residues, moieties or binding units provide the compound or construct with increased half-life, compared to the corresponding amino acid sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect L-13: Compound or construct according to aspect L-12, in which said one or more other groups, residues, moieties or binding units that provide the compound or construct with increased half-life is chosen from the group consisting of serum proteins or fragments thereof, binding units that can bind to serum proteins, an Fc portion, and small proteins or peptides that can bind to serum proteins.

Aspect L-14: Compound or construct according to aspect L-12 or L-13, in which said one or more other groups, residues, moieties or binding units that provide the compound or construct with increased half-life is chosen from the group consisting of human serum albumin or fragments thereof.

Aspect L-15: Compound or construct according to any of aspects L-12 to L-14, in which said one or more other groups, residues, moieties or binding units that provides the compound or construct with increased half-life are chosen from the group consisting of binding units that can bind to serum albumin (such as human serum albumin) or a serum immunoglobulin (such as IgG).

Aspect L-16: Compound or construct according to any of aspects L-12 to L-15, in which said one or more other groups, residues, moieties or binding units that provides the compound or construct with increased half-life are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum albumin (such as human serum albumin) or a serum immunoglobulin (such as IgG).

Aspect L-17: Compound or construct according to any of aspects L-12 to L-16, in which said one or more other groups, residues, moieties or binding units that provides the compound or construct with increased half-life is a Nanobody that can bind to serum albumin (such as human serum albumin) or a serum immunoglobulin (such as IgG).

Aspect L-18: Compound or construct according to any of aspects L-12 to L-17, that has a serum half-life that is at least 1.5 times, preferably at least 2 times, such as at least 5 times, for example at least 10 times or more than 20 times, greater than the half-life of the corresponding amino acid sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect L-19: Compound or construct according to any of aspects L-12 to L-18, that has a serum half-life that is increased with more than 1 hours, preferably more than 2 hours, more preferably more than 6 hours, such as more than 12 hours, or even more than 24, 48 or 72 hours, compared to the corresponding amino acid sequence according to any of aspects A-1 to A-22, B-1 to B-7, C-1 to C-4, D-1 to D-6, E-1 to E-13, F-1 to F-25 or G-1 per se or Nanobody according to any of aspects H-1 to H-22 per se, respectively.

Aspect L-20: Compound or construct according to any of aspects L-12 to L-19, that has a serum half-life in human of at least about 12 hours, preferably at least 24 hours, more preferably at least 48 hours, even more preferably at least 72 hours or more; for example, of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect L-21: Monovalent construct, comprising or essentially consisting of one amino acid sequence according to any of aspects A-1 to A-22, B-1 to B-7, C-1 to C-4, D-1 to D-6, E-1 to E-13, F-1 to F-25 or G-1 and/or one Nanobody according to any of aspects H-1 to H-22.

Aspect L-22: Monovalent construct according to aspect L-21, in which said amino acid sequence of the invention is chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Aspect L-23: Monovalent construct, comprising or essentially consisting of one Nanobody according to any of aspects H-1 to H-22.

Aspect M-1: Nucleic acid or nucleotide sequence, that encodes an amino acid sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22, a polypeptide according to any of aspects K-1 to K-21, a compound or construct according to any of aspects L-1 to L-20 that is such that it can be obtained by expression of a nucleic acid or nucleotide sequence encoding the same, or a monovalent construct according to any of aspects L-21 to L-23.

Aspect M-2: Nucleic acid or nucleotide sequence according to aspect M-1, that is in the form of a genetic construct.

Aspect N-1: Host or host cell that expresses, or that under suitable circumstances is capable of expressing, an amino acid sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22, a polypeptide according to any of aspects K-1 to K-21, a compound or construct according to any of aspects L-1 to L-20 that is such that it can be obtained by expression of a nucleic acid or nucleotide sequence encoding the same, or a monovalent construct according to any of aspects L-21 to L-23; and/or that comprises a nucleic acid or nucleotide sequence according to aspect M-1 or a genetic construct according to aspect M-2.

Aspect O-1: Composition comprising at least one amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, monovalent construct according to any of aspects L-21 to L-23, or nucleic acid or nucleotide sequence according to aspects M-1 or M-2.

Aspect O-2: Composition according to aspect O-1, which is a pharmaceutical composition.

Aspect O-3: Composition according to aspect O-2, which is a pharmaceutical composition, that further comprises at least one pharmaceutically acceptable carrier, diluent or excipient and/or adjuvant, and that optionally comprises one or more further pharmaceutically active polypeptides and/or compounds.

Aspect P-1: Method for producing an amino acid sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22, a polypeptide according to any of aspects K-1 to K-21, a compound or construct according to any of aspects L-1 to L-20 that is such that it can be obtained by expression of a nucleic acid or nucleotide sequence encoding the same, or a monovalent construct according to any of aspects L-21 to L-23, said method at least comprising the steps of:
a) expressing, in a suitable host cell or host organism or in another suitable expression system, a nucleic acid or nucleotide sequence according to aspect M-1, or a genetic construct according to aspect M-2;
optionally followed by:
b) isolating and/or purifying the amino acid sequence according to any of aspects A-1 to A-22, B-1 to B-7, C-1 to C-4, D-1 to D-6, E-1 to E-13, F-1 to F-25 or G-1, the Nanobody according to any of aspects H-1 to H-22, the polypeptide according to any of aspects K-1 to K-21, the compound or construct according to any of aspects L-1 to L-20, or the monovalent construct according to any of aspects L-21 to L-23 thus obtained.

Aspect P-2: Method for producing an amino acid sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22, a polypeptide according to any of aspects K-1 to K-21, a compound or construct according to any of aspects L-1 to L-20 that is such that it can be obtained by expression of a nucleic acid or nucleotide sequence encoding the same, or a monovalent construct according to any of aspects L-21 to L-23, said method at least comprising the steps of:
a) cultivating and/or maintaining a host or host cell according to aspect N-1 under conditions that are such that said host or host cell expresses and/or produces at least one amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, or monovalent construct according to any of aspects L-21 to L-23;
optionally followed by:
b) isolating and/or purifying the amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, or monovalent construct according to any of aspects L-21 to L-23 thus obtained.

Aspect Q-1: Method for screening amino acid sequences directed against OX40L that comprises at least the steps of:
  a) providing a set, collection or library of nucleic acid sequences encoding amino acid sequences;
  b) screening said set, collection or library of nucleic acid sequences for nucleic acid sequences that encode an amino acid sequence that can bind to and/or has affinity for OX40L and that is cross-blocked or is cross blocking a Nanobody of the invention, e.g. one of SEQ ID NO: 179 to 185 (Table-1), or a humanized Nanobody of the invention, e.g. one of SEQ ID NO's: 199 to 226, or a polypeptide or construct of the invention, e.g. one of SEQ ID NO: 186 to 198 (see Table A-3) and 227 to 234 (Table A-4); and
  c) isolating said nucleic acid sequence, followed by expressing said amino acid sequence.

Aspect R-1: Method for the prevention and/or treatment of at least one inflammatory disease and/or disorder such as e.g. asthma, allergic asthma, chronic colitis, Crohn's disease, inflammatory bowel disease, and/or atherosclerosis said method comprising administering, to a subject in need thereof, a pharmaceutically active amount of at least one amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, monovalent construct according to any of aspects L-21 to L-23; or composition according to aspect O-2 or O-3.

Aspect R-2: Method for the prevention and/or treatment of at least one disease or disorder that is associated with OX40L, with its biological or pharmacological activity, and/or with the biological pathways or signalling in which OX40L is involved, said method comprising administering, to a subject in need thereof, a pharmaceutically active amount of at least one amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, monovalent construct according to any of aspects L-21 L-23; or composition according to aspect O-2 or O-3.

Aspect R-3: Method for the prevention and/or treatment of at least one disease or disorder that can be prevented and/or treated by administering, to a subject in need thereof, at least one amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, monovalent construct according to any of aspects L-21 to L-23; or composition according to aspect O-2 or O-3, said method comprising administering, to a subject in need thereof, a pharmaceutically active amount of at least one at least one amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, monovalent construct according to any of aspects L-21 to L-23; or composition according to aspect O-2 or O-3.

Aspect R-4: Method for immunotherapy, said method comprising administering, to a subject in need thereof, a pharmaceutically active amount of at least one amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, monovalent construct according to any of aspects L-21 to L-23; or composition according to aspect O-2 or O-3.

Aspect R-5: Use of an amino acid sequence according to any of aspects A-1 to A-22, B-1 to B-7, C-1 to C-4, D-1 to D-6, E-1 to E-13, F-1 to F-25 or G-1, a Nanobody according to any of aspects H-1 to H-22, a polypeptide according to any of aspects K-1 to K-21, a compound or construct according to any of aspects L-1 to L-20, or a monovalent construct according to any of aspects L-21 to L-23 in the preparation of a pharmaceutical composition for prevention and/or treatment of at least one inflammatory disease and/or disorder such as e.g. asthma, allergic asthma, chronic colitis, Crohn's disease, inflammatory bowel disease, and/or arthrosclerosis;
  and/or for use in one or more of the methods according to aspects R-1 to R-4.

Aspect R-6: Amino acid sequence according to any of aspects A-1 to A-22, B-1 to B-7, C-1 to C-4, D-1 to D-6, E-1 to E-13, F-1 to F-25 or G-1, Nanobody according to any of aspects H-1 to H-22, polypeptide according to any of aspects K-1 to K-21, compound or construct according to any of aspects L-1 to L-20, monovalent construct according to any of aspects L-21 or L-23; or composition according to aspect O-2 or O-3 for the prevention and/or treatment of at least one inflammatory disease and/or disorders such as e.g. asthma, allergic asthma, chronic colitis, Crohn's disease, inflammatory bowel disease, and/or arthrosclerosis.

Aspect S-1: Part or fragment of an amino acid sequence according to any of aspects A-1 to A-22, B-1 to B-7, C-1 to C-4, D-1 to D-6, E-1 to E-13, F-1 to F-25 or G-1, or of a Nanobody according to any of aspects H-1 to H-22.

Aspect S-2: Part or fragment according to aspect S-1, that can specifically bind to OX40L.

Aspect S-3: Part of fragment according to any of aspects S-1 or S-2, that can specifically bind to OX40L with a dissociation constant ($K_D$) of $10^{-5}$ to $10^{-12}$ moles/litre or less, and preferably $10^{-7}$ to $10^{-12}$ moles/litre or less and more preferably $10^{-8}$ to $10^{-12}$ moles/litre.

Aspect S-4: Part or fragment according to any of aspects S-1 to S-3, that can specifically bind to OX40L with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect S-5: Part or fragment according to any of aspects S-1 to S-4, that can specifically bind to OX40L with a rate of dissociation ($k_{off}$-rate) between $1$ $s^{-1}$ and $10^{-6}$ $s^{-1}$ preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect S-6: Compound or construct, that comprises or essentially consists of one or more parts or fragments according to any of aspects S-1 to S-4, and optionally further comprises one or more other groups, residues, moieties or binding units, optionally linked via one or more linkers.

Aspect S-7: Compound or construct according to aspect S-6, in which said one or more other groups, residues, moieties or binding units are amino acid sequences.

Aspect S-8: Compound or construct according to aspect S-6 or S-7, in which said one or more linkers, if present, are one or more amino acid sequences.

Aspect S-9: Nucleic acid or nucleotide sequence, that encodes a part or fragment according to any of aspects S-1 to S-5 or a compound or construct according to any of aspect S-6 to S-8.

Aspect S-10: Composition, comprising at least one part or fragment according to any of aspects S-1 to S-5, compound or construct according to any of aspects S-6 to S-8, or nucleic acid or nucleotide sequence according to aspect S-9.

Aspect T-1: Derivative of an amino acid sequence according to any of aspects A-1 to A-22, B-1 to B-7, C-1 to C-4, D-1 to D-6, E-1 to E-13, F-1 to F-25 or G-1, or of a Nanobody according to any of aspects H-1 to H-22.

Aspect T-2: Derivative according to aspect T-1, that can specifically bind to OX40L.

Aspect T-3: Derivative according to aspect T-1 or T-2, that can specifically bind to OX40L with a dissociation constant ($K_D$) of $10^{-5}$ to $10^{-12}$ moles/litre or less, and preferably $10^{-7}$ to $10^{-12}$ moles/litre or less and more preferably $10^{-8}$ to $10^{-12}$ moles/litre.

Aspect T-4: Derivative according to any of aspects T-1 to T-3, that can specifically bind to OX40L with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect T-5: Derivative according to any of aspects T-1 to T-4, that can specifically bind to OX40L with a rate of dissociation ($k_{off}$ rate) between 1 $s^{-1}$ and $10^{-6}$ $s^{-1}$ preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect T-6: Derivative of a polypeptide according to any of aspects K-1 to K-21 or compound or construct according to any of aspects L-1 to L-23.

Aspect T-7: Derivative according to aspect T-6, that can specifically bind to OX40L.

Aspect T-8: Derivative according to any of aspects T-6 or T-7, that can specifically bind to OX40L with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

Aspect T-9: Derivative according to any of aspects T-6 to T-8, that can specifically bind to OX40L with a rate of association ($k_{on}$-rate) of between $10^2$ $M^{-1}s^{-1}$ to about $10^7$ $M^{-1}s^{-1}$, preferably between $10^3$ $M^{-1}s^{-1}$ and $10^7$ $M^{-1}s^{-1}$, more preferably between $10^4$ $M^{-1}s^{-1}$ and $10^7$ $M^{-1}s^{-1}$, such as between $10^5$ $M^{-1}s^{-1}$ and $10^7$ $M^{-1}s^{-1}$.

Aspect T-10: Derivative according to any of aspects T-6 to T-9, that can specifically bind to OX40L with a rate of dissociation ($k_{off}$ rate) between 1 $s^{-1}$ and $10^{-6}$ $s^{-1}$ preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect T-11: Derivative according to any of aspects T-1 to T-10, that has a serum half-life that is at least 1.5 times, preferably at least 2 times, such as at least 5 times, for example at least 10 times or more than 20 times, greater than the half-life of the corresponding amino acid sequence according to any of aspects A-1 to A-22, B-1 to B-7, C-1 to C-4, D-1 to D-6, E-1 to E-13, F-1 to F-25 or G-1 per se, Nanobody according to any of aspects H-1 to H-22 per se, polypeptide according to any of aspects K-1 to K-21 or compound or construct according to any of aspects L-1 to L-23 per se.

Aspect T-12: Derivative according to any of aspects T-1 to T-11, that has a serum half-life that is increased with more than 1 hours, preferably more than 2 hours, more preferably more than 6 hours, such as more than 12 hours, or even more than 24, 48 or 72 hours, compared to the corresponding amino acid sequence according to any of aspects A-1 to A-22, B-1 to B-7, C-1 to C-4, D-1 to D-6, E-1 to E-13, F-1 to F-25 or G-1 per se, Nanobody according to any of aspects H-1 to H-23 per se, polypeptide according to any of aspects K-1 to K-21 or compound or construct according to any of aspects L-1 to L-23 per se, respectively.

Aspect T-13: Derivative according to any of aspects T-1 to T-12, that has a serum half-life in human of at least about 12 hours, preferably at least 24 hours, more preferably at least 48 hours, even more preferably at least 72 hours or more; for example, at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

Aspect T-14: Derivative according to any of aspects T-1 to T-13, that is a pegylated derivative.

Aspect T-15: Compound or construct, that comprises or essentially consists of one or more derivatives according to any of aspects T-1 to T-14, and optionally further comprises one or more other groups, residues, moieties or binding units, optionally linked via one or more linkers.

Aspect T-16: Compound or construct according to aspect T-15, in which said one or more other groups, residues, moieties or binding units are amino acid sequences.

Aspect T-17: Compound or construct according to aspect T-16, in which said one or more linkers, if present, are one or more amino acid sequences.

Aspect T-18: Nucleic acid encoding a compound or construct according to aspect T-16 or T-17.

Aspect T-19: Composition, comprising at least one derivative to any of aspects T-1 to T-14, compound or construct according to any of aspects T-15 to T-17, or nucleic acid or nucleotide sequence according to aspect T-18.

Specifically Preferred Embodiments

1. Nanobody that is directed against and/or that can specifically bind to hOX40L (SEQ ID NO: 175).
2. Nanobody according to embodiment 1, that is in essentially isolated form.
3. Nanobody according to any of embodiments 1 to 2 that can specifically bind to hOX40L (SEQ ID NO: 175) with a rate of dissociation ($k_{off}$ rate) between $10^{-2}$ $s^{-1}$ and $10^{-6}$ $s^{-1}$.
4. Nanobody according to any of embodiments 1 to 3 that can specifically bind to hOX40L (SEQ ID NO: 175) with an affinity less than 1 nM.
5. Nanobody that can specifically bind to hOX40L (SEQ ID NO: 175) and has an IC50 value in the alphascreen assay with 0.12 nM hOX40L (SEQ ID NO: 175) and 0.2 nM OX40/Fc of less than 10 nM.
6. Nanobody that can specifically bind to hOX40L (SEQ ID NO: 175) and has an IC50 value in the FACS assay of less than 50 nM.

7. Nanobody that can specifically bind to hOX40L (SEQ ID NO: 175) and has an IC50 value in the T-cell activation assay using human donors that is less than 200 nM, more preferably less than 100 nM, most preferred less than 10 nM.
8. Nanobody according to any of embodiments 1 to 7, that
   i) has at least 80% amino acid identity with at least one of the amino acid sequences of SEQ ID NO's: 179 to 185 or 199 to 226, in which for the purposes of determining the degree of amino acid identity, the amino acid residues that form the CDR sequences are disregarded; and in which:
   ii) preferably one or more of the amino acid residues at positions 11, 37, 44, 45, 47, 83, 84, 103, 104 and 108 according to the Kabat numbering are chosen from the Hallmark residues mentioned in Table B-2.
9. Nanobody according to any of embodiments 1 to 8, in which:
   CDR1 is chosen from the group consisting of:
   a) the amino acid sequences of SEQ ID NO's: 133 to 139;
   b) amino acid sequences that have at least 80% amino acid identity with at least one of the amino acid sequences of SEQ ID NO's: 133 to 139;
   c) amino acid sequences that have 3, 2, or 1 amino acid difference with at least one of the amino acid sequences of SEQ ID NO's: 133 to 139;
   and/or
   CDR2 is chosen from the group consisting of:
   d) the amino acid sequences of SEQ ID NO's: 147 to 153;
   e) amino acid sequences that have at least 80% amino acid identity with at least one of the amino acid sequences of SEQ ID NO's: 147 to 153;
   f) amino acid sequences that have 3, 2, or 1 amino acid difference with at least one of the amino acid sequences of SEQ ID NO's: 147 to 153;
   and/or CDR3 is chosen from the group consisting of:
   g) the amino acid sequences of SEQ ID NO's: 161 to 167;
   h) amino acid sequences that have at least 80% amino acid identity with at least one of the amino acid sequences of SEQ ID NO's: 161 to 167;
   i) amino acid sequences that have 3, 2, or 1 amino acid difference with at least one of the amino acid sequences of SEQ ID NO's: 161 to 167.
10. A polypeptide that comprises of one or more Nanobodies according to any of embodiments 1 to 9, and optionally further comprises one or more peptidic linkers.
11. The polypeptide according to embodiment 10, that is chosen from the group consisting of SEQ ID NO's: 186 to 198 and 227 to 234 or from the group consisting of from amino acid sequences that have more than 80% sequence identity with at least one of the amino acid sequences of SEQ ID NO's: 186 to 198 and 227 to 234.
12. The polypeptide according to embodiment 10 or 11, that is chosen from the group consisting of SEQ ID NO's: 186 to 198 and 227 to 234.
13. The polypeptide according to embodiment 10 or 11, that can specifically bind to hOX40L (SEQ ID NO: 175) and has an IC50 value in the T-cell activation assay using human donors that is less than the IC50 of the benchmark Fab, wherein the benchmark IgG from which the Fab is derived from has the following light and heavy chains: SEQ ID NO: 177 and 178.
14. The polypeptide according to embodiment 10 or 11, that can specifically bind to hOX40L (SEQ ID NO: 175) and has an IC50 value in the T-cell activation assay using human donors that is less than 200 nM, more preferably less than 100 nM, even more preferably less than 50 nM, even more preferably less than 10 nM, most preferred less than 5 nM.
15. Method for producing a Nanobody according to any of embodiments 1 to 9, said method at least comprising the steps of expressing, in a suitable host cell or host organism or in another suitable expression system, a nucleic acid or nucleotide sequence encoding a Nanobody according to any of embodiments 1 to 9.
16. Method for screening amino acid sequences directed against hOX40L (SEQ ID NO: 175) that comprises at least the steps of:
   a) providing a set, collection or library of nucleic acid sequences encoding amino acid sequences;
   b) screening said set, collection or library of nucleic acid sequences for nucleic acid sequences that encode an amino acid sequence that can bind to and/or has affinity for hOX40L (SEQ ID NO: 175) and that is cross-blocked or is cross blocking a Nanobody with one of SEQ ID NO's: 179 to 185, or a humanized Nanobody thereof, e.g. with one of SEQ ID NO's: 199 to 226, or a polypeptide with one of SEQ ID NO's: 186 to 198 and 227 to 234; and
   c) isolating said nucleic acid sequence, followed by expressing said amino acid sequence.
17. Nanobody according to any of embodiments 1 to 9 or a polypeptide according to any of embodiments 10 to 14 for use as a medicament.
18. Nanobody according of any of embodiments 1 to 9 or a polypeptide according to any of embodiments 10 to 14 for use in the treatment of asthma, allergic asthma, chronic colitis, Crohn's disease, inflammatory bowel disease, and/or arthrosclerosis.
19. A pharmaceutical composition for the treatment of asthma, allergic asthma, chronic colitis, Crohn's disease, inflammatory bowel disease, and/or arthrosclerosis comprising a Nanobody according to any of embodiments 1 to 9 or a polypeptide according to any of embodiments 10 to 14, and a pharmaceutically acceptable excipient.
20. Method for the prevention and/or treatment of at least one inflammatory disease and/or disorder such as e.g. asthma, allergic asthma, chronic colitis, Crohn's disease, inflammatory bowel disease, and/or arthrosclerosis, said method comprising administering, to a subject in need thereof, a pharmaceutically active amount of at least one Nanobody according to any of embodiments 1 to 9 or a polypeptide according to any of embodiments 10 to 14.
21. Nanobody according to any of embodiments 1 to 9 or a polypeptide according to any of embodiments 10 to 14 for use in a patient with severe persistent allergic asthma, chronic colitis, Crohn's disease, inflammatory bowel disease, and/or atherosclerosis who remain symptomatic despite optimized standard treatment.
22. A pharmaceutical composition for the treatment of a patient with severe persistent allergic asthma, chronic colitis, Crohn's disease, inflammatory bowel disease, and/or atherosclerosis who remain symptomatic despite optimized standard treatment, said treatment comprising administering a Nanobody according to any of embodiments 1 to 9 or a polypeptide according to any of embodiments 10 to 14, and a pharmaceutically acceptable excipient.
23. Method for the prevention and/or treatment of a patient with severe persistent allergic asthma, chronic colitis, Crohn's disease, inflammatory bowel disease, and/or atherosclerosis who remain symptomatic despite optimized standard treatment, said method comprising administer-

EXAMPLES

Example 1: Identification of OX40L Blocking Nanobodies 1.1 Immunizations

Three llamas (No. 285, 286 and 287) were immunized, according to standard protocols, with 4 intramuscular injections in the neck (100 or 50 μg/dose at biweekly intervals) of human (h) OX40L (extracellular domain expressed in NS0 mouse myeloma cells; R&D Systems, Minneapolis, Minn., USA), formulated in Complete Freund's Adjuvant (day 0) or Incomplete Freund's Adjuvant (following immunizations) (Difco, BD Biosciences, San Jose, Calif., USA). Another three llamas (No. 181b, 185b and 189b) were immunized, according to standard protocols, with 4 subcutaneous injections in the bow ($2\times10^7$ cells/dose at biweekly intervals) of CAKI cells overexpressing hOX40L, formulated in PBS. The CAKI (camel kidney) cells (Nguyen, Desmyter, Muyldermans, (2001) Adv. Immunol. 79: 261-296) were stably transfected with an expression vector for full length human OX40L (SEQ ID NO: 175) using Cell Line Nucleofector® Kit V (Amaxa VCA-1003; Lonza, Cologne, Germany). Cells expressing the highest levels of hOX40L on their membrane were sorted with FACSAria™ cell sorter (BD Biosciences) using PE (phycoerythrin) conjugated mouse anti-hOX40L (BD Bioscience) and subsequently cultured in RPMI 1640+10% Fetal Calf Serum+1% Penicillin/Streptomycin+300 μg/ml G418 (Invitrogen, Carlsbad, Calif., USA).

At day 46 or day 50 serum was collected from llamas immunized with recombinant protein or cells respectively to define antibody titers against hOX40L by ELISA and FACS. In ELISA, 96-well Maxisorp plates (Nunc, Wiesbaden, Germany) were coated with hOX40L. After blocking and adding diluted sera samples, the presence of anti-OX40L antibodies was demonstrated using mouse anti-llama IgG1, 2 and 3 antisera (in house produced) and HRP (horseradish peroxidase) conjugated rabbit anti-mouse IgG (Dako, Glostrup, Denmark) and a subsequent enzymatic reaction in the presence of the substrate TMB (3,3',5,5'-tetramentylbenzidine) (Promega, Madison, Wis., USA). In FACS, binding of antibodies present in sera of immunized llamas to Chinese Hamster Ovary (CHO) cells overexpressing hOX40L was investigated. CHO K1 (ATCC) cells were stably transfected as described. Cells expressing medium and high levels of hOX40L on their membrane were sorted as described and cultured in RPMI 1640+10% Fetal Calf Serum+1% Penicillin/Streptomycin+1 mg/ml G418. Cells were resuspended in diluted serum samples. After washing the presence of anti-OX40L antibodies was demonstrated in FACSArray™ (BD Biosciences) using goat anti-llama IgG (Bethyl Laboratories, Montgomery, Tex., USA) and PE conjugated donkey anti-goat IgG (Jackson Immuno Research, West Grove, Pa., USA). Both in ELISA and in FACS high antibody serum titers against hOX40L were detected for all llamas.

1.2 Library Construction

Peripheral blood mononuclear cells were prepared from serum samples of days 46 and 50 or of days 21, 45 and 50 for llamas immunized with recombinant protein or cells respectively using Ficoll-Paque Plus (GE Healthcare, Uppsala, Sweden) according to the manufacturer's instructions. Except for llamas 181b and 185b, also a LN (lymph node) biopsy was taken on day 45 or 46. Next, total RNA was extracted from the peripheral blood mononuclear cells and from the LN using Rneasy Midi Kit (Qiagen, Venlo, The Netherlands) following manufacturer instructions and used as starting material for RT-PCR to amplify Nanobody encoding gene fragments. These fragments were cloned into a house made phagemid vector, allowing production of recombinant phage particles, after infection with helper phage, which display the Nanobodies as geneIII fusion proteins on the surface of the phage particles. Phage was prepared according to standard methods and stored after filter sterilization at 4° C. for further use.

1.3 Selections

Phage libraries obtained from llamas No. 285, 286 and 287 were used for different selection strategies.

In a first and second selection round, biotinylated hOX40L [R&D Systems; biotinylated in house according to manufacturer instructions using Sulfo-NHS-LC-Biotin (Pierce, Rockford, Ill., USA)] at 100, 10, 1, 0.1, 0.01 nM was incubated with the phage libraries and subsequently captured on Streptavidin Dynabeads (Invitrogen). Following extensive washing, bound phages were eluted with either 1 mg/ml trypsin or 1 μM hOX40/Fc chimera (extracellular domain of hOX40 fused to Fc of human IgG, expressed in NS0 mouse myeloma cells; R&D Systems).

In another first selection, CHO cells or CAKI expressing hOX40L (cell generation is described above) were incubated with the phage libraries. After extensive washing, bound phages were eluted from the cells by resuspension in 1 mg/ml trypsin. In a subsequent second selection, phage libraries were incubated with CAKI cells expressing hOX40L (cell generation is described above). After extensive washing, bound phages were eluted as in the first selection round.

Phage libraries obtained from llamas No. 181b, 185b and 189b were used for a first and second round selection on CHO cells expressing hOX40L as described above.

In all selections, enrichment was observed. The output from the selections was rescued in E. coli TG1 cells. Colonies were picked and grown in 96 deep well plates (1 ml volume) and induced by adding IPTG for expression of soluble Nanobodies containing a C-terminal c-myc and $His_6$ tag. Periplasmic extracts (volume: ~100 μl) were prepared according to standard methods 1.4 Screening for OX40L Blocking Nanobodies in Alphascreen Assay The periplasmic extracts were screened in an Alphascreen assay to evaluate the blocking capacity of the expressed Nanobodies. This assay relies on the use of Donor and Acceptor beads which can be conjugated to biological molecules. When a biological interaction between molecules brings the beads into proximity, excited singlet oxygen molecules that are produced upon laser excitation at 680 nm by a photosensitizer in the Donor bead, diffuse across to react with a chemiluminiscer in the acceptor bead that further activates fluorophores which subsequently emit light at 520-620 nm. If the Nanobody inhibits binding of OX40L to OX40, fluorescent output will decrease.

Acceptor beads (Perkin Elmer, Waltham, Mass., USA) were conjugated with anti-human Fc Nanobodies (prepared in house) according to manufacturer instructions. To evaluate the neutralizing capacity of anti-hOX40L Nanobodies, the periplasmic extracts were pre-incubated with 0.37 nM biotinylated hOX40L for 15 min at room temperature. To this mixture, first the anti-human Fc conjugated acceptor beads and hOX40/Fc (0.2 nM final concentration) were added and incubated for 1 hour at room temperature. Second, streptavidin donor beads (Perkin Elmer) were added and incubated for an additional 1 hour. Fluorescence was measured by reading plates on the EnVision Multilabel Plate Reader (Perkin Elmer) using an excitation wavelength of 680 nm and an emission wavelength of 520 nm. Decrease in fluorescence signal indicates that the binding of biotinylated OX40L to the OX40 receptor is blocked by the Nanobody expressed in the periplasmic extract.

From this screening, inhibiting Nanobodies were selected and sequenced. Sequencing analysis revealed 29 Nanobody families, of which 7 were isolated from llamas immunized with recombinant protein and 22 families, of which 11 contain only one member, were isolated from llamas immunized with CAKI cells.

1.5 Binding of OX40L Blocking Nanobodies to Cell Expressed OX40L

Binding of the OX40L blocking Nanobodies to hOX40L expressed on the membrane of cells was determined in a binding FACS assay. CHO cells expressing full length hOX40L (see above) or wild type CHO K1 cells were resuspended in diluted periplasmic extract and incubated for 30 min at 4° C. After washing bound Nanobodies were detected in FACSArray™ using mouse anti-c-myc (Serotec, Dusseldorf, Germany) and PE conjugated goat anti-mouse IgG (Jackson Immuno Research). Strong and specific binding signals on CHO cells expressing hOX40L were demonstrated for all members of 6 families obtained from llamas immunized with recombinant protein and 14 families obtained from llamas immunized with cells. A relative weak binding signal was obtained for all OX40L blocking Nanobodies of the remaining families.

Example 2: Characterization of OX40L Blocking Nanobodies in Alphascreen, Competition FACS and T-Cell Activation Assay 2.1 Nanobody Expression and Purification 7 inhibitory Nanobodies (3 obtained from recombinant protein immunizations and 4 from cell immunizations) selected from the screening described in example 1 were further purified and characterized (SEQ ID NO's: 179 to 185, see also Table A-1). Selected Nanobodies were expressed in *E. coli* as c-myc, $His_6$-tagged proteins in a culture volume of 250 mL. Expression was induced by addition of 1 mM IPTG and allowed to continue for 4 hours at 37° C. After spinning the cell cultures, periplasmic extracts were prepared by freeze-thawing of the pellets and resuspension in PBS. These extracts were used as starting material for immobilized metal ion affinity chromatography (IMAC) using a HisTrap™ crude column (GE Healthcare). Nanobodies were eluted from the column using imidazole step gradient from 20 mM to 250 mM. In a next step the Nanobodies were desalted using HiPrep™ 26/10 desalting columns (GE Healthcare) in D-PBS (Invitrogen). Finally, lipopolysaccharides (LPS) were removed through incubation for 1 hour at room temperature with 50 mM octyl-β-D-glucopiranoside (OGP; Sigma, Bornem, Belgium) and gel filtration on Superdex 75 10/300GL column (GE Healthcare).

2.2 OX40L Blocking Benchmark Antibody Generation

In all assays for characterization of OX40L blocking Nanobodies described below, the potency was compared with a benchmark OX40L blocking mAb (monoclonal antibody) (benchmark IgG (SEQ ID NO: 177 (heavy chain)+SEQ ID NO: 178 (light chain)). A pEE mammalian expression vector containing DNA coding for benchmark antibody was constructed by first cloning the DNA coding for the heavy chain and light chain into pEE6.4 and pEE12.4 respectively (Lonza, Basel, Switzerland) and then constructing a double-gene vector. Human embryonic kidney cells (HEK293T; DSMZ, Braunschweig, Germany) were grown in DMEM+Glutamaxl medium (Invitrogen) supplemented with 10% fetal bovine serum (FBS) and 1% Penicillin/Streptomycin. HEK293T cells were transiently transfected with the plasmid expressing the heavy and light chain of anti-OX40L benchmark mAb using poly-ethylene imine (Polysciences, Eppelheim, Germany) and DMEM+Glutamaxl medium according to manufacturer's instructions and the conditioned medium was harvested after 5 days incubation at 37° C. in a $CO_2$ incubator. The medium was centrifuged and the supernatant was purified on Mabselect Sure column (GE Healthcare), eluted with 50 mM $Na_3$Citrate pH 3.0, immediately neutralized with 1M Tris-HCl pH 9 and dialyzed against PBS.

The Fab fragment of the benchmark was prepared by papain digest of the benchmark IgG (SEQ ID NO: 177 (heavy chain)+SEQ ID NO: 178 (light chain)). Briefly, the IgG was incubated for 4 hours at 37° C. in digestion buffer (0.1M $Na_2HPO_4$; 0.1M $KH_2PO_4$; pH: 7.3) containing 15 mM cystein, 2 mM EDTA and papain (1/100 of total amount IgG). Undigested IgG and Fc fragment were immediately removed on a Mabselect Sure column and the flow-through was further purified via size exclusion on a Superdex 75 10/300GL column and subsequently via affinity chromatography using a CaptureSelect Fab kappa matrix (BAC, Naarden, The Netherlands). Fab fragments were eluted with 100 mM glycin pH2.5, immediately neutralized by the addition of 1M Tris-HCl pH7.5 and dialyzed against PBS.

2.3 Nanobodies Block the Binding of OX40L to its Cognate Receptor OX40 in Alphascreen The purified Nanobodies were characterized in an Alphascreen assay to evaluate their blocking capacity and compare this with a benchmark OX40L blocking antibody.

Acceptor beads were conjugated with anti-human Fc Nanobodies and hOX40L was biotinlyated as described in Example 1. A dilution series of anti-OX40L Nanobodies or anti-OX40L benchmark Fab starting from 250 nM up to 0.9 pM was pre-incubated with 120 pM biotinylated hOX40L during 15 minutes at RT. To this mixture, first the anti-human Fc conjugated acceptor beads and hOX40/Fc (0.2 nM final concentration) were added and incubated for 1 hour at room temperature. Next, streptavidin donor beads were added and incubated for an additional 1 hour. Fluorescence was measured by reading plates on the EnVision Multilabel Plate Reader using an excitation wavelength of 680 nm and an emission wavelength of 520 nm.

Preincubation of all Nanobodies with biotinylated hOX40L reduced fluorescence intensity at 520 nm, demonstrating that the Nanobodies can effectively inhibit OX40L binding to OX40 in a dose-dependent manner. The calculated IC50 values are shown in Table C-1, and vary from 112 pM for OX40L18E09 up to 540 pM for OX40L19A07.

2.4 Nanobodies Block the Binding of OX40 to CHO Cells Expressing OX40L in FACS

The purified Nanobodies were characterized in a competition FACS assay to evaluate their blocking capacity using native OX40L expressed on cells.

A dilution series of anti-OX40L Nanobodies or anti-OX40L benchmark Fab starting from 1.2 µM up to 6.8 pM was pre-incubated with 3.1 nM hOX40/Fc and $2 \times 10^5$ hOX40L expressing cells for 30 min at 4° C. After washing bound hOX40/Fc was detected in FACSArray™ using PE conjugated anti-human IgG (Jackson Immuno Research).

All Nanobodies reduced fluorescence intensity, demonstrating that the Nanobodies can effectively inhibit OX40 binding to native, membrane expressed OX40L in a dose-dependent manner. The calculated IC50 values are shown in Table C-1, and vary from 1.61 nM for OX40L15B07 up to 16.55 nM for OX40L19A07.

2.5 Nanobodies Block OX40L Mediated Effector Memory T-Cell Activation

The purified Nanobodies were characterized in a T-cell activation assay to evaluate their capacity of blocking OX40L mediated activation of effector memory T-cells.

CD45RA-CCR7-effector memory T-cells were isolated from buffy coats (Red Cross, Ghent, Belgium) from healthy donors in two steps. First, the total T-cell population was isolated using RosetteSep Human T-cell Enrichment Cocktail (StemCell Technologies, Vancouver, Canada) and Ficoll-Paque™ PLUS (GE Healthcare) following manufacturer instructions. In a second step a negative selection for CD45RA-CCR7-cells was performed by staining CD45RA+ CCR7+ cells with mouse anti-human CD45RA-biotin (BD Biosciences) and rat anti-human CCR7-biotin (BS Biosciences) and incubation with Dynabeads Biotin Binder (Invitrogen) according to manufacturer instructions.

Wells of a microtiterplate (Greiner, Frickenhausen, Germany) were coated overnight at 4° C. with 31.25 ng/ml anti-CD3 mAb OKT-3 (eBioscience, San Diego, USA). After washing the plate, $2 \times 10^5$ CD45RA-CCR7-effector memory T-cells, $1 \times 10^4$ hOX40L expressing CHO cells or wild type CHO cells (irradiated with gamma scintillator at 3000 RAD; UZ Gent, Belgium) and dilution series of anti-OX40L Nanobodies or anti-OX40L benchmark Fab starting from 2 pM in medium (RPMI+10% Fetal Calf Serum+1% Penicillin/Streptomycin) were added simultaneously and incubated for 3 days at 37° C. in $CO_2$ incubator.

Production of IL4 by CD45RA-CCR7-effector memory T-cells was measured in ELISA. Wells of a Maxisorp plate (Nunc, Langenselbold, Germany) were coated overnight at 4° C. with 2 µg/ml anti-human IL4 (ELISA Capture) (BD Biosciences). After washing and blocking of the coated wells, a Y dilution of cell supernatant was added together with 1 µg/ml biotinylated anti-human IL4 (BD Biosciences) and incubated for 2.5 hours at room temperature. As a standard, ½ serial dilutions of recombinant human IL4 (BD Biosciences) starting from 625 µg/ml were included. Detection was done using HRP conjugated streptavidin (Dako) and TMB One Solution (Promega). The reaction was stopped with $H_2SO_4$ and the OD was read at 450 nm.

All Nanobodies effectively inhibit OX40L mediated CD45RA-CCR7-effector memory T-cell activation. The calculated IC50 values are shown in Table C-2 for 4 human donors and vary from 36-49 nM for OX40L18E09 up to 596-618 nM for OX40L19A07.

Example 3: Binding Specificity of OX40L Blocking Nanobodies 3.1 OX40L Blocking Nanobodies Bind Specifically to Cell Membrane Expressed Human and Cynomolgus OX40L OX40L of human (hOX40L) and cynomolgus monkey (cynoOX40L) was expressed on CHO cells as full length, membrane-bound protein. Transfection of CHO K1 with the respective expression plasmid DNA and selection of clones with high expression levels was performed as described in Example 1. Binding of the Nanobodies to the cell surface expressed OX40L was assessed by FACS analysis of cells as described below.

A dilution series of anti-OX40L Nanobodies or anti-OX40L benchmark Fab starting from 200 nM was pre-incubated with $2 \times 10^5$ either hOX40L or cynoOX40L expressing CHO cells for 30 min at 4° C. After washing bound Nanobodies were detected in FACSArray™ using mouse anti-c-myc and PE conjugated goat anti-mouse IgG.

All Nanobodies showed dose-dependent binding to both hOX40L and cynoOX40L expressed on CHO cells (Table C-3).

3.2 OX40L Blocking Nanobodies do not Bind to TNF Family Members TNF-Alpha, CD40L, CD30L, RANKL or TRAIL The binding of OX40L blocking Nanobodies to other TNF family members was tested in a competition ELISA.

Biotinylated hOX40L was captured on a Maxisorp plate coated with 2 µg/ml neutravidin. A fixed concentration of Nanobody [EC50 concentration as determined in binding ELISA to neutravidin captured hOX40L (data not shown): ranging from 1.3 nM to 4.7 nM] was pre-incubated for 1 hour at room temperature with a concentration series, starting from 100 fold molar excess, of hTNF-alpha (in house produced), hCD40L (PeproTech, Rocky Hill, N.J., USA), hCD30L (R&D Systems), human Receptor Activator for Nuclear Factor κ B Ligand (hRANKL; PeproTech), human tumor necrosis factor-related apoptosis inducing ligand (hTRAIL; R&D Systems) or hOX40L as positive control, before they were added to the plate. Binding of the Nanobodies to neutravidin captured hOX40L was detected with polyclonal rabbit anti-VHH antiserum (in house produced) and HRP conjugated goat anti-rabbit IgG (Dako). Detection was done using sTMB (SDT Reagents, Baesweiler, Germany), the reaction was stopped with 1M HCl and absorbance was determined at 450 nm.

Binding of the Nanobodies to hOX40L captured on neutravidin was only inhibited by exogenously added hOX40L and was not affected by the addition of the other ligands. Results obtained for OX40L01E07 are shown in FIG. 1 and are representative for all 7 Nanobodies tested.

Example 4: Characterization of Trivalent Bispecific Anti-OX40L Nanobodies in Alphascreen, Competition FACS and T-Cell Activation Assay 4.1 Construction and Expression of Trivalent Bispecific Anti-OX40L Nanobodies OX40L01B11, OX40L01E07, OX40L01E10, OX40L15B07, OX40L18E09, OX40L19D08 and OX40L19A07 were formatted as trivalent bispecific anti-OX40L Nanobodies. The trivalent molecules comprise two identical anti-OX40L Nanobody building blocks and one anti-human serum albumin (HSA) Nanobody, ALB11, for half life extension. ALB11 was either positioned in the middle or at the C-terminus of the trivalent constructs, and the linker between the building blocks was either 9GS ($Gly_4SerGly_3Ser$) or 35GS (($Gly_4Ser)_5$). The sequences of the trivalent bispecific anti-OX40L Nanobodies are shown in Table A-3 (SEQ ID NO's: 186 to 198). These constructs were expressed in *Pichia pastoris* X-33. A 40 ml pre-culture in YPD medium (20% peptone, 10% yeast extract and 2% dextrose) was incubated for 8 hours at 28° C. at 250 rpm. Fresh medium (500 ml BGCM; 2% peptone, 1% yeast extract, 0.2 M K-phosphate pH 6, 1% glycerol, 1.3% Yeast Nitrogen Base (Invitrogen), 0.2 mgiotin] was inoculated to an $OD_{600nm}$ of 0.08 and incubated overnight at 28° C. at 200 rpm. The cells were centrifuged when the $20<OD_{600nm}<25$ and the pellet was resuspended in 160 ml BMCM medium (2.3% peptone, 1.2% yeast extract, 0.2 M K phosphate pH 6, 1.3% Yeast Nitrogen Base, 0.06 mg biotin, 0.5% methanol). The culture was incubated for 48 hours at 28° C., 200 rpm and during that time methanol was added 4 times. The culture was centrifuged and the supernatant was used as starting material for IMAC using a HisTrap™ crude column (GE Healthcare) in the case when a c-myc, $His_6$ tag was present at the C-terminus. In the case when there were no tags present, the Nanobodies were purified using MEP Hypercell (Pall) or MabSelectSure (GE Healthcare) resin. If necessary, lipopolysaccharides were removed by incubation with OGP and purification via SEC using HiLoad_16/60_Superdex75 column (GE Healthcare).

4.2 Inhibition of OX40L Binding to OX40 by Trivalent Bispecific Anti-OX40 Nanobodies in AlphaScreen The trivalent Nanobodies (OX40L003, OX40L004, OX40L005, OX40L006, OX40L007, OX40L008, OX40L009, OX40L033, OX40L034, OX40L035, OX40L036, OX40L037, OX40L038) were compared to their monovalent counterparts in the AlphaScreen assay to evaluate whether they could also block OX40L binding to its cognate receptor.

AlphaScreen was performed as described in example 2, using 31 pM biotinylated hOX40L and 80 pM OX40/Fc. All trivalent Nanobodies blocked OX40L binding to the OX40 receptor in a dose dependent way with increased potency as compared to the corresponding monovalent molecules (see Table C-4). The calculated IC50 values for the trivalent Nanobodies varied from 11 pM for OX40L038 up to 95 pM for OX40L008.

In addition, the potency of the trivalent Nanobodies was also determined in presence of HSA. Nanobodies were pre-incubated for 1 hour at room temperature with 5 pM HSA (Sigma, Bornem, Belgium) prior to the addition of beads and hOX40/Fc. Final concentration of HSA in the assay was 1 µM. As shown in Table C-4, the potency of all trivalent Nanobodies for blocking OX40L-OX40 interaction was not significantly affected in the presence of HSA.

4.3 Inhibition of OX40 Binding to OX40L Expressed on CHO Cell Membranes by Trivalent Bispecific Anti-OX40L Nanobodies in FACS The trivalent Nanobodies (OX40L003, OX40L004, OX40L005, OX40L006, OX40L007, OX40L008, OX40L009) were compared to their monovalent counterparts in a competition FACS assay to evaluate whether they could also block binding of OX40 to OX40L expressed on CHO cell membrane.

The competition FACS assay was performed as described in example 2. All trivalent Nanobodies effectively inhibited OX40 binding to native, membrane expressed OX40L in a dose-dependent manner with potencies comparable with the corresponding monovalent molecules (see Table C-4). This might be explained by the low sensitivity of the assay due to high expression level of hOX40L on the CHO cells.

4.4 Binding to HSA

The affinity of the trivalent Nanobodies (OX40L003, OX40L004, OX40L005, OX40L006, OX40L007, OX40L008, OX40L009, OX40L034) for HSA was measured in BIAcore T100 instrument. HSA was immobilized via amine coupling on a CM-5 sensorchip at 626RU. Different concentrations of Nanobodies, ranging between 2 nM and 400 nM, were injected at 45 µl/min for 2 min, including a dissociation time of 10 min and regeneration of the surface with 10 mM Glycine-HCl pH1.5. Fitting was done using the 1:1 binding model and kinetic parameters are listed in Table C-5. The affinity of all trivalent Nanobodies for HSA is comparable.

4.5 Inhibition of OX40L Mediated Effector Memory T-Cell Activation by Trivalent Bispecific Anti-OX40L Nanobodies The trivalent Nanobodies (OX40L003, OX40L004, OX40L005, OX40L006, OX40L007, OX40L008, OX40L009, OX40L033, OX40L034, OX40L035, OX40L036, OX40L037, OX40L038) were compared to their monovalent counterparts in a T-cell activation assay to evaluate their capacity of blocking OX40L mediated activation of effector memory T-cells.

Figure 2A:
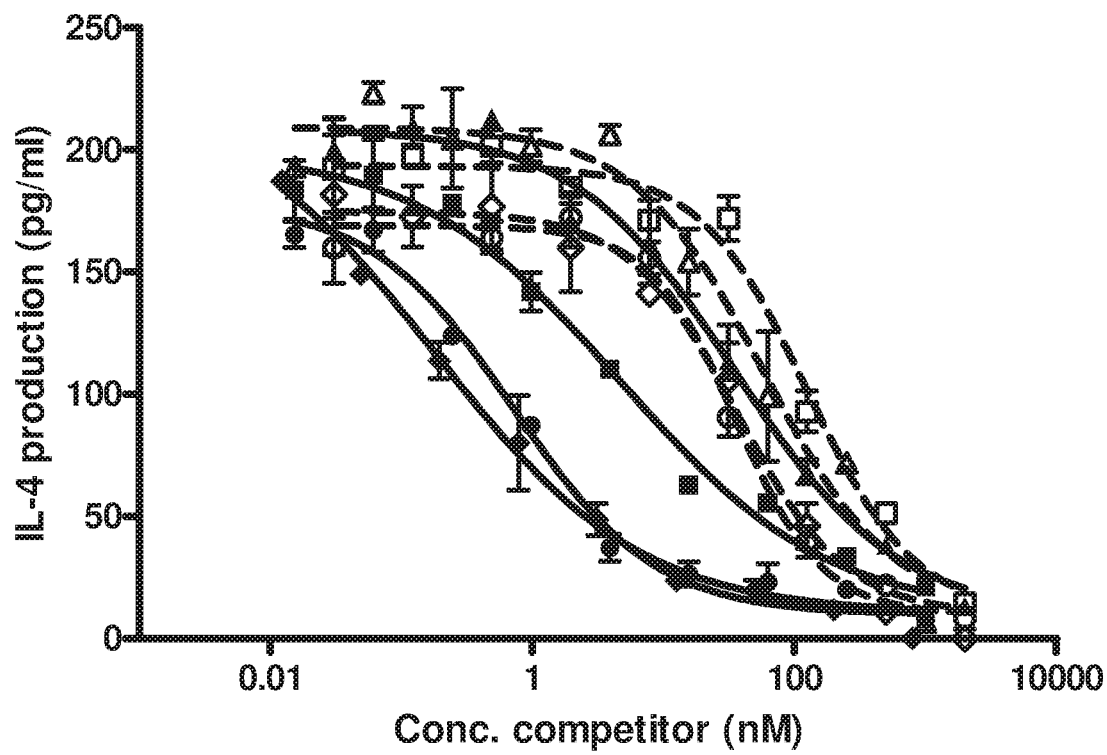
FIGS. 2A-2B: Inhibition of OX40L mediated effector memory T-cell activation by monovalent and trivalent bispecific anti-OX40L Nanobodies. $2 \times 10^5$ CD45RA-CCR7-effector memory T-cells, $1 \times 10^4$ hOX40L expressing CHO cells and dilution series of anti-OX40L Nanobodies or anti-OX40L benchmark were incubated for 3 days at 37° C. IL-4 production was measured in ELISA. All monovalent Nanobodies and benchmark Fab are shown with dotted lines and open symbols: OX40L01E07 (□), OX40L18E09 (○) and OX40L19D08 (¯) in FIG. 2A; OX40L01E10 (□), OX40L15B07 (○), OX40L01B11 (¯) in FIG. 2B, benchmark Fab (r). All trivalent bispecific Nanobodies and the benchmark IgG are shown with solid lines and symbols: OX40L003 (■), OX40L004 (•) and OX40L005 (♦) in FIG. 2A; OX40L006 (■), OX40L007 (•) and OX40L009 (¯) in FIG. 2B, benchmark IgG (▲).
Figure 2B:
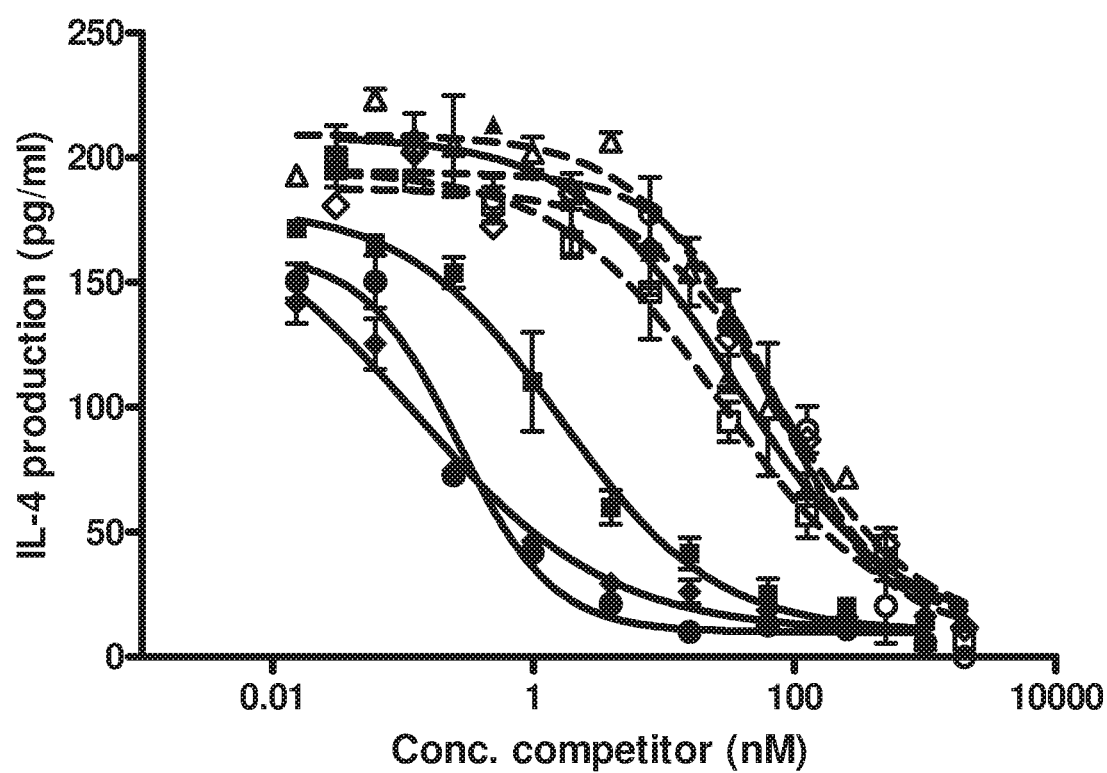

The T-cell activation assay was performed as described in Example 2, using four different human donors (donor 1-4). To investigate the influence of HSA binding on the potency of trivalent anti-OX40L Nanobodies, the same T-cell activation was performed in an additional 4 donors (donor 5-8) in the presence of 10% human serum (HS). The calculated IC50 values are shown in Table C-6. The inhibition curves obtained for donor 3 are shown in FIG. 2 and are representative for all donors tested.

All trivalent Nanobodies effectively inhibit OX40L mediated CD45RA-CCR7-effector memory T-cell activation with increased potencies compared to the monovalent Nanobodies. For the trivalent Nanobodies containing the OX40L01E07 building block, the potency in presence of HSA was increased when the ALB11 was at the C-terminal position. Furthermore, a 35GS linker between the last anti-OX40L building block and ALB11 (OX40L034) was preferred above a 9GS linker (OX40L033). Also for OX40L01E10, the formats with ALB11 at C-terminus had higher potency in presence of HSA, but there was no clear difference between OX40L035 and OX40L036. Finally, for the OX40L15B07 containing trivalent Nanobodies, all formats had similar potency in the presence of HSA, regardless of the position of ALB11 and the linker length.

Example 5: Epitope Binning of Anti-OX40L Nanobodies

Epitope binning of the 7 Nanobodies was determined using Surface Plasmon Resonance on a Biacore T100 instrument. The experiment was performed in HBS-EP+ running-buffer at 25° C. Recombinant hOX40L (R&D Systems) was immobilized on a Sensorchip CM5 via amine coupling at a level of app. 1200 RU. A first injection at 10 µl/min for 2 min with 500 nM of the Nanobody was performed. After a dissociation of 10 sec, a dual injection was performed at 10 µl/min for 2 min, starting with 1 µM of the same Nanobody to ensure saturation of the surface, followed by a mixture of 1 µM of the Nanobody and 500 nM of anti-OX40L benchmark Fab. After 10 min dissociation, regeneration of the surface was performed by injection of 50 mM NaOH for 5-25 sec at 100 µl. Based on the data shown in Table C-7, it was concluded that OX40L01B11 and the anti-OX40L benchmark Fab recognize the same or overlapping epitope on hOX40L or they are sterically hindering each other as they could not bind simultaneously to hOX40L. The data also indicate that the epitope of the other Nanobodies does not completely overlap with the epitope of anti-OX40L benchmark Fab and/or to a smaller or larger extend sterical hindrance is present dependent on the Nanobody injected.

In addition, it was investigated to what extend the 7 anti-OX40L Nanobodies have a different or identical or overlapping epitope. Standard conditions were as described above. Recombinant hOX40L was immobilized on a Sensorchip CM5 via amine coupling at a level of app. 1300 RU. A dual injection was performed at 10 µl/min for 2 min, starting with 500 nM of the first Nanobody, followed by 500 nM of the second Nanobody. After 10 min dissociation, regeneration of the surface was performed by injection of 50 mM NaOH for 5-20 sec at 100 µl/min. As shown in Table C-8, significant binding responses were obtained by injecting OX40L19D08, OX40L19A07 and OX40L01E07 after a first injection with OX40L01B11. Furthermore, OX40L15B07 and OX40L18E09 cannot bind simultaneously to hOX40L.

Example 6: Sequence Optimization of Anti-OX40L Nanobodies

In general, during Nanobody sequence optimization, parental wild type Nanobody® sequences are mutated to yield Nanobody® sequences that are more identical to human VH3-JH germline consensus sequences. Specific amino acids in the framework regions that differ between the Nanobody® and the human VH3-JH germline consensus are altered to the human counterpart in such a way that the protein structure, activity and stability are kept intact. To investigate this, all sequence optimization variants were compared with the parental Nanobody in four different assays: (i) determination of the melting temperature (Tm) in a Thermal Shift Assay (TSA), (ii) analysis of in vitro potency in hOX40L/hOX40 competition Alphascreen under native conditions as well as after heating for 1 min at Tm+10° C., (iii) analysis of in vitro potency in T-cell activation assay and (iv) analytical size exclusion (SEC) analysis.

In the TSA assay, Nanobodies were diluted to a concentration of 0.2 mg/ml and melting temperature (Tm) was determined at different pH by stepwise increase in temperature in presence of Sypro Orange, a dye that binds to Trp residues that become exposed upon unfolding of the protein, using the Lightcycler (Roche) for detection. The OX40L/hOX40 Alphascreen was exactly performed as described in Example 2. The T-cell activation assay was essentially performed as described in Example 2, but 5 nM rec hOX40L instead of hOX40L expressing CHO cells and 2 µg/ml anti-CD3 mAb OKT-3 was used. In SEC analysis, the Nanobodies were analyzed on a Phenomenex matrix to allow detection of multimers, aggregates or 'stickyness'.

6.1 Sequence Optimization of OX40L15B07

For sequence optimization of OX40L15B07, the following mutations were investigated: E1D, A14P, H39Q, R40A, T41P, E43K, G60A, F62S, I71R, A74S, N82bS, K83R and Q108L. Starting from a basic variant, i.e. OX40L15B07 (A14P, K83R, Q108L), a library was constructed including 7 additional mutations (parental or human residue) spread over 7 individual positions: H39Q, R40A, T41P, E43K, I71R, A74S and N82bS. The library was cloned in an in-house E. coli expression vector and periplasmic extracts containing soluble Nanobodies of 400 clones were screened in a hOX40L/hOX40 competition Alphascreen, as described in Example 1. Sequence analysis revealed that only the H39Q mutation resulted in a dramatic loss of potency, whereas all other mutations did not affect the potency in this Alphascreen. In addition, a BIAcore off-rate analysis was performed on BIAcore T100. For this, rec. hOX40L was immobilized on a CM-5 sensorchip. Periplasmic extracts (10-fold diluted) were injected at 45 µl/min for 120s, followed by a dissociation phase of 600s. The chip was regenerated with 50 mM NaOH. A ~2-fold increase in off-rate was demonstrated for R40A, T41P and E43K mutations. All other mutations investigated did not affect the off-rate.

Next, different sequence optimization variants (OX40L030, OX40L040-50, OX40L053, OX40L054, OX40L055, OX40L056, OX40L069, OX40L070, OX40L071, OX40L082 and OX40L083; SEQ ID NO's: 206-226; Table A-2) were constructed and produced as described in Example 2. As summarized in Table C-11, E1D, A14P, A74S, K83R and Q108L mutations had no clear effect on potency or thermal stability. In contrast, a ~6-fold drop in potency (T-cell assay) and a 5° C. drop in Tm were observed for R40A. T41P and E43K resulted in a ~2- and ~3-fold drop in potency and a 1.5-3° C. and 1-4° C. drop in Tm respectively. The mutations G60A and F62S did not affect the Tm, but G60A resulted in a ~3.5-fold drop in potency. Finally, I71R and N82bS resulted in a drop in Tm of 5° C. and 2° C. respectively, but did not affect potency. Regardless of the observed decrease in Tm, the potency of native and heat-treated samples measured in Alphascreen was similar for each variant.

Furthermore, the behaviour of OX40L030, OX40L082 and OX40L083 in analytic SEC on Phenomenex matrix was similar to that of OX40L15B07. No significant aggregation or stickyness was observed, although for OX40L082 a very small prepeak was observed, which might be due to dimerization (data not shown).

6.2 Sequence Optimization of OX40L01B11

For sequence optimization of OX40L01B11, the following mutations were investigated: E1D, A14P, V23A, A74S, K83R and Q108L (amino acid position referring to Kabat numbering scheme). An OX40L01B11 variant containing all mutations (OX40L075; SEQ ID NO: 199; Table A-2) was constructed and produced as described in Example 2. As shown in Table C-9, the mutations had no effect on the potency in a hOX40L/hOX40 competition Alphascreen, but a small drop in Tm of 2° C. compared to the parental OX40L01B11, and an entailed 6-fold drop in potency after heat-treatment of OX40L075 was observed. The behaviour of OX40L075 in analytical SEC on Phenomenex matrix was similar to that of OX40L01B11; no aggregation or stickyness was observed (data not shown).

6.3 Sequence Optimization of OX40L01E07

For sequence optimization of OX40L01E07, the following mutations were investigated: E1D, A14P, A74S, K83R, L105Q and Q108L. Six OX40L01E07 variants (OX40L024, OX40L025, OX40L026, OX40L027, OX40L028 and OX40L039; SEQ ID NO's: 200-205; Table A-2) were constructed and produced as described in Example 2. All the mutations were permissive for in vitro potency in both native conditions and after heat-treatment. No significant negative effect on physical stability was observed (Table C-10). The behaviour of all variants in analytic SEC on Phenomenex matrix was similar to that of OX40L01E07; no aggregation or stickyness was observed (data not shown).

Example 7: Characterization of Trivalent Bispecific Sequence Optimized Anti-OX40L Nanobodies in Alphascreen and T-Cell Activation Assay 7.1 Construction and Expression of Trivalent Bispecific Sequence Optimized Anti-OX40L Nanobodies Sequence optimized variants of OX40L01B11, OX40L01E07 and OX40L15B07 were formatted as trivalent bispecific sequence optimized anti-OX40L Nanobodies. The trivalent molecules comprised two identical anti-OX40L Nanobody building blocks and one anti-HSA Nanobody, ALB11, for half life extension. ALB11 was either positioned in the middle or at the C-terminus of the trivalent constructs, and the linker between the building blocks was either 9GS or 35GS. The sequences of the trivalent bispecific sequence optimized anti-OX40L Nanobodies are shown in Table A-4 (SEQ ID NOs: 227-234).

7.2 Inhibition of OX40L Mediated Effector Memory T-Cell Activation by Trivalent Bispecific Sequence Optimized Anti-OX40L Nanobodies The in vitro potency of the trivalent bispecific sequence optimized anti-OX40L Nanobodies (OX40L032, OX40L051, OX40L079, OX40L080, OX40L084, OX40L085 and OX40L086) was compared with the potency of the corresponding wild type formatted Nanobodies and the anti-OX40L benchmark in the T-cell activation assay. The assay was performed as described in Example 4, in the presence of 10% fetal bovine serum or 10% human serum. The data obtained with five different human donors (donor 9-13) are shown in Table C-12. The trivalent sequence optimized Nanobodies OX40L079 and OX40L080 had similar potencies compared to that of wild type OX40L003 in absence of HSA. For both Nanobodies there was a shift in potency in presence of HSA, which was slightly more pronounced when ALB11 building block was in the middle position (OX40L080) compared to when it was at the C-terminus (OX40L079). When comparing OX40L003 with OX40L080, however, it seems that 35GS linkers instead of 9GS linkers between the respective anti-OX40L building blocks on the one hand and ALB11 on the other hand decreased the 'HSA-effect'.

The trivalent bispecific sequence optimized Nanobodies OX40L032, OX40L051 and OX40L086 had similar potency compared with wild type OX40L009, both in presence and absence of HSA. Furthermore, the E1D mutation included in OX40L086 did not affect the potency.

Although a ~2-fold decrease in potency in Alphascreen was observed for sequence optimized variant OX40L082 compared with the parental Nanobody OX40L15B07 (see Example 6), upon formatting (OX40L084), the potency was similar compared to wild type OX40L007. For another sequence optimized variant, OX40L083, a ~6-fold drop in potency was observed in Alphascreen (see Example 6), which was translated in a 15- to 20-fold drop in potency in the T-cell assay for the trivalent OX40L085 compared with wild type OX40L007. For neither OX40L084 nor OX40L085 the potency in presence of HSA was affected.

7.3 Binding to HSA

The affinity of the trivalent bispecific sequence optimized Nanobodies (OX40L032, OX40L051, OX40L079, OX40L080, OX40L084 and OX40L085) for HSA was measured in BIAcore T100 instrument. HSA was immobilized via amine coupling on a CM-5 sensorchip at 626RU. Different concentrations of Nanobodies, ranging between 2 nM and 400 nM, were injected at 45 μl/min for 2 min, including a dissociation time of 10 min and regeneration of the surface with 10 mM Glycine-HCl pH1.5. Fitting was done using the 1:1 binding model and kinetic parameters are listed in Table C-13. The affinity of all trivalent Nanobodies for HSA was comparable and the position of ALB11 did not seem to have an influence on the affinity for HSA.

Tables

TABLE A-1

Preferred VHH sequences or Nanobody sequences (also referred herein as a sequence with a particular name or SEQ ID NO: X, wherein X is a number referring to the relevant amino acid sequence):

| Name | SEQ ID NO: X, wherein X= | Amino acid sequence |
| --- | --- | --- |
| OX40L15B07 | 179 | EVQLVESGGGLVQAGGSLRLSCAASRSIGRLDRMGWYRHRTGEPREL VATITGGSSINYGDFVKGRFTISIDNAKNTVYLQMNNLKPEDTAVYYCN FNKYVTSRDTWGQGTQVTVSS |
| OX40L01B11 | 180 | EVQLVESGGGLVQAGGSLRLSCVASGRSFSTYIMGWFRQAPGKEREF VATISRSGITTRSADSVKGRFTISRDNAKNTVYLQMNSLKPEDTAVYYC AAGPYVEQTLGLYQTLGPWDYWGQGTQVTVSS |
| OX40L01E07 | 181 | EVQLVESGGGLVQAGGSLRLSCAASGRTFSSIYAKGWFRQAPGKEREF VAAISRSGRSTSYADSVKGRFTISRDNAKNTVYLQMNSLKPEDTAVYYC AAVGGATTVTASEWDYWGLGTQVTVSS |
| OX40L01E10 | 182 | EVQLVESGGGLVQAGDSLRLSCAASGLTFSSFAMGWFRQAPGKEREF VAAISRSGYGTSFADSVRDRIISRDNAKNTVTLHLSRLKPEDTAVYYCA AEHTLGRPSRSQINYLYWGQGTQVTVSS |
| OX40L18E09 | 183 | EVQLVESGGGLVQAGGSLRLSCAASRNILSLNTMGWYRHAPGKPREL VARISSNSKTDYADSVKGRFTISRDNAKNTVLLQMNSLKPEDTGVYYC NLNVWRTSSDYWGQGTQVTVSS |
| OX40L19A07 | 184 | EVQLVESGGGLVQAGGSLRLSCAASGFTLDDYAIAWFRQAPGKEREG VSRIKISNGRTTYAGSVKGRFTISSDNAKNTVYLQMNSLNAEDTAVYYC AADRSSLLFGSNWDRKARYDYWGQGTQVTVSS |
| OX40L19D08 | 185 | EVQLVESGGGLVQAGASLRLSCAASGRRFISNYAMGWFRQAPGQER AFVAAISRSGSITYYTDSVKGRFSISRDYAKSTVYLQMDNLKPEDTAVYY CAADGGAVRDLTTNLPDYWGRGTQVTVSS |

TABLE A-2

Sequence optimized Nanobody sequences

| Name | SEQ ID NO | Amino acid sequence |
| --- | --- | --- |
| OX40L075 | 199 | EVQLVESGGGLVQPGGSLRLSCAASGRSFSTYIMGWFRQAPGKEREFVA TISRSGITTRSADSVKGRFTISRDNSKNTVYLQMNSLRPEDTAVYYCAAGP YVEQTLGLYQTLGPWDYWGQGTLVTVSS |
| OX40L024 | 200 | EVQLVESGGGLVQPGGSLRLSCAASGRTFSSIYAKGWFRQAPGKEREFV AAISRSGRSTSYADSVKGRFTISRDNAKNTVYLQMNSLRPEDTAVYYCAA VGGATTVTASEWDYWGLGTLVTVSS |
| OX40L025 | 201 | EVQLVESGGGLVQPGGSLRLSCAASGRTFSSIYAKGWFRQAPGKEREFV AAISRSGRSTSYADSVKGRFTISRDNSKNTVYLQMNSLRPEDTAVYYCAA VGGATTVTASEWDYWGLGTLVTVSS |
| OX40L026 | 202 | EVQLVESGGGLVQPGGSLRLSCAASGRTFSSIYAKGWFRQAPGKEREFV AAISRSGRSTSYADSVKGRFTISRDNAKNTVYLQMNSLRPEDTAVYYCAA VGGATTVTASEWDYWGQGTLVTVSS |

TABLE A-2-continued

Sequence optimized Nanobody sequences

| Name | SEQ ID NO | Amino acid sequence |
|---|---|---|
| OX40L027 | 203 | EVQLVESGGGLVQPGGSLRLSCAASGRTFSSIYAKGWFRQAPGKEREFV<br>AAISRSGRSTSYADSVKGRFTISRDNSKNTVYLQMNSLRPEDTAVYYCAA<br>VGGATTVTASEWDYWGQGTLVTVSS |
| OX40L028 | 204 | DVQLVESGGGLVQPGGSLRLSCAASGRTFSSIYAKGWFRQAPGKEREFV<br>AAISRSGRSTSYADSVKGRFTISRDNAKNTVYLQMNSLRPEDTAVYYCAA<br>VGGATTVTASEWDYWGLGTLVTVSS |
| OX40L039 | 205 | DVQLVESGGGLVQPGGSLRLSCAASGRTFSSIYAKGWFRQAPGKEREFV<br>AAISRSGRSTSYADSVKGRFTISRDNSKNTVYLQMNSLRPEDTAVYYCAA<br>VGGATTVTASEWDYWGQGTLVTVSS |
| OX40L030 | 206 | DVQLVESGGGLVQAGGSLRLSCAASRSIGRLDRMGWYRHRTGEPRELV<br>ATITGGSSINYGDFVKGRFTISIDNAKNTVYLQMNNLKPEDTAVYYCNFN<br>KYVTSRDTWGQGTQVTVSS |
| OX40L040 | 207 | DVQLVESGGGLVQPGGSLRLSCAASRSIGRLDRMGWYRHRTGEPRELV<br>ATITGGSSINYGDFVKGRFTISRDNSKNTVYLQMNSLRPEDTAVYYCNFN<br>KYVTSRDTWGQGTLVTVSS |
| OX40L041 | 208 | DVQLVESGGGLVQPGGSLRLSCAASRSIGRLDRMGWYRHATGEPRELV<br>ATITGGSSINYGDFVKGRFTISRDNSKNTVYLQMNSLRPEDTAVYYCNFN<br>KYVTSRDTWGQGTLVTVSS |
| OX40L042 | 209 | DVQLVESGGGLVQPGGSLRLSCAASRSIGRLDRMGWYRHRPGEPRELV<br>ATITGGSSINYGDFVKGRFTISRDNSKNTVYLQMNSLRPEDTAVYYCNFN<br>KYVTSRDTWGQGTLVTVSS |
| OX40L043 | 210 | DVQLVESGGGLVQPGGSLRLSCAASRSIGRLDRMGWYRHRTGKPRELV<br>ATITGGSSINYGDFVKGRFTISRDNSKNTVYLQMNSLRPEDTAVYYCNFN<br>KYVTSRDTWGQGTLVTVSS |
| OX40L044 | 211 | DVQLVESGGGLVQPGGSLRLSCAASRSIGRLDRMGWYRHAPGEPRELV<br>ATITGGSSINYGDFVKGRFTISRDNSKNTVYLQMNSLRPEDTAVYYCNFN<br>KYVTSRDTWGQGTLVTVSS |
| OX40L045 | 212 | DVQLVESGGGLVQPGGSLRLSCAASRSIGRLDRMGWYRHATGKPRELV<br>ATITGGSSINYGDFVKGRFTISRDNSKNTVYLQMNSLRPEDTAVYYCNFN<br>KYVTSRDTWGQGTLVTVSS |
| OX40L046 | 213 | DVQLVESGGGLVQPGGSLRLSCAASRSIGRLDRMGWYRHRPGKPRELV<br>ATITGGSSINYGDFVKGRFTISRDNSKNTVYLQMNSLRPEDTAVYYCNFN<br>KYVTSRDTWGQGTLVTVSS |
| OX40L047 | 214 | DVQLVESGGGLVQPGGSLRLSCAASRSIGRLDRMGWYRHAPGKPRELV<br>ATITGGSSINYGDFVKGRFTISRDNSKNTVYLQMNSLRPEDTAVYYCNFN<br>KYVTSRDTWGQGTLVTVSS |
| OX40L048 | 215 | DVQLVESGGGLVQPGGSLRLSCAASRSIGRLDRMGWYRHRTGEPRELV<br>ATITGGSSINYADFVKGRFTLSRDNSKNTVYLQMNSLRPEDTAVYYCNFN<br>KYVTSRDTWGQGTLVTVSS |
| OX40L049 | 216 | DVQLVESGGGLVQPGGSLRLSCAASRSIGRLDRMGWYRFHTGEPRELV<br>ATITGGSSINYGDSVKGRFTISRDNSKNTVYLQMNSLRPEDTAVYYCNFN<br>KYVTSRDIWGQGTLVTVSS |
| OX40L050 | 217 | DVQLVESGGGLVQPGGSLRLSCAASRSIGRLDRMGWYRHRTGEPRELV<br>ATITGGSSINYADSVKGRFTISRDNSKNTVYLQMNSLRPEDTAVYYCNFN<br>KYVTSRDTWGQGTLVTVSS |
| OX40L053 | 218 | DVQLVESGGGLVQPGGSLRLSCAASRSIGRLDRMGWYRHRTGEPRELV<br>ATITGGSSINYGDFVKGRFTISIDNSKNTVYLQMNSLRPEDTAVYYCNFNK<br>YVTSRDTWGQGTLVTVSS |
| OX40L054 | 219 | DVQLVESGGGLVQPGGSLRLSCAASRSIGRLDRMGWYRHRTGEPRELV<br>ATITGGSSINYGDFVKGRFTISRDNAKNTVYLQMNSLRPEDTAVYYCNFN<br>KYVTSRDTWGQGTLVTVSS |
| OX40L055 | 220 | DVQLVESGGGLVQPGGSLRLSCAASRSIGRLDWVGWYRHRTGEPRELV<br>ATITGGSSINYGDFVKGRFTISRDNSKNTVYLQMNNLRPEDTAVYYCNFN<br>KYVTSRDTWGQGTLVTVSS |
| OX40L056 | 221 | DVQLVESGGGLVQPGGSLRLSCAASRSIGRLDRMGWYRHRPGKPRELV<br>ATITGGSSINYADSVKGRFTISRDNSKNTVYLQMNSLRPEDTAVYYCNFN<br>KYVTSRDTWGQGTLVTVSS |

TABLE A-2-continued

Sequence optimized Nanobody sequences

| Name | SEQ ID NO | Amino acid sequence |
|---|---|---|
| OX40L069 | 222 | DVQLVESGGGLVQPGGSLRLSCAASRSIGRLDRMGWYRHRPGKPRELV ATITGGSSINYADSVKGRFTISIDNSKNTVYLQMNSLRPEDTAVYYCNFNK YVTSRDTWGQGTLVTVSS |
| OX40L070 | 223 | DVQLVESGGGLVQPGGSLRLSCAASRSIGRLDRMGWYRHRPGKPRELV ATITGGSSINYADSVKGRFTISRDNSKNTVYLQMNNLRPEDTAVYYCNFN KYVTSRDTWGQGTLVTVSS |
| OX40L071 | 224 | DVQLVESGGGLVQPGGSLRLSCAASRSIGRLDWVGWYRHRPGKPRELV ATITGGSSINYADSVKGRFTISIDNSKNTVYLQMNNLRPEDTAVYYCNFN KYVTSRDTWGQGTLVTVSS |
| OX40L082 | 225 | EVQLVESGGGLVQPGGSLRLSCAASRSIGRLDRMGWYRHRPGEPRELVA TITGGSSINYGDSVKGRFTISIDNSKNTVYLQMNSLRPEDTAVYYCNFNKY VISRDTWGQGTLVTVSS |
| OX40L083 | 226 | EVQLVESGGGLVQPGGSLRLSCAASRSIGRLDRMGWYRHRPGKPRELV ATITGGSSINYGDSVKGRFTISIDNSKNTVYLQMNSLRPEDTAVYYCNFNK YVTSRDTWGQGTLVTVSS |

TABLE A-3

Preferred polypeptide or compound sequences (also referred herein as a sequence with a particular name or SEQ ID NO: X, wherein X is a number referring to the relevant amino acid sequence):

| Name | SEQ ID NO: X, wherein X= | Amino acid sequence |
|---|---|---|
| OX40L003 (OX40L01E07-9GS-Alb8-9GS-OX40L01E07) | 186 | EVQLVESGGGLVQAGGSLRLSCAASGRTFSSIYAKGWFRQAPGKEREFVAAISRSGRSTSYADSVKGRFTISRDNAKNTVYLQMNSLKPEDTAVYYCAAVGGATTVTASEWDYWGLGTQVTVSSGGGGSGGGSEVQLVESGGGLVQPGNSLRLSCAASGFTFSSFGMSWVRQAPCKGLEWVSSISGSGSDTLYADSVKGRFTISRDNAKTTLYLQMNSLRPEDTAVYYCTIGGSLSRSSQGTLVTVSSGGGGSGGGSGGGSEVQLVESGGGLVQAGGSLRLSCAASGRTFSSIYAKGWFRQAPGKEREFVAAISRSGRSTYADSVKGRFTISRDNAKNTVYLQMNSLKPEDTAVYYCAAVGGATTVTASEWDYWGLGTQVTVSS |
| OX40L004 (OX40L18E09-9GS-Alb8-9GS-OX40L18E09) | 187 | EVQLVESGGGLVQAGGSLRLSCAASRNILSLNTMGWYRHAPGKPRELVARISSNSKTDYADSVKGRFTISRDNAKNTVLLQMNSLKPEDTGVYYCNLNVWRTSSDYWGQGTQVTVSSGGGGSGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQAGGSLRLSCAASRNILSLNTMGWYRHAPGKPRELVARISSNSKTDYADSVKGRFTISRDNAKNTVLLQMNSLKPEDTGVYYCNLNVWRTSSDYWGQGTQVTVSS |
| OX40L005 (OX40L19D08-9GS-Alb8-9GS-OX40L19D08) | 188 | EVQLVESGGGLVQAGASLRLSCAASGRRFISNYAMGWFRQAPGQERAFVAAISRSGSITYYTDSVKGRFSISRDYAKSTVYLQMDNLKPEDTAVYYCAADGGAVRDLTTNLPDYWGRGTQVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSGGGSEVQLVESGGGLVQAGASLRLSCAASGRRFISNYAMGWFRQAPGQERAFVAAISRSGSITYYTDSVKGRFSISRDYAKSTVYLQMDNLKPEDTAVYYCAADGGAVRDLTTNLPDYWGRGTQVTVSS |
| OX40L006 (OX40L01E10-9GS-Alb8-9GS-OX40L01E10) | 189 | EVQLVESGGGLVQAGDSLRLSCAASGLTFSSFAMGWFRQAPGKEREFVAAISRSGYGTSEADSVRDRFIISRDNAKNTVTLHLSRLKPEDTAVYYCAAEHUGRPSRSQINYLYWGQGTQVTVSSGGGGSGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQAGDSLRLSCAASGLTFSSFAMGWFRQAPGKEREFVAAISRSGYGTSEADSVRDRHISRDNAKNTVTLHLSRLKPEDTAVYYCAAEHTLGRPSRSQINYLYWGQGTQVTVSS |
| OX40L007 (OX40L15B07-9GS-Alb8-9GS-OX40L15B07) | 190 | EVQLVESGGGLVQAGGSLRLSCAASRSIGRLDRMGWYRHRTGEPRELVATITGGSSINYGDFVKGRFTISDNAKNTVYLQMNNLKPEDTAVYYCNFNKYVTSRDTWGQGTQVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVIVSSGGGGSGGGSEVQLVESGGGLVQAGGSLRLSCAASRSIGRLDRMGWYRHRTGEPPRELVATITGGSSINYGDEVKGRETISDNAKNTVYLQMNNLKPEDTAVYYCNFNKYVTSRDTWGQGTQVTVSS |
| OX40L008 (OX40L19A07-9GS-Alb8-9GS-OX40L19A07) | 191 | EVQLVESGGGLVQAGGSLRLSCAASGFTLDDYAIAWFRQAPGKEREGVSRIKISNGRTTYAGSVKGRFTISDNAKNTVYLQMNSLNAEDTAVYYCAADRSSLLEGSNWDRKARYDWGQGTQVTVSSGGGGSGGGSEVQLVESGGGLVQPGNSLRLSCAASGFTESSEGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQAGGSLRLSCAASGFTLDDYAIAWFRQAPGKEREGVSRIKISNGRTTYAGSVKGRFTISSDNAKNTVYLQMNSLNAEDTAVYYCAADRSSLLFGSNWDRKARYDWGQGTQVTVSS |
| OX40L009 (OX40L19A07-9GS-Alb8-9GS-OX40L19A07) | 192 | EVQLVESGGGLVQAGGSLRLSCAASGETLDDYAIAWERQAPGKEREGVSRIKISNGRTTYAGSVKGRFTISSDNAKNTVYLQMNSLNAEDTAVYYCAADRSSLLEGSNWDRKARYDWGQGTQVTVSSGGGGSGGGSEVQLVESGGGLVQPGNSLRLSCAASGFTESSEGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQAGGSLRLSCAASGETLDDYAIAWFROAPGKEREGVSRIKINGRTTYAGSVKGRFTISSDNAKNTVYLKAADRSSLLIGSNWDRKARYDWGQGTQVTVSS |

TABLE A-3-continued

Preferred polypeptide or compound sequences (also referred herein as a sequence with a particular name or SEQ ID NO: X, wherein X is a number referring to the relevant amino acid sequence):

| Name | SEQ ID NO: X, wherein X= | Amino acid sequence |
|---|---|---|
| OX40L033 (OX40L01E07 (Q108L)-35GS-OX40L01E07 (Q108L)-9GS-ALB11) | 193 | EVQLVESGGGLVQAGGSLRLSCAASGRTFSSIYAKGWERQAPGKEREEVAAISRSGRSTSYADSVKGRFTISRDNAKNTVYLQMNSLKPEDTAVYYCAAVGGATTVTASEWDYWGLGTLVTVSSGGGGSGGGGSGGGGSGGGGSGGGGSEVQLVESGGGLVQAGGSLRLSCAASGRTFSSIYAKGWERQAPGKEREFVAAISRSGRSTSYADSVKGRFTISRDNAKNTVYLQMNSLKPEDTAVYYCAAVGGATTVTASEWDYWGLGTLVTVSSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| OX40L034 (OX40L01E07 (Q108L)-35GS-OX40L01E07 (Q108L)-35GS-ALB11) | 194 | EVQLVESGGGLVQAGGSLRLSCAASGRTFSSIYAKGWERQAPGKEREEVAAISRSGRSTSYADSVKGRFTISRDNAKNTVYLQMNSLKPEDTAVYYCAAVGGATTVTASEWDYWGLETLVTVSSGGGGSGGGGSGGGGSGGGGSGGGGSEVQLVESGGGLVQAGGSLRLSCAASGRTFSSIYAKGWERQAPGKEREEVAAISRSGRSTSYADSVKGRFTISRDNAKNTVYLQMNSLKPEDTAVYYCAAVGGATTVTASEWDYWGLETLVTVSSGGGGSGGGGSGGGGSGGGGSGGGGSEVQLVESGGGLVQPGNSLRLSCAASGETESSEGMSWVRQAPGKGLEWVSSISGSGSDTLYADSVKGRFTISRDNAKTTLYLQMNSLRPEDTAVYYCTIGGSLSRSSQGTLVTVSS |
| OX40L035 (OX40L01E10 (Q108L)-35GS-OX40L01E10 (Q108L)-9GS-ALB11) | 195 | EVQLVESGGGLVQAGDSLRLSCAASGLTESSFAMGWERQAPGKEREFVAAISRSGYGTSEADSVRDRFIISRDNAKNTVTLHLSRLKPEDTAVYYCAAEHUGRPSRSQINYLYWGQGTLTFSSFAMGWERQAPGKEREEVAAISRSGYGTSEADSVRDRFIISRDNAKNTVTLHLSRLKPEDTAVYYCAAEHTLGRPSRSQINYLYWGQGTLVTVSSGGGGSGGGGSEVQLVESGGGLVQPGNSLRLSCAASGFTESSEGMSWVRQAPGKGLEWVSSISGSGSDTLYADSVKGRETISRDNAKTTLYLQMNSLRPEDTAVYKTIGGSLSRSSQGTLVTVSS |
| OX40L036 (OX40L01E10 (Q108L)-35GS-OX40L01E10 (Q108L)-35GS-ALB11) | 196 | EVQLVESGGGLVQAGDSLRLSCAASGLTFSSFAMGWERQAPGKEREQAPGKEREEVAAISRSGYGTSEADSVRDRFIISRDNAKNTVTLHLSRLKPEDTAVYYCAAEHTLGRPSRSQINYLYWGQGTLVTVSSGGGGSGGGGSGGGGSGGGGSGGGGSEVQLVESGGGLVQAGDSLRLSCAASGLTFSSFAMGWFRQAPGKERENAAISRSGYGTSEADSVRDRFIISRDNAKNTVLFHSRLKPEDTAWYCAAEHTLGRPSRSQINYLYWGQQTLVTVSSGGGGSGGGGSGGGGSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAWYCTIGGSLSRSSQGTLVTVSS |
| OX40L037 (OX40L015B07 (Q108L)-35GS-OX40L0154B07 (Q108L)-9GS-ALB11) | 197 | EVQLVESGGGLVQAGGSLRLSCAASRSIGRLDRMGWYRHRTGEPRELVATITGGSSINYGDRAGRFTISIDNAKNIVYLQMNNLKPEDTAWYCNFNKYVTSRDTWGQGTLVTVSSGGGGSGGGGSGGGGSGGGGSGGGGSEVQLVESGGLVQAGGSLRLSCAASRSIGRLDRMGWYRHRTGEPRELVATITGGSSINYGDFVKGRFTISIDNAKNTVYLQMNNLKPEDTAVYYCNFNKYVISRDTWGQGTLVTVSSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| OX40L038 (OX40L015B07 (Q108L)-35GS-OX40L015B07 (Q108L)-35GS-ALB11) | 198 | EVQLVESGGGLVQAGGSLRLSCAASRSIGRLDRMGWYRHRTGEPRELVATITGGSSINYGDFVKGRFTISIDNAKNTVYLQMNNLKPEDTAWYCNFNKYVTSRDTWGQGTLVTVSSGGGGSGGGGSGGGGSGGGGSGGGGSEVQLVESGGGLVQAGGSLRLSCAASRSIGRLDRMGWYRHRTGEPRELVATITGGSSINYGDFVKGRFTISIDNAKNTVYLQMNNLKPEDTAWYCNFNKYVTSRDTWGQGTLVTVSSGGGGSGGGGSGGGGSGGGGSGGGGSEVQLVESGGGINQPGNSLRLSCAASGFTFSSFGMSWVRQAPGKGLEWVSSISGSGDTLYADSVKGRFTISRDNAKTTLYLQMNSLRPEDTAWYCTIGGSLSRSSQGTLVTVSS |

TABLE A-4

Preferred sequence optimized polypeptide or compound sequences

| Name | SEQ ID NO | Amino acid sequence |
|---|---|---|
| OX40L032 (OX40L01B11 (A14P, V23A, A74S, K83R, Q108L))-35GS-OX40L01B11 (A14P, V23A, A74S, K83R, Q108L) | 227 | EVQLVESGGGLVQPGGSLRLSCAASGRSFSTYIMGWFRQAPGKEREFVAATISRSGITTRSADSVKGRFTISRDNSKNT VYLQMNSLRPEDTAVYKAAGPYVEQTLGLYQTLGPWDYWGQGTLVTVSSGGGGSGGGGSGGGGSGGGGSGGGGSGGG GGSGGGGSGGGGSGGGGSEVQLVESGGGLVQPGGSLRLSCAASGFSTYIMGWFRQAPGKEREFVATISRSGGGGSGGGG VKGRFTISRDNSKNTVYLQMNSLRPEDTAVYCCAAGPYVEQTLGLYQTLGPWDYWGQGTLVTVSSGGGGSGGGGS SGGGGSGGGGSGGGGSGGGGSEVQLVESGGGLVQPGGSLRLSCAASGFTFSSFGMSWVRQAPGKGLE WVSSISGGSGDTLYADSVKGRFTISRDNAKTTLYLQMNSLRPEDTAVYYCTIGGSLSRSSQGTLVTVSS |
| OX40L051 (OX40L01B11 (A14P, V23A, A74S, K83R, Q108L))-35GS-ALB11-35GS-OX40L01B11 (A14P, V23A, A74S, K83R, Q108L) | 228 | EVQLVESGGGLVQPGGSLRLSCAASGRSFSTYIMGWFRQAPGKEREFVAATISRSGITTRSADSVKGRFTISRDNSK VYLQMNSLRPEDTAVYCCAAGPYVEQTLGLYQTLGPWDYWGQGTLVTVSSGGGGSGGGGSGGGGSGGGGSGGG GGSGGGGSGGGGSEVQLVESGGGLVQPGGSLRLSCAASGFTESSFGMSWVRQAPGKGLEWVSSISGGSGDTLYA DSVKGRFTISRDNAKTTLYLQMNSLRPEDTAVYYCTIGGSLSRSSFSTYIMGWFRQAPGKEREFVATISRSGITTRSADS VKGRFTISRDNSKNTVYLQMNSLRPEDTAVYCCAAGPYVEQTLGLYQTLGPMDYWGQGTLVTVSS |
| OX40L079 (OX40L01E07 (E1D, A14P, A74S, K83R, L105Q, Q108L))-35GS-OX40L01E07 (A14P, A74S, K83R, L105Q, Q108L) | 229 | DVQLVESGGGLVQPGGSLRLSCAASGRTFSSIYAKGWFRQAPGKEREFVAAISRSGRSTSYADSVKGRFTISRDNSK NTVYLQMNSLRPEDTAVYCCAAVGATTVTASEWDYWGQGTLVTVSSGGGGSGGGGSGGGGSGGGGSGGGGSGGGGS GRFTISRDNSKNTVYLQMNSLRPEDTAVYKAAVGATTVTASEWDYWGQGTLVTVSSGGGGSGGGGSGGGGSGGGGS GGGGSGGGGSGGGGSGGGGSEVQLVESGGGLVQPGGSLRLSCAASGFTFSSFGMSWVRQAPGKGLEWVSSISG SGSDTLYADSVKGRFTISRDNAKTTLYLQMNSLRPEDTAVYYCTIGGSLSRSSQGTLVTVSS |
| OX40L080 (OX40L01E07 (E1D, A14P, A74S, K83R, L105Q, Q108L))-35GS-ALB11-35GS-OX40L01E07 (A14P, A74S, K83R, L105Q, Q108L) | 230 | DVQLVESGGGLVQPGGSLRLSCAASGRTFSSIYAKGWFRQAPGKEREFVAAISRSGRSTSYADSVKGRFTISRDNSK NTVYLQMNSLRPEDTAVYCCAAVGATTVTASEWDYWGQGTLVTVSSGGGGSGGGGSGGGGSGGGGSGGGGS GGGSGGGGSEVQLVESGGGLVQPGGSLRLSCAASGFTFSSFGMSWVRQAPGKGLEWVSSISGGSGDTLYADSVK GRFTISRDNAKTTLYLQMNSLRPEDTAVYYCTIGGSLSRSSQGTINTVSSGGGGSGGGGSGGGGSGGGGSGGGGS GGGSGGGGSGGGGSEVQLVESGGGLVQPGGSLRLSCAASGRTFSSIYAKGWFRQAPGKEREFVAAISRSGRSTSYADSVK GRFTISRDNSKNTVYLQMNSLRPEDTAVYCCAAVGATTVTASEWDYWGQGTLVTVSS |
| OX40L084 (OX40L15B07 (E1D, A14P, T41P, F62S, A74S, N82bS, K83R, Q108L))-9GS-ALB11-9GS-OX40L15B07 (A14P, T41P, F62S, A74S, N82bS, K83R, Q108L) | 231 | DVQLVESGGGLVQPGGSLRLSCAASRSIGRLDRMGWYRHRPGEPRELVATITGGSSINYGDSVKGRFTISDNSKNT VYLQMNSLRPEDTAVYYCNFNKYVTSRDTWGQGTLVTVSSGGGGSGGGGSEVQLVESGGGLVQPGNSLRLSCAAS GHTSSFGMSWVRQAPGKGLEWVSSISGGSGDTLYADSVKGRFTISRDNAKTILYLQMNSLRPEDTAVYYCTIGGSL SRSSQGTLVTVSSGGGGSVKGRFTISIDNSKNTVLQMNSLRPEDTAVYCNFNKYVTSRDTWGQGTLVTVSS SSINYGDSVKGRFTISIDNSKNTVYLQMNSLRPEDTAVYYCNFNKYVTSRDTWGQGTLVTVSS |
| OX40L085 (OX40L15B07 (E1D, A14P, T41P, E43K, F62S, A74S, N82bS, K83R, Q108L))-9GS-ALB11-9GS-OX40L15B07 (A14P, T41P, E43K, F62S, A74S, N82bS, K83R, Q108L) | 232 | DVQLVESGGGLVQPGGSLRLSCAASRSIGRLDRMGWYRHRPGEPRELVATITGGSSINYGDSVKGRFTISIDNSKNT VYLQMNSLRPEDTAVYYCNFNKYVTSRDTWGQGTLVTVSSGGGGSGGGGSEVQLVESGGGLVQPGNSLRLSCAAS GFTFSSFGMSWVRQAPGKGLEWVSSISGGSGDTLYADSVKGRFTISRDNAKTTLYLQMNSLRPEDTAVYKTIGGSL SRSSCIGTLVTVSSGGGGSGGGGSEVQLVESGGGLVQPGGSLRLSCAASRSIGRLDRMGWYRHRPGKPRELVATITGG SSINYGDSVKGRFTISIDNSKNTVVLQNANSLRPEDTAVYYCNFNKYVTSRDTWQGTLVTVSS |
| OX40L086 (OX40L01B11 (E1D, A14P, V23A, A74S, K83R, Q108L))-35GS-OX40L01B11 (A14P, V23A, A74S, K83R, Q108L) | 233 | DVQLVESGGGLVQPGGSLRLSCAASGRSFSTYIMGWFRQAPGKEREFVAATISRSGITTRSADSVKGRFTISRDNSKNT VYLQMNSLRPEDTAVYCCAAGPYVEQTLGLYQTLGPWDYWGQGTLVTVSSGGGGSGGGGSGGGGSGGGGSGGG GGSGGGGSGGGGSEVQLVESGGGLVQPGNSLRLSCAASGFTESSFVTSWVRQAPGKGLEWVSSISGGSGDTLYA DSVKGRFTISRDNAKTTLYLQMNSLRPEDTAVYYCTIGGSLSRSSQGTLVTVSSGGGGSGGGGSGGGGSGGGG VKGRFTISRDNSKNTVYLQMNSLRPEDTAVYCCAAGPYVEQTLGLYQTLGPMDYWGQGTLVTVSS |

TABLE A-4-continued

Preferred sequence optimized polypeptide or compound sequences

| Name | SEQ ID NO | Amino acid sequence |
|---|---|---|
| OX40L095 (OX40L01B11 (E1D, A14P, V23A, A74S, K83R, Q108L)-9GS-ALB11-9GS-OX40L01B11 (A14P, V23A, A74S, K83R, Q108L)) | 234 | DVQLVESGGGLVQPGSLRLSCAASGRSFSTYIMGWFRQAPGKEREFVATISRSGITTRSADSVKGRFTISRDNSKNT VYLQMNSLRPEDTAVYYCAAGPYVEQTLGLYQTLGPWDYWGQGTLVTVSSGGGSGGGSEVQLVESGGGLVQP GNSLRLSCAASGFTFSSFGMSWVRQAPGKGLEWVSSISGSGSDTLYADSVKGRFTISRDNAKTTLYLQMNSLRPEDT AVYYCTIGGSLSRSSQGTLVTVSSGGGSGGGSEVQLVESGGGLVQPGGSLRLSCAASGRSFSTYIMGWFRQAPGK EREFVATISRSGITTRSADSVKGRFTISRDNSKNTVYLQMNSLRPEDTAVYYCAAGPYVEQTLGLYQTLGPWDYWG QGTLVTVSS |

TABLE A-5

Further sequences

| Name | SEQ ID NO: | Amino acid sequence |
|---|---|---|
| human OX40L | 175 | MERVQPLEENVGNAARPRFERNKLLLVASVIQGLGLLLCFTYICLHFSAL QVSHRYPRIQSIKVQFTEYKKEKGFILTSQKEDEIMKVQNNSVIINCDGFY LISLKGYFSQEVNISLHYQKDEEPLFQLKKVRSVNSLMVASLTYKKVYLN VTTDNTSLDDFHVNGGELILIHQNPGEFCVL |
| cynomolgus OX40L | 176 | MERVQPLEENVGNAARPRFERNLLLVASVIQGLGLLLCFTYICLHFSAL QVSHQYPRIQSIKVQFTEYKKEEGFILTSQKEDEIMKVQNNSVIINCDGFY LISLKGYFSQEVNISLHYQKDEEPLFQLKKVRSVNSLMVASLTYKDKVYLN VTTDNTSLDDFHVNGGELILIHQNPGEFCVL |
| OX40L benchmark antibody heavy chain | 177 | EVQLLESGGGLVQPGGSLRLSCAASGFTFNSYAMSWVRQAPGKGLEW VSIISGSGGFTYYADSVKGRFTISRDNSRTTLYLQMNSLRAEDTAVYKA KDRLVAPGTFDYWGQGALVTVSSASTKGPSVFPLAPSSKSTSGGTAALG CLVKDYFPEPTVSWNSGALTSGVHTFPAVLQSSGLYSLSSVVTVPSSSL GTQTYICNVNHPSNTKVDKKVEPKSCDKTHTCPPCPAPELLGGPSVFLF PPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKG QPREPQVYTLPPSRDELTKNQVSLTCLVKGFYPSDIAVEWESNGQPENN YKTTPVLDSDGSFFLYSKLTVDKSRWQQGNVFSCSVMHEALHNHYTQ KSLSLSPGK |
| OX40L benchmark antibody light chain | 178 | DIQMTQSPSSLSASVGDRVTITCRASQGISSWLAWYQQKPEKAPKSLIY AASSLQSGVPSRFSGSGSGTDFTLTISSLQPEDFATYYCQQYNSYPYTFG QGTKLEIKRTVAAPSVFIPPSDEQLKSGTASVVCLLNNFYPREAKVQWK VDNALQSGNSQESVTEQDSKDSTYSLSSTLTLSKADYEKHKVYACEVTH QGLSSPVTKSFNRGEC |

TABLE C-1

Blocking capacity of Nanobodies in AlphaScreen and FACS

| ID | hOX40L/hOX40 AlphaScreen IC50(pM) | FACS IC50(nM) |
|---|---|---|
| OX40L01B11 | 375 | 5.61 |
| OX40L01E07 | 423 | 8.89 |
| OX40L01E10 | 490 | 9.11 |
| OX40L15B07 | 300 | 1.61 |
| OX40L18E09 | 112 | 1.73 |
| OX40L19A07 | 540 | 16.55 |
| OX40L19D08 | 285 | 3.31 |
| benchmark Fab | 1970 | 217.28 |

TABLE C-2

IC50 values for Nanobodies in OX40L mediated T-cell activation assay

| ID | donor 1 IC50 (nm) | donor 2 IC50 (nm) | donor 3 IC50 (nm) | donor 4 IC50 (nm) |
|---|---|---|---|---|
| OX40L01B11 | 230 | 188 | 80 | 220 |
| OX40L01E07 | 260 | 320 | 125 | 169 |
| OX40L01E10 | 110 | 159 | 27 | 12 |
| OX40L15B07 | 236 | 249 | 73 | n.d. |
| OX40L18E09 | 36 | 45 | 36 | 49 |
| OX40L19A07 | 596 | 618 | n.d. | n.d. |
| OX40L19D08 | 90 | 132 | 36 | 96 |
| Benchmark Fab | 80 | 131 | 58 | 85 | nd: not determined

TABLE C-3

Binding of Nanobodies to cell expressed OX40L

| ID | Binding to CHO-hOX40L EC50 (nm) | Binding to CHO-cynoOX40L EC50 (nm) |
|---|---|---|
| OX40L01B11 | 2.94 | 3.39 |
| OX40L01E07 | 4.03 | 4.90 |
| OX40L01E10 | 3.77 | 5.54 |
| OX40L15B07 | 2.43 | 3.23 |
| OX40L18E09 | 2.26 | 3.80 |
| OX40L19A07 | 5.67 | 5.34 |
| OX40L19D08 | 2.85 | 3.40 |

TABLE C-4

Potency of trivalent Nanobodies in AlphaScreen and FACS

| | hOX40L/hOX40 AlphaScreen | | |
|---|---|---|---|
| ID | IC50(pM) | IC50(pM) in presence of HSA | FACS IC50(nM) |
| OX40L01E10 | 264 | n.d. | 12 |
| OX40L006 | 70 | 122 | 18 |
| OX40L035 | 35 | 35 | n.d. |
| OX40L036 | 40 | 40 | n.d. |
| OX40L01B11 | 278 | n.d. | 5 |
| OX40L009 | 17 | 22 | 2 |
| OX40L01E07 | 229 | n.d. | 11 |
| OX40L003 | 61 | 85 | 16 |
| OX40L033 | 50 | 50 | n.d. |
| OX40L034 | 40 | 40 | n.d. |
| OX40L18E09 | 41 | n.d. | 2 |
| OX40L004 | 20 | 25 | 4 |
| OX40L19A07 | 355 | n.d. | 13 |
| OX40L008 | 95 | 126 | 17 |
| OX40L19D08 | 133 | n.d. | 4 |
| OX40L005 | 32 | 41 | 7 |
| OX40L15B07 | 125 | n.d. | 2 |
| OX40L007 | 14 | 17 | 2 |

TABLE C-4-continued

Potency of trivalent Nanobodies in AlphaScreen and FACS

| | hOX40L/hOX40 AlphaScreen | | |
|---|---|---|---|
| ID | IC50(pM) | IC50(pM) in presence of HSA | FACS IC50(nM) |
| OX40L037 | 13 | 13 | n.d. |
| OX40L038 | 11 | 11 | n.d. | nd: not determined

TABLE C-5

Binding of trivalent Nanobodies to Human Serum Albumin

| ID | ka 1/Ms | kd 1/s | KD nM |
|---|---|---|---|
| OX40L006 | 1.30E+05 | 4.70E-03 | 36.6 |
| OX40L009 | 1.80E+05 | 4.70E-03 | 25.8 |
| OX40L003 | 7.30E+05 | 5.00E-03 | 6.9 |
| OX40L034 | 9.30E+05 | 6.00E-03 | 6.4 |
| OX40L004 | 5.00E+05 | 4.20E-03 | 8.3 |
| OX40L008 | 4.40E+05 | 3.90E-03 | 8.8 |
| OX40L005 | 3.70E+05 | 4.70E-03 | 12.9 |
| OX40L007 | 3.30E+05 | 4.90E-03 | 14.9 |

TABLE C-6

IC50 values for trivalent Nanobodies in OX40L mediated T-cell activation assay

| ID | donor 1 IC50 (nM) | donor 2 IC50 (nM) | donor 3 IC50 (nM) | donor 4 IC50 (nM) | donor 5 IC50 (nM) + 10% HS | donor 6 IC50 (nM) + 10% HS | donor 7 IC50 (nM) + 10% HS | donor 8 IC50 (nM) + 10% HS |
|---|---|---|---|---|---|---|---|---|
| OX40L006 | 3.6 | 3.4 | 1.6 | 1.1 | 27.2 | 10.4 | nd | 2.9 |
| OX40L035 | nd | nd | nd | nd | 7.1 | 1.6 | nd | 1.4 |
| OX40L036 | nd | nd | nd | nd | 10.6 | 0.7 | 1.0 | 1.7 |
| OX40L009 | nd | nd | 0.1 | 0.03 | nd | nd | nd | nd |
| QX40L003 | 18.8 | 6.4 | 4.7 | 5.2 | nd | nd | 48.3 | 12.5 |
| OX40L033 | nd | nd | nd | nd | 11.9 | 2.4 | 3.5 | 2.3 |
| OX40L034 | nd | nd | nd | nd | 8.3 | nd | 0.8 | 0.8 |
| OX40L004 | nd | nd | 0.7 | 0.8 | nd | nd | nd | nd |
| OX40L008 | nd | nd | nd | nd | nd | nd | nd | nd |
| QX40L005 | nd | nd | 0.2 | 2.8 | nd | nd | nd | nd |
| OX40L007 | nd | nd | 0.3 | 0.3 | 1.1 | 0.8 | 1.6 | 0.3 |
| OX40L037 | nd | nd | nd | nd | 1.4 | 0.6 | 0.8 | 1.0 |
| OX40L038 | nd | nd | nd | nd | 0.8 | 1.6 | nd | 0.6 |
| benchmark Fab | 80.2 | 130.9 | 57.6 | 85.2 | nd | nd | nd | nd |
| benchmark IgG | 69.1 | 57.2 | 35.1 | 5.6 | nd | nd | nd | nd | nd: not determine
HS: human serum

TABLE C-7

Competition of Nanobodies with anit-OX40L benchmark Fab

| ID | Additional binding of LC001 Fab (RU) | % of expected LC001Fab binding |
|---|---|---|
| OX40L01B11 | 14 | 4 |
| OX40L01E10 | 109 | 27 |
| OX40L15B07 | 80 | 20 |
| OX40L18E09 | 70 | 18 |
| OX40L19D08 | 218 | 55 |
| OX40L19A07 | 160 | 40 |
| OX40L01E07 | 232 | 58 |

TABLE C-8

Competition of Nanobodies with each other

| First injection | Second injection | Binding Level sample 1 (RU) | Binding Level sample 2 (RU) | Binding Level sample 2 − sample 1 (RU) |
|---|---|---|---|---|
| OX40L01B11 | HBS-EP+ | 440 | 383 | −57 |
| | OX40L01B11 | 373 | 380 | 7 |
| | OX40L01E10 | 349 | 342 | −7 |
| | OX40L15B07 | 332 | 324 | −9 |
| | OX40L18E09 | 319 | 312 | −7 |
| | OX40L19D08 | 309 | 468 | 159 |
| | OX40L19A07 | 301 | 371 | 70 |
| | OX40L01E07 | 292 | 486 | 194 |
| OX40L01E10 | HBS-EP+ | 211 | 185 | −26 |
| | OX40L01B11 | 220 | 296 | 76 |
| | OX40L01E10 | 207 | 215 | 8 |
| | OX40L15B07 | 219 | 237 | 17 |
| | OX40L18E09 | 224 | 245 | 21 |
| | OX40L19D08 | 226 | 275 | 49 |
| | OX40L19A07 | 227 | 239 | 12 |
| | OX40L01E07 | 227 | 289 | 62 |
| OX40L15B07 | HBS-EP+ | 195 | 155 | −40 |
| | OX40L01B11 | 199 | 259 | 61 |
| | OX40L01E10 | 185 | 190 | 5 |
| | OX40L15B07 | 194 | 198 | 5 |
| | OX40L18E09 | 197 | 207 | 11 |
| | OX40L19D08 | 197 | 239 | 42 |
| | OX40L19A07 | 198 | 207 | 9 |
| | OX40L01E07 | 198 | 232 | 55 |
| OX40L18E09 | HBS-EP+ | 185 | 168 | −16 |
| | OX40L01B11 | 190 | 238 | 48 |
| | OX40L01E10 | 178 | 176 | −2 |
| | OX40L15B07 | 187 | 189 | 2 |
| | OX40L18E09 | 190 | 195 | 5 |
| | OX40L19D08 | 192 | 224 | 33 |

TABLE C-8-continued

Competition of Nanobodies with each other

| First injection | Second injection | Binding Level sample 1 (RU) | Binding Level sample 2 (RU) | Binding Level sample 2 − sample 1 (RU) |
|---|---|---|---|---|
| | OX40L19A07 | 192 | 194 | 2 |
| | OX40L01E07 | 192 | 238 | 45 |
| OX40L19D08 | HBS-EP+ | 222 | 184 | −38 |
| | OX40L01B11 | 227 | 433 | 205 |
| | OX40L01E10 | 215 | 202 | −13 |
| | OX40L15B07 | 224 | 217 | −7 |
| | OX40L18E09 | 227 | 225 | −3 |
| | OX40L19D08 | 229 | 236 | 7 |
| | OX40L19A07 | 229 | 205 | −24 |
| | OX40L01E07 | 229 | 252 | 23 |
| OX40L19A07 | HBS-EP+ | 175 | 160 | −15 |
| | OX40L01B11 | 178 | 358 | 180 |
| | OX40L01E10 | 166 | 183 | 17 |
| | OX40L15B07 | 174 | 200 | 26 |
| | OX40L18E09 | 176 | 206 | 30 |
| | OX40L19D08 | 177 | 224 | 47 |
| | OX40L19A07 | 177 | 183 | 6 |
| | OX40L01E07 | 177 | 240 | 63 |
| OX40L01E07 | HBS-EP+ | 220 | 212 | −9 |
| | OX40L01B11 | 194 | 399 | 205 |
| | OX40L01E10 | 188 | 193 | 5 |
| | OX40L15B07 | 186 | 198 | 12 |
| | OX40L18E09 | 185 | 200 | 15 |
| | OX40L19D08 | 184 | 187 | 3 |
| | OX40L19A07 | 182 | 179 | −3 |
| | OX40L01E07 | 181 | 192 | 11 |

TABLE C-9

Potency and melting temperature of OX40L01B11 variant

| | Alphascreen hOX40L/hOX40: IC50 (nM) | | TSA |
|---|---|---|---|
| ID | Native | Tm + 10° C. | $T_m$ (°) at pH 7.5 |
| OX40L01B11 | 0.54 | 0.6 | 69.79 |
| OX40L075 | 0.31 | 1.9 | 67.3 |

TABLE C-10

Potency and melting temperature of OX40L01E07 variants

| | Alphascreen hOX40L/hOX40: IC50 (pM) | | T cell assay with rec. hOX40L: | TSA |
|---|---|---|---|---|
| ID | Native | Tm + 10° C. | IC50 (nM) | Tm (° C.) at pH 7.5 |
| OX40L01E07 | 100 | 100 | 1.48 | 73.2 |
| OX40L024 | 70 | 70 | 1.54 | 71.1 |
| OX40L025 | 60 | 50 | 1.15 | 71.5 |
| OX40L026 | 50 | 60 | 2.46 | 76.1 |
| OX40L027 | 70 | 70 | 1.43 | 76.5 |
| OX40L028 | 70 | 70 | 2.3 | 71.9 |
| OX40L039 | 50 | 50 | 1.6 | 76.1 |

TABLE C-11

Potency and melting temperature of OX40L15B07 variants

| | Alphascreen hOX40L/hOX40: $IC_{50}$ (nM)- assay1 | Alphascreen hOX40L/hOX40: $IC_{50}$ (nM)- assay 2 | | Alphascreen hOX40L/hOX40: $IC_{50}$ (nM)- assay 3 | | T cell assay with rec. hOX40L | TSA Tm (° C.) |
|---|---|---|---|---|---|---|---|
| ID | Native | Native | Tm + 10° C. | Native | Tm + 10° C. | $IC_{50}$ (nM) | at pH 7.5) |
| OX40L15B07 | 0.102 | 0.066 | 0.103 | 0.077 | nd | 10 | 69.85 |
| OX40L030 | 0.076 | nd | nd | 0.143 | 0.143 | 11 | 70.67 |
| OX40L040 | 0.046 | 0.092 | 0.084 | 0.102 | 0.082 | 9 | 63.6 |
| OX40L041 | 0.127 | 0.22 | 0.262 | nd | nd | 64 | 58.2 |
| OX40L042 | 0.057 | nd | nd | nd | nd | 18 | 66.1 |
| OX40L043 | 0.101 | 0.134 | 0.156 | nd | nd | 29 | 64.85 |
| OX40L044 | 0.065 | nd | nd | nd | nd | 76 | 60.28 |
| OX40L045 | 0.152 | nd | nd | nd | nd | 133 | 62.36 |
| OX40L046 | 0.084 | 0.256 | 0.221 | nd | nd | 57 | 67.76 |
| OX40L047 | 0.269 | 0.735 | 0.557 | nd | nd | 126 | 65.68 |
| OX40L048 | 0.093 | 0.314 | 0.314 | nd | nd | 32 | 63.19 |
| OX40L049 | 0.035 | nd | nd | nd | nd | 12 | 63.99 |
| OX40L050 | 0.046 | 0.145 | 0.164 | nd | nd | 43 | 63.6 |
| OX40L053 | nd | nd | nd | 0.118 | 0.126 | nd | 68.57 |
| OX40L054 | nd | nd | nd | 0.079 | 0.094 | nd | 63.58 |
| OX40L055 | nd | nd | nd | 0.091 | 0.106 | nd | 65.66 |
| OX40L056 | nd | 1.124 | 1.124 | 1.124 | 1.124 | 135 | 67.32 |
| OX40L082 | nd | nd | nd | 0.14 | 0.14 | nd | 71.87 | nd: not determined

TABLE C-12

IC50 values obtained for trivalent sequence optimized Nanobodies in OX40L mediated T-cell activation assay

| ID | donor 9 IC50 (nM) + 10% FBS | donor 9 IC50 (nM) + 10% HS | donor 10 IC50 (nM) + 10% FBS | donor 10 IC50 (nM) + 10% HS | donor 11 IC50 (nM) + 10% FBS | donor 11 IC50 (nM) + 10% HS | donor 12 IC50 (nM) + 10% FBS | donor 12 IC50 (nM) + 10% HS | donor 13 IC50 (nM) + 10% FBS | donor 13 IC50 (nM) + 10% HS |
|---|---|---|---|---|---|---|---|---|---|---|
| OX40L003 | nd | nd | nd | nd | 10.9 | 106.0 | 11.0 | 64.2 | nd | nd |
| OX40L034 | nd | nd | nd | nd | 6.4 | 26.4 | 7.9 | 24.5 | nd | nd |
| OX40L079 | nd | nd | nd | nd | 5.3 | 19.3 | 5.5 | 7.1 | nd | nd |
| OX40L080 | nd | nd | nd | nd | 6.9 | 30.5 | 6.2 | 13.4 | nd | nd |
| OX40L007 | nd | nd | 7.9 | 11.5 | nd | nd | 3.0 | nd | 4.1 | 9.8 |
| OX40L084 | nd | nd | 15.2 | 13.9 | nd | nd | 3.6 | 5.0 | 12.0 | 7.8 |
| OX40L085 | nd | nd | 123.0 | 49.4 | nd | nd | 62.8 | nd | nd | nd |
| OX40L009 | 5.6 | 9.9 | 7.7 | 20.3 | nd | nd | nd | nd | nd | nd |
| OX40L032 | 5.2 | 8.9 | 9.4 | 12.1 | nd | nd | nd | nd | nd | nd |
| OX40L051 | 4.0 | 3.9 | 5.8 | 7.9 | nd | nd | nd | nd | 2.3 | 3.6 |
| OX40L086 | nd | nd | nd | nd | nd | nd | nd | nd | 4.2 | 5.1 |
| anti-OX40L benchmark IgG | nd | nd | 203.0 | 161.0 | 61.2 | 30.2 | 22.1 | 42.9 | 84.4 | 120.5 | nd: not determined

TABLE C-13

Binding of trivalent sequence optimiezed Nanobodies to Human Serum Albumin

| | BIAcore kinetic analysis on HSA | | |
|---|---|---|---|
| ID | ka (1/Ms) | kd (1/s) | KD (nM) |
| OX40L003 | 7.30E+05 | 5.00E−03 | 6.9 |
| OX40L034 | 9.30E+05 | 6.00E−03 | 6.4 |
| OX40L079 | 6.90E+05 | 6.00E−03 | 8.7 |
| OX40L080 | 7.20E+05 | 5.40E−03 | 7.6 |
| OX40L007 | 3.30E+05 | 4.90E−03 | 14.9 |
| OX40L084 | 4.20E+05 | 4.10E−03 | 9.7 |
| OX40L085 | 8.00E+05 | 3.90E−03 | 4.9 |
| OX40L009 | 1.80E+05 | 4.70E−03 | 25.8 |
| OX40L0032 | 1.80E+05 | 6.00E−03 | 33 |
| OX40L051 | 1.90E+05 | 5.30E−03 | 27 |

The invention claimed is:

1. Immunoglobulin single variable domain that specifically binds to OX40L (SEQ ID NO: 175), in which
CDR1 is chosen from the group consisting of:
a) SEQ ID NO: 135;
b) amino acid sequences that have 3, 2, or 1 amino acid difference with at least one of the amino acid sequences of SEQ ID NO: 135;
and
CDR2 is chosen from the group consisting of:
c) SEQ ID NO: 149;
d) amino acid sequences that have 3, 2, or 1 amino acid difference with at least one of the amino acid sequences of SEQ ID NO: 149;
and
CDR3 is chosen from the group consisting of:
e) SEQ ID NO: 163;
f) amino acid sequences that have 3, 2, or 1 amino acid difference with at least one of the amino acid sequences of SEQ ID NO: 163,
wherein the immunoglobulin single variable domain is a VH domain, a VHH, a partially humanized VHH or a fully humanized VHH.

2. Immunoglobulin single variable domain according to claim 1, that can specifically bind to OX40L (SEQ ID NO: 175):
with a dissociation constant ($K_D$) of $10^{-5}$ to $10^{-12}$ moles/litre or less,
with a rate of association ($k_{on}$-rate) of between $10^2$ $M^{-1}s^{-1}$ to about $10^7$ $M^{-1}s^{-1}$,
with a rate of dissociation ($k_{off}$ rate) between 1 $s^{-1}$ and $10^{-6}$ $s^{-1}$,
with an affinity less than 500 nM,
having an IC50 value in an Amplified Luminescent Proximity Homogenous Assay with 0.12 nM hOX40L and 0.2 nM OX40/Fc of less than 10 nM,
having an IC50 value in the FACS assay of less than 100 nM, and/or
having an IC50 value in the T-cell activation assay using human donors that is less than the IC50 of the benchmark Fab produced by papain digest of the benchmark IgG of which SEQ ID NO: 177 and 178 represent the polypeptides of the heavy and light chain, respectively.

3. Immunoglobulin single variable domain according to claim 1, that is chosen from the group consisting of SEQ ID NO's: 181 and 200-205, immunoglobulin single variable domains that cross-block the binding to OX40L of at least one of the amino acid sequences of SEQ ID NOs: 181 and 200-205, and immunoglobulin single variable domains that are cross-blocked from binding to OX40L by at least one of the amino acid sequences of SEQ ID NOs: 181 and 200-205.

4. Polypeptide that comprises or essentially consists of one or more immunoglobulin single variable domains according to claim 1.

5. Polypeptide according to claim 4, which further comprises one or more other residues or binding units, optionally linked via one or more peptidic linkers.

6. Polypeptide according to claim 4, in which said one or more other residues or binding units are chosen from the group consisting of immunoglobulin sequences, domain antibodies, and single domain antibodies.

7. Polypeptide according to claim 4, which is a multivalent construct, a multispecific construct, a multiparatopic construct, and/or has an increased half-life, compared to the corresponding immunoglobulin single variable domain.

8. Polypeptide according to claim 7, in which said one or more other binding units provide the polypeptide with increased half-life, compared to the immunoglobulin single variable domain.

9. Polypeptide according to claim 8, in which said one or more other binding units that provides the polypeptide with increased half-life are chosen from the group consisting of binding units that can bind to serum albumin, human serum albumin, a serum immunoglobulin, IgG, domain antibodies, single domain antibodies, single domain antibodies that can bind to serum albumin, and single domain antibodies that can bind to human serum albumin.

10. Polypeptide according to claim 4, that is chosen from the group consisting of SEQ ID NO's: 186, 193, 194, 229, and 230.

11. Nucleic acid or nucleotide sequence, that encodes an immunoglobulin single variable domain according to claim 1.

12. Host or host cell that expresses, or that under suitable circumstances is capable of expressing, an immunoglobulin single variable domain according to claim 1.

13. Composition comprising at least one immunoglobulin single variable domain according to claim 1.

14. Composition according to claim 13, further comprising a carrier.

15. Method for producing an immunoglobulin single variable domain according to claim 1, said method at least comprising the steps of:
a) expressing, in a suitable host cell or host organism or in another suitable expression system, a nucleic acid or nucleotide sequence encoding the immunoglobulin single variable domain;
optionally followed by:
b) isolating and/or purifying the immunoglobulin single variable domain.

* * * * *